US008981188B2

(12) United States Patent
Manjunath et al.

(10) Patent No.: US 8,981,188 B2

(45) Date of Patent: Mar. 17, 2015

(54) PRODUCTION OF HIGH TRYPTOPHAN MAIZE BY CHLOROPLAST TARGETED EXPRESSION OF ANTHRANILATE SYNTHASE

(75) Inventors: Siva Manjunath, Chesterfield, MO (US); Santiago Xavier Navarro, St. Louis, MO (US); William D. Rapp, Wildwood, MO (US); Xiaohong Shi, Ballwin, MO (US); Marguerite J. Varagona, Ballwin, MO (US); Jennifer L. Winson, Godfrey, IL (US); Guangning Ye, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 361 days.

(21) Appl. No.: 13/425,415

(22) Filed: Mar. 20, 2012

(65) Prior Publication Data

US 2012/0246762 A1 Sep. 27, 2012

Related U.S. Application Data

(63) Continuation of application No. 11/836,690, filed on Aug. 9, 2007, now Pat. No. 8,138,393.

(60) Provisional application No. 60/837,200, filed on Aug. 11, 2006.

(51) Int. Cl.

| | |
|---|---|
| ***A01H 5/00*** | (2006.01) |
| ***A01H 5/10*** | (2006.01) |
| ***C12P 21/04*** | (2006.01) |
| ***C07H 21/04*** | (2006.01) |
| ***C12N 15/82*** | (2006.01) |
| ***C12Q 1/68*** | (2006.01) |
| ***A23K 1/00*** | (2006.01) |
| ***A23L 1/212*** | (2006.01) |
| ***A23L 1/182*** | (2006.01) |
| ***A23L 1/20*** | (2006.01) |
| ***C12N 9/88*** | (2006.01) |

(52) U.S. Cl.

CPC .............. *C12N 9/88* (2013.01); *C12N 15/8214* (2013.01); *C12N 15/8254* (2013.01)

USPC ....... 800/320.1; 800/278; 800/287; 536/23.4; 435/6.12; 435/69.8; 435/468; 435/412; 435/424; 426/627; 426/630; 426/615

(58) Field of Classification Search

None

See application file for complete search history.

(56) References Cited

U.S. PATENT DOCUMENTS

| | | | | |
|---|---|---|---|---|
| 5,188,642 | A | | 2/1993 | Shah et al. |
| 5,545,545 | A | | 8/1996 | Gengenbach et al. |
| 5,728,925 | A | | 3/1998 | Herrera-Estrella et al. |
| 6,118,047 | A | * | 9/2000 | Anderson et al. ............ 800/278 |
| 6,248,876 | B1 | | 6/2001 | Barry et al. |
| 6,271,016 | B1 | | 8/2001 | Anderson et al. |
| 6,515,201 | B2 | | 2/2003 | Anderson et al. |
| 7,217,865 | B2 | | 5/2007 | Weaver et al. |
| 7,288,403 | B2 | | 10/2007 | Anderson et al. |
| 7,705,215 | B1 | | 4/2010 | Adams et al. |
| 7,714,189 | B2 | | 5/2010 | Manjunath et al. |
| 8,138,393 | B2 | | 3/2012 | Manjunath et al. |
| 2003/0167514 | A1 | | 9/2003 | Anderson et al. |
| 2003/0213010 | A1 | | 11/2003 | Weaver et al. |
| 2007/0028321 | A1 | | 2/2007 | Manjunath et al. |

FOREIGN PATENT DOCUMENTS

| | | | | |
|---|---|---|---|---|
| WO | WO 97/26366 | | | 7/1997 |
| WO | WO 02/090497 | | | 11/2002 |
| WO | WO 03/092363 | | | 11/2003 |
| WO | WO 03/092363 | A2 | * | 11/2003 |

OTHER PUBLICATIONS

U.S. Appl. No. 60/837,200, filed Aug. 11, 2006, Manjunath et al.

U.S. Appl. No. 08/113,561, filed Aug. 25, 1993, Adams et al.

U.S. Appl. No. 11/836,690, filed Mar. 20, 2012, Manjunath et al.

Archer et al., "Current views of chloroplast import and hypotheses on the origin of the transport mechanism," *J. Bioenerg Biomembr*, 22:789-810, 1990.

Bae et al., "Rhizobium meliloti anthranilate synthase gene: cloning, sequence, and expression in *Escherichia coli*," *J. of Bacteriology*, 171(6):3471-3478, 1989.

Schnell et al., "Signal peptide analogs derived from two chloroplast precursors interact with the signal recognition system of the chloroplast envelope," *J. Bio. Chem.*, 266(5):3335-3342, 1991

Silva-Filho et al., "Mitochondrial and chloroplast targeting sequences in tandem modify protein import specificity in plant organelles," *Plant Mol. Biol.*, 30:769-780, 1996.

* cited by examiner

*Primary Examiner* — David T Fox

*Assistant Examiner* — Lee A Visone

(74) *Attorney, Agent, or Firm* — Dentons US LLP; Chunping Li, Esq.

(57) ABSTRACT

Novel expression vectors and constructs encoding a chloroplast transit peptide (CTP) operably linked to a monomeric anthranilate synthase are provided. Additionally, novel polynucleotide sequences encoding monomeric anthranilate synthases are provided. Also provided are methods for increasing the levels of free tryptophan in transgenic plants containing the expression vectors and constructs.

9 Claims, 19 Drawing Sheets

PRODUCTION OF HIGH TRYPTOPHAN MAIZE BY CHLOROPLAST TARGETED EXPRESSION OF ANTHRANILATE SYNTHASE

This application is a continuation of U.S. application Ser. No. 11/836,690, filed Aug. 9, 2007, now U.S. Pat. No. 8,138,393; which application claims the priority of U.S. Provisional Patent Application Ser. No. 60/837,200, filed Aug. 11, 2006; each of the entire disclosures of which applications are specifically incorporated herein by reference in their entirety.

BACKGROUND OF THE INVENTION

1. Field of the Invention

The invention relates to methods and compositions for expressing and localizing anthranilate synthase in plant cells.

2. Description of Related Art

In maize, anthranilate synthase exists as a two-subunit enzyme which catalyzes the first reaction branching from the aromatic amino acid pathway to the biosynthesis of tryptophan in the chloroplast. It has been shown to be an important enzyme in the regulation of tryptophan production in plants. Anderson et al. (U.S. Pat. No. 6,118,047) demonstrated that over expression of a tryptophan-insensitive α-subunit of anthranilate synthase from maize led to an increased level of tryptophan in transgenic maize plants. Recently, it has been shown that monomeric forms of anthranilate synthases from prokaryotic sources are capable of increasing tryptophan levels in transgenic soybeans and corn (U.S. patent application Ser. No. 10/138,927, issued as U.S. Pat. No. 7,217,865, and Ser. No. 10/430,011, published as US Patent Application Publication 20030213010).

Most proteins which participate in the biosynthetic pathways within the chloroplast are nuclear-encoded and are synthesized in the cytosol. Correct targeting of these proteins to the plastids is thus essential for their biosynthetic function. In most cases, this targeting is achieved by the presence of an N-terminal extension, called a chloroplast transit peptide (CTP) or plastid transit peptide. Transgenes from bacterial sources must have a sequence encoding a CTP sequence fused to a sequence encoding an expressed polypeptide if the expressed polypeptide is to be compartmentalized in the chloroplast. Accordingly, transport of an exogenous polypeptide to a chloroplast is accomplished by means of operably linking a polynucleotide sequence encoding a CTP sequence to the 5' region of a polynucleotide encoding the exogenous polypeptide.

For many purposes in the manipulation and transformation of plant cells with a monomeric anthranilate synthase, it will be desirable that the gene that is introduced into the plant cell results in a product that is translocated to the plastid and functions in the plastid. Not all CTPs, however, are able to accomplish this translocation with equal efficacy. The identification of efficient and effective CTPs for successful expression and localization of anthranilate synthase in monocotyledonous plants, and in particular maize plants, is needed in the art.

SUMMARY OF THE INVENTION

In one aspect, the present invention provides polynucleotides encoding polypeptides comprising chloroplast transit peptides (CTPs) fused to monomeric anthranilate synthases (AS), wherein the chloroplast transit peptides are capable of compartmentalizing the anthranilate synthase in the plastid fraction of a plant cell. When such anthranilate synthase nucleic acids are expressed in a transgenic plant, elevated levels of tryptophan can be achieved within the cells of the plant. In one embodiment of the present invention, expression vectors and constructs containing these polynucleotides are provided. The recombinant plant cells that contain such expression vectors and constructs are also part of the present invention. The transgenic plant cells, seeds and feed products obtained by the expression of proteins using the sequences, constructs and methods of the present invention are further considered part of the invention.

In another aspect, the present invention provides methods for increasing the free tryptophan content in monocotyledonous plants. In one embodiment, the method comprises transforming a monocotyledonous plant with a polynucleotide encoding a polypeptide comprising a chloroplast transit peptide fused to a monomeric anthranilate synthase, wherein the chloroplast transit peptide functions to localize or compartmentalize the anthranilate synthase activity in the plastid of the plant cell.

In yet another aspect, the invention provides novel isolated polynucleotides encoding monomeric anthranilate synthases from *Agrobacterium* and *Sinorhizobium* sources. In one embodiment aspect of the present invention, expression vectors comprising these novel polynucleotides are provided. In yet other embodiments, host cells, transgenic plant cells, transgenic plants, seeds from the transgenic plants and resulting feed products containing these expression vectors are also considered part of the present invention.

DETAILED DESCRIPTION OF THE INVENTION

Figure 1:
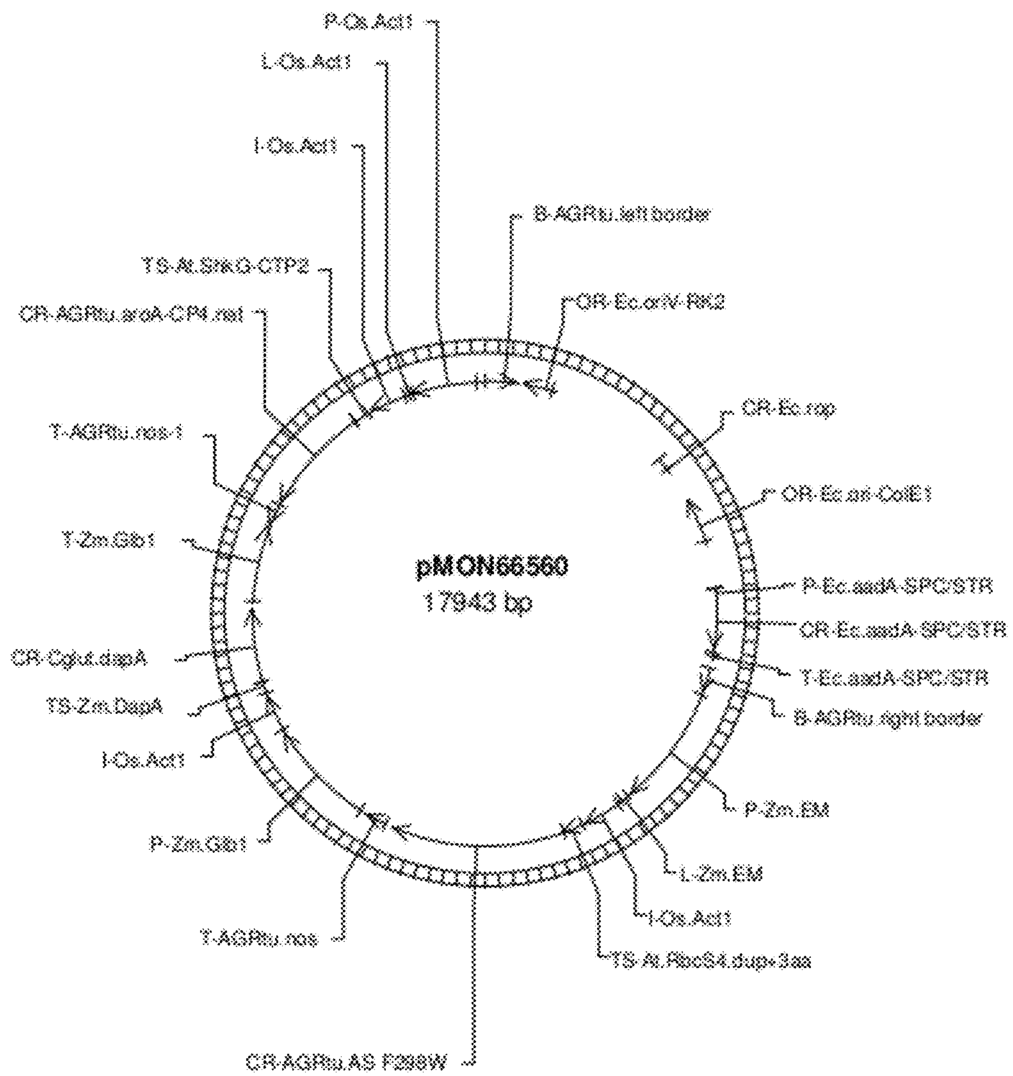
FIG. 1 depicts a restriction map of plasmid pMON66560

In accordance with the invention, compositions are provided for expressing and transporting a monomeric anthranilate synthase to the plastids of a plant cell. The invention in particular provides novel polynucleotide sequences that will find use in increasing the free tryptophan content in the cells of transformed plants. Additionally, novel polynucleotides encoding monomeric anthranilate synthase polypeptides from *Agrobacterium* and *Sinorhizobium* are provided.

The invention provides polynucleotides encoding polypeptides comprising chloroplast transit peptides (CTPs) fused to monomeric anthranilate synthases (AS), wherein the chloroplast transit peptides are capable of compartmentalizing the anthranilate synthase in the plastid fraction of a plant cell. When such anthranilate synthase nucleic acids are expressed in a transgenic plant, elevated levels of tryptophan can be achieved within the cells of the plant. In one aspect of the present invention, expression vectors and constructs containing these polynucleotides are provided. The recombinant plant cells that contain such expression vectors and constructs are also part of the present invention. The transgenic plant cells, seeds and feed products obtained by the expression of proteins using the sequences, constructs and methods of the present invention are also considered part of the invention.

In yet another aspect of the present invention, a method of increasing the free tryptophan content in monocotyledonous plants is provided. In one embodiment the method comprises transforming a monocotyledonous plant with a polynucleotide encoding a polypeptide comprising a chloroplast transit peptide fused to a monomeric anthranilate synthase, wherein the chloroplast transit peptide is capable of compartmentalizing the anthranilate synthase activity in the plastid of the plant cell.

The present invention is additionally directed to novel isolated polynucleotides encoding monomeric anthranilate synthases from *Agrobacterium* and *Sinorhizobium* sources. In one aspect of the present invention, expression vectors comprising these novel polynucleotides are provided. In yet other embodiments, host cells, transgenic plant cells, transgenic plants, seeds from the transgenic plants and resulting feed products containing these expression vectors are also considered part of the present invention.

A transgenic plant or seed that shows a desired trait, for example, increased tryptophan levels of the present invention, comprises a particular exogenous DNA inserted into the genome of the transgenic plant that imparts the desired trait. The trait being a measurable change from the naturally occurring trait in a control plant, for example, a plant or seed of substantially the same genotype that lacks that particular exogenous DNA. The enhanced desired trait may be measured by comparing the trait in a transgenic plant or seed with the particular exogenous DNA associated with the enhanced desired trait to the trait in a control plant or seed. "High tryptophan maize" therefore refers to a corn (maize) plant with increased tryptophan levels in any plant part, preferably a seed; the seed may also be referred to herein as a kernel or a grain.

Anthranilate synthase (AS; EC 4.1.3.27) catalyzes the first reaction branching from the aromatic amino acid pathway to the biosynthesis of tryptophan in plants, fungi, and bacteria. In plants, the chemical processes for the biosynthesis of tryptophan are compartmentalized in the chloroplast. Since anthranilate synthase is a nuclear-encoded protein that is synthesized in the cytosol, it must be transported by some means into the chloroplast to participate in the biosynthesis of tryptophan. Additionally, the endogenous anthranilate synthase that is native to wild type or nontransgenic plants is sensitive to feedback inhibition by the accumulation of tryptophan during the biosynthetic process. In this way, the tryptophan content of nontransgenic plant cells is limited to a relatively low level. For example, in nontransgenic corn, tryptophan levels are typically less than 25 parts per million (ppm) in the seed of the plant; usually in the 8 to 10 ppm range. The present invention provides novel polynucleotides encoding feedback-insensitive monomeric anthranilate synthase polypeptides from *Agrobacterium* and *Sinorhizobium* which are fused to a chloroplast transit peptide capable of targeting the anthranilate synthase to the plastids. The present invention further provides DNA constructs and seeds that contain at least one of the plant expression cassettes of the DNA constructs of the present inventions in its genome, wherein the seed has a higher tryptophan content than seeds not containing the construct.

Increased tryptophan may be exhibited in the plant cell by accumulation of increased amounts (greater than 25 ppm) of the amino acid in the kernel and may be measured by any suitable method, such as that of mass spectrophotometry or high performance liquid chromatography, of appropriately extracted tissue. A transgenic corn kernel of the present invention with increased tryptophan is especially useful as a feed or food product, a meal or meal product, or protein products, or source of other products processed from the kernel that contain a higher tryptophan content than nontransgenic kernels of a similar variety.

Any of the plants or parts thereof of the present invention may be processed to produce a feed (e.g. silage), meal, protein or oil preparation. A particularly preferred plant part for this purpose is a seed. In a preferred embodiment the feed, meal, protein or oil preparation is designed for use in feeding farm animals (livestock). Methods to produce feed, meal, protein and oil preparations are known in the art, for example, U.S. Pat. Nos. 4,957,748; 5,100,679; 5,219,596; 5,936,069; 6,005,076; 6,146,669; and 6,156,227, herein incorporated by reference in their entirety. In a preferred embodiment, the protein preparation is a high protein preparation. The high protein preparation preferably has a protein content of greater than 5% w/v, more preferably 10% w/v, and even more preferably 15% w/v.

Isolated Polynucleotides and Polypeptides

The present invention provides, in one embodiment, isolated polynucleotides encoding chloroplast transit peptides (CTPs; plastid transit peptides) fused to monomeric anthranilate synthases. The term "plastid" means a class of plant cell organelles comprising proplastids, leucoplasts, amyloplasts, chromoplasts, and chloroplasts. In the context of the present invention, the phrase "transit peptide" means a polypeptide that directs the transport of a nuclear encoded protein to a plastid. Typically, the CTP or transit peptide sequence is located at the N-terminus of a polypeptide.

Polynucleotides encoding monomeric anthranilate synthases, and polynucleotides encoding CTPs or plastid transit peptides are "isolated" in that they have been substantially separated or purified away from other nucleic acid sequences with which the nucleic acid is normally associated in the cell of the organism in which the nucleic acid naturally occurs, i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids. The term "substantially purified", as used herein, refers to a molecule separated from other molecules normally associated with it in its native state. More preferably, a substantially purified molecule is the predominant species present in a preparation. A substantially purified molecule may be greater than 60% free, preferably 75% free, more preferably 90% free from the other molecules (exclusive of solvent) present in the natural mixture. The term "substantially purified" is not intended to encompass molecules present in their native state. Such isolated polynucleotides can also be "recombinant" in that they have been combined with exogenous polynucleotides. For example, a recombinant DNA molecule can be an isolated polynucleotide that is operably linked to an exogenous promoter, or to a promoter that is endogenous to the host cell.

As used herein, an "exogenous" polynucleotide is a DNA sequence that has been introduced into a host cell, and that is preferably not identical to any DNA sequence present in the cell in its native, untransformed state. An "endogenous" or "native" polynucleotide is a DNA sequence that is naturally present in a host cell or organism. Likewise, an "exogenous" polypeptide is a protein sequence that is encoded by an isolated DNA that has been introduced into a host cell, and that is preferably not identical to any DNA sequence present in the cell in its native, untransformed state. An "endogenous" or "native" polypeptide is a protein that is naturally present in a host cell or organism.

Of particular interest are polypeptides representing CTP sequences of the present invention which are capable of correctly compartmentalizing the monomeric anthranilate synthase polypeptide in the plastid of the transformed plant cell. The CTP sequence may be derived from a gene encoding a plastid-targeted protein from maize or from other plant species including, but not limited to, *Ruta graveolens, Oryza sativa*, and *Arabidopsis thaliana*. Chloroplast transit peptide sequences are known in the art and include the targeting sequences of *Arabidopsis thaliana* ribulose-1,5-bisphosphate carboxylase (rubisco) small subunit 1 (At-CTP1; Silva-Filho et al. (1996); Schnell et al. (1991); *Arabidopsis thaliana* 5-(enolpyruvyl)shikimate-3-phosphate synthase (At-CTP2; Archer et al. (1990); *Zea mays* anthranilate synthase-alpha 1 (Zm-ASA1-CTP) and alpha 2 (Zm-ASA2-CTP) subunits; *Zea mays* dihydrodipicolinate synthase (Zm-DHDPS-CTP); *Oryza sativa* ADP glucose pyrophosphorylase (Os-Waxy (Os-Wx)-CTP; and *Ruta graveolens* anthranilate synthase alpha subunit (Rg-ASA short-CTP and Rg-ASA long-CTP). For descriptions of the use of chloroplast transit peptides see U.S. Pat. Nos. 5,188,642 and 5,728,925, both of which are incorporated herein by reference.

Exemplary isolated polynucleotides encoding chloroplast transit peptides (CTPs) of the invention include DNAs comprising the following nucleotide SEQ ID NOs:

SEQ ID NO:1: Nucleic acid sequence encoding At-CTP2 (C/M) (*Arabidopsis thaliana* 5-(enolpyruvyl) shikimate-3-phosphate synthase) with modified cleavage site (C/M);

SEQ ID NO:2: Nucleic acid sequence encoding At-CTP2 (E/K) with native cleavage site (E/K);

SEQ ID NO:3: Nucleic acid sequence encoding At-CTP2 (E/K)+10 amino acids from mature *Arabidopsis* EPSPS synthase;

SEQ ID NO:4: Nucleic acid sequence encoding At-CTP2 (E/K)+5 amino acids from mature *Arabidopsis* EPSPS synthase;

SEQ ID NO:5: Nucleic acid sequence encoding Zm-ASA1-CTP (*Zea mays* anthranilate synthase α1 subunit);

SEQ ID NO:6: Nucleic acid sequence encoding Zm-ASA1-CTP+20 amino acids from mature *Zea mays* anthranilate synthase α1 subunit;

SEQ ID NO:7: Nucleic acid sequence encoding Zm-ASA2-CTP (*Zea mays* anthranilate synthase α2 subunit);

SEQ ID NO:8: Zm-ASA2-CTP+5 amino acids from mature *Zea mays* anthranilate synthase α2 subunit;

SEQ ID NO:9: Nucleic acid sequence encoding Zm-ASA2-CTP+18 amino acids from mature *Zea mays* anthranilate synthase α2 subunit;

SEQ ID NO:10: Nucleic acid sequence encoding Os-Wx-CTP (*Oryza sativa* ADP glucose pyrophosphorylase);

SEQ ID NO:11: Nucleic acid sequence encoding Os-Wx-CTP+5 amino acids from mature *Oryza sativa* ADP glucose pyrophosphorylase;

SEQ ID NO:12: Nucleic acid sequence encoding Os-Wx-CTP+20 amino acids from mature *Oryza sativa* ADP glucose pyrophosphorylase;

SEQ ID NO:13: Nucleic acid sequence encoding Rg-AS short-CTP (*Ruta graveolens* anthranilate synthase α subunit; Met1 to Ser72);

SEQ ID NO:14: Nucleic acid sequence encoding Rg-AS long-CTP (Ruta graveolens anthranilate synthase α subunit; Met1 to Ser92);

SEQ ID NO:15: Nucleic acid sequence encoding Zm-DHDPS-CTP (*Zea mays* dihydrodipicolinate synthase);

SEQ ID NO:16: Zm-DHDPS-CTP+9 amino acids from mature *Zea mays* dihydrodipicolinate synthase;

SEQ ID NO:17: Nucleic acid sequence encoding Zm-DHDPS-CTP+20 amino acids from mature *Zea mays* dihydrodipicolinate synthase;

SEQ ID NO:18: Nucleic acid sequence encoding Zm-DHDPS-CTP+3 amino acids from mature *Zea mays* dihydrodipicolinate synthase; and SEQ ID NO:19: Nucleic acid sequence encoding *Arabidopsis thaliana* rubisco small subunit gene chloroplast transit peptide, CTP1.

The present invention also contemplates any isolated nucleic acid encoding a chloroplast transit peptide (CTP) comprising, for example, any one of the following amino acid sequences:

SEQ ID NO:20: At-CTP2(C/M) (*Arabidopsis thaliana* 5-(enolpyruvyl) shikimate-3-phosphate synthase) with modified cleavage site (C/M);

SEQ ID NO:21: At-CTP2(E/K) with native cleavage site (E/K);

SEQ ID NO:22 At-CTP2(E/K)+10 amino acids from mature *Arabidopsis* EPSPS synthase;

SEQ ID NO:23 At-CTP2(E/K)+5 amino acids from mature *Arabidopsis* EPSPS synthase;

SEQ ID NO:24 Zm-ASA1-CTP (*Zea mays* anthranilate synthase α1 subunit);

SEQ ID NO:25 Zm-ASA1-CTP+20 amino acids from mature *Zea mays* anthranilate synthase al subunit;

SEQ ID NO:26 Zm-ASA2-CTP (*Zea mays* anthranilate synthase α2 subunit);

SEQ ID NO:27 Zm-ASA2-CTP+5 amino acids from mature *Zea mays* anthranilate synthase α2 subunit;

SEQ ID NO:28 Zm-ASA2-CTP+18 amino acids from mature *Zea mays* anthranilate synthase α2 subunit;

SEQ ID NO:29 Os-Wx-CTP (*Oryza sativa* ADP glucose pyrophosphorylase);

SEQ ID NO:30 Os-Wx-CTP+5 amino acids from mature *Oryza sativa* ADP glucose pyrophosphorylase;

SEQ ID NO:31 Os-Wx-CTP+20 amino acids from mature *Oryza sativa* ADP glucose pyrophosphorylase;

SEQ ID NO:32 Rg-AS short-CTP (*Ruta graveolens* anthranilate synthase α subunit; Met1 to Ser72);

SEQ ID NO:33 Rg-AS long-CTP (*Ruta graveolens* anthranilate synthase α subunit; Met1 to Ser92);

SEQ ID NO:34 Zm-DHDPS-CTP (*Zea mays* dihydrodipicolinate synthase)

SEQ ID NO:35 Zm-DHDPS-CTP+9 amino acids from mature *Zea mays* dihydrodipicolinate synthase;

SEQ ID NO:36 Zm-DHDPS-CTP+20 amino acids from mature *Zea mays* dihydrodipicolinate synthase;

SEQ ID NO:37 Zm-DHDPS-CTP+3 amino acids from mature *Zea mays* dihydrodipicolinate synthase; and SEQ ID NO:38 *Arabidopsis thaliana* rubisco small subunit gene, CTP1.

Isolated polynucleotides encoding chloroplast transit peptides (CTPs) of the invention fused to green fluorescent protein (GFP), to anthranilate synthases, or to anthranilate synthase fused to GFP include DNAs comprising the following nucleotide SEQ ID NOs:

SEQ ID NO:39 Nucleic acid sequence encoding At-CTP2 fused to green fluorescent protein (GFP);

SEQ ID NO:40 Nucleic acid sequence encoding Zm-ASA2-CTP fused to green fluorescent protein (GFP);

SEQ ID NO:41 Nucleic acid sequence encoding Os-Wx-CTP fused to green fluorescent protein (GFP);

SEQ ID NO:42 Nucleic acid sequence encoding Rg-AS short-CTP fused to green fluorescent protein (GFP);

SEQ ID NO:43 Nucleic acid sequence encoding Zm-DHDPS-CTP fused to green fluorescent protein (GFP);

SEQ ID NO:44 Nucleic acid sequence encoding Zm-DHDPS-CTP+5 amino acids from mature *Zea mays* dihydrodipicolinate synthase fused to GFP;

SEQ ID NO:45 Nucleic acid sequence encoding At-CTP2 with native cleavage site E/K fused to *Rhizobium meliloti* anthranilate synthase;

SEQ ID NO:46 Nucleic acid sequence encoding At-CTP2+10 amino acids from mature *Arabidopsis* EPSPS synthase fused to *Rhizobium meliloti* anthranilate synthase;

SEQ ID NO:47 Nucleic acid sequence encoding Zm-ASA2-CTP fused to *Rhizobium meliloti* anthranilate synthase;

SEQ ID NO:48 Nucleic acid sequence encoding Zm-ASA2-CTP+18 amino acids from mature *Zea mays* anthranilate synthase α2 subunit fused to *Rhizobium meliloti* anthranilate synthase; and SEQ ID NO:49 Nucleic acid sequence encoding Zm-ASA2-CTP+18 amino acids from mature *Zea mays* anthranilate synthase α2 subunit (the first 65 amino acids encoded by the Zm-ASA2 gene) fused to *Agrobacterium tumefaciens* monomeric anthranilate synthase fused to green fluorescent protein.

Sequences representative of chloroplast transit peptides (CTPs) of the invention fused to green fluorescent protein (GFP) or anthranilate synthases include amino acids comprising the following polypeptide SEQ ID NOs:

SEQ ID NO:50 At-CTP2 fused to green fluorescent protein (GFP);

SEQ ID NO:51 Zm-ASA2-CTP fused to green fluorescent protein (GFP);

SEQ ID NO:52 Os-Wx-CTP fused to green fluorescent protein (GFP);

SEQ ID NO:53 Rg-AS short-CTP fused to green fluorescent protein (GFP);

SEQ ID NO:54 Zm-DHDPS-CTP fused to green fluorescent protein (GFP);

SEQ ID NO:55 Zm-DHDPS-CTP+5 amino acids from mature *Zea mays* dihydrodipicolinate synthase fused to GFP;

SEQ ID NO:56 At-CTP2 with native cleavage site E/K fused to *Rhizobium meliloti* anthranilate synthase;

SEQ ID NO:57 At-CTP2+10 amino acids from mature *Arabidopsis* EPSPS synthase fused to *Rhizobium meliloti* anthranilate synthase;

SEQ ID NO:58 Zm-ASA2-CTP fused to *Rhizobium meliloti* anthranilate synthase;

SEQ ID NO:59 Zm-ASA2-CTP+18 amino acids from mature *Zea mays* anthranilate synthase α2 subunit fused to *Rhizobium meliloti* anthranilate synthase; and SEQ ID NO:60 Zm-ASA2-CTP+18 amino acids from mature *Zea mays* anthranilate synthase α2 subunit (the first 65 amino acids encoded by the Zm-ASA2 gene) fused to *Agrobacterium tumefaciens* monomeric anthranilate synthase fused to green fluorescent protein.

Certain oligonucleotides are also useful for the practice of the present invention, for example, oligonucleotides comprising SEQ ID NOs: 61-198 are useful in the construction of transfection vectors for transient protoplast assays; and oligonucleotides comprising SEQ ID NOs: 226-231 are useful as PCR primers.

Another aspect of the present invention relates to isolated monomeric anthranilate synthases (AS) and fragments thereof; and their use in methods for obtaining plants that produce elevated levels of free L-tryptophan. Overproduction of free L-tryptophan in transgenic plants containing such polypeptides results from the introduction and expression of a nucleic acid encoding anthranilate synthase, or a domain thereof. Such anthranilate synthase nucleic acids include wild type or mutant α-domains, or monomeric forms of anthranilate synthase. A monomeric form of anthranilate synthase comprises at least two anthranilate synthase domains in a single polypeptide chain, e.g., an α-domain linked to a β-domain.

Native plant anthranilate synthases are generally quite sensitive to feedback inhibition by L-tryptophan and analogs thereof. Such inhibition constitutes a key mechanism for regulating the tryptophan synthetic pathway. Therefore, an anthranilate synthase or a domain thereof that is highly active, more efficient or that is inhibited to a lesser extent by tryptophan or an analog thereof will likely produce elevated levels of tryptophan. According to the invention, the anthranilate synthases from *Agrobacterium tumefaciens* and *Sinorhizobium meliloti* are particularly useful for producing high levels of tryptophan. Isolated monomeric anthranilate synthases of the present invention additionally include deregulated forms and fragments thereof. Such deregulated forms include the S51C allele of *Sinorhizobium* as described herein; the F298W, V48F, V48Y, S51F and S51C alleles of *Agrobacterium* anthranilate synthase, as described in U.S. Patent Application 2003097677; and the codon-optimized form of the *Agrobacterium* anthranilate synthase S51C allele as described in U.S. patent application Ser. No. 11/503,532, entitled "High Tryptophan Maize", each of which are herein incorporated by reference in their entirety. These alleles are deregulated for feedback inhibition from tryptophan.

To generate high levels of tryptophan in a plant or a selected host cell, the selected anthranilate synthase nucleic acid is isolated and may be manipulated in vitro to include regulatory signals required for gene expression in plant cells or other cell types. Because the tryptophan biosynthetic pathway in plants is reported to be present within plastids, the exogenous anthranilate synthase nucleic acids are either introduced into plastids or are modified by adding a nucleic acid segment encoding an amino-terminal plastid transit peptide. Such a plastid transit peptide can direct the anthranilate synthase gene product into plastids.

In order to alter the biosynthesis of tryptophan, the nucleic acid encoding an anthranilate synthase activity must be introduced into plant cells or other host cells and these transformed cells identified, either directly or indirectly. An entire anthranilate synthase or a useful portion or domain thereof can be used. The anthranilate synthase is stably incorporated into the plant cell genome. The transcriptional signals controlling expression of the anthranilate synthase must be recognized by and be functional within the plant cells or other host cells. That is, the anthranilate synthase must be transcribed into messenger RNA (mRNA), and the mRNA must be stable in the plant cell nucleus and be transported intact to the cytoplasm for translation. The anthranilate synthase mRNA must have appropriate translational signals to be recognized and properly translated by plant cell ribosomes. The polypeptide gene product must substantially escape proteolytic attack in the cytoplasm, be transported into the correct cellular compartment (e.g. a plastid) and be able to assume a three-dimensional conformation that will confer enzymatic activity. The anthranilate synthase must further be able to function in the biosynthesis of tryptophan and its derivatives; that is, it must be localized near the native plant enzymes catalyzing the flanking steps in biosynthesis (presumably in a plastid) in order to obtain the required substrates and to pass on the appropriate product.

Even if all these conditions are met, successful overproduction of tryptophan is not a predictable event. The expression of some transgenes may be negatively affected by nearby chromosomal elements. If the high level of tryptophan is achieved by mutation to reduce feedback inhibition, there may be other control mechanisms compensating for the reduced regulation at the anthranilate synthase step. There may be mechanisms that increase the rate of breakdown of the accumulated amino acids. Tryptophan and related amino acids must also be overproduced at levels that are not toxic to the plant. Finally, the introduced trait must be stable and heritable in order to permit commercial development and use.

Isolation and identification of polynucleotides encoding anthranilate synthases is described in U.S. patent application Ser. No. 10/138,927, published as U.S. Patent Application Publication 20030097677 and issued as U.S. Pat. No. 7,217,865; and Ser. No. 10/430,011, published as U.S. Patent Application Publication 20030213010, which are herein incorporated by reference in their entirety.

Exemplary isolated DNAs encoding anthranilate synthases of the present invention include DNAs comprising the following nucleotide SEQ ID NOs:

SEQ ID NO: 199 *Agrobacterium tumefaciens* wild type anthranilate synthase;

SEQ ID NO: 201 *Agrobacterium tumefaciens* F298W mutant allele;

SEQ ID NO: 203 *Agrobacterium tumefaciens* S51F mutant allele;

SEQ ID NO: 205 *Agrobacterium tumefaciens* S51C mutant allele;

SEQ ID NO: 207 *Agrobacterium tumefaciens* codon-optimized S51C mutant allele;

SEQ ID NO: 209 *Sinorhizobium meliloti* anthranilate synthase wild type; and

SEQ ID NO: 211 *Sinorhizobium meliloti* anthranilate synthase S51C mutant allele.

The present invention also contemplates any isolated nucleic acid encoding an anthranilate synthase comprising, for example, any one of the following amino acid sequences:

SEQ ID NO: 200 *Agrobacterium tumefaciens* wild type anthranilate synthase;

SEQ ID NO: 202 *Agrobacterium tumefaciens* F298W mutant;

SEQ ID NO: 204 *Agrobacterium tumefaciens* S51F mutant;

SEQ ID NO: 206 *Agrobacterium tumefaciens* S51C mutant;

SEQ ID NO: 208 *Agrobacterium tumefaciens* codon-optimized S51C mutant;

SEQ ID NO: 210 *Sinorhizobium meliloti* anthranilate synthase wild type;

SEQ ID NO: 212 *Sinorhizobium meliloti* anthranilate synthase S51C mutant.

As used herein with respect to anthranilate synthase, the term "monomeric" means that two or more anthranilate synthase domains are incorporated in a functional manner into a single polypeptide chain. The monomeric anthranilate synthase may be assembled in vivo into a dimeric form. Monomeric anthranilate synthase polynucleotides and polypeptides can be isolated from various organisms such as *Agrobacterium tumefaciens, Anabaena* M22983*, Azospirillum brasilense, Brucella melitensis, Euglena gracilis, Mesorhizobium loti, Nostoc* sp. PCC7120 or *Rhizobium meliloti* (*Sinorhizobium meliloti*). Alternatively, monomeric anthranilate synthase nucleic acids and polypeptides can be constructed from a combination of domains selected from any convenient monomeric or multimeric anthranilate synthase gene. Such organisms include, for example, *Agrobacterium tumefaciens, Anabaena M*22983, *Arabidopsis thaliana, Azospirillum brasilense, Brucella melitensis, Mesorhizobium loti, Nostoc* sp. PCC7120, *Rhizobium meliloti* (*Sinorhizobium meliloti*), *Rhodopseudomonas palustris, Ruta graveolens, Sulfolobus solfataricus, Salmonella typhimurium, Serratia marcescens*, soybean, rice, cotton, maize, or any gene encoding a subunit or domain of anthranilate synthase. Nucleic acids encoding the selected domains can be linked recombinantly. For example, a nucleic acid encoding the C-terminus of an α-domain can be linked to a nucleic acid encoding the N-terminus of the β-domain, or vice versa, by forming a phosphodiester bond. As an alternative, such single domain polypeptides can be linked chemically. For example, the α-domain can be linked via its C-terminus to the N-terminus of the β-domain, or vice versa, by forming a peptide bond.

As used herein, an anthranilate synthase that is "deregulated to feedback inhibition by tryptophan" is an anthranilate synthase that retains greater than about 10% more activity than a corresponding "wild-type" or native susceptible anthranilate synthase, when the deregulated and "wild type" anthranilate synthases are exposed to equivalent amounts of tryptophan or an amino acid analog of tryptophan. Preferably the deregulated anthranilate synthase retains greater than about 20% more activity than a corresponding "wild-type" or native susceptible anthranilate synthase.

Fragments and variants of the polypeptides are also considered to be a part of the present invention. A fragment is a variant polypeptide that has an amino acid sequence that is entirely the same as part but not all of the amino acid sequence of the previously described polypeptides. The fragments can be "free-standing" or comprised within a larger polypeptide of that the fragment forms a part or a region, most preferably as a single continuous region. Preferred fragments are biologically active fragments that are those fragments that mediate activities of the polypeptides of the invention, including those with similar activity or improved activity or with a decreased activity. Also included are those fragments that are antigenic or immunogenic in an animal, for the purpose of generating antibodies useful in a detection method, for example, an enzyme-linked immunosorbent assay.

Variants of the polypeptides also include polypeptides that vary from the sequences set forth in the Sequence Listing by conservative amino acid substitutions, substitution of a residue by another with like characteristics. In general, such substitutions are among Ala, Val, Leu and Ile; between Ser and Thr; between Asp and Glu; between Asn and Gln; between Lys and Arg; or between Phe and Tyr. Particularly preferred are variants in which 5 to 10; 1 to 5; 1 to 3 or one amino acid(s) are substituted, deleted, or added, in any combination.

Functional anthranilate synthase DNA sequences and functional anthranilate synthase polypeptides that exhibit 80%, more preferably 85%, even more preferably 90% to 95% and most preferably 96% to 99%, sequence identity to the DNA sequences and amino acid sequences explicitly described herein are also within the scope of the present invention. For example, 85% amino acid identity means that 85% of the amino acids are identical when the 2 sequences are aligned for maximum matching. Gaps (in either of the 2 sequences being matched) are allowed in maximizing matching; gap lengths of 5 or less are preferred with 2 or less being more preferred.

The polynucleotides of the present invention can be used, for example, in the construction of recombinant expression vectors useful for the transformation of plant host cells, as further discussed herein.

Plant Transformation Vectors

Of interest in the present invention, is the use of the polynucleotide sequences, or polynucleotides, in recombinant expression vectors to direct the transcription and translation of the polynucleotide sequences encoding monomeric AS fused to a CTP in a plant host cell.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

The term "operably linked" refers to a functional linkage between a promoter and a second sequence, wherein the promoter initiates and mediates transcription of DNA sequences corresponding to the second sequence. As used herein, "operably linked" also refers to a functional linkage between 2 or more distinct nucleotide sequences such that the nucleic acid sequences being linked are contiguous and, where necessary to join two protein coding regions, contiguous and in the same reading frame. For example, operably linking the CTP-coding sequences with the nucleotide sequence encoding a monomeric anthranilate synthase may require the manipulation of one or more of the DNA sequences, such as a convenient restriction site or a linker sequence that may permit better recognition of the amino-terminal transit sequence.

Such polynucleotides can be amplified using cDNA, mRNA or genomic DNA as a template and appropriate oligonucleotide primers according to standard PCR amplification techniques. Alternatively, they can be synthesized using standard synthetic techniques, such as an automated DNA synthesizer.

An expression vector minimally comprises a polynucleotide sequence which encodes a polypeptide that is expressed in a host cell. Typically, an expression vector is placed under the control of certain regulatory elements including promoters, tissue specific regulatory elements, and enhancers. Such an expression vector is said to be "operably linked to" the regulatory elements.

The expression vectors of the present invention generally comprise a promoter, functional in a plant cell, operably linked to a nucleic acid sequence encoding an anthranilate synthase, fused to a chloroplast transit peptide (CTP) of the present invention and a transcriptional termination region functional in a plant host cell.

Exemplary expression vectors of the present invention include DNAs having the following SEQ ID NOs:

SEQ ID NO: 213, nucleic acid sequence encoding pMON68065, the expression vector for Zm-ASA2-CTP+18::AgroAS(S51C) non-optimized mutant allele;

SEQ ID NO: 214, nucleic acid sequence encoding pMON68066, the expression vector for Zm-ASA2-CTP+18::AgroAS(S51C) non-native optimized (nno) mutant allele;

SEQ ID NO: 215, nucleic acid sequence encoding pMON69757, the expression vector for the construct containing the AgroAS(F298W) mutant allele;

SEQ ID NO: 216, nucleic acid sequence encoding pMON69770, the expression vector for the construct containing the AgroAS(S51C) non-optimized mutant allele with an alternate 3' UTR;

SEQ ID NO: 217, nucleic acid sequence encoding pMON69768, the expression vector for the construct containing the AgroAS(S51F) mutant allele;

SEQ ID NO: 218, nucleic acid sequence encoding pMON78850, the expression vector for the construct containing the *Rhizobium meliloti* anthranilate synthase wild type allele;

SEQ ID NO: 219, nucleic acid sequence encoding pMON78851, the expression vector for the construct containing the *Rhizobium meliloti* anthranilate synthase S51C allele.

By "host cell" is meant a cell that contains a vector and supports the replication, and/or transcription or transcription and translation (expression) of the expression construct. Host cells for use in the present invention can be monocotyledonous plant cells or bacterial cells. An example of a bacterial host cell of the present invention is *Agrobacterium*. In a preferred embodiment, host cells are maize cells.

As used herein, a "transgenic plant" is a plant having an exogenous polynucleotide stably introduced into its genome, for example, the nuclear or plastid polynucleotides from another organism.

The terms "seeds" and "kernels" are understood to be equivalent in meaning. The term kernel is frequently used in describing the seed of a corn or rice plant. In all plants the seed is the mature ovule consisting of a seed coat, embryo, aleurone, and an endosperm.

Of particular interest is the use of the polynucleotides of the present invention for the preparation of recombinant expression vectors to encode a monomeric AS fused with a CTP in a host plant cell, wherein the CTP directs the localization of the AS to the plastid fraction of the plant host cell. Plant expression constructs generally comprise a promoter functional in a plant host cell operably linked to a nucleic acid sequence of the present invention and a transcriptional termination region functional in a plant host cell.

As used herein "promoter" means a region of DNA sequence that is essential for the initiation of transcription of RNA from DNA. Promoters are located upstream of DNA to be transcribed and have regions that act as binding sites for RNA polymerase and have regions that work with other factors to promote RNA transcription. More specifically, basal promoters in plants comprise canonical regions associated with the initiation of transcription, such as CAAT and TATA boxes. In the present invention, preferred promoter molecules and 5' UTR molecules allow for transcription in seed cells or tissues at a rate or level greater than in other cells and tissues of the plant. Those skilled in the art will recognize that there are a number of constitutive and tissue specific promoters that are functional in plant cells, and have been described in the literature. For example, promoters are described in U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142 and 5,530,196 (35S promoter); U.S. Pat. No. 6,433,252 (maize L3 oleosin promoter, P-Zm.L3); U.S. Pat. No. 6,429,357 (rice actin 2 promoter as well as a rice actin 2 intron); U.S. Pat. No. 5,837,848 (root specific promoter); U.S. Pat. No. 6,294,714 (light inducible promoters); U.S. Pat. No. 6,140,078 (salt inducible promoters); U.S. Pat. No. 6,252,138 (pathogen inducible promoters); U.S. Pat. No. 6,175,060 (phosphorus deficiency inducible promoters); U.S. Pat. No. 6,635,806 (gamma-coixin promoter, P-Cl.Gcx); U.S. patent application Ser. No. 10/732,721 (maize embryo-specific promoter ZmEM; emb5); U.S. Pat. No. 7,151,204 (maize chloroplast aldolase promoter); SEQ ID NO: 220 (Barley Per1 promoter); SEQ ID NO: 221 (maize B32 promoter); SEQ ID NO: 222 (maize Z27 promoter); SEQ ID NO: 223 (maize Globulin 1 promoter; Belanger and Kriz, 1991); and SEQ ID NO: 224 (coixin L-3 promoter), all of which are incorporated herein by reference.

Constitutive promoters such as the CaMV35S promoter derived from the cauliflower mosaic virus (U.S. Pat. Nos. 5,858,741 and 5,322,938) or the FMV35S promoter derived from figwort mosaic virus (U.S. Pat. No. 5,378,619) yield high levels of expression in most plant organs. Enhanced or duplicated versions of the CaMV35S and FMV35S promoters are useful in the practice of this invention, for example the enhanced CaMV35S (e35S) (Odell, et al., 1985); U.S. Pat. No. 5,378,619). In addition, it may also be preferred to bring about expression of the protein of interest in specific tissues of the plant, such as leaf, stem, root, tuber, seed endosperm, seed embryos, fruit, etc., and the promoter chosen should have the desired tissue and developmental specificity.

Regulatory transcript termination regions may be provided in plant expression vectors of the present invention as well. Transcript termination regions may be provided by the gene sequence of the endogenous anthranilate synthase or a convenient transcription termination region derived from a different gene source. These transcription termination regions are commonly referred to as 3' untranslated regions or 3' UTRs. Examples of 3' UTR regions are the nopaline synthase 3' region (nos 3'; Fraley et al., 1983), the wheat heat shock protein, hsp17 (T-Ta.Hsp17), the 3' region of the glutelin gene of *Oryza sativa* (Os-gt1; SEQ ID NO: 225), a 3' UTR from a zein gene, such as Z27 3' UTR (Lopes et al., 1995), maize globulin 1 (T-Zm.Glb1), and T-Ps.RbcS2:E9 (pea rubisco small subunit), those disclosed in WO0011200A2 and other 3' UTRs known in the art which can be tested and used in combination with an anthranilate synthase coding region fused to a chloroplast transit peptide. The skilled artisan will recognize that any convenient transcript termination region that is capable of terminating transcription in a monocot plant cell may be employed in the constructs of the present invention.

Moreover, transcription enhancers or duplications of enhancers can be used to increase expression from a particular promoter. Examples of such enhancers include, but are not limited to a maize hsp70 intron (also referred to as Zm.DnaK) (U.S. Pat. No. 5,424,412 Brown, et al.), the Adh intron1 (Callis et al., 1987), a rice actin intron (McElroy et al., 1991; U.S. Pat. No. 5,641,876), sucrose synthase intron (Vasil et al., 1989), a TMV omega element (Gallie et al., 1999), and the CaMV 35S enhancer or an octopine synthase enhancer (U.S. Pat. No. 5,290,924). As the DNA sequence between the transcription initiation site and the start of the coding sequence, i.e., the untranslated leader sequence, can influence gene expression, one may also wish to employ a particular leader sequence. Any leader sequence available to one of skill in the art may be employed. Preferred leader sequences direct optimum levels of expression of the attached gene, for example, by increasing or maintaining mRNA stability and/or by preventing inappropriate initiation of translation (Joshi, 1987). The choice of such sequences is at the discretion of those of skill in the art. Sequences that are derived from genes that are highly expressed in monocots, and in particular maize and rice, are contemplated.

Assays to determine the efficiency by which the isolated CTP sequences of the invention target a protein of interest to a plastid are well known in the art. By way of example, a reporter gene such as β-glucuronidase (GUS), chloramphenicol acetyl transferase (CAT), or green fluorescent protein (GFP) may be operably linked to the CTP sequence. This gene fusion is placed behind the control of a suitable promoter, ligated into a transformation vector, and transformed into a plant cell. Following an adequate period of time for expression and localization into the plastid, the plastid fraction is extracted and reporter activity assayed. The ability of the isolated CTP sequences to target and deliver the reporter protein to the plastid is thus evaluated and compared to other known CTP sequences; see Silva-Filho et al. (1996).

Plant Cell Transformation

A plant cell, tissue, organ, or plant into which the recombinant expression vector of the present invention has been introduced is considered transformed, transfected, or transgenic. A transgenic or transformed plant cell or plant also includes progeny of the plant cell or plant and progeny produced from a breeding program employing such a transgenic plant as a parent in a cross and exhibiting an altered phenotype resulting from the presence of an introduced nucleic acid sequence.

The term “introduced” in the context of inserting a nucleic acid sequence into a cell, means “transfection”, or “transformation” or “transduction” and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, the term “plant” includes reference to whole plants, plant organs (for example, leaves, stems, roots, etc.), seeds, and plant cells and progeny of same. Plant cell, as used herein includes, without limitation, seed suspension cultures, embryos, meristematic regions, callus tissue, leaves, roots, shoots, gametophytes, sporophytes, pollen, and microspores. The class of plants that can be used in the methods of the present invention is generally monocotyledonous plants. A preferred plant of the present invention is maize.

As used herein, “transgenic plant” includes reference to a plant that comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression vector. “Transgenic” is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic.

Thus a plant having within its cells a heterologous polynucleotide is referred to herein as a transgenic plant. The heterologous polynucleotide can be either stably integrated into the genome, or can be extra-chromosomal. Preferably, the polynucleotides of the present invention are stably integrated into the genome such that the polynucleotides are passed on to successive generations. The polynucleotides are integrated into the genome alone or as part of a recombinant expression vector.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species, or, if from the same species, is substantially modified from its original form by deliberate human intervention.

The particular methods used for the transformation of the host plant cell are not critical to the present invention. The transformation of the plant is preferably permanent, i.e., by integration of the introduced expression constructs into the host plant genome, so that the introduced constructs are passed onto successive plant generations. The skilled artisan will recognize that a wide variety of transformation techniques exist in the art. Any technique that is suitable for the target host plant can be employed within the scope of the present invention. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to, calcium-phosphate-DNA co-precipitation, electroporation, microinjection, *Agrobacterium* infection, liposomes or microprojectile transformation (i.e., the gene gun).

With respect to microprojectile bombardment (U.S. Pat. Nos. 5,550,318; 5,538,880; and 5,610,042; each of which is specifically incorporated herein by reference in its entirety), particles are coated with polynucleotides and delivered into cells by a propelling force. Exemplary particles include those comprised of tungsten, platinum, and preferably, gold. A useful method for delivering DNA into plant cells by particle acceleration is the Biolistics® Particle Delivery System (Bio-Rad, Hercules, Calif.), which can be used to propel particles coated with DNA or cells through a screen, such as a stainless steel or NYTEX screen, onto a filter surface covered with monocot plant cells cultured in suspension. Microprojectile bombardment techniques are widely applicable, and may be used to transform virtually any plant species. Examples of species that have been transformed by microprojectile bombardment include monocot species such as corn (PCT Publication WO95/06128), barley, wheat (U.S. Pat. No. 5,563,055, incorporated herein by reference in its entirety), rice, oat, rye, sugarcane, and sorghum; as well as a number of dicots including tobacco, soybean (U.S. Pat. No. 5,322,783, incorporated herein by reference in its entirety), sunflower, peanut, cotton, tomato, and legumes in general (U.S. Pat. No. 5,563,055, incorporated herein by reference in its entirety) The skilled artisan can refer to the literature for details and select suitable techniques for use in the methods of the present invention.

Normally, included with the expression vector of the present invention will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

Where *Agrobacterium* is used for plant cell transformation, a vector may be used that may be introduced into the *Agrobacterium* host for homologous recombination with T-DNA or the Ti- or Ri-plasmid present in the *Agrobacterium* host. The Ti- or Ri-plasmid containing the T-DNA for recombination may be armed (capable of causing gall formation) or disarmed (incapable of causing gall formation), the latter being permissible, so long as the vir genes are present in the transformed *Agrobacterium* host. The armed plasmid can give a mixture of normal plant cells and gall.

In some instances where *Agrobacterium* is used as the vehicle for transforming host plant cells, the expression or transcription construct bordered by the T-DNA border region(s) will be inserted into a broad host range vector capable of replication in *E. coli* and *Agrobacterium*, there being broad host range vectors described in the literature. Commonly used is pRK2 or derivatives thereof. See, for example, Ditta et al. (1980) and EPA 0 120 515, that are incorporated herein by reference. Alternatively, one may insert the sequences to be expressed in plant cells into a vector containing separate replication sequences, one of which stabilizes the vector in *E. coli*, and the other in *Agrobacterium*. See, for example, McBride and Summerfelt (1990), wherein the pRiHR1 (Jouanin et al., 1985) origin of replication is utilized and provides for added stability of the plant expression vectors in host *Agrobacterium* cells.

Included with the expression construct and the T-DNA will be one or more markers that allow for selection of transformed *Agrobacterium* and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using *Agrobacterium*, explants may be combined and incubated with the transformed *Agrobacterium* for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed may be used to establish repetitive generations.

There are several possible ways to obtain the plant cells of this invention that contain multiple expression vectors. Any means for producing a plant comprising a vector or polynucleotide sequence of the present invention, and at least one other vector having another polynucleotide sequence encoding a separate enzyme are encompassed by the present invention. For example, the expression vector of the present invention can be used to transform a plant at the same time as the second construct either by inclusion of both expression vectors in a single plant transformation vector (plasmid) or by using separate plant transformation vectors, each of which express desired genes. The second vector can be introduced into a plant that has already been transformed with the first expression vector, or alternatively, transformed plants, one having the first construct and one having the second construct, can be crossed, using standard breeding techniques, to bring the constructs together in the same plant.

Methods

The present invention provides a method of increasing free tryptophan levels in a seed of a transgenic plant. In one embodiment, the method of increasing tryptophan comprises introducing into a plant cell a nucleic acid sequence encoding a monomeric anthranilate synthase operably linked to a CTP that is capable of targeting or localizing the monomeric anthranilate synthase to the chloroplast of the plant cell. The monomeric anthranilate synthase of the present invention is a deregulated form of the enzyme that is insensitive to feedback inhibition by tryptophan.

As used herein, "increased" or "elevated" levels of free tryptophan in a plant cell, plant tissue, plant part or plant are levels that are about 2 to 200 times, preferably about 5 to 150 times, and more preferably about 10 to 100 times, the levels found in an untransformed plant cell, plant tissue, plant part or plant, i.e., one where the genome has not been altered by the presence of a polynucleotide encoding a chloroplast transit peptide fused to a monomeric anthranilate synthase. For example, the levels of free L-tryptophan in a transformed plant seed are compared with those in an untransformed plant seed ("the starting material").

A further aspect of the present invention is to provide a relatively high throughput method for predicting the ability of a CTP to correctly compartmentalize a monomeric AS to the plastids of plant cells. The present invention provides a visualization method utilizing transient expression in maize protoplasts, or maize developing embryos, of a green fluorescent protein (GFP) fused with various monomeric AS and various CTPs. A GFP is capable of producing a green fluorescence, absorbing in the UV to blue range with a peak at 395 nm and emitting in the green range with a peak at 510 nm. This method allows for the visualization of the localization of the AS::GFP polypeptide. A result where greater than 50% of the localization is in the plastid would be a positive predictor of the ability of the CTP to successfully compartmentalize monomeric AS.

The present invention further provides a method of making a nutritionally enhanced corn feed product comprising processing a seed of a corn plant of the present invention into a meal, protein or oil.

Additionally, the present invention provides a method for detecting unique DNA sequences belonging to any of the CTP::AS sequence combinations described herein in a transgenic plant cell, or in a feed or meal product derived from such a transgenic plant cell. The genome of such a transgenic plant cell, or a feed or meal product derived from such a transgenic plant cell, produces an amplicon diagnostic for an expression vector containing any of the unique CTP::AS DNA sequences when tested in a DNA amplification method to amplify a DNA molecule from DNA extracted from such a transgenic plant cell, or a feed or meal product derived from such a transgenic plant cell. As used herein, an "amplicon" is a piece of DNA that has been synthesized using amplification techniques such as PCR or LCR. An "amplicon" is also understood in its common usage to be a PCR product.

The invention now being generally described, it will be more readily understood by reference to the following examples that are included for purposes of illustration only and are not intended to limit the present invention.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Localization of an Anthranilate Synthase Comprising a CTP1 Chloroplast Transit Peptide This example demonstrates that the protein product of a transgene encoding a CTP1 chloroplast transit peptide fused to the amino terminus of an *Agrobacterium* anthranilate synthase allele is not targeted efficiently to embryo plastids in transgenic maize.

The plant transformation vector pMON66560 (FIG. 1) encodes a fusion protein comprising the chloroplast transit peptide sequence from the *Arabidopsis* rubisco small subunit gene, CTP1 (encoded by SEQ ID NO: 19) fused to the amino-terminus of AgroAS(F298W (encoded by SEQ ID NO: 201), and driven by a maize embryo-specific promoter (ZmEM).

To isolate the plastid fraction from embryos of immature kernels from transgenic maize plants, several ears were harvested at 25-27 days after pollination (DAP). The homozygous F3 transgenic maize plants contained the plant transformation vector pMON66560 (FIG. 1).

Approximately 2.5 g of embryos were placed on ice as they were excised from kernels. The embryos were then rinsed 3 times in cold, sterile water, followed by a rinse in cold PIM buffer (20 mM Hepes/NaOH, 0.5M sorbitol, 10 mM KCl, 1 mM $MgCl_2$, 1 mM EDTA, 10 mM DTT, pH7.4). The embryos and subsequent fractions were kept cold during all isolation steps.

The embryos were then transferred to a petri dish containing 5 ml PIM, and chopped finely using single edge razor blades until the consistency of the chopped embryos resembled sand. The chopped embryos were filtered through 1 layer of Miracloth™ (Calbiochem Corporation, La Jolla, Calif.) into a 50 ml conical tube and brought to a total volume of 20 ml with PIM. A small aliquot of this filtered homogenate (designated fraction H) was stored at ⁻80° C. prior to analysis. The filtered homogenate was then centrifuged at 750×g for 5 minutes to pellet the plastids. The supernatant was poured off, and a small aliquot (designated S1) stored at ⁻80° C. An aliquot of 2.5 ml of PIM was then added to the pelleted plastids, and the pellets were resuspended using a small, soft-haired paint brush. After a small aliquot was removed and frozen (fraction designated P1), 2.5 ml of the resuspended pellets were layered onto each of two discontinuous Percoll gradients. The gradient tubes consisted of 6 ml 35% Percoll/PIM layered onto 3 ml 75% Percoll/PIM. The gradient tubes were then centrifuged for 8 minutes at 1000×g. The resulting plastid bands at the 35%/75% interface were collected and transferred to another 15 ml tube, and 5 ml 1×PIM was added to each tube. After centrifuging at 750×g for 5 minutes, the supernatant was removed, and both pellets were resuspended in 0.25 ml PIM. The resuspended pellet fraction containing the purified plastids was designated P2 and was stored at −80° C. prior to analysis.

The presence of the AS protein in the four isolated fractions (H, S1, P1 and P2) was analyzed by western blot analysis, using methods well known in the art. Briefly, the protein fractions were separated by SDS-PAGE on 4-12% Bio-Rad Criterion Bis-Tris gels (Bio-Rad Laboratories, Hercules, Calif.), loading 18 μg protein/lane. Following electrophoresis, the proteins were transferred to nitrocellulose, and duplicate blots were subjected to standard protocols for western blotting including blocking, primary antibody incubation (primary antibodies described below), washing, secondary antibody incubation (conjugated to horse radish peroxidase), washing, and chemiluminescent detection. The primary antibodies used in the blot analysis were raised in goat against (a) the anthranilate synthase α-2 subunit from maize, a known plastid localized protein; (b) pea glutamine synthetase 1 (GS1), a cytosolic form of glutamine synthase (GS) (Tingey et al., 1987); and (c) *Agrobacterium* anthranilate synthase. The antibodies, termed anti-maize ASα, anti-pea GS1 and anti-Agro AS, respectively, were prepared using standard methodology known in the art.

Figure 2:
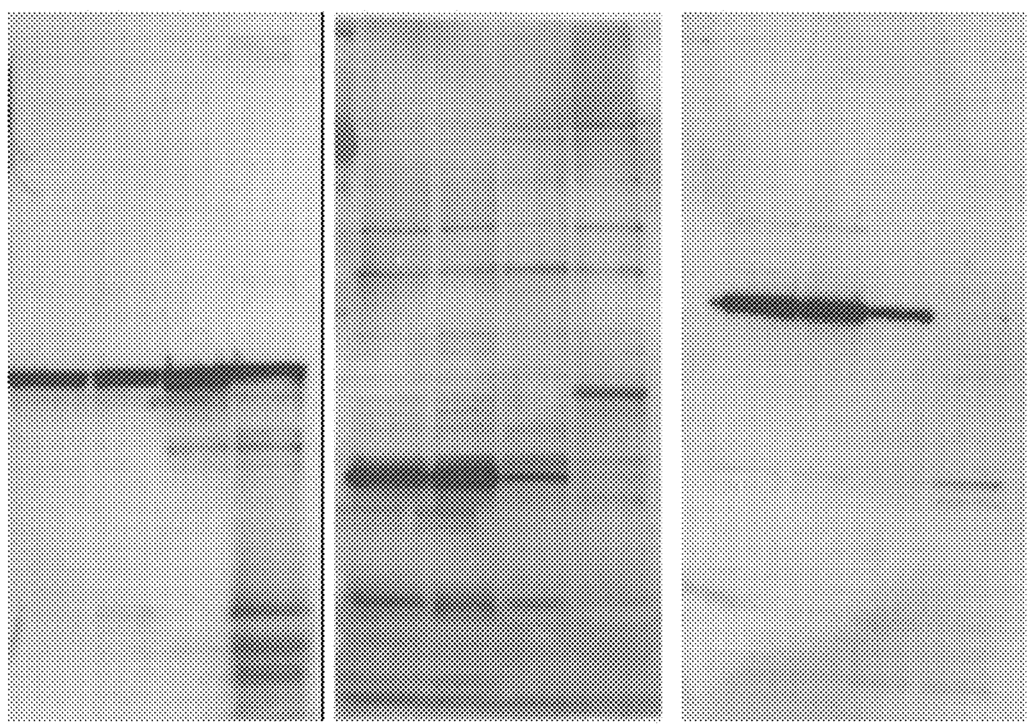
FIG. 2 depicts a western blot analysis of plastid fractions of transgenic corn cells containing the plant transformation vector pMON66560

The results (FIG. 2) demonstrate that the anti-maize ASα antibody, while recognizing bands corresponding to maize anthranilate synthase α-2 subunit in all four fractions, was enriched in plastid fractions P1 and P2. In contrast, anti-pea GS1 antibody recognized a band corresponding to a protein of the expected size in fractions H and S1, a smaller amount of protein in the crude P1 plastid fraction, and barely detectable amounts in the purified plastids, P2 fraction. This pattern of partitioning of glutamine synthetase is consistent with its localization to the cytosol. Anti-Agro AS antibody recognized a protein of the expected size which displays a pattern that resembles the cytosolic marker GS1 in all 4 fractions, indicating it is also localized primarily in the cytosol, despite the fact that the coding sequence included the CTP1 sequence. The results indicate that CTP1 would not be useful in expression vectors for compartmentalizing the protein in the plastid of maize embryo cells. Additionally, the results suggest that not all chloroplast transit peptides have the ability to successfully localize a monomeric AS to the plastids of maize cells.

Example 2

Additional Transit Peptide Sequences for Localization of Anthranilate Synthase This example describes the design of the various CTP sequences that were incorporated in the construction of the protoplast transfection vectors containing the maize anthranilate synthase-green fluorescent protein (Zm-AS::GFP) fusions and the control::GFP fusions detailed in Example 3; and which were evaluated in the transient expression assay systems which are described in Example 4.

TABLE 1

CTP variants

| CTP Name | SEQ ID NO: | Brief Description of CTP |
|---|---|---|
| At-CTP2(C/M) | 1 | At-CTP2 (*Arabidopsis thaliana* 5-(enolpyruvyl) shikimate-3-phosphate synthase) with modified cleavage site (C/M) |
| At-CTP2(E/K) | 2 | At-CTP2 with native cleavage site (E/K) |
| At-CTP2(E/K) + 10 | 3 | At-CTP2 + 10 amino acids from mature *Arabidopsis* EPSPS synthase |
| At-CTP2(E/K) + 5 | 4 | At-CTP2 + 5 amino from mature *Arabidopsis* EPSPS synthase |
| Zm-ASA1-CTP | 5 | Zm-ASA1 CTP (*Zea mays* anthranilate synthase α1 subunit) |
| Zm-ASA1-CTP + 20 | 6 | Zm-ASA1 CTP + 20 amino acids from mature *Zea mays* anthranilate synthase α1 subunit |
| Zm-ASA2-CTP | 7 | Zm-ASA2 CTP (*Zea mays* anthranilate synthase α2 subunit) |
| Zm-ASA2-CTP + 5 | 8 | Zm-ASA2 CTP + 5 amino acids from mature *Zea mays* anthranilate synthase α2 subunit |
| Zm-ASA2-CTP + 18 | 9 | Zm-ASA2 CTP + 18 amino acids from mature *Zea mays* anthranilate synthase α2 subunit |
| Os-Wx-CTP | 10 | Os-Wx CTP (*Oryza sativa* ADP glucose pyrophosphorylase) |
| Os-Wx-CTP + 5 | 11 | Os-Wx CTP + 5 amino acids from mature *Oryza sativa* ADP glucose pyrophosphrylase |
| Os-Wx-CTP + 20 | 12 | Os-Wx CTP + 20 amino acids from mature *Oryza sativa* ADP glucose pyrophosphrylase |
| Rg-AS short-CTP | 13 | Rg-AS short-CTP (*Ruta graveolens* anthranilate synthase α subunit; Met1 to Ser72) |
| Rg-AS long-CTP | 14 | Rg-AS long-CTP (*Ruta graveolens* anthranilate synthase α subunit CTP; Met1 to Ser92) |
| Zm-DHDPS-CTP | 15 | Zm-DHDPS CTP (*Zea mays* dihydrodipicolinate synthase) |
| Zm-DHDPS-CTP + 9 | 16 | Zm-DHDPS CTP + 9 amino acids from mature *Zea mays* dihydrodipicolinate synthase |
| Zm-DHDPS-CTP + 20 | 17 | Zm-DHDPS CTP + 20 amino acids from mature *Zea mays* dihydrodipicolinate synthase |
| Zm-DHDPS-CTP + 3 | 18 | Zm-DHDPS CTP + 3 amino acids from mature *Zea mays* dihydrodipicolinate synthase |

Example 3

Construction of Transformation Vectors

This example describes the construction of the protoplast transfection vectors containing the maize anthranilate synthase::green fluorescent protein (Zm-AS::GFP) fusions and the control::GFP fusions that were used in the transient protoplast and embryo assays described in Example 4. Two general strategies were employed to construct these vectors.

Figure 3:
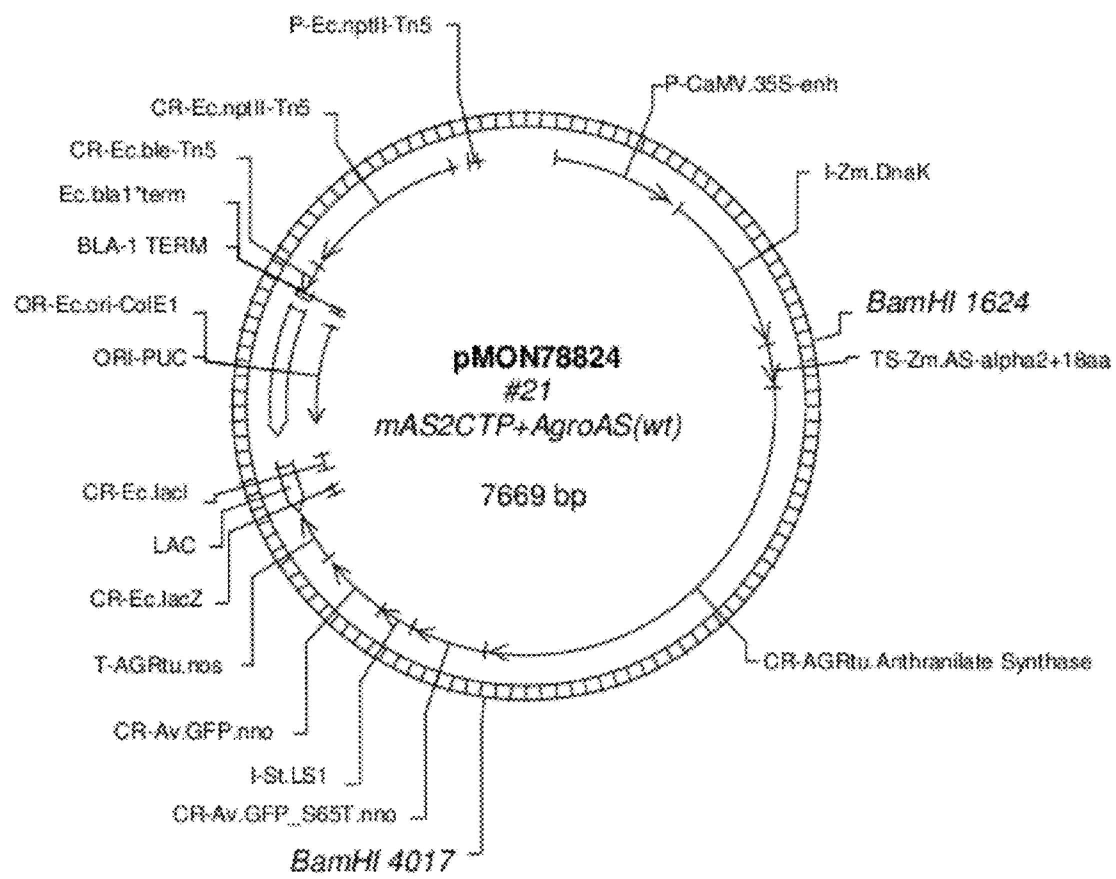
FIG. 3 depicts a restriction map of plasmid pMON78824

The first strategy involved PCR amplification of the CTP-AS coding sequence with the introduction of a restriction site to facilitate the addition of the GFP coding sequence. The first strategy is exemplified by the construction of pMON78824 (FIG. 3). The plasmid pMON78824 was constructed by PCR amplification of a DNA fragment containing the Zm-ASA2 CTP-coding sequence using the plasmid pMON66574 as a template. BamHI restriction sites were incorporated into the primers AS25 and AS 3' (SEQ ID NOs: 63 and 61, respectively) to allow insertion of the fragment in frame with the GFP coding sequence contained in the plasmid pMON30098. The PCR product was cloned into the pCRII vector (Invitrogen Corporation, Carlsbad, Calif.), according to manufacturer's instructions contained in the TA cloning kit (Invitrogen), resulting in plasmid pMON82553. The sequence integrity was confirmed by DNA sequencing using methodologies well known in the art.

The Zm-ASA2 CTP-fragment was then excised from pMON82553 using BamHI, and inserted into the BamHI site of the plasmid pMON30098 to create pMON78824. The resulting plasmid pMON78824 encoded a fusion protein (SEQ ID NO: 60) comprising: a) the first 65 amino acids encoded by the Zm-ASA2 gene; b) *Agrobacterium tumefaciens* monomeric anthranilate synthase; and c) the GFP coding region, all under the control of the e35S promoter.

Additional protoplast transformation vectors containing various GFP translational fusions were constructed in a similar manner using standard PCR and cloning methods, well known in the art. The transfection vector IDs (pMON number), general description of the fusion protein included in the transfection vector, PCR primers used, and PCR template are summarized in Table 2.

TABLE 2

Summary of the strategy 1 plasmid vectors constructed for protoplast transfection assays

| Transfection Vector ID | General description of fusion protein | PCR primers | SEQ ID NO: | PCR template |
|---|---|---|---|---|
| pMON30098 | Base vector provides GFP sequence for transfection vectors | n/a | | n/a |
| pMON79960 | CTP1::GFP | CTP1 5'<br>CTP1 3' | 61<br>62 | pMON66559 |
| pMON79961 | CTP1::AgroAS(F298W)::GFP | CTP1 5'<br>AS 3' | 61<br>63 | pMON66559 |
| pMON78818 | No CTP:: AgroAS(F298W)::GFP | AS 5'<br>AS 3' | 64<br>63 | pMON79961 |
| pMON78820 | Zm-ASA2(includes CTP)::GFP | AS25<br>AS23 | 65<br>66 | pMON64201 |
| pMON78822 | No CTP: mature Zm-ASA2::GFP | AS2MAT<br>AS23 | 67<br>66 | pMON64201 |
| pMON78824 | Zm-ASA2-CTP + 18::AgroAS(wt)::GFP | AS25<br>AS 3' | 65<br>63 | pMON66574 |
| pMON78140 | Os-Wx-CTP::GFP | RW-5<br>RW-3 | 68<br>69 | pMON66356 |
| pMON78139 | Rg-AS short-CTP::GFP | Ruta-5<br>Ruta-3 | 70<br>71 | pMON66575 |
| pMON78143 | Rg-AS short-CTP::AgroAS(F298W)::GFP | Ruta XbaI<br>AgroBsiWI | 72<br>73 | pMON66575 |
| pMON78142 | Rg-AS long-CTP::AgroAS(F298W)::GFP | Ruta XbaI<br>AgroBsiWI | 72<br>73 | pMON66571 |
| pMON69763 | DHDPS + 3 - CTP::AgroAS(F298W)::GFP | DHDPS-67146-5'<br>DHDPS-67146-3' | 74<br>75 | pMON67146 |
| pMON69774 | At-CTP2(EK)::*Rhizobium meliloti* anthranilate synthase::GFP | 5'Xba1-CTP2-N1<br>3'Xba1-CTP2-N1 | 76<br>77 | pMON78834 |
| pMON69775 | At-CTP2 + 10::*Rhizobium meliloti* anthranilate synthase::GFP | 3'Xba1-CTP2-N2<br>3'Xba1-CTP2-N3 | 78<br>79 | pMON78834 |
| pMON69776 | Zm-ASA2-CTP::*Rhizobium meliloti* anthranilate synthase::GFP | 5'-Xba1-ZmAS2-N1<br>3'-Xba1-ZmAS2-N1 | 80<br>81 | pMON69754 |
| pMON69777 | Zm-ASA2-CTP + 18::*Rhizobium meliloti* anthranilate synthase::GFP | 5'-Xba1-ZmAS1-N1<br>3'-Xba1-ZmAS2-N2 | 82<br>83 | pMON69754 |

The second strategy used for protoplast transformation vector construction involved the assembly of sequences corresponding to various CTPs, and fusing these sequences to the N-terminal coding sequence of AgroAS(F298W) (SEQ ID NO: 201). The CTP coding sequences were generated using sets of overlapping primers in a PCR-based assembly reaction based on a method of Withers-Martinez et. al. (1999). An example of this second strategy is the generation of plasmid pMON78832 (FIG. 4) containing an expression vector encoding an At-CTP2::AgroAS(F298W)::GFP fusion protein.

The first step of this second strategy is to synthesize a shuttle vector containing the AgroAS(F298W) coding sequence that was modified for in-frame fusions to various CTPs to its N-terminus and GFP to its C-terminus. To this end, a PCR amplification reaction was done using pMON79961 as the template, and the oligonucleotide primers AS5A (SEQ ID NO: 84) and AS 3' (SEQ ID NO: 63), using methods well known in the art. The resulting 2.2 kb PCR-product, containing the AgroAS(F298W) coding sequence was agarose gel-purified, ligated into the pCRII vector, and transformed into competent *E. coli* cells using the Invitrogen TA cloning kit (Invitrogen). The resulting intermediate plasmid was named WDRAPP01.0005, and was sequenced to confirm the presence of the 2.2 kb PCR product. The 2.2 kb insert was then excised from plasmid WDRAPP01.0005 using BamHI and cloned into the BamHI site in the plasmid pBluescriptII SK+ to generate the plasmid pMON82554.

The second step of this second strategy involved the synthesis of At-CTP2-AgroAS(F298W) N-terminal coding sequence. To this end, the following 14 oligonucleotide primers, listed in Table 3, were prepared.

TABLE 3

| Oligonucleotide Primers | |
|---|---|
| Oligo Name | SEQ ID NO: |
| At-CTP2-Agro N1-1 | SEQ ID NO: 85 |
| At-CTP2-Agro N1-2 | SEQ ID NO: 86 |
| At-CTP2-Agro N1-3 | SEQ ID NO: 87 |
| At-CTP2-Agro N1-4 | SEQ ID NO: 88 |
| At-CTP2-Agro N1-5 | SEQ ID NO: 89 |
| At-CTP2-Agro N1-6 | SEQ ID NO: 90 |
| At-CTP2-Agro N1-7 | SEQ ID NO: 91 |
| At-CTP2-Agro N1-8 | SEQ ID NO: 92 |
| At-CTP2-Agro N1-9 | SEQ ID NO: 93 |
| At-CTP2-Agro N1-10 | SEQ ID NO: 94 |
| At-CTP2-Agro N1-11 | SEQ ID NO: 95 |
| At-CTP2-Agro N1-12 | SEQ ID NO: 96 |
| At-CTP2-Agro N1-13 | SEQ ID NO: 97 |
| At-CTP2-Agro N1-14 | SEQ ID NO: 98 |

Stock solutions (100 μmoles/L) were made for each of the 14 oligonucleotides described in Table 5 by dissolving the requisite amounts in distilled water. An oligonucleotide mixture (At-CTP2 N1 oligo mix) was then prepared by combining 5 μl of each individual oligonucleotide solution. The PCR amplification was carried out using the following conditions:

Primary PCR

Mix 1:

1 microliter CTP2 N1 oligo mix 1 microliter 4 dNTP mix (Roche, 10 millimolar each)

23 microliter water

Mix 2:

6 microliters 25 mM $MgCl_2$ 5 microliters PCR buffer (w/out $MgCl_2$)

0.75 microliters Expand Hi-Fi enzyme mix (Roche)

13.25 microliters water

Mix 1 and Mix 2 were combined in a thin-walled PCR tube and the PCR reaction was carried out as follows:

1) 94° C./2 min
2) 94° C./30 sec
3) 45° C./30 sec
4) 72° C./30 sec
5) Go to step 2 four more times
6) 72° C./2 min
7) 4° C./hold Secondary PCR Mix 3:

1 microliter of primary PCR reaction 1.5 microliter N1-1 oligo (10 picomoles/microliter)

1.5 microliter N1-14 oligo (10 picomoles/microliter)

1 microliter dNTP mix 20 microliter water

Mix 4:

6 microliters 25 mM $MgCl_2$ 5 microliters PCR buffer (w/out $MgCl_2$)

0.75 microliters Expand Hi-Fi enzyme mix (Roche)

13.25 microliters water

Figure 4:
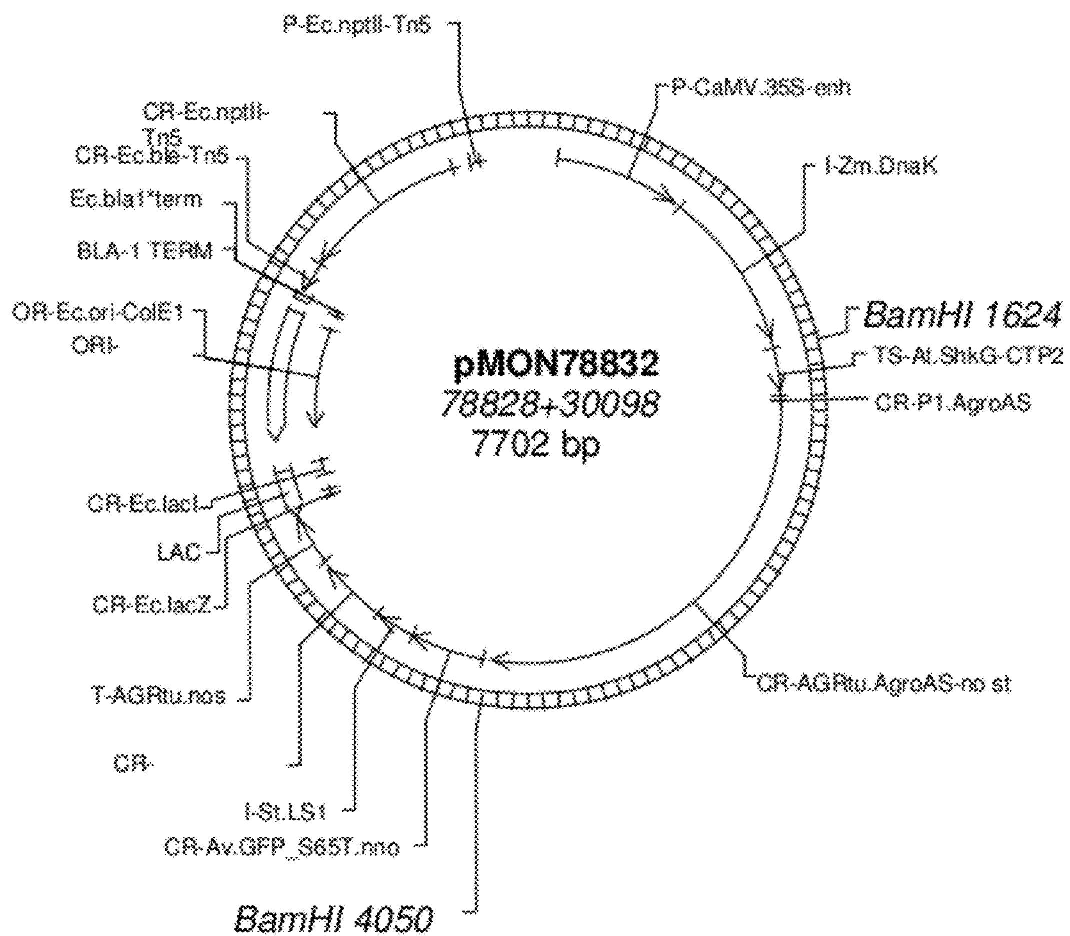
FIG. 4 depicts a restriction map of plasmid pMON78832
Figure 5:
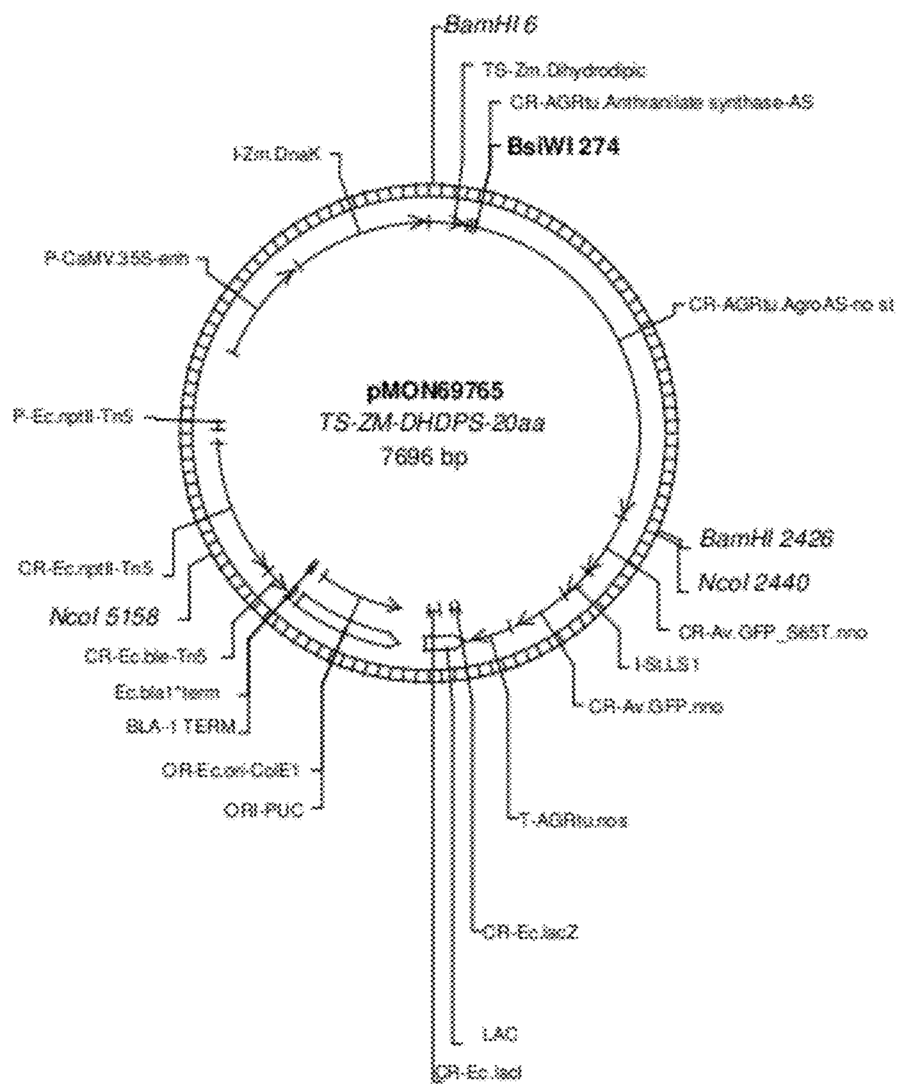
FIG. 5 depicts a restriction map of plasmid pMON69765

Mix 1 and Mix 2 were combined in a thin-walled PCR tube and the PCR reaction was carried out as follows:

Mix 3 and Mix 4 were combined in a thin-walled PCR tube and the PCR reaction was carried out as follows:

1) 94° C./2 min
2) 94° C./30 sec
3) 55° C./30 sec
4) 72° C./30 sec
5) Go to step 2 24 more times
6) 72° C./2 min
7) 4° C./hold The resulting PCR product of the correct size (~0.3 kb) was agarose gel-purified and ligated into the pCRII vector (Invitrogen TA cloning kit, Invitrogen) as described above. After confirming the sequence, the plasmid was digested with NcoI and BsiWI, and cloned into pMON82554, replacing a fragment which had previously been removed at the NcoI and BsiWI site. The resulting intermediate plasmid was then digested with BamH1 to generate a fragment that was then cloned into pMON30098. This resulting plasmid vector comprised the e35S promoter::hsp70 intron::At-CTP2:AgroAS (F298W)::GFP::nos 3' UTR genetic elements (pMON78832; FIG. 4).

Several variants of each CTP were built in the manner described above by adding the DNA sequence of the corresponding mature protein that encodes 3 to 20 amino acids at the 3' end of the CTP. For each pCRII vector containing a CTP variant, the fragment between the NcoI and BSiWI restriction sites of the pCRII vector was subsequently removed from the vector and cloned between the NcoI and BsiWI sites of the pMON82554 shuttle vector as described above. Each of these vectors was subsequently digested with BamHI to generate a fragment that was then cloned into the BamHI site of pMON30098 as described above to provide the remaining genetic elements of the final plasmid vector. The final plasmid vectors containing these CTP variants fused to GFP and the remaining genetic elements of the vector are listed in Table 4 along with the primers that were used in their construction.

TABLE 4

| Summary of the strategy 2 plasmid vectors constructed for protoplast transfection assays | | | |
|---|---|---|---|
| pMON | CTP::GFP variants | Primer Name | SEQ ID NO |
| pMON78832 | At-CTP2(C/M)::AgroAS(F298W)::GFP | CTP2- N1-1 | 85 |
| | | CTP2- N1-2 | 86 |
| | | CTP2- N1-3 | 87 |
| | | CTP2- N1-4 | 88 |
| | | CTP2- N1-5 | 89 |

TABLE 4-continued

Summary of the strategy 2 plasmid vectors constructed for protoplast transfection assays

| pMON | CTP::GFP variants | Primer Name | SEQ ID NO |
|---|---|---|---|
| | | CTP2- N1-6 | 90 |
| | | CTP2- N1-7 | 91 |
| | | CTP2- N1-8 | 92 |
| | | CTP2- N1-9 | 93 |
| | | CTP2- N1-10 | 94 |
| | | CTP2- N1-11 | 95 |
| | | CTP2- N1-12 | 96 |
| | | CTP2- N1-13 | 97 |
| | | CTP2- N1-14 | 98 |
| pMON78833 | At-CTP2(E/K)::AgroAS(F298W)::GFP | CTP2- N1-1 | 85 |
| | | CTP2- N1-2 | 86 |
| | | CTP2- N1-3 | 87 |
| | | CTP2- N1-4 | 88 |
| | | CTP2- N1-5 | 89 |
| | | CTP2- N2-6 | 99 |
| | | CTP2- N1-7 | 91 |
| | | CTP2- N1-8 | 92 |
| | | CTP2- N2-9 | 100 |
| | | CTP2- N1-10 | 94 |
| | | CTP2- N1-11 | 95 |
| | | CTP2- N1-12 | 96 |
| | | CTP2- N1-13 | 97 |
| | | CTP2- N1-14 | 98 |
| pMON78834 | At-CTP2 + 10::AgroAS(F298W)::GFP | CTP2- N1-1 | 85 |
| | | CTP2- N1-2 | 86 |
| | | CTP2- N1-3 | 87 |
| | | CTP2- N1-4 | 88 |
| | | CTP2- N1-5 | 89 |
| | | CTP2- N3-6A | 101 |
| | | CTP2- N3-6B | 102 |
| | | CTP2- N1-7 | 91 |
| | | CTP2- N1-8 | 92 |
| | | CTP2- N3-9A | 103 |
| | | CTP2- N3-9B | 104 |
| | | CTP2- N1-10 | 94 |
| | | CTP2- N1-11 | 95 |
| | | CTP2- N1-12 | 96 |
| | | CTP2- N1-13 | 97 |
| | | CTP2- N1-14 | 98 |
| pMON78835 | At-CTP2 + 5::AgroAS(F298W)::GFP | CTP2- N1-1 | 85 |
| | | CTP2- N1-2 | 86 |
| | | CTP2- N1-3 | 87 |
| | | CTP2- N1-4 | 88 |
| | | CTP2- N1-5 | 89 |
| | | CTP2- N4-6 | 105 |
| | | CTP2- N1-7 | 91 |
| | | CTP2- N1-8 | 92 |
| | | CTP2- N4-9 | 106 |
| | | CTP2- N1-10 | 94 |
| | | CTP2- N1-11 | 95 |
| | | CTP2- N1-12 | 96 |
| | | CTP2- N1-13 | 97 |
| | | CTP2- N1-14 | 98 |
| pMON78138 | Zm-ASA1-CTP::AgroAS(F298W)::GFP | ASA1-1-1T | 107 |
| | | ASA1-1-2T | 108 |
| | | ASA1-1-3T | 109 |
| | | CTP2- N1-7 | 91 |
| | | ASA1-1-5B | 110 |
| | | ASA1-1-4B | 111 |
| | | ASA1-1-3B | 112 |
| | | ASA1-1-2B | 113 |
| | | CTP2- N1-8 | 92 |
| pMON78141 | Zm-ASA1-CTP + 20::AgroAS(F298W)::GFP | ASA1-1-1T | 107 |
| | | ASA1-1-2T | 108 |
| | | ASA1-20-3T | 114 |
| | | ASA1-20-4T | 115 |
| | | CTP2- N1-7 | 91 |
| | | ASA1-1-5B | 110 |
| | | ASA1-1-4B | 111 |
| | | ASA1-1-3B | 112 |
| | | ASA1-20-3B | 116 |
| | | ASA1-20-2B | 117 |
| | | CTP2- N1-8 | 92 |

TABLE 4-continued

Summary of the strategy 2 plasmid vectors constructed for protoplast transfection assays

| pMON | CTP::GFP variants | Primer Name | SEQ ID NO |
|---|---|---|---|
| pMON69760 | Zm-ASA2-CTP::AgroAS(F298W)::GFP | AS2-5'-1 | 118 |
| | | AS2-5'-41 | 119 |
| | | AS2-5'-81 | 120 |
| | | AS2-5'-121 | 121 |
| | | AS2-5'-161 | 122 |
| | | AS2-3'-208 | 123 |
| | | AS2-3'-168 | 124 |
| | | AS2-3'-128 | 125 |
| | | AS2-3'-88 | 126 |
| | | AS2-3'-48 | 127 |
| pMON69761 | Zm-ASA2-CTP + 5aa::AgroAS(F298W)::GFP | AS2-5'-161-5aa | 128 |
| | | AS2-3'-183-5aa | 129 |
| | | AS2-3'-153-5aa | 130 |
| pMON69762 | Zm-ASA2-CTP + 10aa::AgroAS(F298W)::GFP | AS2-5'-161-10aa | 131 |
| | | AS2-5'-196-10aa | 132 |
| | | AS2-3'-198-10aa | 133 |
| | | AS2-3'-163-10aa | 134 |
| pMON69771 | Zm-ASA2-CTP::GFP | AS2GFP-5' | 135 |
| | | AS2GFP-3' | 136 |
| pMON78135 | Os-Wx-CTP::AgroAS(F298W)::GFP | RW-CM-1T | 137 |
| | | RW-CM-2T | 138 |
| | | RW-CM-3T | 139 |
| | | RW-CM-4T | 140 |
| | | RW-CM-5T | 141 |
| | | RW-CM-6T | 142 |
| | | RW-CM-7T | 143 |
| | | RW-CM-8B | 144 |
| | | RW-CM-7B | 145 |
| | | RW-CM-6B | 146 |
| | | RW-CM-5B | 147 |
| | | RW-CM-4B | 148 |
| | | RW-CM-3B | 149 |
| | | RW-CM-2B | 150 |
| | | RW-CM-1B | 151 |
| pMON78136 | Os-Wx-CTP + 5::AgroAS(F298W)::GFP | RW-CM-1T | 137 |
| | | RW-CM-2T | 138 |
| | | RW-CM-3T | 139 |
| | | RW-CM-4T | 140 |
| | | RW-CM-5T | 141 |
| | | RW-CM-6T | 142 |
| | | RW-5-7T | 152 |
| | | RW-5-8T | 153 |
| | | RW-CM-8B | 144 |
| | | RW-CM-7B | 145 |
| | | RW-CM-6B | 146 |
| | | RW-CM-5B | 147 |
| | | RW-CM-4B | 148 |
| | | RW-CM-3B | 149 |
| | | RW-5-2B | 154 |
| | | RW-5-1B | 155 |
| pMON78137 | Os-Wx-CTP + 20::AgroAS(F298W)::GFP | RW-CM-1T | 137 |
| | | RW-CM-2T | 138 |
| | | RW-CM-3T | 139 |
| | | RW-CM-4T | 140 |
| | | RW-CM-5T | 141 |
| | | RW-CM-6T | 142 |
| | | RW-20-7T | 156 |
| | | RW-20-8T | 157 |
| | | RW-20-9T | 158 |
| | | RW-CM-8B | 144 |
| | | RW-CM-7B | 145 |
| | | RW-CM-6B | 146 |
| | | RW-CM-5B | 147 |
| | | RW-CM-4B | 148 |
| | | RW-CM-3B | 149 |
| | | RW-5-2B | 154 |
| | | RW-20-2B | 159 |
| | | RW-20-1B | 160 |
| pMON69758 | Zm-DHDPS-CTP::AgroAS(F298W)::GFP | DHDPS-5'-1 | 161 |
| | | DHDPS-5'-41 | 162 |
| | | DHDPS-5'-81 | 163 |
| | | DHDPS-5'-121 | 164 |
| | | DHDPS-5'-161 | 165 |

TABLE 4-continued

Summary of the strategy 2 plasmid vectors constructed for protoplast transfection assays

| pMON | CTP::GFP variants | Primer Name | SEQ ID NO |
|---|---|---|---|
| | | DHDPS-3'-AgroAS | 166 |
| | | DHDPS-3'-184 | 167 |
| | | DHDPS-3'-140 | 168 |
| | | DHDPS-3'-99 | 169 |
| | | DHDPS-3'-59 | 170 |
| pMON69759 | Zm-DHDPS-CTP + 9aa::AgroAS(F298W)::GFP | DHDPS-5'-161-9aa | 171 |
| | | DHDPS-5'-201-9aa | 172 |
| | | DHDPS-3'-216-9aa | 173 |
| | | DHDPS-3'-176-9aa | 174 |
| pMON69765 | Zm-DHDPS-CTP + 20aa::AgroAS(F298W)::GFP | DHDPS-5'-201-20aa | 175 |
| | | DHDPS-5'-241-20aa | 176 |
| | | DHDPS-3'-249-20aa | 177 |
| | | DHDPS-3'-209-20aa | 178 |
| | | DHDPS-3'-169-20aa | 179 |
| pMON69764 | Zm-DHDPS-CTP + 5aa::AgroAS(F298W)::GFP | DHDPS-5'-161-5aa | 180 |
| | | DHDPS-5'-201-5aa | 181 |
| | | DHDPS-3'-244-5aa | 182 |
| | | DHDPS-3'-204-5aa | 183 |
| | | DHDPS-3'-164-5aa | 184 |
| pMON69772 | Zm-DHDPS-CTP: :GFP | DHDPSGFP-5' | 185 |
| | | DHDPSGFP-3' | 186 |
| pMON69766 | Zm-DHDPS-CTP + 5::GFP | DHDPS-N1 | 187 |
| | | DHDPS-N2 | 188 |
| | | DHDPS-N3 | 189 |
| | | DHDPS-N4 | 190 |
| | | DHDPS-N9 | 191 |
| | | DHDPS-N10 | 192 |
| | | DHDPS-N11 | 193 |
| | | DHDPS-N12 | 194 |
| | | DHDPS-N13 | 195 |
| | | DHDPS-N14 | 196 |
| | | DHDPS-N15 | 197 |
| | | DHDPS-N18 | 198 |

Example 4

Localization of AgroAS and Variants to Plastids

This example describes the two transient expression assay systems used to predict the abilities of different chloroplast transit peptides (CTPs) in plastid targeting of AS::GFP fusion proteins. These assays utilize the protoplast transfection vectors containing the anthranilate synthase-green fluorescent protein (AS::GFP) fusions and the fusions that were described in Example 3.

Two transient expression assay methods were developed to predict the localization of AS::GFP fusion proteins in maize cells. A medium throughput maize protoplast system was used to screen many different CTPs for their ability to target the AS::GFP fusion proteins to the plastids of etiolated maize leaf cells. A lower throughput system of expressing proteins in developing maize embryos was used to confirm the plastid localization pattern seen in the protoplast system. Data from these two assays were then used to predict the abilities of various CTPs in directing the localization of *Agrobacterium* and *Sinorhizobium* AS proteins in transgenic maize embryos.

All constructs tested in the transient assay systems were built with the same genetic elements in a common vector backbone which expressed each gene using the e35S promoter, hsp70 (DnaK) intron and nos 3'UTR.

To ensure that the transient assay systems were functioning correctly, control plasmids were constructed. The controls for cytosolic localization were the vectors containing GFP fusion with no CTP (pMON30098; Tables 2 and 5), AgroAS fusion to GFP (no CTP added) (pMON78818; Tables 2 and 5), and a truncated Zm-ASA2-CTP::GFP fusion lacking the Zm-ASA2-CTP (pMON78822; Tables 2 and 5). The controls used for plastid localization were maize ASA2 fused to GFP (pMON78820; Tables 2 and 5) and At-CTP2 fused to GFP (pMON53173; Table 5). Two additional controls were used to confirm the data from the transgenic plants; CTP1::GFP (pMON79960; Tables 2 and 5) and CTP1::AgroAS (F298W)::GFP (pMON79961; Tables 2 and 5). Localization patterns of GFP or GFP fusion proteins from each of these vectors are reported in Table 5. The data also confirmed the cell fractionation results as described in Example 1, indicating cytosolic localization of the CTP1::AgroAS(F298W)::GFP fusion protein and the inability of CTP1 to target the AgroAS(F298W) to the plastid.

In most of the experiments, an additional control was constructed for each CTP tested. These controls consisted of the tested CTP fused directly to GFP. For example, Zm-ASA2-CTP fused to GFP (pMON69771) to test the Zm-ASA2::AgroAS::GFP fusions. The methods for construction of all of the vectors tested are detailed in Example 3.

Several variations were made for each of the CTPs tested. These variations were distinguished by varying the number of N-terminal amino acids added to the CTP of the native host protein (Table 1). For example, in the Zm-ASA2-CTP series, the experimentally determined CTP fused directly to GFP was used, as well as two additional versions which included 5 and 18 amino acids from the N-terminus of the Zm-ASA2, isolated from the region of the amino-terminus of the mature *Zea mays* anthranilate synthase $\alpha 2$ subunit adjacent to the CTP. The constructs are denoted as Zm-ASA2-CTP+5 (SEQ ID NO: 8) and Zm-ASA2-CTP+18 (SEQ ID NO: 9) in Table 1.

As a primary test, the CTP constructs described in Table 1 were evaluated in an etiolated protoplast system. Leaf mesophyll protoplasts were prepared from etiolated maize seedlings using methods well known in the art (see for example Sheen, 1993).

The different vectors were electroporated into the protoplasts using methods well known in the art. Approximately 18 to 24 hours later, the protoplast cells were counted for GFP fluorescence using confocal microscopy. Briefly, microscopy was performed using a Zeiss Laser Scanning Microscope LSM510 META (Carl Zeiss MicroImaging, Inc., Thornwood, N.Y.) equipped with an Argon Ion laser, green and red Helium-Neon lasers, and a chameleon diode-pumped laser (Coherent Laser Division, Santa Clara, Calif.). Image acquisition and analysis was performed using LSM 5 Image Examiner, version 3.2.0.70 (Carl Zeiss MicroImaging, Inc., Thornwood, N.Y.). Image processing was performed using Adobe Photoshop CS, version 8.0 (Adobe Systems Incorporated, San Jose, Calif.). At least 50 cells for each construct were scored with respect to having GFP fluorescence in the; a) plastids only, b) cytosol only and c) both plastid and cytosol.

As a secondary test, a specific transient assay system was developed to evaluate constructs designed to be expressed in developing maize germ tissue. The constructs evaluated by this test were chosen based upon having a score in the protoplast system of 50% or greater of transformed cells containing plastid only localization. Additional control constructs, as detailed above, were also tested.

Embryos were isolated from surface-sterilized ears from the maize, e.g. HiII or an inbred parent, at approximately 14 days after pollination (DAP). About 20-30 embryos were placed on Petri plates containing N6 medium supplemented with 0.2M sorbitol+0.2M mannitol (Chu, 1978). Following four hours of incubation at room temperature, the embryos were bombarded with 0.6 μm gold particles coated with DNA using the Biolistic™ PDS-1000/He Particle Delivery System (Bio-Rad Corporation). The plates were bombarded twice at 9 cm from the stopping screen to the target shelf, with a rupture pressure of 1100 psi and a gap distance of 1 cm. Following bombardment, the embryos were incubated at 28° C. in the dark overnight before being analyzed by multiphoton confocal microscopy, as described above. At least 50 cells were counted per sample and scored as described for above for the protoplast system.

The results from the localization assays are shown in Table 5. The results indicate that based upon visualization, the following six CTPs effectively target AgroAS to the plastids in maize germ cells: Zm-ASA2-CTP+18 (SEQ ID NO: 9; the CTP component of pMON78824), Rg-AS long-CTP (SEQ ID NO: 14; the CTP component of pMON78142), Rg-AS short-CTP (SEQ ID NO: 13; the CTP component of pMON78143 and pMON78139), At-CTP2 (E/K) (SEQ ID NO: 2; the CTP component of pMON78833), At-CTP2 (E/K)+10 (SEQ ID NO: 3; the CTP component of pMON78834), and Zm-DHDPS-CTP+20 (SEQ ID NO: 17; the CTP component of pMON69765). The results also indicate that not all of the various CTPs assayed were positive for the ability to localize AS::GFP in either the protoplast or the embryo transient expression assays. These results corroborate the results described in Example 1, and indicate the need for identifying useful CTPs for successfully localizing monomeric AS proteins in the chloroplasts of monocotyledonous plants and therefore producing elevated tryptophan levels.

TABLE 5

Results of localization assays

| pMON ID | CTP::AgroAS::GFP variants | Protoplast % Plastid Loc | Embryo % Plastid Loc |
|---|---|---|---|
| 78832 | At-CTP2(C/M)::AgroAS(F298W)::GFP | 68.6 | Not tested |
| 78833 | At-CTP2(E/K)::AgroAS(F298W)::GFP | 64 | 79 |
| 78834 | At-CTP2 + 10::AgroAS(F298W)::GFP | 72 | 35 |
| 78835 | At-CTP2 + 5::AgroAS(F298W)::GFP | 60.6 | Not tested |
| 53173 | Control: At-CTP2::GFP | >80 | 80 |
| 78138 | Zm-ASA1-CTP::AgroAS(F298W)::GFP | 0 | Not tested |
| 78141 | Zm-ASA1-CTP + 20::AgroAS(F298W)::GFP | 0 | Not tested |
| 69760 | Zm-ASA2-CTP::AgroAS(F298W)::GFP | 0 | Not tested |
| 69761 | Zm-ASA2-CTP + 5::AgroAS(F298W)::GFP | 0 | Not tested |
| 78824 | Zm-ASA2-CTP + 18:: AgroAS(wt)::GFP | 100 | 81 |
| 69771 | Control: Zm-ASA2-CTP::GFP | 15 | Not tested |
| 78135 | Os-Wx-CTP::AgroAS(F298W)::GFP | 0 | Not tested |
| 78136 | Os-Wx CTP + 5::AgroAS(F298W)::GFP | 0 | Not tested |
| 78137 | Os-Wx-CTP + 20::AgroAS(F298W)::GFP | 72 | Not tested |
| 78140 | Control: Os-Wx-CTP::GFP | 77 | Not tested |
| 78143 | Rg-AS short-CTP::AgroAS(F298W)::GFP | 87.3 | 54 |
| 78142 | Rg-AS long-CTP::AgroAS(F298W)::GFP | 88.6 | 55 |
| 78139 | Control: Rg-AS short-CTP::GFP | 77.3 | 67 |
| 69758 | Zm-DHDPS-CTP::AgroAS(F298W)::GFP | 0 | Not tested |
| 69759 | Zm-DHDPS-CTP + 9::AgroAS(F298W)::GFP | 3 | Not tested |
| 69765 | Zm-DHDPS-CTP + 20::AgroAS(F298W)::GFP | 71 | 91% in plastid and cytosol; 9% in cytosol only |
| 69763 | Zm-DHDPS-CTP + 3::AgroAS(F298W)::GFP | 0 | 33 |
| 69772 | Control: Zm-DHDPS-CTP::GFP | 0 | 10 |
| 69766 | Control: Zm-DHDPS-CTP + 5::GFP | 30 | Not tested |
| 69774 | At-CTP2(E/K)::*Rhizobium meliloti* anthranilate synthase::GFP | 64 | Not tested |
| 69775 | At-CTP2 + 10::*Rhizobium meliloti* anthranilate synthase::GFP | 72.7 | Not tested |
| 69776 | Zm-ASA2-CTP::*Rhizobium meliloti* anthranilate synthase::GFP | 0 | Not tested |
| 69777 | Zm-ASA2-CTP + 18::*Rhizobium meliloti* anthranilate synthase::GFP | 70.7 | Not tested |
| 78818 | Control: No CTP::AgroAS(F298W)::GFP | 0 | 0 |

TABLE 5-continued

| Results of localization assays | | | |
|---|---|---|---|
| pMON ID | CTP::AgroAS::GFP variants | Protoplast % Plastid Loc | Embryo % Plastid Loc |
| 78820 | Control: Zm-ASA2(includes CTP)::GFP | 70.3 | 85 |
| 78822 | Control: No CTP::mature Zm-ASA2::GFP | * | Not tested |
| 79961 | Control: CTP1::AgroAS(F298W)::GFP | * | 0 |
| 30098 | Control: GFP | * | 0 |
| 79960 | Control: CTP1::GFP | ** | 44 |

* For these controls, no plastid localization was observed in the protoplast transient assay; the data was not quantified.
** For this control, plastid and cytosolic localization was observed but not quantified.

Example 5

Transformation Vectors and Maize Transformation

This example describes the construction of the transformation vectors containing nucleic acid sequences encoding the wild type (wt) and mutant alleles of both *Agrobacterium tumefaciens* and *Rhizobium meliloti* anthranilate synthase (AS) in combination with various chloroplast transport proteins. This example also provides a protocol for transformation of maize with the transformation vectors described herein.

Figure 6:
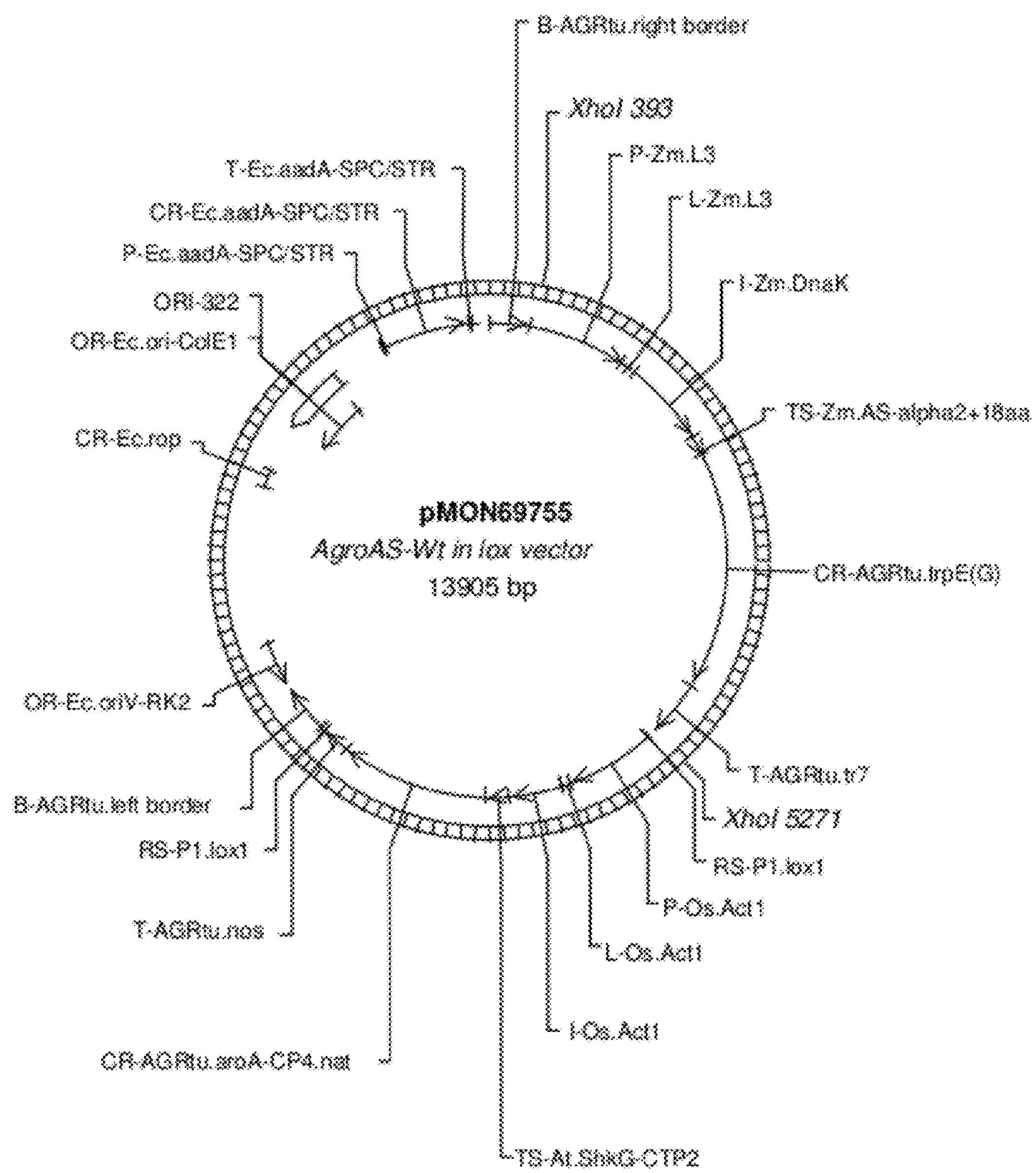
FIG. 6 depicts a restriction map of plasmid pMON69755

For the construction of transformation vectors containing the wild type *Agrobacterium tumefaciens* AS, the AS coding sequence was cut out of plasmid pMON66580 by digesting with XhoI, blunting the ends using mungbean nuclease, and then cutting with BglII to isolate a first fragment. To isolate a second fragment containing maize oleosin promoter, hsp70 intron, and Tr7-3'-UTR, the plasmid pMON69753 was cut with BglII and SmaI. These two fragments were ligated to generate pMON69754. To construct the final transformation vector containing the Zm-ASA2-CTP, pMON69754 was digested with XhoI, and the purified fragment containing maize oleosin promoter, hsp70 intron, Zm-ASA2-CTP fused to –wt, and Tr7-3'UTR was isolated. This fragment was then ligated in the vector pMON78808, which had also been digested with XhoI to generate the final transformation vector pMON69755 (FIG. 6).

For the construction of transformation vectors containing the AgroAS(F298W) mutant allele, pMON66869 was digested with StuI and RsrII to isolate a fragment containing part of the AgroAS(F298W) coding region. Similarly, pMON69754 was also digested with StuI and RsrII to isolate a fragment containing the maize oleosin promoter, hsp70 intron, part of the coding region and Tr7 3'-UTR. The resulting fragments were ligated to generate pMON69756. To construct final transformation vector, pMON69756 was digested with XhoI, and purified the fragment containing maize oleosin promoter, hsp70 intron, Zm-ASA2-CTP fused to AgroAS(F298W), and Tr7-3'UTR. This fragment was then ligated into the XhoI site of pMON78808, to generate pMON69757; SEQ ID NO: 215).

Transformation vectors containing the AgroAS(S51F) coding region (SEQ ID NO: 203) were similarly constructed. For example, the plasmid pMON69754, described above, was digested with BamHI and NcoI to remove the AgroAS coding region. The plasmid pMON58121 was also digested with BamHI and NcoI to isolate the AgroAS(S51F) mutant allele. The resulting fragments were then ligated to generate the intermediate plasmid pMON69767. The final transformation vector, pMON69768, was constructed as described above by digesting pMON69767 with XhoI, and ligating the fragments at the XhoI site of pMON78808.

An example of the construction of transformation vectors containing the AgroAS(S51C) allele is pMON68065. pMON68063 was digested with XhoI restriction enzyme, separated on 1.0% agarose gel, and the 4569 bp DNA fragment that corresponds to the *Zea mays* Oleosin promoter fused to the Zmhsp70 (Zm.DNAK) intron, the AgroAS (S51C) allele and the Os-gt1-3'UTR was isolated from the gel.

pMON78808 DNA was also cut with XhoI restriction enzyme, dephosphorylated using alkaline phosphatase enzyme (New England BioLabs Inc.), and the DNA was purified using a QIAGEN PCR purification kit (QIAGEN Inc.). The XhoI-digested DNA of pMON78808 and the 4569 bp XhoI-digested DNA fragment of pMON68063 were ligated together to generate pMON68065.

An example of the construction of transformation vectors containing the AgroAS(S51C) codon-optimized (AgroAS (S51C)-nno) allele is pMON68066. Codon optimization of the AgroAS(S51C) mutant allele was carried out as described in U.S. patent application Ser. No. 11/503,532, which is herein incorporated by reference). Codon-optimized AgroAS (S51C)-nno DNA was synthesized by the BLUE HERON BIOTECHNOLOGY group (Bothell, Wash., USA). The synthetic DNA was then digested with NcoI and BamHI restriction enzymes, separated on a 1.0% agarose gel, and the 2193 bp DNA fragment corresponding to the AgroAS(S51C)-nno was cut out from the gel and purified as described above. The DNA of pMON68063 was also cut with NcoI and BamHI restriction enzymes and separated on a 1.0% agarose gel. The isolated 5244 bp NcoI/BamHI-digested DNA fragment contains all the genetic elements described in pMON68063 except the AgroAS(S51C) mutant allele. Ligation reactions were carried out by mixing the DNA of the NcoI/BamHI-digested AgroAS(S51C)-nno DNA (2193 bp fragment) and pMON68063 (5244 bp DNA fragment), to generate pMON68064. pMON68064 was then cut with XhoI restriction enzyme, separated on a 1.0% agarose gel, and the 4532 bp DNA fragment that contains the *Zea mays* oleosin promoter fused to the hsp70 (Zm.DNAK) intron, the AgroAS (S51C)-nno and the Os-gt1-3'UTR was purified as described above. The DNA of pMON78808 DNA was also cut with XhoI restriction enzyme, dephosphorylated using alkaline phosphatase enzyme (New England BioLabs Inc., Beverly, Mass.), and purified using a QIAGEN PCR purification kit (QIAGEN Inc., Valencia, Calif.). Ligation reactions were carried out by mixing the dephosphorylated XhoI-cut pMON78808 DNA and the 4532 bp DNA fragment of pMON68064, to generate pMON68066.

Figure 7:
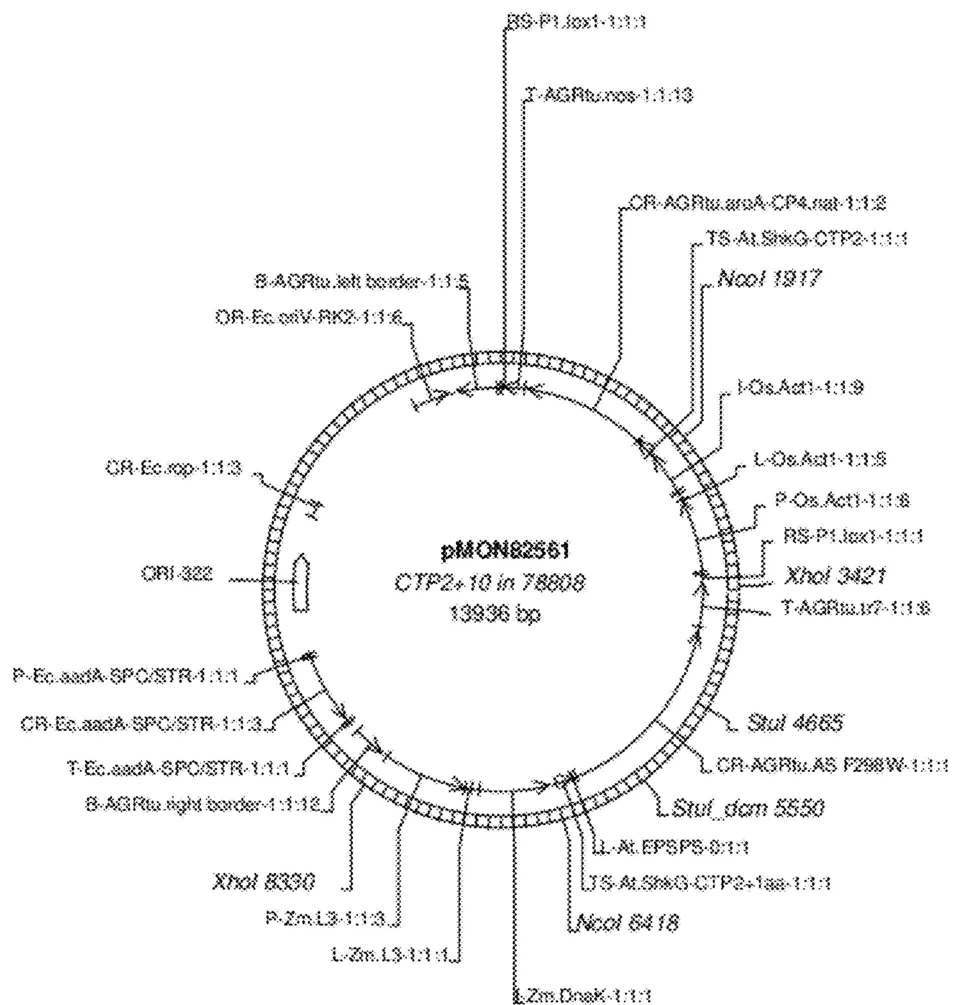
FIG. 7 depicts a restriction map of plasmid pMON82561
Figure 9:
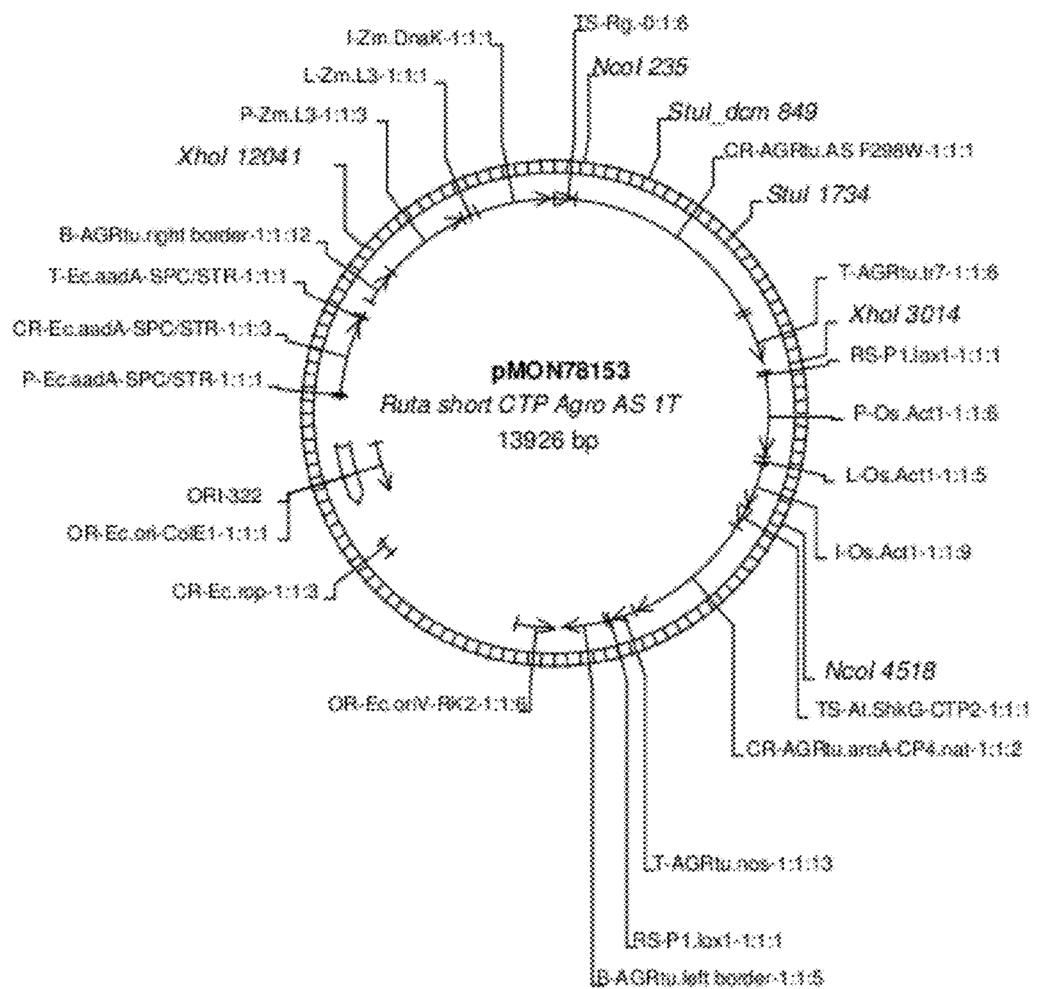
FIG. 9 depicts a restriction map of plasmid pMON78153
Figure 10:
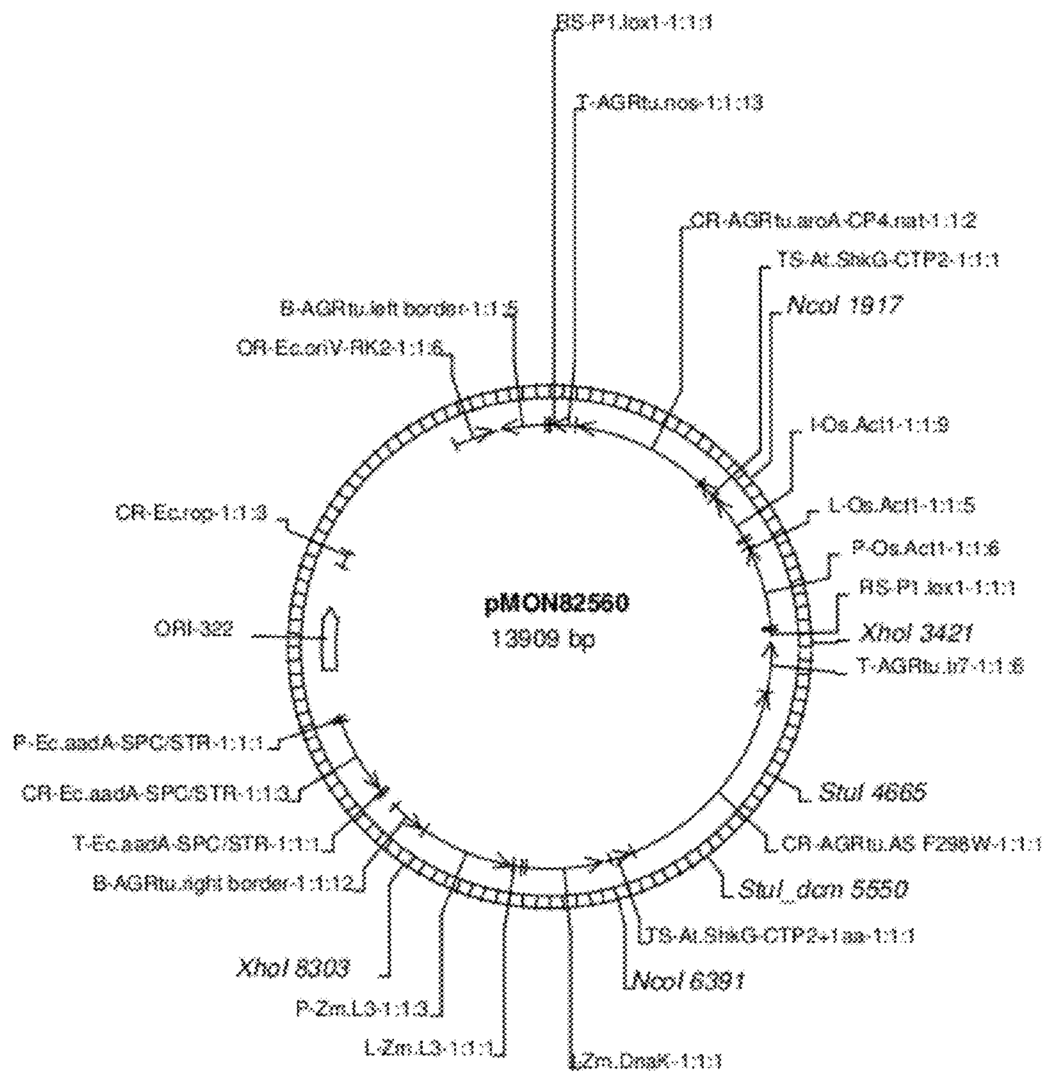
FIG. 10 depicts a restriction map of plasmid pMON82560
Figure 11:
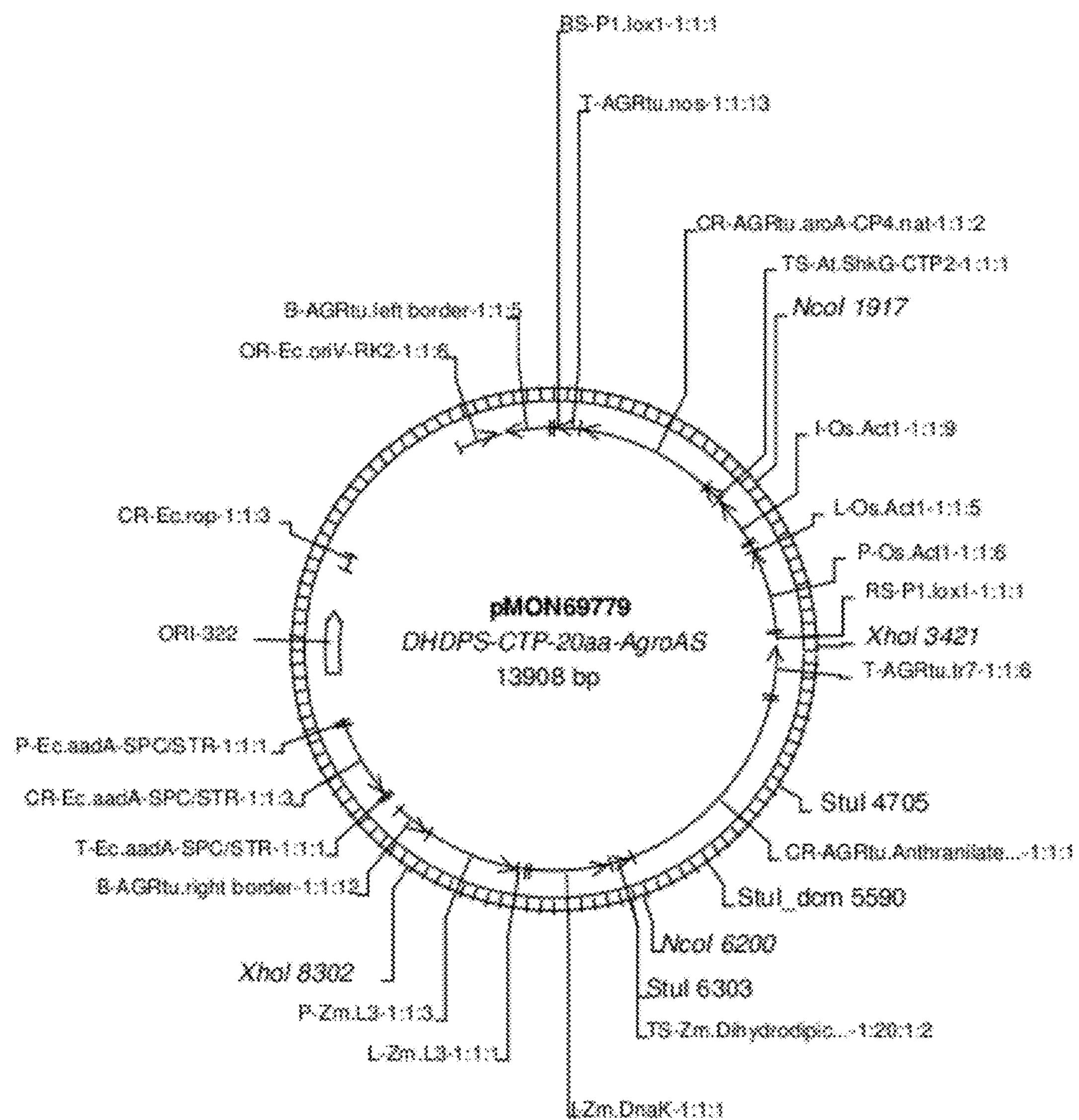
FIG. 11 depicts a restriction map of plasmid pMON69779
Figure 12:
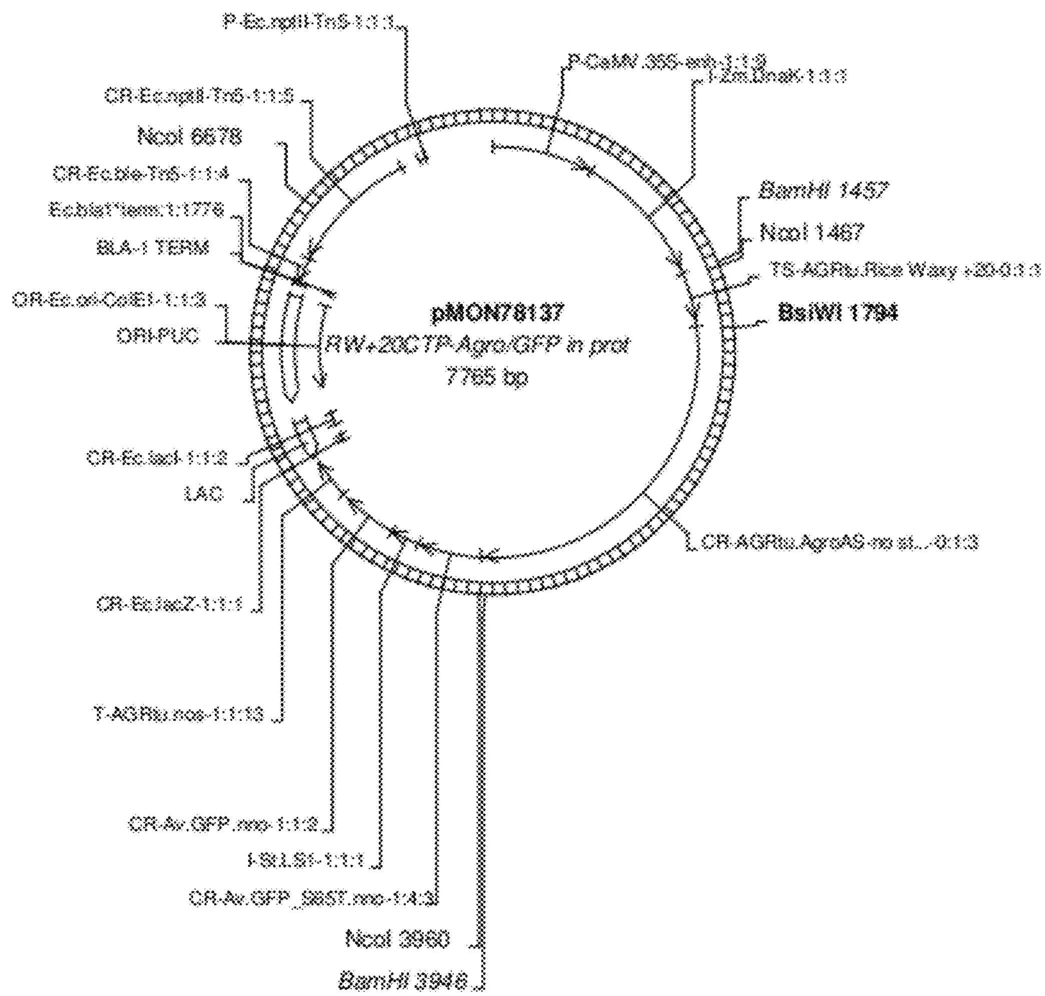
FIG. 12 depicts a restriction map of plasmid pMON78137
Figure 13:
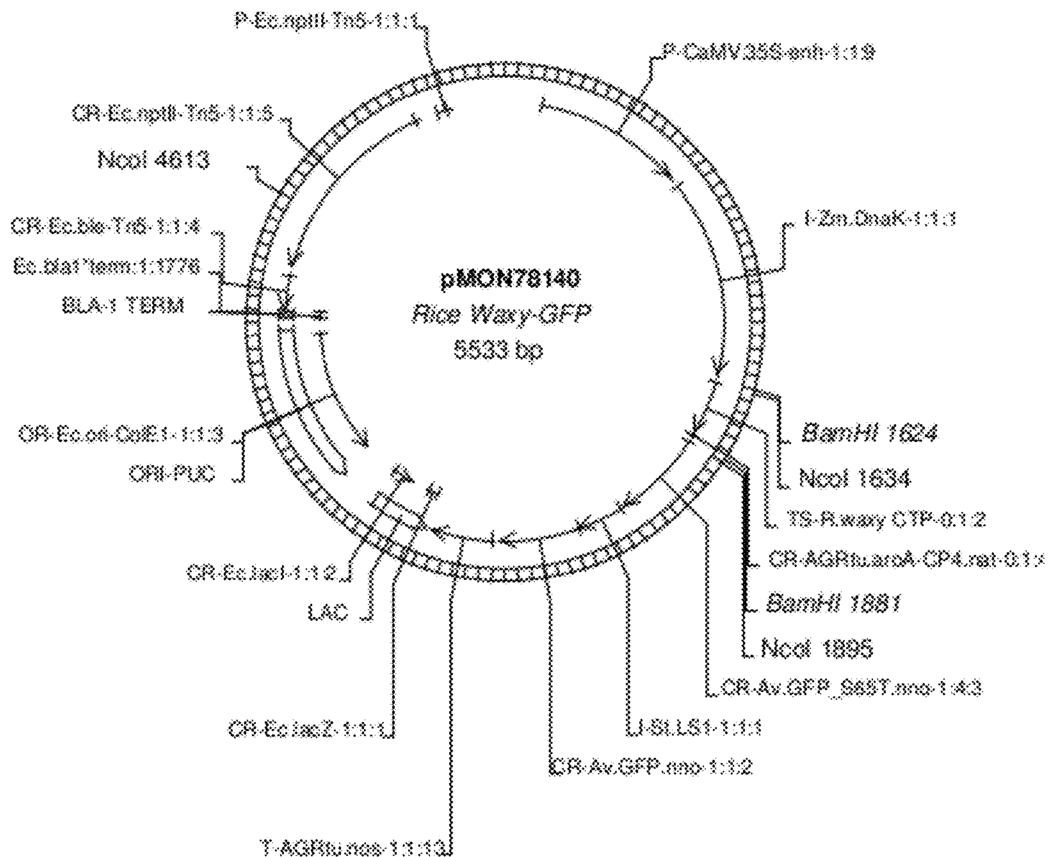
FIG. 13 depicts a restriction map of plasmid pMON78140
Figure 14:
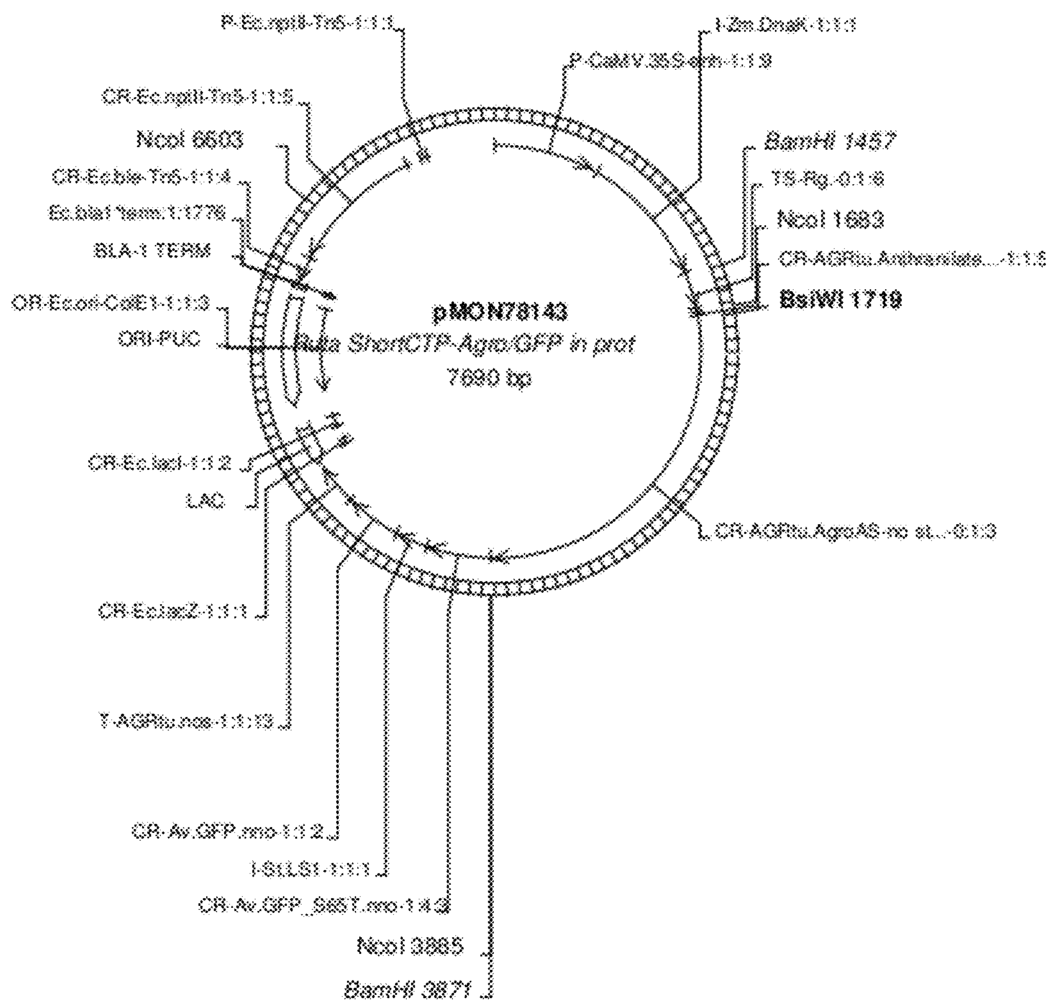
FIG. 14 depicts a restriction map of plasmid pMON78143
Figure 15:
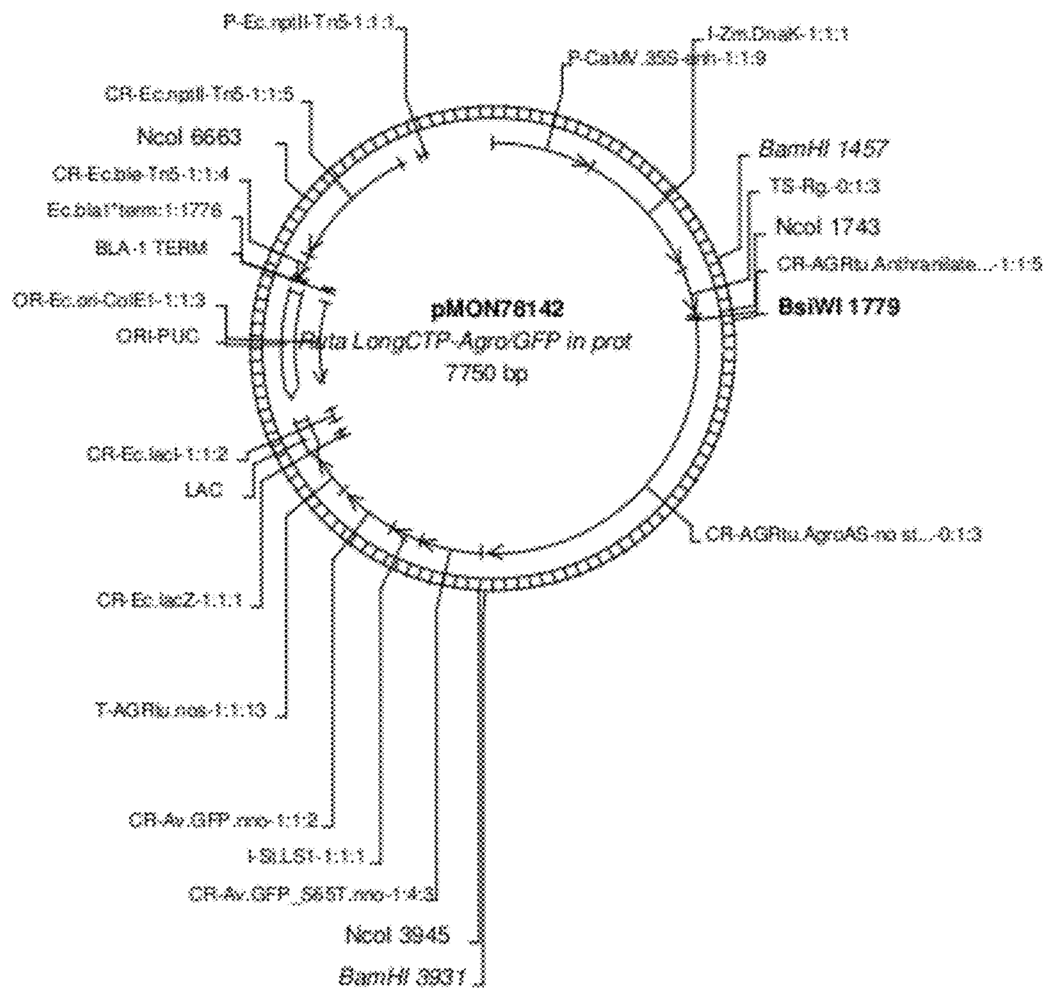
FIG. 15 depicts a restriction map of plasmid pMON78142
Figure 16:
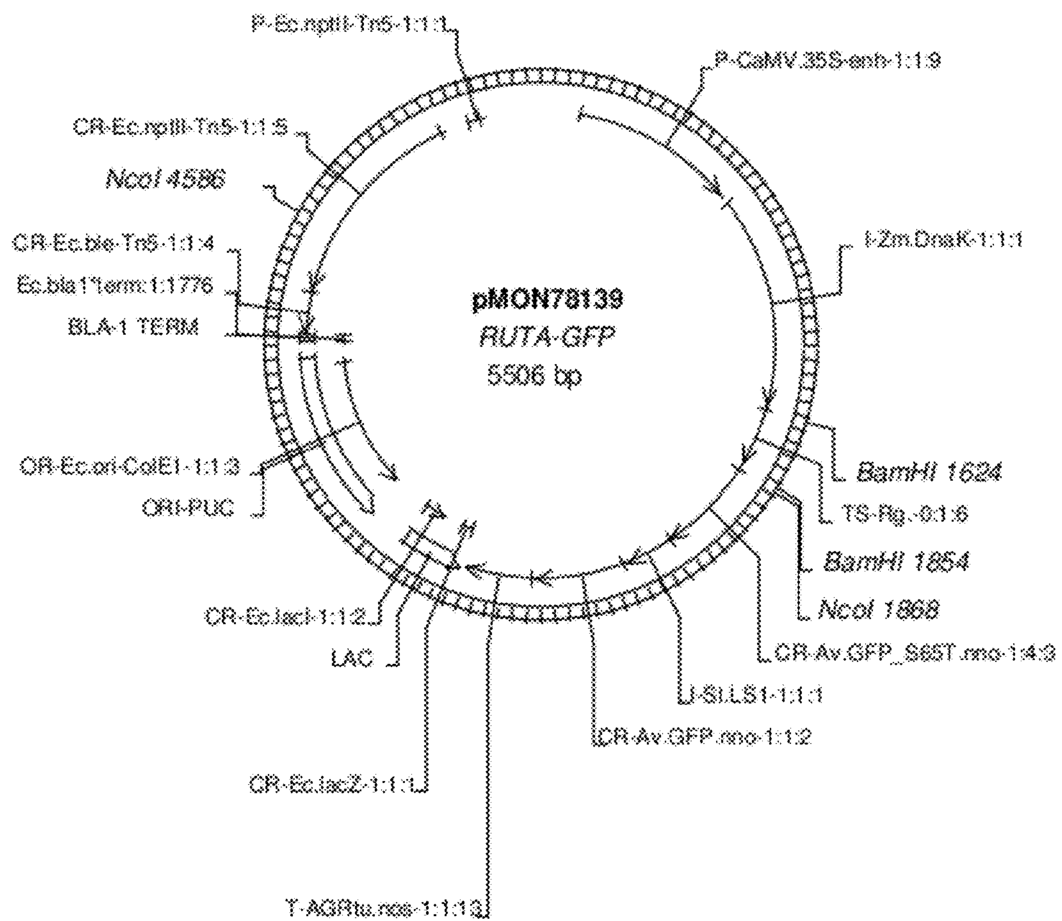
FIG. 16 depicts a restriction map of plasmid pMON78139
Figure 17:
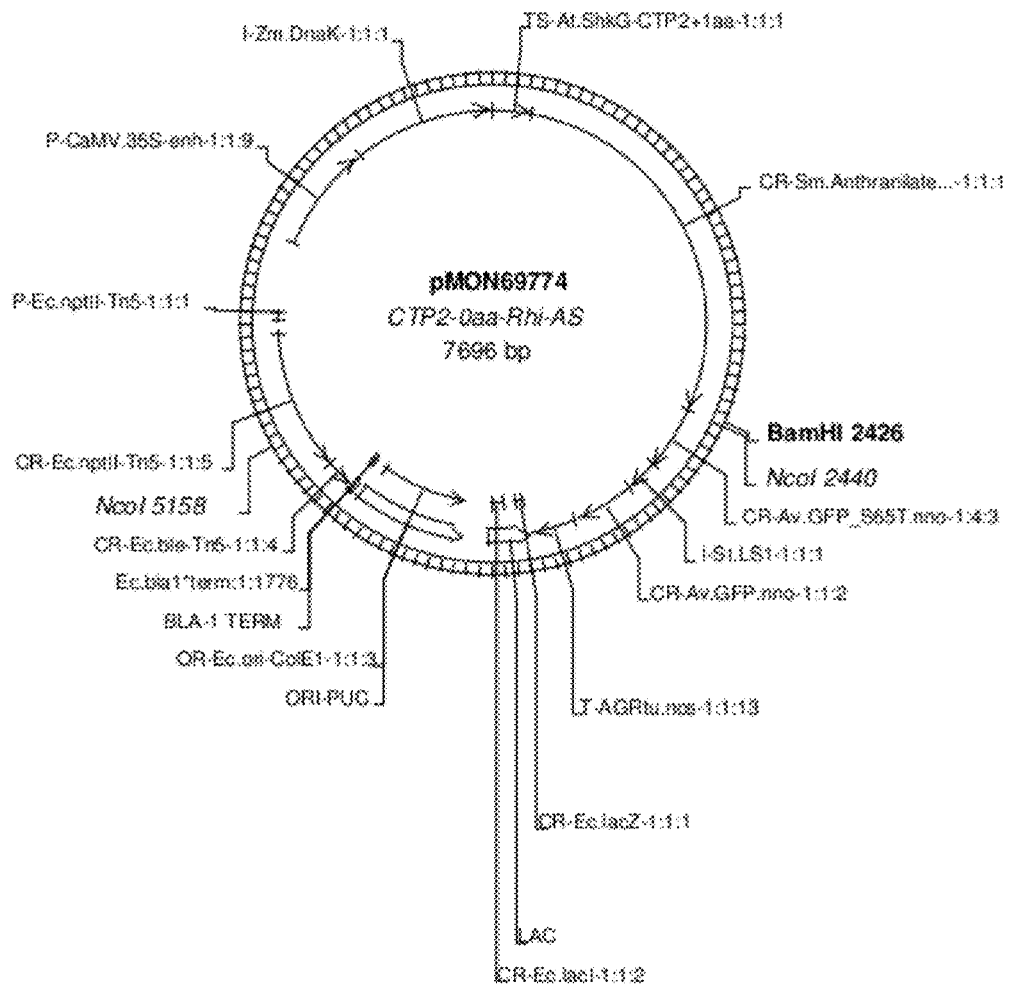
FIG. 17 depicts a restriction map of plasmid pMON69774
Figure 18:
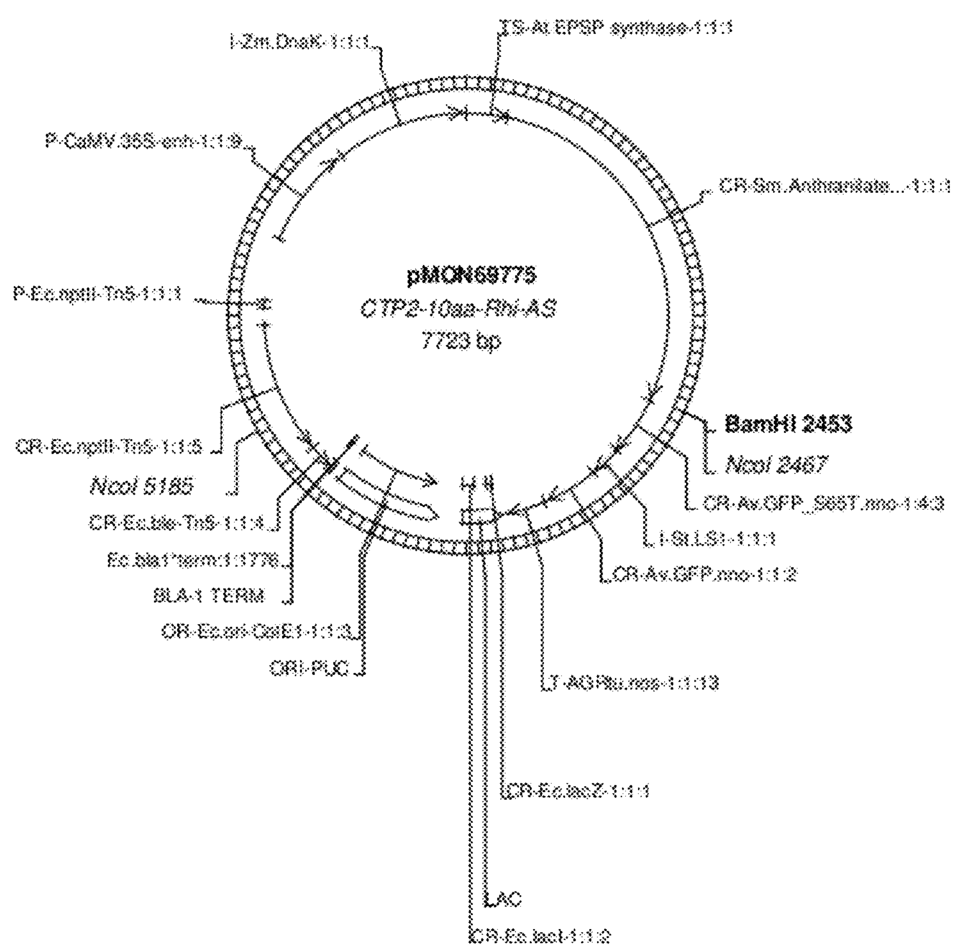
FIG. 18 depicts a restriction map of plasmid pMON69775
Figure 19:
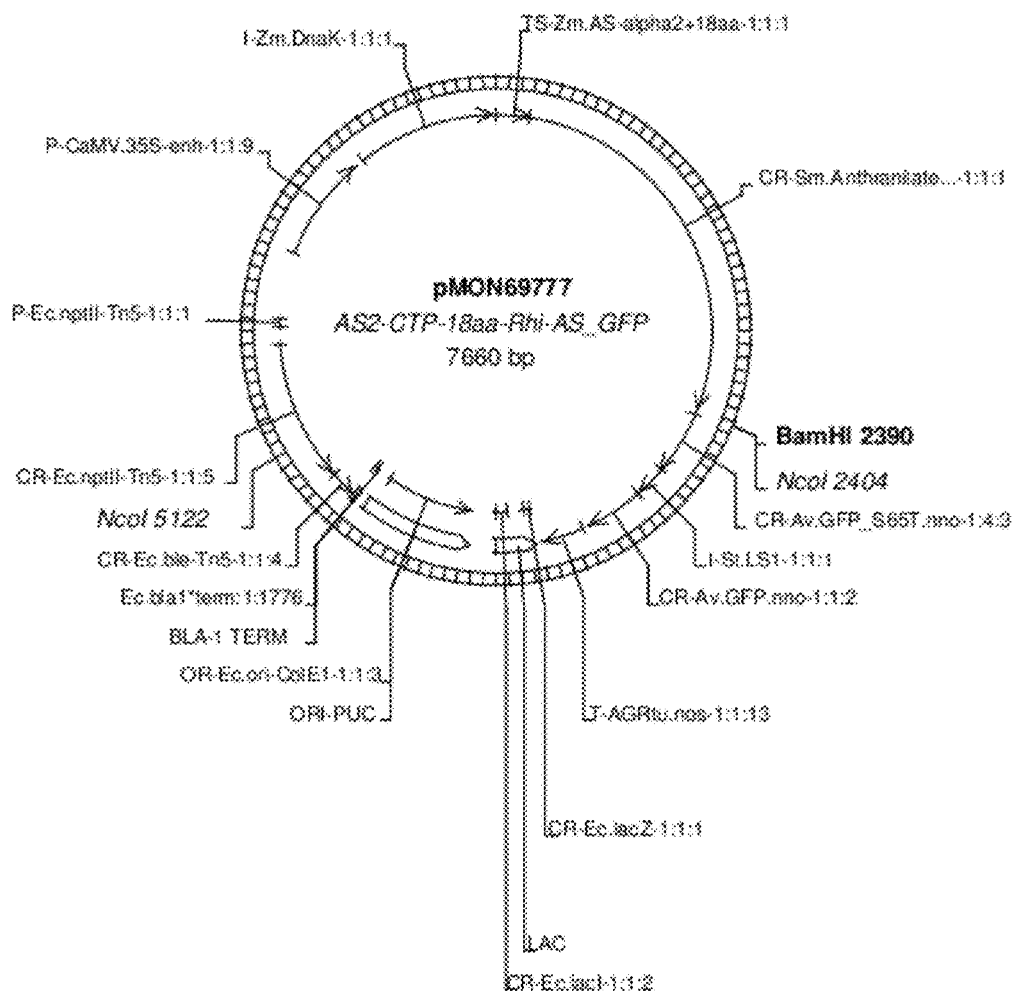
FIG. 19 depicts a restriction map of plasmid pMON69777

The plasmid pMON69769 was used as a base vector to generate various other transformation vectors including pMON82561 (FIG. 7), pMON78152 (FIG. 8), pMON78153 (FIG. 9), pMON82560 (FIG. 10), pMON69779 (FIG. 11), pMON78846, pMON78850, pMON78851, pMON68065, pMON69781, pMON94548, pMON94549, pMON97701, pMON97703 and pMON97705 using similar cloning strategies.

Transformation of Maize

The transformation vectors described above were transformed into maize essentially as described in U.S. Patent Application Publication 20050005327, which is herein incorporated by reference in its entirety. Briefly, ears containing immature embryos are harvested approximately 10 days after pollination and kept refrigerated at 4° C. until use (up to 5 days post-harvest). The preferred embryo size for this method of transformation is ~1.5-2.0 mm. This size is usually achieved 10 days after pollination inside the greenhouse with the growth conditions of an average temperature of 87° F., day length of 14 hours with supplemental lighting supplied by GE 1000 Watt High Pressure Sodium lamps.

Immature embryos are isolated from surface sterilized ears and directly dropped into the prepared *Agrobacterium* cell suspension in a 1.5-mL microcentrifuge tube. The isolation lasts continuously for approximately 5 to 60 minutes. Alternately, embryos are excised directly into inoculation medium (without *Agrobacterium* or acetosyringone) for 5-60 minutes and subsequently inoculated for 5-30 minutes with *Agrobacterium* cell suspension. After the *Agrobacterium* cell suspension is removed using a fine tipped sterile transfer pipette, the immature embryos are transferred onto a crn398 co-culture medium (Table 6). The embryos are then placed on the medium with the scutellum side facing up. The embryos are cultured in a dark incubator (23° C.) for approximately 14-48 hours.

The embryos are then transferred onto a callus induction medium (crn336, Table 6) which contains 0.1 mM glyphosate and 500 mg/L carbenicillin to inhibit *Agrobacterium* in Petri dishes (100 mm×25 mm). The cultures are incubated in a dark culture room/incubator at 30° C. for 2 weeks followed by an additional week in a dark culture room/incubator at 27° C. All the callus pieces are then transferred individually onto the first regeneration medium (crn335, Table 6) which contains 0.1 mM glyphosate and 250 mg/L carbenicillin. The cultures are grown on this medium in a 27° C. culture room with 16 hours light/8 hours dark photoperiod for 7 to 10 days. They are then transferred onto the second regeneration medium (crn333, Table 6) in Petri dishes (100 mm×25 mm) at 27° C. with 16 hours of light for approximately 2 to 3 weeks. All the callus pieces with regenerating shoots and living tissue are then transferred onto either fresh crn333 plates or crn334 PHYTATRAYs (Table 6) or directly transferred to sundae cups containing a rooting medium (crn366, Table 6) to grow further prior to being transferred to soil (approximately 1 to 3 weeks). The regeneration media (crn335, crn333 and crn334) all contain 250 mg/L carbenicillin and 0.1 mM glyphosate.

Plantlets are then transferred to soil, hardened off in a growth chamber at 27° C., 80% humidity, and low light intensity for approximately 1 to 2 weeks, and then transferred to a greenhouse and grown under standard greenhouse conditions. The resulting kernels are collected and analyzed as described below.

TABLE 6

Composition of media used in corn transformation (per Liter).

| Component | Co-culture media (crn398) | Callus induction media (crn336) | First regeneration media (crn335) | Second regeneration media (crn333 (plates)/crn334 (PHYTATRAYs)) | Rooting media (crn366) |
|---|---|---|---|---|---|
| MS salts | 2.17 g | 4.33 g | 4.33 g | 4.33 g | 2.17 g |
| Sucrose | 20 g | 30 g | 30 g | | 20 g |
| Maltose | | | | 20 g | |
| Glucose | 10 g | | | 10 g | |
| 1-Proline | 115 mg | 1.38 g | 1.38 g | | |
| Casamino Acids | | 0.5 g | 0.05 g | | |
| IBA (1 mg/mL stock) | | | | | 0.75 mL |
| 1-Asparagine | | | | 0.15 g | |
| Myo-inositol | | | | 0.1 g | |
| NAA (1 mg/mL stock) | | | | | 0.5 mL |
| Thiamine-HCl (0.5 mg/mL stock) | 1.0 mL | 1.0 mL | | | |
| 2,4-D (1 mg/mL stock) | 3.0 mL | 0.5 mL | | | |
| Silver Nitrate (2 mg/mL stock) | 1.7 mL | 1.7 mL | | | |
| MS Vitamins 100X | 10 mL | 10 mL | | | 5.0 mL |
| MS Fromm 1000X | | | 1.0 mL | 1.0 mL | |
| Carbenicillin (250 mg/mL) | | 2.0 mL | 1.0 mL | 1.0 mL | |
| Glyphosate (0.5M stock) | | 0.2 mL | 0.2 mL | 0.2 mL | 0.2 mL |
| Phytagel | | 3.0 g | 3.0 g | 3.0 g | 3.0 g |
| BAP (0.5 mg/mL stock) | | 0.02 mL | 7.0 mL | | |
| Acetosyringone (1.0.M) | 0.2 mL | | | | |
| Agarose Low EEO | 5.5 g | | | | |

Example 6

Methods for Immunolocalization of AS and Quantification of Tryptophan in Maize Kernels This example describes the analytical procedures used in immunolocalization studies and quantification of free tryptophan levels in kernels from maize events transformed with the CTP-constructs described in Example 5.

Figure 8:
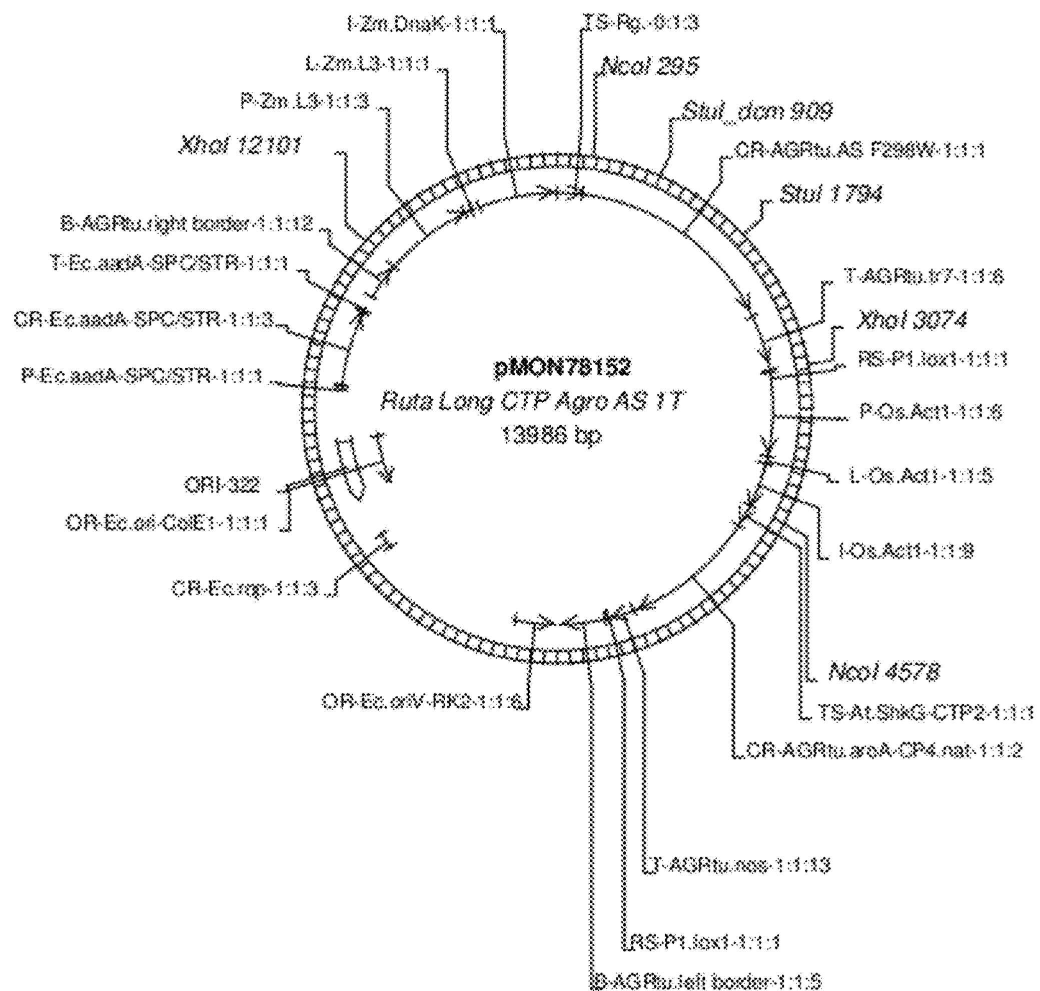
FIG. 8 depicts a restriction map of plasmid pMON78152

The kernels from F1 stage transgenic plants harboring different constructs were separately harvested at 26 DAP. These constructs included pMON69755 (FIG. 6), pMON69779 (FIG. 11), pMON82560 (FIG. 10), pMON82561 (FIG. 7), pMON78153 (FIG. 9) and pMON78152 (FIG. 8). Eight to ten embryos were isolated from each transgenic line of these constructs, fixed in 3.7% formaldehyde solution, and stored at 4° C., prior to being analyzed for the localization of the expressed proteins by the immunolabeling study described below.

Genomic DNA was also extracted from endosperm of these transgenic kernels using DNeasy™ plant Kit (Cat. No. 69104, Qiagen, Waltham, Mass.). PCR amplifications were performed to identify the positive and negative kernels using the oligonucleotide primers maize AS2-5' and maize AS2-3' designated SEQ ID NO: 226 and SEQ ID NO: 227 respectively in the Sequence Listing.

The corn embryos described above were incubated in 500 μl 0.05% Triton X-100 for 30 minutes. Scutellum tissue sections were sliced into sections 20 μm thick using a Leica VT 1000S Vibrating-blade microtome (Leica Microsystems GmbH, Nussloch Germany) equipped with a sapphire knife, and then washed 3 times in PBS buffer (137 mM NaCl, 3 mM KCl, 8 mM $Na_2HPO_4$ and 1.5 mM $KH_2PO_4$) containing 10 mM glycine, for 10 minutes per wash.

The tissue sections were then incubated in enzymatic mixture (4% pectinase, 2% cellulase) for 40 minutes at 28° C. The tissues were then blocked with undiluted serum for 15 minutes, using goat serum (Sigma Cat. No. G-9023; Sigma Chemical Company, St. Louis, Mo.) for AgroAS detection and rabbit serum (Sigma R-9133) for maize AS. The tissue sections were then incubated overnight at 4° C., with gentle shaking, in either 1% rabbit anti-his AgroAS or goat anti-maize AS in PBS buffer.

Following the overnight incubation, the tissues were washed in PBS buffer containing 10 mM glycine for 20 minutes and incubated again in the respective undiluted serums for 15 minutes at room temperature. The tissues were then incubated in the dark with Alexa-conjugate secondary antibody for 2 hours at room temperature. The dilution factors were 1:1000 for AlexaFluor® 532 (Molecular Probes, Inc., Eugene, Oreg.) goat anti-rabbit-conjugate secondary antibody for AgroAS protein and 1:1000 AlexaFluor® 488 (Molecular Probes, Inc.) rabbit anti-goat for Zm AS protein. Following the incubation, the tissues were washed 3 times in PBS containing 10 mM glycine for 10 minutes per wash. The tissues were then counterstained with calcofluor white for cell walls (Sigma) solution (2.5 mg/ml in stock, diluted 1:50 with distilled water) and Hoechst stain for nuclei (Molecular Probes Inc.) for 15 minutes in dark with shaking. The stained tissues were then washed for 10 minutes in distilled water prior to mounting.

The results indicate that when the samples were probed with both AgroAS (red fluorescence at 543 nm) and control Zm AS antibody (green fluorescence at 488 nm) with the channels merged, the appearance of yellow color suggested co-localization of the proteins in plastids (data not shown).

To extract the amino acid fraction, 30 mg of ground kernels were placed in a centrifuge vial. One milliliter of 5% trichloroacetic acid was added to each sample. The samples were mixed by vortexing, and placed at 4° C. overnight. The samples were then mixed again and spun in a microcentrifuge for 15 minutes at 14,000 rpm. Some of the supernatant was then removed, placed in an HPLC vial and sealed. Samples were kept at 4° C. prior to analysis.

The amino acid analysis was performed as described in the Agilent Technical Publication, "Amino Acid Analysis Using Zorbax Eclipse-AAA Columns and the Agilent 1100 HPLC", Mar. 17, 2000. The analysis pre-derivatizes the amino acids with o-pthaldialdehyde (OPA) then separates the OPA conjugates by reverse phase chromatography. The separation was done using an Agilent 1100 series HPLC system (Agilent, Palo Alto, Calif.) with an Eclipse XDB-C18 5 μm, 4.6×150 mm column, and a flow rate of 1.2 ml/minute. Amino acid concentrations were measured using fluorescence: excitation at 340 nm, emission at 450 nm. Elution was with a gradient of HPLC Buffers A and B according to Table 7, where HPLC Buffer A was 40 mM $Na_2HPO_4$, pH 7.8 and HPLC Buffer B was 9:9:2:: Methanol:Acetonitrile:Water.

TABLE 7

| Amino Acid Elution | | | | | |
|---|---|---|---|---|---|
| Time | 0 | 20 | 21 | 26 | 27 |
| % Buffer A | 95 | 35 | 0 | 0 | 0 |
| % Buffer B | 5 | 65 | 100 | 100 | 100 |

Amino acid standards were prepared or purchased in concentrations ranging from 0 to 100 μg/ml. Proline analysis required an additional derivatization step using 9-fluorenylmethyl-chloroformate (FMOC). Results, as shown in Table 8, were reported in ppm.

Example 7

Analysis of Free Tryptophan Levels in Maize

This example sets forth the analysis of free tryptophan levels in maize plants transformed with the expression vectors described in Example 5.

The F1 kernels were analyzed for free tryptophan as described in Example 6. The results from some of the transformed plants, shown in Table 8 below, indicate that the CTPs that demonstrated the ability to successfully target the GFP in the transient expression assays (data shown in Table 5) had higher levels of free tryptophan in transformed plants. Additionally, the CTPs that did not demonstrate the ability to localize the GFP in the plastid had lower levels of free tryptophan. These results indicate that not all CTPs can direct the localization of monomeric AS to the plastid and hence increase free tryptophan levels.

TABLE 8

Average free tryptophan levels in F3 homozygous transgenic maize plants.

| Construct | Vector Description | Event ID | Average of Tryptophan ppm | StdDev of Tryptophan ppm |
|---|---|---|---|---|
| PMON30167 | Vector only | RAG 120 | 11 | 1 |
| Parent line | | Non-transgenic | 11 | 2 |
| PMON69755 | Zm-ASA2-CTP + 18:_wt AS | ZM_S100593 | 118 | 8 |
| | | ZM_S101241 | 99 | 45 |
| | | ZM_S103021 | 58 | 18 |
| | | ZM_S103022 | 63 | 6 |
| | | ZM_S98891 | 122 | 26 |
| PMON69757 | Zm-ASA2-CTP + 18:_F298W | ZM_S100715 | 352 | 42 |
| | | ZM_S101226 | 310 | 16 |
| | | ZM_S99658 | 286 | 37 |
| | | ZM_S99679 | 242 | 16 |
| | | ZM_S99787 | 319 | 22 |
| PMON69768 | Zm-ASA2-CTP + 18:_S51F | ZM_S104037 | 227 | 18 |
| | | ZM_S104038 | 129 | 11 |
| | | ZM_S104052 | 174 | 18 |
| | | ZM_S105091 | 258 | 30 |
| | | ZM_S105105 | 254 | 53 |
| PMON69770 | Zm-ASA2-CTP + 18:_S51C | ZM_S102618 | 677 | 174 |
| | | ZM_S102637 | 649 | 84 |
| | | ZM_S103233 | 585 | 190 |
| | | ZM_S103234 | 612 | 197 |
| | | ZM_S103245 | 632 | 160 |
| | | ZM_S103257 | 667 | 106 |
| | | ZM_S103261 | 430 | 106 |
| | | ZM_S103277 | 684 | 251 |
| PMON69779 | ZM-DHDPS-CTP + 20:_F298W | ZM_S115297 | 150 | 16 |
| | | ZM_S115309 | 129 | 32 |
| | | ZM_S115313 | 123 | 30 |
| | | ZM_S115314 | 148 | 15 |
| | | ZM_S116346 | 145 | 12 |
| PMON67146 | Zm-DHDPS-CTP + 3:_F298W | ZM_S67192 | 49 | 47 |
| | | ZM_S67201 | 41 | 49 |
| | | ZM_S67209 | 51 | 48 |
| PMON78152 | Rg long-CTP:_F298W | ZM_S111632 | 68 | 12 |
| | | ZM_S112752 | 53 | 13 |
| | | ZM_S112777 | 69 | 22 |
| | | ZM_S113086 | 89 | 36 |
| | | ZM_S113096 | 280 | 43 |
| PMON78153 | Rg short-CTP:_F298W | ZM_S113911 | 326 | 14 |
| | | ZM_S113927 | 258 | 99 |
| | | ZM_S113946 | 280 | 54 |
| | | ZM_S113953 | 241 | 47 |
| | | ZM_S114105 | 271 | 79 |
| PMON82560 | At-CTP2(E/K) + 1:_F298W | ZM_S115009 | 353 | 93 |
| | | ZM_S115027 | 340 | 24 |
| | | ZM_S115029 | 393 | 25 |
| | | ZM_S115066 | 358 | 113 |
| | | ZM_S115070 | 361 | 91 |
| PMON82561 | At-CTP2(E/K) + 10:_F298W | ZM_S113026 | 156 | 37 |
| | | ZM_S113029 | 192 | 27 |
| | | ZM_S113033 | 147 | 50 |
| | | ZM_S113194 | 145 | 40 |
| | | ZM_S113833 | 169 | 24 |
| PMON66559 | CTP1:_F298W | ZM_S44537 | 10 | 2 |
| | | ZM_S44538 | 8 | 1 |
| | | ZM_S44540 | 11 | 3 |
| | | ZM_S44542 | 8 | 0 |
| | | ZM_S46820 | 9 | 2 |
| | | ZM_S46828 | 9 | 2 |
| | | ZM_S46833 | 10 | 2 |
| | | ZM_S46841 | 9 | 1 |
| | | ZM_S46842 | 10 | 2 |
| | | ZM_S46848 | 11 | 3 |
| | | ZM_S46855 | 10 | 2 |
| | | ZM_S46859 | 10 | 2 |
| | | ZM_S46861 | 9 | 1 |
| | | ZM_S46865 | 9 | 1 |
| | | ZM_S46873 | 8 | 1 |
| | | ZM_S46877 | 9 | 3 |
| | | ZM_S46878 | 10 | 1 |
| PMON68065 | Zm-ASA2-CTP + 18:_S51C | ZM_S138234 | 435 | 42 |
| | | ZM_S142738 | 512 | 95 |
| | | ZM_S137274 | 514 | 78 |
| | | ZM_S139817 | 529 | 108 |

TABLE 8-continued

| Average free tryptophan levels in F3 homozygous transgenic maize plants. | | | | |
|---|---|---|---|---|
| Construct | Vector Description | Event ID | Average of Tryptophan ppm | StdDev of Tryptophan ppm |
| | | ZM_S134462 | 587 | 71 |
| | | ZM_S142742 | 594 | 135 |
| | | ZM_S142745 | 594 | 90 |
| | | ZM_S142725 | 613 | 87 |
| | | ZM_S142747 | 651 | 93 |
| | | ZM_S142728 | 814 | 395 |
| PMON68066 | Zm-ASA2-CTP + 18:_S51C_nno | ZM_S134079 | 436 | 132 |
| | | ZM_S133073 | 656 | 127 |
| | | ZM_S133076 | 774 | 57 |
| | | ZM_S134078 | 904 | 119 |
| | | ZM_S134080 | 917 | 268 |
| | | ZM_S133092 | 928 | 255 |
| | | ZM_S133080 | 943 | 154 |
| | | ZM_S133098 | 960 | 321 |
| | | ZM_S133099 | 1002 | 556 |
| | | ZM_S133082 | 1023 | 129 |
| | | ZM_S133433 | 1100 | 138 |
| | | ZM_S133093 | 1110 | 136 |
| | | ZM_S133089 | 1289 | 139 |
| | | ZM_S133434 | 1352 | 101 |
| PMON78850 | At-CTP2(E/K) + 1: *Rhizobium*_wt | ZM_S127477 | 45 | 4 |
| | | ZM_S129898 | 32 | 6 |
| | | ZM_S129905 | 35 | 3 |
| | | ZM_S129913 | 45 | 5 |
| | | ZM_S129917 | 40 | 7 |
| PMON78851 | At-CTP2(E/K) + 1: *Rhizobium*_S51C | ZM_S128450 | 595 | 103 |
| | | ZM_S128451 | 547 | 96 |
| | | ZM_S128458 | 983 | 31 |
| | | ZM_S128461 | 477 | 85 |
| | | ZM_S128463 | 548 | 72 |
| | | ZM_S128464 | 547 | 100 |
| | | ZM_S128466 | 503 | 39 |
| | | ZM_S128467 | 603 | 126 |
| | | ZM_S128469 | 532 | 69 |

Example 8

Production of Meal and Feed Products

This example sets forth methods for production of meal and feed products containing the expression vectors which have been described in Example 5.

Any of the plants or parts thereof of the present invention may be processed to produce a feed, meal, protein, or oil preparation, including feed, meal, protein and oil preparations high in total tryptophan content. A particularly preferred plant part for this purpose is a seed. In a preferred embodiment the feed, meal, protein or oil preparation is designed for livestock animals or humans, or both. Methods to produce feed, meal, protein and oil preparations are known in the art. See, for example, U.S. Pat. Nos. 4,957,748; 5,100,679; 5,219,596; 5,936,069; 6,005,076; 6,146,669; and 6,156,227. In a preferred embodiment, the feed, meal, protein or oil preparation is a high tryptophan preparation. Such a high tryptophan preparation preferably has a tryptophan content of greater than about 200 to 400 ppm, more preferably 400 to 600 ppm, and even more preferably 600 to 800 ppm.

Example 9

Methods for Detecting a CTP::As Transgene

This sets forth methods that may be used to detect the presence in transgenic plant cells, or feed or meal products derived from such transgenic plant cells, of unique sequences belonging to a construct containing any of the CTP::AS sequence combinations described herein.

PCR Amplification of CTP::AS DNA

Genomic DNA from transgenic plant cells, or from feed or meal products derived from such transgenic plant cells, can be extracted using the QIAGEN DNeasy™ Plant mini kit (Cat #69104; QIAGEN Inc.) according to manufacturer's protocol. The PCR reaction mixture generally may include about 100 mg of the extracted genomic DNA, 1×PCR reaction buffer (Expand High Fidelity PCR System, Cat #1732641; Roche Inc., Nutley, N.J.), 0.2 mM dNTP, 5 picomoles of each primer, 3.5 units of High Fidelity Taq polymerase enzyme, and water to a final volume of 50 μl. For example, the primer pairs of SEQ ID NO: 228 and SEQ ID NO: 229; or SEQ ID NO: 230 and SEQ ID NO: 231 can be used to amplify the extracted DNA to produce an amplicon that is diagnostic for DNA from the Zm-ASA2+18-CTP::AgroAS construct of a plant cell that has been transformed with pMON68066. The reaction mixture is subjected to various temperature cycles that may include: denaturing at 95° C., annealing at 60° C., and extension at 72° C., for 35 cycles. After 35 cycles of PCR, about 10 μl of the reaction mixture is separated on a 1.0% agarose gel. The presence of a 2649 base pair fragment (with primer pair SEQ ID NO: 228 and SEQ ID NO: 229) or a 2735 base pair fragment (with primer pair SEQ ID NO: 230 and SEQ ID NO: 231) indicates that the plant cell, feed or meal product comprises the Zm-ASA2+18-CTP fused to the AS allele. It is well within the means of one of ordinary skill in the art to recognize and design additional PCR primer pairs that would be useful in the detection of unique sequences belonging to a construct containing any of the other CTP::AS sequence combinations described herein.

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations may be applied to the materials and methods described herein without departing from the concept, spirit and scope of the invention. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. patents, applications and application publications: U.S. application Ser. No. 09/757,089; U.S. application Ser. No. 10/138,927; U.S. application Ser. No. 10/430,011; U.S. application Ser. No. 10/732,721; U.S. application Ser. No. 11/503,532; U.S. Pat. No. 4,957,748; U.S. Pat. No. 4,957,748; U.S. Pat. No. 5,100,679; U.S. Pat. No. 5,100,679; U.S. Pat. No. 5,188,642; U.S. Pat. No. 5,219,596; U.S. Pat. No. 5,219,596; U.S. Pat. No. 5,290,924; U.S. Pat. No. 5,322,783; U.S. Pat. No. 5,322,938; U.S. Pat. No. 5,322,938; U.S. Pat. No. 5,352,605; U.S. Pat. No. 5,359,142; U.S. Pat. No. 5,378,619; U.S. Pat. No. 5,378,619; U.S. Pat. No. 5,424,412; U.S. Pat. No. 5,530,196; U.S. Pat. No. 5,538,880; U.S. Pat. No. 5,550,318; U.S. Pat. No. 5,563,055; U.S. Pat. No. 5,610,042; U.S. Pat. No. 5,641,876; U.S. Pat. No. 5,728,925; U.S. Pat. No. 5,837,848; U.S. Pat. No. 5,858,741; U.S. Pat. No. 5,936,069; U.S. Pat. No. 5,936,069; U.S. Pat. No. 6,005,076; U.S. Pat. No. 6,005,076; U.S. Pat. No. 6,118,047; U.S. Pat. No. 6,140,078; U.S. Pat. No. 6,146,669; U.S. Pat. No. 6,146,669; U.S. Pat. No. 6,156,227; U.S. Pat. No. 6,156,227; U.S. Pat. No. 6,175,060; U.S. Pat. No. 6,177,611; U.S. Pat. No. 6,232,526; U.S. Pat. No. 6,252,138; U.S. Pat. No. 6,294,714; U.S. Pat. No. 6,426,446; U.S. Pat. No. 6,429,357; U.S. Pat. No. 6,429,362; U.S. Pat. No. 6,433,252; U.S. Pat. No. 6,437,217; U.S. Pat. No. 6,635,806; U.S. Pat. No. 5,641,876; U.S. Pat. No. 7,151,204; U.S. Pat. No. 7,217,865; U.S. Publn. 20030097677; U.S. Publn. 20030213010; U.S. Publn. 20050005327

Archer et al., *J. Bioenerg. Biomemb.,* 22:789-810, 1990.

Belanger and Kriz, *Genetics* 129:863-872, 1991.

Callis et al., *Genes Dev.,* 1:1183-1200, 1987.

Chu, In: *Proceedings of Symposium on Plant Tissue Culture*, Science Press, Beijing, China, 43-50, 1978.

Ditta et al., *Proc. Nat. Acad. Sci. USA,* 77:7347-7351, 1980.

EPA 0 120 515

Fraley et al., *Proc. Natl. Acad. Sci. USA,* 80:4803-4807, 1983.

Gallie et al., *The Plant Cell,* 1:301-311, 1989.

Joshi, *Nucleic Acids Res.,* 15:6643-6653, 1987.

Jouanin et al., *Mol. Gen. Genet.,* 201:370-374, 1985.

Lopes et al., *Mol Gen Genet.,* 247:603-613, 1995.

McBride and Summerfelt, *Plant Mol. Biol.,* 14:269-276, 1990.

McElroy et al., *Mol. Gen. Genet.,* 231(1):150-160, 1991.

Odell, et al. *Nature,* 313:810-812, 1985.

PCT Appln. WO 0011200A2

PCT Appln. WO 95/06128

Schnell et al., *J. Biol. Chem.,* 266(5):3335-3342, 1991.

Sheen, *EMBO J.,* 12:3497-3505, 1993.

Silva-Filho et al., *Plant Mol. Biol.,* 30:769-780, 1996.

Silva-Filho et al., *Plant Mol. Biol.,* 30:769-780, 1996.

Tingey et al., *EMBO J.,* 6:1-9, 1987.

Vasil et al., *Plant Physiol.,* 91:1575-1579, 1989.

Withers-Martinez et. al., *Protein Engineering,* 12:1113-1120, 1999.

---

What is claimed is:

1. A nutritionally enhanced corn feed product comprising corn plants or plant parts thereof comprising an expression vector comprising a polynucleotide molecule encoding a chloroplast transit peptide fused to a monomeric anthranilate synthase that is feedback insensitive to tryptophan, wherein the chloroplast transit peptide is heterologous to the monomeric anthranilate synthase, wherein:

a) the chloroplast transit peptide comprises the polypeptide sequence of SEQ ID NO: 28; or b) the polynucleotide molecule encoding the chloroplast transit peptide comprises SEQ ID NO: 9;

wherein said chloroplast transit peptide provides enhanced targeting of said monomeric anthranilate synthase to a chloroplast of a plant cell when compared to the targeting of said anthranilate synthase by chloroplast transit peptide 1 (CTP1) of SEQ ID NO:19; and wherein said corn feed product has enhanced levels of at least tryptophan when compared to a corn feed product from a plant of the same genotype but lacking said polynucleotide molecule.

2. The feed product of claim 1, wherein said plant parts comprise corn seeds.

3. The feed product of claim 1, wherein said polynucleotide encoding a chloroplast transit peptide comprises SEQ ID NO: 9, and said polynucleotide encoding a monomeric anthranilate synthase comprises SEQ ID NO: 207.

4. The feed product of claim 1, wherein said chloroplast transit peptide is capable of compartmentalizing said monomeric anthranilate synthase to a plastid in said plant cell.

5. The feed product of claim 1, defined as comprising a nucleic acid which produces an amplicon diagnostic for an expression vector comprising a polynucleotide molecule encoding a chloroplast transit peptide fused to a monomeric anthranilate synthase, wherein:

a) the chloroplast transit peptide comprises the polypeptide sequence of SEQ ID NO:28; or b) the polynucleotide molecule encoding the chloroplast transit peptide comprises SEQ ID NO:9 when tested in a DNA amplification method.

6. A nutritionally enhanced corn feed product of claim 1, prepared from corn plants or plant parts thereof comprising tryptophan levels that are greater than 200 to 400 ppm, 400 to 600 ppm, or 600 to 800 ppm.

7. The feed product of claim 6, wherein said plant parts comprise corn seeds.

8. The feed product of claim 1, wherein the expression vector comprises a promoter functional in plants operably linked to said polynucleotide encoding the chloroplast transit peptide fused to the monomeric anthranilate synthase.

9. The feed product of claim 8, wherein said promoter is a constitutive, inducible, seed-specific, or tissue-preferred promoter.

* * * * *

SEQUENCE LISTING

```
<160> NUMBER OF SEQ ID NOS: 231

<210> SEQ ID NO 1
<211> LENGTH: 228
<212> TYPE: DNA
<213> ORGANISM: Arabidopsis thaliana

<400> SEQUENCE: 1

atggcgcaag ttagcagaat ctgcaatggt gtgcagaacc catctcttat ctccaatctc      60

tcgaaatcca gtcaacgcaa atctccctta tcggtttctc tgaagacgca gcagcatcca     120

cgagcttatc cgatttcgtc gtcgtgggga ttgaagaaga gtgggatgac gttaattggc     180

tctgagcttc gtcctcttaa ggtcatgtct tctgtttcca cggcgtgc                  228


<210> SEQ ID NO 2
<211> LENGTH: 231
<212> TYPE: DNA
<213> ORGANISM: Arabidopsis thaliana

<400> SEQUENCE: 2

atggcgcaag ttagcagaat ctgcaatggt gtgcagaacc catctcttat ctccaatctc      60

tcgaaatcca gtcaacgcaa atctccctta tcggtttctc tgaagacgca gcagcatcca     120
```

```
cgagcttatc cgatttcgtc gtcgtgggga ttgaagaaga gtgggatgac gttaattggc    180

tctgagcttc gtcctcttaa ggtcatgtct tctgtttcca cggcggagaa a             231


<210> SEQ ID NO 3
<211> LENGTH: 258
<212> TYPE: DNA
<213> ORGANISM: Arabidopsis thaliana

<400> SEQUENCE: 3

atggcgcaag ttagcagaat ctgcaatggt gtgcagaacc catctcttat ctccaatctc     60

tcgaaatcca gtcaacgcaa atctccctta tcggtttctc tgaagacgca gcagcatcca    120

cgagcttatc cgatttcgtc gtcgtgggga ttgaagaaga gtgggatgac gttaattggc    180

tctgagcttc gtcctcttaa ggtcatgtct tctgtttcca cggcggagaa agcgtcggag    240

attgtacttc aacccatt                                                  258


<210> SEQ ID NO 4
<211> LENGTH: 243
<212> TYPE: DNA
<213> ORGANISM: Arabidopsis thaliana

<400> SEQUENCE: 4

atggcgcaag ttagcagaat ctgcaatggt gtgcagaacc catctcttat ctccaatctc     60

tcgaaatcca gtcaacgcaa atctccctta tcggtttctc tgaagacgca gcagcatcca    120

cgagcttatc cgatttcgtc gtcgtgggga ttgaagaaga gtgggatgac gttaattggc    180

tctgagcttc gtcctcttaa ggtcatgtct tctgtttcca cggcggagaa agcgtcggag    240

att                                                                  243


<210> SEQ ID NO 5
<211> LENGTH: 96
<212> TYPE: DNA
<213> ORGANISM: Zea mays

<400> SEQUENCE: 5

atggccaccg ccagcctcgc gctctcgctg cgcctcgcgc cgtactcgca cccgctgagc     60

ctccgccgcc gcggcgccgc cggcgtcacc tgccgc                               96


<210> SEQ ID NO 6
<211> LENGTH: 156
<212> TYPE: DNA
<213> ORGANISM: Zea mays

<400> SEQUENCE: 6

atggccaccg ccagcctcgc gctctcgctg cgcctcgcgc cgtactcgca cccgctgagc     60

ctccgccgcc gcggcgccgc cggcgtcacc tgccgcgcca ccaccgccac gttccaccag    120

cttgacgccg tcgcggtgag ggaggaggag tccagg                              156


<210> SEQ ID NO 7
<211> LENGTH: 142
<212> TYPE: DNA
<213> ORGANISM: Zea mays

<400> SEQUENCE: 7

atggaatccc tagccgccac ctccgtgttc gcgccctccc gcgtcgccgt cccggcggcg     60

cgggccctgg ttagggcggg gacggtggta ccaaccaggc ggacgagcag ccggagcgga    120

accagcgggg tgaaatgctc ta                                             142
```

<210> SEQ ID NO 8
<211> LENGTH: 191
<212> TYPE: DNA
<213> ORGANISM: Zea mays

<400> SEQUENCE: 8
atggaatccc tagccgccac ctccgtgttc gcgccctccc gcgtcgccgt cccggcggcg 60
cgggccctgg ttagggcggg gacggtggta ccaaccaggc ggacgagcag ccggagcgga 120
accagcgggg tgaaatgctc tgctgccgtg acgccgatgg taacgatcat tcaggatgac 180
ggagcggaga c 191

<210> SEQ ID NO 9
<211> LENGTH: 195
<212> TYPE: DNA
<213> ORGANISM: Zea mays

<400> SEQUENCE: 9
atggaatccc tagccgccac ctccgtgttc gcgccctccc gcgtcgccgt cccggcggcg 60
cgggccctgg ttagggcggg gacggtggta ccaaccaggc ggacgagcag ccggagcgga 120
accagcgggg tgaaatgctc tgctgccgtg acgccgcagg cgagcccagt gattagcagg 180
agcgctgcgg cggcc 195

<210> SEQ ID NO 10
<211> LENGTH: 227
<212> TYPE: DNA
<213> ORGANISM: Oryza sativa

<400> SEQUENCE: 10
gcggctctca ccacgtccca gctcgccacc tcggccaccg gcttcggcat cgccgacagg 60
tcggcgccgt cgtcgctgct ccgccacggg ttccagggcc tcaagccccg cagccccgcc 120
ggcggcgacg cgacgtcgct cagcgtgacg accagcgcgc gcgcgacgcc caagcagcag 180
cggtcggtgc agcgtggcag ccggaggttc ccctccgtcg tcgtgtg 227

<210> SEQ ID NO 11
<211> LENGTH: 242
<212> TYPE: DNA
<213> ORGANISM: Oryza sativa

<400> SEQUENCE: 11
gcggctctca ccacgtccca gctcgccacc tcggccaccg gcttcggcat cgccgacagg 60
tcggcgccgt cgtcgctgct ccgccacggg ttccagggcc tcaagccacg cagcccagcc 120
ggcggcgacg cgacgtcgct cagcgtgacg accagcgcgc gcgcgacgcc caagcagcag 180
cggtcggtgc agcgtggcag ccggaggttc ccatccgtcg tcgtgtacgc caccggcgcc 240
gg 242

<210> SEQ ID NO 12
<211> LENGTH: 291
<212> TYPE: DNA
<213> ORGANISM: Oryza sativa

<400> SEQUENCE: 12
atggcggctc tcaccacgtc ccagctcgcc acctcggcca ccggcttcgg catcgccgac 60
aggtcggcgc cgtcgtcgct gctccgccac gggttccagg gcctcaagcc acgcagccca 120
gccggcggcg acgcgacgtc gctcagcgtg acgaccagcg cgcgcgcgac gcccaagcag 180
cagcggtcgg tgcagcgtgg cagccggagg ttcccatccg tcgtcgtgta cgccaccggc 240
gccggcatga acgtcgtgtt cgtcggcgcc gagatggccc cctggagcaa g 291

<210> SEQ ID NO 13
<211> LENGTH: 215
<212> TYPE: DNA
<213> ORGANISM: Ruta graveolens

<400> SEQUENCE: 13
atgagtgcag cggcaacgtc gatgcaatcc cttaaattct ccaaccgtct ggtcccaccc 60
agtcgccgtc tgtctccggt tccgaacaat gtcacctgca ataacctccc caagtctgca 120
gctcccgtcc ggacagtcaa atgctgcgct tcttcctgga acagtaccat caacggcgcg 180
gccgccacga ccaacggtgc gtccgccgcc agttc 215

<210> SEQ ID NO 14
<211> LENGTH: 275
<212> TYPE: DNA
<213> ORGANISM: Ruta graveolens

<400> SEQUENCE: 14
atgagtgcag cggcaacgtc gatgcaatcc cttaaattct ccaaccgtct ggtcccaccc 60
agtcgccgtc tgtctccggt tccgaacaat gtcacctgca ataacctccc caagtctgca 120
gctcccgtcc ggacagtcaa atgctgcgct tcttcctgga acagtaccat caacggcgcc 180
gccgccacga ccaacggtgc gtccgccgcc agtaacggcg catccacgac caccactaca 240
tatgttagtg atgcaaccag atttatcgac tcttc 275

<210> SEQ ID NO 15
<211> LENGTH: 162
<212> TYPE: DNA
<213> ORGANISM: Zea mays

<400> SEQUENCE: 15
atgatttcgc cgacgaatct cctcccggcg cggaagatca cccctgtctc aaatggcggc 60
gcagcgacgg cgagcccctc ttctccctcg gtggccgcac ggccacggcg actcccttca 120
ggcctccaat ctgtgactgg tagagggaag gtttccttgg ca 162

<210> SEQ ID NO 16
<211> LENGTH: 190
<212> TYPE: DNA
<213> ORGANISM: Zea mays

<400> SEQUENCE: 16
atgatttcgc cgacgaatct cctcccggcg cggaagatca cccctgtctc aaatggcggc 60
gcagcgacgg cgagcccctc ttctccctcg gtggccgcac ggccacggcg actcccttca 120
ggcctccaat ctgtgactgg tagagggaag gtttccttgg cagccatcac tctggatgat 180
taccttccaa 190

<210> SEQ ID NO 17
<211> LENGTH: 222
<212> TYPE: DNA
<213> ORGANISM: Zea mays

<400> SEQUENCE: 17
atgatttcgc cgacgaatct cctcccggcg cggaagatca cccctgtctc aaatggcggc 60
gcagcgacgg cgagcccctc ttctccctcg gtggccgcac ggccacggcg actcccttca 120

```
ggcctccaat ctgtgactgg tagagggaag gtttccttgg cagccatcac tctggatgat    180

taccttccaa tgcgaagcac tgaagtgaag aaccggacat ca                       222


<210> SEQ ID NO 18
<211> LENGTH: 171
<212> TYPE: DNA
<213> ORGANISM: Zea mays

<400> SEQUENCE: 18

atgatttcgc cgacgaatct cctcccggcg cggaagatca cccctgtctc aaatggcggc     60

gcagcgacgg cgagcccctc ttctccctcg gtggccgcac ggccacggcg actcccttca    120

ggcctccaat ctgtgactgg tagagggaag gtttccttgg cagccatcac c             171


<210> SEQ ID NO 19
<211> LENGTH: 261
<212> TYPE: DNA
<213> ORGANISM: Arabidopsis thaliana

<400> SEQUENCE: 19

gcttcctcta tgctctcttc cgctactatg gttgcctctc cggctcaggc cactatggtc     60

gctcctttca acggacttaa gtcctccgct gccttcccag ccacccgcaa ggctaacaac    120

gacattactt ccatcacaag caacggcgga agagttaact gcatgcaggt gtggcctccg    180

attggaaaga agaagtttga gactctctct taccttcctg accttaccga ttccggtggt    240

cgcgtcaact gcatgcaggc c                                              261


<210> SEQ ID NO 20
<211> LENGTH: 76
<212> TYPE: PRT
<213> ORGANISM: Arabidopsis thaliana

<400> SEQUENCE: 20

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75


<210> SEQ ID NO 21
<211> LENGTH: 77
<212> TYPE: PRT
<213> ORGANISM: Arabidopsis thaliana

<400> SEQUENCE: 21

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60
```

```
Pro Leu Lys Val Met Ser Ser Val Ser Thr Ala Glu Lys
65                  70                  75


<210> SEQ ID NO 22
<211> LENGTH: 86
<212> TYPE: PRT
<213> ORGANISM: Arabidopsis thaliana

<400> SEQUENCE: 22

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Glu Lys Ala Ser Glu
65                  70                  75                  80

Ile Val Leu Gln Pro Ile
                85


<210> SEQ ID NO 23
<211> LENGTH: 81
<212> TYPE: PRT
<213> ORGANISM: Arabidopsis thaliana

<400> SEQUENCE: 23

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Glu Lys Ala Ser Glu
65                  70                  75                  80

Ile


<210> SEQ ID NO 24
<211> LENGTH: 32
<212> TYPE: PRT
<213> ORGANISM: Zea mays

<400> SEQUENCE: 24

Met Ala Thr Ala Ser Leu Ala Leu Ser Leu Arg Leu Ala Pro Tyr Ser
1               5                   10                  15

His Pro Leu Ser Leu Arg Arg Arg Gly Ala Ala Gly Val Thr Cys Arg
            20                  25                  30


<210> SEQ ID NO 25
<211> LENGTH: 52
<212> TYPE: PRT
<213> ORGANISM: Zea mays

<400> SEQUENCE: 25

Met Ala Thr Ala Ser Leu Ala Leu Ser Leu Arg Leu Ala Pro Tyr Ser
1               5                   10                  15
```

```
His Pro Leu Ser Leu Arg Arg Arg Gly Ala Ala Gly Val Thr Cys Arg
            20                  25                  30

Ala Thr Thr Ala Thr Phe His Gln Leu Asp Ala Val Ala Val Arg Glu
        35                  40                  45

Glu Glu Ser Arg
    50


<210> SEQ ID NO 26
<211> LENGTH: 47
<212> TYPE: PRT
<213> ORGANISM: Zea mays

<400> SEQUENCE: 26

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Arg Ser Gly Thr Ser Gly Val Lys Cys Ser
        35                  40                  45


<210> SEQ ID NO 27
<211> LENGTH: 63
<212> TYPE: PRT
<213> ORGANISM: Zea mays

<400> SEQUENCE: 27

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Arg Ser Gly Thr Ser Gly Val Lys Cys Ser Ala
        35                  40                  45

Ala Val Thr Pro Met Val Thr Ile Ile Gln Asp Asp Gly Ala Glu
    50                  55                  60


<210> SEQ ID NO 28
<211> LENGTH: 65
<212> TYPE: PRT
<213> ORGANISM: Zea mays

<400> SEQUENCE: 28

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Arg Ser Gly Thr Ser Gly Val Lys Cys Ser Ala
        35                  40                  45

Ala Val Thr Pro Gln Ala Ser Pro Val Ile Ser Arg Ser Ala Ala Ala
    50                  55                  60

Ala
65


<210> SEQ ID NO 29
<211> LENGTH: 75
<212> TYPE: PRT
<213> ORGANISM: Oryza sativa

<400> SEQUENCE: 29

Ala Ala Leu Thr Thr Ser Gln Leu Ala Thr Ser Ala Thr Gly Phe Gly
```

```
1               5                   10                  15

Ile Ala Asp Arg Ser Ala Pro Ser Ser Leu Leu Arg His Gly Phe Gln
            20                  25                  30

Gly Leu Lys Pro Arg Ser Pro Ala Gly Gly Asp Ala Thr Ser Leu Ser
        35                  40                  45

Val Thr Thr Ser Ala Arg Ala Thr Pro Lys Gln Gln Arg Ser Val Gln
    50                  55                  60

Arg Gly Ser Arg Arg Phe Pro Ser Val Val Val
65                  70                  75


<210> SEQ ID NO 30
<211> LENGTH: 80
<212> TYPE: PRT
<213> ORGANISM: Oryza sativa

<400> SEQUENCE: 30

Ala Ala Leu Thr Thr Ser Gln Leu Ala Thr Ser Ala Thr Gly Phe Gly
1               5                   10                  15

Ile Ala Asp Arg Ser Ala Pro Ser Ser Leu Leu Arg His Gly Phe Gln
            20                  25                  30

Gly Leu Lys Pro Arg Ser Pro Ala Gly Gly Asp Ala Thr Ser Leu Ser
        35                  40                  45

Val Thr Thr Ser Ala Arg Ala Thr Pro Lys Gln Gln Arg Ser Val Gln
    50                  55                  60

Arg Gly Ser Arg Arg Phe Pro Ser Val Val Val Tyr Ala Thr Gly Ala
65                  70                  75                  80


<210> SEQ ID NO 31
<211> LENGTH: 96
<212> TYPE: PRT
<213> ORGANISM: Oryza sativa

<400> SEQUENCE: 31

Ala Ala Leu Thr Thr Ser Gln Leu Ala Thr Ser Ala Thr Gly Phe Gly
1               5                   10                  15

Ile Ala Asp Arg Ser Ala Pro Ser Ser Leu Leu Arg His Gly Phe Gln
            20                  25                  30

Gly Leu Lys Pro Arg Ser Pro Ala Gly Gly Asp Ala Thr Ser Leu Ser
        35                  40                  45

Val Thr Thr Ser Ala Arg Ala Thr Pro Lys Gln Gln Arg Ser Val Gln
    50                  55                  60

Arg Gly Ser Arg Arg Phe Pro Ser Val Val Val Tyr Ala Thr Gly Ala
65                  70                  75                  80

Gly Met Asn Val Val Phe Val Gly Ala Glu Met Ala Pro Trp Ser Lys
                85                  90                  95


<210> SEQ ID NO 32
<211> LENGTH: 71
<212> TYPE: PRT
<213> ORGANISM: Ruta graveolens

<400> SEQUENCE: 32

Met Ser Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
            20                  25                  30

Cys Asn Asn Leu Pro Lys Ser Ala Ala Pro Val Arg Thr Val Lys Cys
        35                  40                  45
```

```
Cys Ala Ser Ser Trp Asn Ser Thr Ile Asn Gly Ala Ala Ala Thr Thr
    50                  55                  60

Asn Gly Ala Ser Ala Ala Ser
65                  70


<210> SEQ ID NO 33
<211> LENGTH: 91
<212> TYPE: PRT
<213> ORGANISM: Ruta graveolens

<400> SEQUENCE: 33

Met Ser Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
            20                  25                  30

Cys Asn Asn Leu Pro Lys Ser Ala Ala Pro Val Arg Thr Val Lys Cys
        35                  40                  45

Cys Ala Ser Ser Trp Asn Ser Thr Ile Asn Gly Ala Ala Ala Thr Thr
    50                  55                  60

Asn Gly Ala Ser Ala Ala Ser Asn Gly Ala Ser Thr Thr Thr Thr Thr
65                  70                  75                  80

Tyr Val Ser Asp Ala Thr Arg Phe Ile Asp Ser
                85                  90


<210> SEQ ID NO 34
<211> LENGTH: 54
<212> TYPE: PRT
<213> ORGANISM: Zea mays

<400> SEQUENCE: 34

Met Ile Ser Pro Thr Asn Leu Leu Pro Ala Arg Lys Ile Thr Pro Val
1               5                   10                  15

Ser Asn Gly Gly Ala Ala Thr Ala Ser Pro Ser Ser Pro Ser Val Ala
            20                  25                  30

Ala Arg Pro Arg Arg Leu Pro Ser Gly Leu Gln Ser Val Thr Gly Arg
        35                  40                  45

Gly Lys Val Ser Leu Ala
    50


<210> SEQ ID NO 35
<211> LENGTH: 63
<212> TYPE: PRT
<213> ORGANISM: Zea mays

<400> SEQUENCE: 35

Met Ile Ser Pro Thr Asn Leu Leu Pro Ala Arg Lys Ile Thr Pro Val
1               5                   10                  15

Ser Asn Gly Gly Ala Ala Thr Ala Ser Pro Ser Ser Pro Ser Val Ala
            20                  25                  30

Ala Arg Pro Arg Arg Leu Pro Ser Gly Leu Gln Ser Val Thr Gly Arg
        35                  40                  45

Gly Lys Val Ser Leu Ala Ala Ile Thr Leu Asp Asp Tyr Leu Pro
    50                  55                  60


<210> SEQ ID NO 36
<211> LENGTH: 74
<212> TYPE: PRT
<213> ORGANISM: Zea mays
```

<400> SEQUENCE: 36

```
Met Ile Ser Pro Thr Asn Leu Leu Pro Ala Arg Lys Ile Thr Pro Val
1               5                   10                  15

Ser Asn Gly Gly Ala Ala Thr Ala Ser Pro Ser Ser Pro Ser Val Ala
            20                  25                  30

Ala Arg Pro Arg Arg Leu Pro Ser Gly Leu Gln Ser Val Thr Gly Arg
        35                  40                  45

Gly Lys Val Ser Leu Ala Ala Ile Thr Leu Asp Asp Tyr Leu Pro Met
    50                  55                  60

Arg Ser Thr Glu Val Lys Asn Arg Thr Ser
65                  70
```

<210> SEQ ID NO 37
<211> LENGTH: 57
<212> TYPE: PRT
<213> ORGANISM: Zea mays

<400> SEQUENCE: 37

```
Met Ile Ser Pro Thr Asn Leu Leu Pro Ala Arg Lys Ile Thr Pro Val
1               5                   10                  15

Ser Asn Gly Gly Ala Ala Thr Ala Ser Pro Ser Ser Pro Ser Val Ala
            20                  25                  30

Ala Arg Pro Arg Arg Leu Pro Ser Gly Leu Gln Ser Val Thr Gly Arg
        35                  40                  45

Gly Lys Val Ser Leu Ala Ala Ile Thr
    50                  55
```

<210> SEQ ID NO 38
<211> LENGTH: 87
<212> TYPE: PRT
<213> ORGANISM: Arabidopsis thaliana

<400> SEQUENCE: 38

```
Ala Ser Ser Met Leu Ser Ser Ala Thr Met Val Ala Ser Pro Ala Gln
1               5                   10                  15

Ala Thr Met Val Ala Pro Phe Asn Gly Leu Lys Ser Ser Ala Ala Phe
            20                  25                  30

Pro Ala Thr Arg Lys Ala Asn Asn Asp Ile Thr Ser Ile Thr Ser Asn
        35                  40                  45

Gly Gly Arg Val Asn Cys Met Gln Val Trp Pro Pro Ile Gly Lys Lys
    50                  55                  60

Lys Phe Glu Thr Leu Ser Tyr Leu Pro Asp Leu Thr Asp Ser Gly Gly
65                  70                  75                  80

Arg Val Asn Cys Met Gln Ala
                85
```

<210> SEQ ID NO 39
<211> LENGTH: 1134
<212> TYPE: DNA
<213> ORGANISM: Arabidopsis thaliana

<400> SEQUENCE: 39

```
atggcgcaag ttagcagaat ctgcaatggt gtgcagaacc catctcttat ctccaatctc      60

tcgaaatcca gtcaacgcaa atctccctta tcggtttctc tgaagacgca gcagcatcca     120

cgagcttatc cgatttcgtc gtcgtgggga ttgaagaaga gtgggatgac gttaattggc     180

tctgagcttc gtcctcttaa ggtcatgtct tctgtttcca cggcgtgcat gggcaagggc     240
```

```
gaggaactgt tcactggcgt ggtcccaatc ctggtggaac tggatggtga tgtgaacggg    300
cacaagttct ccgtcagcgg agagggtgaa ggtgatgcca cctacggaaa gctcaccctg    360
aagttcatct gcactaccgg aaagctccct gttccgtggc caaccctcgt caccactttc    420
acctacggtg ttcagtgctt ctcccggtac ccagatcaca tgaagcagca tgacttcttc    480
aagagcgcca tgcccgaagg ctacgtgcaa gaaaggacta tctctttcaa ggatgacggg    540
aactacaaga cacgtgccga agtcaagttc gaaggtgata ccctggtgaa ccgcatcgag    600
ctgaaaggta agtttctgct tctacctttg atatatatat aataattatc attaattagt    660
agtaatataa tatttcaaat atttttttca aaataaaaga atgtagtata tagcaattgc    720
ttttctgtag tttataagtg tgtatatttt aatttataac ttttctaata tatgaccaaa    780
atttgttgat gtgcaggtat cgatttcaag gaagatggaa acatcctcgg acacaagctg    840
gagtacaact acaactccca caacgtatac atcacggccg acaagcagaa gaacggcatc    900
aaggctaact tcaagatcag gcacaacatc gaagatggaa gcgtgcaact ggcggaccac    960
taccagcaga acacgcccat cggcgatggc cctgtcctgc tgccggacaa ccattacctg   1020
tccacgcaat ctgccctctc caaggacccc aacgagaaga gggaccacat ggtcctgctg   1080
gagttcgtga cggctgctgg gatcacgcat ggcatggatg aactctacaa gtga         1134
```

<210> SEQ ID NO 40
<211> LENGTH: 1060
<212> TYPE: DNA
<213> ORGANISM: Zea mays

<400> SEQUENCE: 40

```
atggaatccc tagccgccac ctccgtgttc gcgccctccc gcgtcgccgt cccggcggcg     60
cgggccctgg ttagggcggg gacggtggta ccaaccaggc ggacgagcag ccggagcgga    120
accagcgggg tgaaatgctc ggatccagga gcaaccatgg caagggcgag gaactgttca    180
ctggcgtggt cccaatcctg gtggaactgg atggtgatgt gaacgggcac aagttctccg    240
tcagcggaga gggtgaaggt gatgccacct acggaaagct caccctgaag ttcatctgca    300
ctaccggaaa gctccctgtt ccgtggccaa ccctcgtcac cactttcacc tacggtgttc    360
agtgcttctc ccggtaccca gatcacatga agcagcatga cttcttcaag agcgcatgcc    420
cgaaggctac gtgcaagaaa ggactatctc tttcaaggat gacgggaact acaagacacg    480
tgccgaagtc aagttcgaag gtgataccct ggtgaaccgc atcgagctga aaggtaagtt    540
tctgcttcta cctttgatat atatataata attatcatta attagtagta atataatatt    600
tcaaatattt ttttcaaaat aaaagaatgt agtatatagc aattgctttt ctgtagttta    660
taagtgtgta tattttaatt tataactttt ctaatatatg accaaaattt gttgatgtgc    720
aggtatcgat ttcaaggaag atggaaacat cctcggacac aagctggagt acaactacaa    780
ctcccacaac gtatacatca cggccgacaa gcagaagaac ggcatcaagg ctaacttcaa    840
gatcaggcac aacatcgaag atggaagcgt gcaactggcg gaccactacc agcagaacac    900
gcccatcggc gatggccctg tcctgctgcc ggacaaccat tacctgtcca cgcaatctgc    960
cctctccaag gaccccaacg agaagaggga ccacatggtc ctgctggagt tcgtgacggc   1020
tgctgggatc acgcatggca tggatgaact ctacaagtga                         1060
```

<210> SEQ ID NO 41
<211> LENGTH: 606
<212> TYPE: DNA
<213> ORGANISM: Oryza sativa

<400> SEQUENCE: 41

```
gcggctctca ccacgtccca gctcgccacc tcggccaccg gcttcggcat cgccgacagg     60
tcggcgccgt cgtcgctgct ccgccacggg ttccagggcc tcaagccccg cagccccgcc    120
ggcggcgacg cgacgtcgct cagcgtgacg accagcgcgc gcgcgacgcc caagcagcag    180
cggtcggtgc agcgtggcag ccggaggttc ccctccgtcg tcgtgtgatg ggcaagggcg    240
aggaactgtt cactggcgtg gtcccaatcc tggtggaact ggatggtgat gtgaacgggc    300
acaagttctc cgtcagcgga gagggtgaag gtgatgccac ctacggaaag ctcaccctga    360
agttcatctg cactaccgga aagctccctg ttccgtggcc aaccctcgtc accactttca    420
cctacggtgt tcagtgcttc tcccggtacc cagatcacat gaagcagcat gacttcttca    480
agagcgccat gcccgaaggc tacgtgcaag aaaggactat ctctttcaag gatgacggga    540
actacaagac acgtgccgaa gtcaagttcg aaggtgatac cctggtgaac cgcatcgagc    600
tgaaag                                                               606
```

<210> SEQ ID NO 42
<211> LENGTH: 1140
<212> TYPE: DNA
<213> ORGANISM: Ruta graveolens

<400> SEQUENCE: 42

```
atgagtgcag cggcaacgtc gatgcaatcc cttaaattct ccaaccgtct ggtcccaccc     60
agtcgccgtc tgtctccggt tccgaacaat gtcacctgca ataacctccc caagtctgca    120
gctcccgtcc ggacagtcaa atgctgcgct tcttcctgga acagtaccat caacggcgcg    180
gccgccacga ccaacggtgc gtccgccgcc agttccgcgg atccaggagc aaccatgggc    240
aagggcgagg aactgttcac tggcgtggtc ccaatcctgg tggaactgga tggtgatgtg    300
aacgggcaca agttctccgt cagcggagag ggtgaaggtg atgccaccta cggaaagctc    360
accctgaagt tcatctgcac taccggaaag ctccctgttc cgtggccaac cctcgtcacc    420
actttcacct acggtgttca gtgcttctcc cggtacccag atcacatgaa gcagcatgac    480
ttcttcaaga gcgccatgcc cgaaggctac gtgcaagaaa ggactatctc tttcaaggat    540
gacgggaact acaagacacg tgccgaagtc aagttcgaag gtgataccct ggtgaaccgc    600
atcgagctga aggtaagtt tctgcttcta cctttgatat atatataata attatcatta    660
attagtagta atataatatt tcaaatattt ttttcaaaat aaaagaatgt agtatatagc    720
aattgctttt ctgtagttta taagtgtgta tattttaatt tataactttt ctaatatatg    780
accaaaattt gttgatgtgc aggtatcgat ttcaaggaag atggaaacat cctcggacac    840
aagctggagt acaactacaa ctcccacaac gtatacatca cggccgacaa gcagaagaac    900
ggcatcaagg ctaacttcaa gatcaggcac aacatcgaag atggaagcgt gcaactggcg    960
gaccactacc agcagaacac gcccatcggc gatggccctg tcctgctgcc ggacaaccat   1020
tacctgtcca cgcaatctgc cctctccaag gaccccaacg agaagaggga ccacatggtc   1080
ctgctggagt tcgtgacggc tgctgggatc acgcatggca tggatgaact ctacaagtga   1140
```

<210> SEQ ID NO 43
<211> LENGTH: 1083
<212> TYPE: DNA
<213> ORGANISM: Zea mays

<400> SEQUENCE: 43

```
atgatttcgc cgacgaatct cctcccggcg cggaagatca cccctgtctc aaatggcggc      60
gcagcgacgg cgagcccctc ttctccctcg gtggccgcac ggccacggcg actcccttca     120
ggcctccaat ctgtgactgg tagagggaag gtttccttgg cggatccagg agcaaccatg     180
ggcaagggcg aggaactgtt cactggcgtg gtcccaatcc tggtggaact ggatggtgat     240
gtgaacgggc acaagttctc cgtcagcgga gagggtgaag gtgatgccac ctacggaaag     300
ctcaccctga agttcatctg cactaccgga aagctccctg ttccgtggcc aaccctcgtc     360
accactttca cctacggtgt tcagtgcttc tcccggtacc cagatcacat gaagcagcat     420
gacttcttca agagcgccat gcccgaaggc tacgtgcaag aaaggactat ctctttcaag     480
gatgacggga actacaagac acgtgccgaa gtcaagttcg aaggtgatac cctggtgaac     540
cgcatcgagc tgaaaggtaa gtttctgctt ctacctttga tatatatata ataattatca     600
ttaattagta gtaatataat atttcaaata ttttttcaa aataaaagaa tgtagtatat     660
agcaattgct tttctgtagt ttataagtgt gtatatttta atttataact tttctaatat     720
atgaccaaaa tttgttgatg tgcaggtatc gatttcaagg aagatggaaa catcctcgga     780
cacaagctgg agtacaacta caactcccac aacgtataca tcacggccga caagcagaag     840
aacggcatca aggctaactt caagatcagg cacaacatcg aagatggaag cgtgcaactg     900
gcggaccact accagcagaa cacgcccatc ggcgatggcc ctgtcctgct gccggacaac     960
cattacctgt ccacgcaatc tgccctctcc aaggacccca acgagaagag ggaccacatg    1020
gtcctgctgg agttcgtgac ggctgctggg atcacgcatg gcatggatga actctacaag    1080
tga                                                                  1083
```

<210> SEQ ID NO 44
<211> LENGTH: 1098
<212> TYPE: DNA
<213> ORGANISM: Zea mays

<400> SEQUENCE: 44

```
atgatttcgc cgacgaatct cctcccggcg cggaagatca cccctgtctc aaatggcggc      60
gcagcgacgg cgagcccctc ttctccctcg gtggccgcac ggccacggcg actcccttca     120
ggcctccaat ctgtgactgg tagagggaag gtttccttgg cagccatcac tctggaggat     180
ccaggagcaa ccatgggcaa gggcgaggaa ctgttcactg gcgtggtccc aatcctggtg     240
gaactggatg gtgatgtgaa cgggcacaag ttctccgtca gcggagaggg tgaaggtgat     300
gccacctacg gaaagctcac cctgaagttc atctgcacta ccggaaagct ccctgttccg     360
tggccaaccc tcgtcaccac tttcacctac ggtgttcagt gcttctcccg gtacccagat     420
cacatgaagc agcatgactt cttcaagagc gccatgcccg aaggctacgt gcaagaaagg     480
actatctctt tcaaggatga cgggaactac aagacacgtg ccgaagtcaa gttcgaaggt     540
gataccctgg tgaaccgcat cgagctgaaa ggtaagtttc tgcttctacc tttgatatat     600
atataataat tatcattaat tagtagtaat ataatatttc aaatattttt ttcaaaataa     660
aagaatgtag tatatagcaa ttgcttttct gtagtttata agtgtgtata ttttaattta     720
taacttttct aatatatgac caaaatttgt tgatgtgcag gtatcgattt caaggaagat     780
ggaaacatcc tcggacacaa gctggagtac aactacaact cccacaacgt atacatcacg     840
gccgacaagc agaagaacgg catcaaggct aacttcaaga tcaggcacaa catcgaagat     900
ggaagcgtgc aactggcgga ccactaccag cagaacacgc ccatcggcga tggccctgtc     960
ctgctgccgg acaaccatta cctgtccacg caatctgccc tctccaagga ccccaacgag    1020
```

aagagggacc acatggtcct gctggagttc gtgacggctg ctgggatcac gcatggcatg 1080
gatgaactct acaagtga 1098

<210> SEQ ID NO 45
<211> LENGTH: 2420
<212> TYPE: DNA
<213> ORGANISM: Arabidopsis thaliana

<400> SEQUENCE: 45
atggcgcaag ttagcagaat ctgcaatggt gtgcagaacc catctcttat ctccaatctc 60
tcgaaatcca gtcaacgcaa atctccctta tcggtttctc tgaagacgca gcagcatcca 120
cgagcttatc cgatttcgtc gtcgtgggga ttgaagaaga gtgggatgac gttaattggc 180
tctgagcttc gtcctcttaa ggtcatgtct tctgtttcca cggcggagaa aatggcagcg 240
gtaattctag aagacggcgc ggagagttat accacgaagg gtggcatcgt cgtcacccgc 300
aggcggcgtg aggcatccta cagcgacgcg atcgccggtt atgtcgaccg gctggacgaa 360
cgccgcggcg cggtcttttc ctcgaactac gaatatcccg gccgctatac ccgctgggac 420
actgcggtgg tcgacccgcc gcttgccatc tcctccttcg gtcgctcgct ctggatcgaa 480
gcctataacg aacgcggcga agtgctgctg gcgctgatcg ccgaggatct gaagtccgtt 540
gccgacatca cgctcggctc acttgccgcc cgccgcctcg acctcaccat caacgagccc 600
gatcgtgtct tcaccgagga agagcggtcg aagatgccga cggtctttac ggttcttcgc 660
gcggtgacga acctcttcca ctcggaggag gactcgaacc tcggcctcta tggcgccttc 720
ggctacgacc tcgccttcca gttcgatgcg atcgaactga agctttcgcg tccggacgac 780
cagcgcgaca tggttctctt tctgccggac gagatccttg tggtcgatca ctatgcggcc 840
aaggcctgga tcgaccgcta cgatttcgcc agggagaacc tttcgaccga gggcaaggca 900
gcggacattg ctcccgagcc gttccgcagc gtcgacagca tcccgccgca cggggatcac 960
cgcccgggcg aatatgccga gctcgtcgtc aaggcgaagg aaagcttccg tcgcggcgat 1020
cttttcgaag tggtgccggg gcagaaattc tacgagcgct gcgaaagccg cccgtccgag 1080
atttccaacc ggctgaaggc gatcaatccg tcgccctatt ccttcttcat caatctcggc 1140
aaccaggaat atctcgtcgg tgcttcgccg gagatgttcg tgcgcgtttc cggccggcgc 1200
atcgagacct gcccgatctc cggtacgatc aagcgcggcg acgatccgat cgccgacagc 1260
gagcagatcc tgaagctctt gaactcgaag aaggacgagt ccgagctcac catgtgctcg 1320
gacgtcgacc gcaacgacaa gagccgggtc tgcgtgccgg gctcggtcaa ggtgatcggc 1380
cggcgtcaga tcgagatgta ttcgcggctg atccacacgg tcgatcacat cgaggggcgc 1440
ctgcgcgacg atatggacgc cttcgacggg ttcctcagcc acgcctgggc ggtgaccgtt 1500
accggcgcgc caaagctctg ggccatgcgc ttcatcgaga gccacgagaa gagcccgcgt 1560
gcctggtatg gcggcgcgat cggcatggtc ggcttcaacg gcgacatgaa taccgggctg 1620
accttgcgta ccatccgcat caaggacggg atcgccgagg tgagggcggg tgcgacgctc 1680
ctctatgatt ccaatccgga agaagaagaa gccgaaaccg aactgaaggc ctctgccatg 1740
attgcagcca tccgcgacgc gaaatccgca aacagcgcca aatccgcgcg cgatgtcgcc 1800
gccgtcggcg ccggagtcag catcctgctc gtcgatcacg aggacagctt cgtccatacc 1860
ctcgcgaact acttccgcca gaccggcgcg tccgtcacca ccgtgcgcac gccggtggcc 1920
gaggaaatct tcgaccgggt caagccggac ctcgtcgtgc tttcgcccgg tcccggcacc 1980

```
ccgaaggact tcgactgcaa ggcgacgatc aagaaggcgc gggcgcggga cctgccgatc   2040
ttcggcgtct gcctggggct gcaggcgctc gcggaggcct atggcggcga ccttcgtcaa   2100
ctggcgatcc cgatgcatgg gaagccctcg cgcatccgcg tgctcgaacc cggcatcgtc   2160
ttctccggcc tcggcaagga ggtgacggtc gggcgctatc attcgatttt cgccgatccg   2220
tccaacctgc cgcgcgaatt cgtgatcacg gccgaaagcg aagatggtac gatcatgggc   2280
atcgaacaca gcaaggagcc ggtggcggcc gtgcagttcc atccggaatc gatcatgacg   2340
ctgggcggcg acgccggcat gcggatgatc gagaacgtgg ttgcccatct cgccaagcgg   2400
gcgaagacca aggcagcctg                                               2420
```

<210> SEQ ID NO 46
<211> LENGTH: 2447
<212> TYPE: DNA
<213> ORGANISM: Arabidopsis thaliana

<400> SEQUENCE: 46

```
atggcgcaag ttagcagaat ctgcaatggt gtgcagaacc catctcttat ctccaatctc     60
tcgaaatcca gtcaacgcaa atctccctta tcggtttctc tgaagacgca gcagcatcca    120
cgagcttatc cgatttcgtc gtcgtgggga ttgaagaaga gtgggatgac gttaattggc    180
tctgagcttc gtcctcttaa ggtcatgtct tctgtttcca cggcggagaa agcgtcggag    240
attgtacttc aacccattat ggcagcggta attctagaag acggcgcgga gagttatacc    300
acgaagggtg gcatcgtcgt cacccgcagg cggcgtgagg catcctacag cgacgcgatc    360
gccggttatg tcgaccggct ggacgaacgc cgcggcgcgg tcttttcctc gaactacgaa    420
tatcccggcc gctatacccg ctgggacact gcggtggtcg acccgccgct tgccatctcc    480
tccttcggtc gctcgctctg gatcgaagcc tataacgaac gcggcgaagt gctgctggcg    540
ctgatcgccg aggatctgaa gtccgttgcc gacatcacgc tcggctcact tgccgcccgc    600
cgcctcgacc tcaccatcaa cgagcccgat cgtgtcttca ccgaggaaga gcggtcgaag    660
atgccgacgg tctttacggt tcttcgcgcg gtgacgaacc tcttccactc ggaggaggac    720
tcgaacctcg gcctctatgg cgccttcggc tacgacctcg ccttccagtt cgatgcgatc    780
gaactgaagc tttcgcgtcc ggacgaccag cgcgacatgg ttctctttct gccggacgag    840
atccttgtgg tcgatcacta tgcggccaag gcctggatcg accgctacga tttcgccagg    900
gagaaccttt cgaccgaggg caaggcagcg gacattgctc ccgagccgtt ccgcagcgtc    960
gacagcatcc cgccgcacgg ggatcaccgc ccgggcgaat atgccgagct cgtcgtcaag   1020
gcgaaggaaa gcttccgtcg cggcgatctt ttcgaagtgg tgccggggca gaaattctac   1080
gagcgctgcg aaagccgccc gtccgagatt tccaaccggc tgaaggcgat caatccgtcg   1140
ccctattcct tcttcatcaa tctcggcaac caggaatatc tcgtcggtgc ttcgccggag   1200
atgttcgtgc gcgtttccgg ccggcgcatc gagacctgcc cgatctccgg tacgatcaag   1260
cgcggcgacg atccgatcgc cgacagcgag cagatcctga agctcttgaa ctcgaagaag   1320
gacgagtccg agctcaccat gtgctcggac gtcgaccgca acgacaagag ccgggtctgc   1380
gtgccgggct cggtcaaggt gatcggccgg cgtcagatcg agatgtattc gcggctgatc   1440
cacacggtcg atcacatcga ggggcgcctg cgcgacgata tggacgcctt cgacgggttc   1500
ctcagccacg cctgggcggt gaccgttacc ggcgcgccaa agctctgggc catgcgcttc   1560
atcgagagcc acgagaagag cccgcgtgcc tggtatggcg gcgcgatcgg catggtcggc   1620
ttcaacggcg acatgaatac cgggctgacc ttgcgtacca tccgcatcaa ggacgggatc   1680
```

```
gccgaggtga gggcgggtgc gacgctcctc tatgattcca atccggaaga agaagaagcc   1740

gaaaccgaac tgaaggcctc tgccatgatt gcagccatcc gcgacgcgaa atccgcaaac   1800

agcgccaaat ccgcgcgcga tgtcgccgcc gtcggcgccg gagtcagcat cctgctcgtc   1860

gatcacgagg acagcttcgt ccataccctc gcgaactact tccgccagac cggcgcgtcc   1920

gtcaccaccg tgcgcacgcc ggtggccgag gaaatcttcg accgggtcaa gccggacctc   1980

gtcgtgcttt cgcccggtcc cggcaccccg aaggacttcg actgcaaggc gacgatcaag   2040

aaggcgcggg cgcgggacct gccgatcttc ggcgtctgcc tggggctgca ggcgctcgcg   2100

gaggcctatg gcggcgacct tcgtcaactg gcgatcccga tgcatgggaa gccctcgcgc   2160

atccgcgtgc tcgaacccgg catcgtcttc tccggcctcg gcaaggaggt gacggtcggg   2220

cgctatcatt cgattttcgc cgatccgtcc aacctgccgc gcgaattcgt gatcacggcc   2280

gaaagcgaag atggtacgat catgggcatc gaacacagca aggagccggt ggcggccgtg   2340

cagttccatc cggaatcgat catgacgctg ggcggcgacg ccggcatgcg gatgatcgag   2400

aacgtggttg cccatctcgc caagcgggcg aagaccaagg cagcctg                 2447
```

```
<210> SEQ ID NO 47
<211> LENGTH: 2330
<212> TYPE: DNA
<213> ORGANISM: Zea mays

<400> SEQUENCE: 47

atggaatccc tagccgccac ctccgtgttc gcgccctccc gcgtcgccgt cccggcggcg     60

cgggccctgg ttagggcggg gacggtggta ccaaccaggc ggacgagcag ccggagcgga    120

accagcgggg tgaaatgctc tatggcagcg gtaattctag aagacggcgc ggagagttat    180

accacgaagg gtggcatcgt cgtcacccgc aggcggcgtg aggcatccta cagcgacgcg    240

atcgccggtt atgtcgaccg gctggacgaa cgccgcggcg cggtcttttc ctcgaactac    300

gaatatcccg gccgctatac ccgctgggac actgcggtgg tcgacccgcc gcttgccatc    360

tcctccttcg gtcgctcgct ctggatcgaa gcctataacg aacgcggcga agtgctgctg    420

gcgctgatcg ccgaggatct gaagtccgtt gccgacatca cgctcggctc acttgccgcc    480

cgccgcctcg acctcaccat caacgagccc gatcgtgtct tcaccgagga agagcggtcg    540

aagatgccga cggtctttac ggttcttcgc gcggtgacga acctcttcca ctcggaggag    600

gactcgaacc tcggcctcta tggcgccttc ggctacgacc tcgccttcca gttcgatgcg    660

atcgaactga agctttcgcg tccggacgac cagcgcgaca tggttctctt tctgccggac    720

gagatccttg tggtcgatca ctatgcggcc aaggcctgga tcgaccgcta cgatttcgcc    780

agggagaacc tttcgaccga gggcaaggca gcggacattg ctcccgagcc gttccgcagc    840

gtcgacagca tcccgccgca cggggatcac cgcccgggcg aatatgccga gctcgtcgtc    900

aaggcgaagg aaagcttccg tcgcggcgat cttttcgaag tggtgccggg gcagaaattc    960

tacgagcgct gcgaaagccg cccgtccgag atttccaacc ggctgaaggc gatcaatccg   1020

tcgccctatt ccttcttcat caatctcggc aaccaggaat atctcgtcgg tgcttcgccg   1080

gagatgttcg tgcgcgtttc cggccggcgc atcgagacct gcccgatctc cggtacgatc   1140

aagcgcggcg acgatccgat cgccgacagc gagcagatcc tgaagctctt gaactcgaag   1200

aaggacgagt ccgagctcac catgtgctcg gacgtcgacc gcaacgacaa gagccgggtc   1260

tgcgtgccgg gctcggtcaa ggtgatcggc cggcgtcaga tcgagatgta ttcgcggctg   1320
```

```
atccacacgg tcgatcacat cgaggggcgc ctgcgcgacg atatggacgc cttcgacggg   1380

ttcctcagcc acgcctgggc ggtgaccgtt accggcgcgc caaagctctg ggccatgcgc   1440

ttcatcgaga gccacgagaa gagcccgcgt gcctggtatg gcggcgcgat cggcatggtc   1500

ggcttcaacg gcgacatgaa taccgggctg accttgcgta ccatccgcat caaggacggg   1560

atcgccgagg tgagggcggg tgcgacgctc ctctatgatt ccaatccgga agaagaagaa   1620

gccgaaaccg aactgaaggc ctctgccatg attgcagcca tccgcgacgc gaaatccgca   1680

aacagcgcca aatccgcgcg cgatgtcgcc gccgtcggcg ccggagtcag catcctgctc   1740

gtcgatcacg aggacagctt cgtccatacc ctcgcgaact acttccgcca gaccggcgcg   1800

tccgtcacca ccgtgcgcac gccggtggcc gaggaaatct tcgaccgggt caagccggac   1860

ctcgtcgtgc tttcgcccgg tcccggcacc ccgaaggact tcgactgcaa ggcgacgatc   1920

aagaaggcgc gggcgcggga cctgccgatc ttcggcgtct gcctggggct gcaggcgctc   1980

gcggaggcct atggcggcga ccttcgtcaa ctggcgatcc cgatgcatgg gaagccctcg   2040

cgcatccgcg tgctcgaacc cggcatcgtc ttctccggcc tcggcaagga ggtgacggtc   2100

gggcgctatc attcgatttt cgccgatccg tccaacctgc cgcgcgaatt cgtgatcacg   2160

gccgaaagcg aagatggtac gatcatgggc atcgaacaca gcaaggagcc ggtggcggcc   2220

gtgcagttcc atccggaatc gatcatgacg ctgggcggcg acgccggcat gcggatgatc   2280

gagaacgtgg ttgcccatct cgccaagcgg gcgaagacca aggcagcctg              2330
```

<210> SEQ ID NO 48
<211> LENGTH: 2384
<212> TYPE: DNA
<213> ORGANISM: Zea mays

<400> SEQUENCE: 48

```
atggaatccc tagccgccac ctccgtgttc gcgccctccc gcgtcgccgt cccggcggcg     60

cgggccctgg ttagggcggg gacggtggta ccaaccaggc ggacgagcag ccggagcgga    120

accagcgggg tgaaatgctc tgctgccgtg acgccgcagg cgagcccagt gattagcagg    180

agcgctgcgg cggcgatggc agcggtaatt ctagaagacg gcgcggagag ttataccacg    240

aagggtggca tcgtcgtcac ccgcaggcgg cgtgaggcat cctacagcga cgcgatcgcc    300

ggttatgtcg accggctgga cgaacgccgc ggcgcggtct tttcctcgaa ctacgaatat    360

cccggccgct atacccgctg ggacactgcg gtggtcgacc cgccgcttgc catctcctcc    420

ttcggtcgct cgctctggat cgaagcctat aacgaacgcg gcgaagtgct gctggcgctg    480

atcgccgagg atctgaagtc cgttgccgac atcacgctcg gctcacttgc cgcccgccgc    540

ctcgacctca ccatcaacga gcccgatcgt gtcttcaccg aggaagagcg gtcgaagatg    600

ccgacggtct ttacggttct tcgcgcggtg acgaacctct tccactcgga ggaggactcg    660

aacctcggcc tctatggcgc cttcggctac gacctcgcct tccagttcga tgcgatcgaa    720

ctgaagcttt cgcgtccgga cgaccagcgc gacatggttc tctttctgcc ggacgagatc    780

cttgtggtcg atcactatgc ggccaaggcc tggatcgacc gctacgattt cgccagggag    840

aacctttcga ccgagggcaa ggcagcggac attgctcccg agccgttccg cagcgtcgac    900

agcatcccgc cgcacgggga tcaccgcccg ggcgaatatg ccgagctcgt cgtcaaggcg    960

aaggaaagct tccgtcgcgg cgatcttttc gaagtggtgc cggggcagaa attctacgag   1020

cgctgcgaaa gccgcccgtc cgagatttcc aaccggctga aggcgatcaa tccgtcgccc   1080

tattccttct tcatcaatct cggcaaccag gaatatctcg tcggtgcttc gccggagatg   1140
```

```
ttcgtgcgcg tttccggccg gcgcatcgag acctgcccga tctccggtac gatcaagcgc   1200
ggcgacgatc cgatcgccga cagcgagcag atcctgaagc tcttgaactc gaagaaggac   1260
gagtccgagc tcaccatgtg ctcggacgtc gaccgcaacg acaagagccg ggtctgcgtg   1320
ccgggctcgg tcaaggtgat cggccggcgt cagatcgaga tgtattcgcg gctgatccac   1380
acggtcgatc acatcgaggg gcgcctgcgc gacgatatgg acgccttcga cgggttcctc   1440
agccacgcct gggcggtgac cgttaccggc gcgccaaagc tctgggccat gcgcttcatc   1500
gagagccacg agaagagccc gcgtgcctgg tatggcggcg cgatcggcat ggtcggcttc   1560
aacggcgaca tgaataccgg gctgaccttg cgtaccatcc gcatcaagga cgggatcgcc   1620
gaggtgaggg cgggtgcgac gctcctctat gattccaatc cggaagaaga agaagccgaa   1680
accgaactga aggcctctgc catgattgca gccatccgcg acgcgaaatc cgcaaacagc   1740
gccaaatccg cgcgcgatgt cgccgccgtc ggcgccggag tcagcatcct gctcgtcgat   1800
cacgaggaca gcttcgtcca taccctcgcg aactacttcc gccagaccgg cgcgtccgtc   1860
accaccgtgc gcacgccggt ggccgaggaa atcttcgacc gggtcaagcc ggacctcgtc   1920
gtgctttcgc ccggtcccgg caccccgaag gacttcgact gcaaggcgac gatcaagaag   1980
gcgcgggcgc gggacctgcc gatcttcggc gtctgcctgg ggctgcaggc gctcgcggag   2040
gcctatggcg gcgaccttcg tcaactggcg atcccgatgc atgggaagcc ctcgcgcatc   2100
cgcgtgctcg aacccggcat cgtcttctcc ggcctcggca aggaggtgac ggtcgggcgc   2160
tatcattcga ttttcgccga tccgtccaac ctgccgcgcg aattcgtgat cacggccgaa   2220
agcgaagatg gtacgatcat gggcatcgaa cacagcaagg agccggtggc ggccgtgcag   2280
ttccatccgg aatcgatcat gacgctgggc ggcgacgccg gcatgcggat gatcgagaac   2340
gtggttgccc atctcgccaa gcgggcgaag accaaggcag cctg                    2384
```

<210> SEQ ID NO 49
<211> LENGTH: 2379
<212> TYPE: DNA
<213> ORGANISM: Zea mays

<400> SEQUENCE: 49

```
atggaatccc tagccgccac ctccgtgttc gcgccctccc gcgtcgccgt cccggcggcg     60
cgggccctgg ttagggcggg gacggtggta ccaaccaggc ggacgagcag ccggagcgga    120
accagcgggg tgaaatgctc tgctgccgtg acgccgcagg cgagcccagt gattagcagg    180
agcgctgcgg cggccgtaac gatcattcag gatgacggag cggagaccta cgagacgaaa    240
ggcggcatcc aggtcagccg aaagcgccgg cccaccgatt atgccaacgc catcgataat    300
tacatcgaaa agcttgattc ccatcgcggc gcggtttttt cgtccaacta tgaatatccg    360
ggccgttaca cccgctggga tacggccatc gtcgatccgc cgctcggcat ttcctgtttt    420
ggccgcaaga tgtggatcga agcctataat ggccgcggcg aagtgctgct cgatttcatt    480
acggaaaagc tgaaggcgac acccgatctc accctcggcg cttcctcgac ccgccggctc    540
gatcttaccg tcaacgaacc ggaccgtgtc ttcaccgaag aagaacgctc gaaaatcccg    600
acggtcttca ccgctctcag agccatcgtc gacctcttct attcgagcgc ggattcggcc    660
atcggcctgt tcggtgcctt cggttacgat ctcgccttcc agttcgacgc gatcaagctt    720
tcgctggcgc gtccggaaga ccagcgtgac atggtgctgt ttctgcccga tgaaatcctc    780
gtcgttgatc actattccgc caaggcctgg atcgaccgtt acgatttcga gaaggacggc    840
```

```
atgacgacgg acggcaaatc ctccgacatt acccccgatc ccttcaagac caccgatacc     900
atcccgccca agggcgatca ccgtcccggc gaatattccg agcttgtggt gaaggccaag     960
gaaagcttcc gccgcggcga cctgttcgag gtcgttcccg gccagaaatt catggagcgt    1020
tgcgaaagca atccgtcggc gatttcccgc cgcctgaagg cgatcaaccc gtcgccctat    1080
tccttcttca tcaatctcgg cgatcaggaa tatctggtcg gcgcctcgcc ggaaatgttc    1140
gtgcgcgtct ccggccgtcg catcgagacc tgcccgatat caggcaccat caagcgcggc    1200
gacgatccga ttgccgacag cgagcagatt ttgaaactgc tcaactcgaa aaaggacgaa    1260
tccgaactga ccatgtgctc ggacgtggac cgcaacgaca agagccgcgt ctgcgagccg    1320
ggttcggtga aggtcattgg ccgccgccag atcgagatgt attcacgcct catccacacc    1380
gtcgatcaca tcgaaggccg cctgcgcgac gatatggacg cctttgacgg tttcctcagc    1440
cacgcctggg ccgtcaccgt caccggtgca ccaaagctgt gggccatgcg cttcatcgaa    1500
ggtcatgaaa agagcccgcg cgcctggtat ggcggtgcga tcggcatggt cggcttcaac    1560
ggcgacatga ataccggcct gacgctgcgc accatccgga tcaaggacgg tattgccgaa    1620
gtgcgcgccg gcgcgaccct gctcaatgat tccaacccgc aggaagaaga agccgaaacc    1680
gaactgaagg cctccgccat gatatcagcc attcgtgacg caaaaggcac caactctgcc    1740
gccaccaagc gtgatgccgc caaagtcggc accggcgtca agatcctgct cgtcgaccac    1800
gaagacagct tcgtgcacac gctggcgaat tatttccgcc agacgggcgc gacggtctcg    1860
accgtcagat caccggtcgc agccgacgtg ttcgatcgct tccagccgga cctcgttgtc    1920
ctgtcgcccg gacccggcag cccgacggat ttcgactgca aggcaacgat caaggccgcc    1980
cgcgcccgcg atctgccgat cttcggcgtt tgcctcggtc tgcaggcatt ggcagaagcc    2040
tatggcggcg agctgcgcca gcttgctgtg cccatgcacg gcaagccttc gcgcatccgc    2100
gtgctggaac ccggcctcgt cttctccggt ctcggcaagg aagtcacggt cggtcgttac    2160
cattcgatct tcgccgatcc cgccaccctg ccgcgtgatt tcatcatcac cgcagaaagc    2220
gaggacggca cgatcatggg catcgaacac gccaaggaac cggtggccgc cgttcagttc    2280
cacccggaat cgatcatgac gctcggacag gacgcgggca tgcggatgat cgagaatgtc    2340
gtggtgcatc tgacccgcaa ggcgaagacc aaggccgcg                          2379
```

<210> SEQ ID NO 50
<211> LENGTH: 314
<212> TYPE: PRT
<213> ORGANISM: Arabidopsis thaliana

<400> SEQUENCE: 50

```
Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys Met Gly Lys Gly
65                  70                  75                  80

Glu Glu Leu Phe Thr Gly Val Val Pro Ile Leu Val Glu Leu Asp Gly
                85                  90                  95

Asp Val Asn Gly His Lys Phe Ser Val Ser Gly Glu Gly Glu Gly Asp
```

```
            100                 105                 110

Ala Thr Tyr Gly Lys Leu Thr Leu Lys Phe Ile Cys Thr Thr Gly Lys
        115                 120                 125

Leu Pro Val Pro Trp Pro Thr Leu Val Thr Thr Phe Thr Tyr Gly Val
    130                 135                 140

Gln Cys Phe Ser Arg Tyr Pro Asp His Met Lys Gln His Asp Phe Phe
145                 150                 155                 160

Lys Ser Ala Met Pro Glu Gly Tyr Val Gln Glu Arg Thr Ile Ser Phe
                165                 170                 175

Lys Asp Asp Gly Asn Tyr Lys Thr Arg Ala Glu Val Lys Phe Glu Gly
            180                 185                 190

Asp Thr Leu Val Asn Arg Ile Glu Leu Lys Gly Ile Asp Phe Lys Glu
        195                 200                 205

Asp Gly Asn Ile Leu Gly His Lys Leu Glu Tyr Asn Tyr Asn Ser His
    210                 215                 220

Asn Val Tyr Ile Thr Ala Asp Lys Gln Lys Asn Gly Ile Lys Ala Asn
225                 230                 235                 240

Phe Lys Ile Arg His Asn Ile Glu Asp Gly Ser Val Gln Leu Ala Asp
                245                 250                 255

His Tyr Gln Gln Asn Thr Pro Ile Gly Asp Gly Pro Val Leu Leu Pro
            260                 265                 270

Asp Asn His Tyr Leu Ser Thr Gln Ser Ala Leu Ser Lys Asp Pro Asn
        275                 280                 285

Glu Lys Arg Asp His Met Val Leu Leu Glu Phe Val Thr Ala Ala Gly
    290                 295                 300

Ile Thr His Gly Met Asp Glu Leu Tyr Lys
305                 310


<210> SEQ ID NO 51
<211> LENGTH: 290
<212> TYPE: PRT
<213> ORGANISM: Zea mays

<400> SEQUENCE: 51

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Arg Ser Gly Thr Ser Gly Val Lys Cys Ser Asp
        35                  40                  45

Pro Gly Ala Thr Met Gly Lys Gly Glu Glu Leu Phe Thr Gly Val Val
    50                  55                  60

Pro Ile Leu Val Glu Leu Asp Gly Asp Val Asn Gly His Lys Phe Ser
65                  70                  75                  80

Val Ser Gly Glu Gly Glu Gly Asp Ala Thr Tyr Gly Lys Leu Thr Leu
                85                  90                  95

Lys Phe Ile Cys Thr Thr Gly Lys Leu Pro Val Pro Trp Pro Thr Leu
            100                 105                 110

Val Thr Thr Phe Thr Tyr Gly Val Gln Cys Phe Ser Arg Tyr Pro Asp
        115                 120                 125

His Met Lys Gln His Asp Phe Phe Lys Ser Ala Met Pro Glu Gly Tyr
    130                 135                 140

Val Gln Glu Arg Thr Ile Ser Phe Lys Asp Asp Gly Asn Tyr Lys Thr
145                 150                 155                 160
```

```
Arg Ala Glu Val Lys Phe Glu Gly Asp Thr Leu Val Asn Arg Ile Glu
                165                 170                 175

Leu Lys Gly Ile Asp Phe Lys Glu Asp Gly Asn Ile Leu Gly His Lys
            180                 185                 190

Leu Glu Tyr Asn Tyr Asn Ser His Asn Val Tyr Ile Thr Ala Asp Lys
        195                 200                 205

Gln Lys Asn Gly Ile Lys Ala Asn Phe Lys Ile Arg His Asn Ile Glu
    210                 215                 220

Asp Gly Ser Val Gln Leu Ala Asp His Tyr Gln Gln Asn Thr Pro Ile
225                 230                 235                 240

Gly Asp Gly Pro Val Leu Leu Pro Asp Asn His Tyr Leu Ser Thr Gln
                245                 250                 255

Ser Ala Leu Ser Lys Asp Pro Asn Glu Lys Arg Asp His Met Val Leu
            260                 265                 270

Leu Glu Phe Val Thr Ala Ala Gly Ile Thr His Gly Met Asp Glu Leu
        275                 280                 285

Tyr Lys
    290


<210> SEQ ID NO 52
<211> LENGTH: 201
<212> TYPE: PRT
<213> ORGANISM: Oryza sativa

<400> SEQUENCE: 52

Ala Ala Leu Thr Thr Ser Gln Leu Ala Thr Ser Ala Thr Gly Phe Gly
1               5                   10                  15

Ile Ala Asp Arg Ser Ala Pro Ser Ser Leu Leu Arg His Gly Phe Gln
            20                  25                  30

Gly Leu Lys Pro Arg Ser Pro Ala Gly Gly Asp Ala Thr Ser Leu Ser
        35                  40                  45

Val Thr Thr Ser Ala Arg Ala Thr Pro Lys Gln Gln Arg Ser Val Gln
    50                  55                  60

Arg Gly Ser Arg Arg Phe Pro Ser Val Val Val Met Gly Lys Gly Glu
65                  70                  75                  80

Glu Leu Phe Thr Gly Val Val Pro Ile Leu Val Glu Leu Asp Gly Asp
                85                  90                  95

Val Asn Gly His Lys Phe Ser Val Ser Gly Glu Gly Glu Gly Asp Ala
            100                 105                 110

Thr Tyr Gly Lys Leu Thr Leu Lys Phe Ile Cys Thr Thr Gly Lys Leu
        115                 120                 125

Pro Val Pro Trp Pro Thr Leu Val Thr Thr Phe Thr Tyr Gly Val Gln
    130                 135                 140

Cys Phe Ser Arg Tyr Pro Asp His Met Lys Gln His Asp Phe Phe Lys
145                 150                 155                 160

Ser Ala Met Pro Glu Gly Tyr Val Gln Glu Arg Thr Ile Ser Phe Lys
                165                 170                 175

Asp Asp Gly Asn Tyr Lys Thr Arg Ala Glu Val Lys Phe Glu Gly Asp
            180                 185                 190

Thr Leu Val Asn Arg Ile Glu Leu Lys
        195                 200


<210> SEQ ID NO 53
<211> LENGTH: 316
<212> TYPE: PRT
<213> ORGANISM: Ruta graveolens
```

<400> SEQUENCE: 53

```
Met Ser Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
            20                  25                  30

Cys Asn Asn Leu Pro Lys Ser Ala Ala Pro Val Arg Thr Val Lys Cys
        35                  40                  45

Cys Ala Ser Ser Trp Asn Ser Thr Ile Asn Gly Ala Ala Ala Thr Thr
    50                  55                  60

Asn Gly Ala Ser Ala Ala Ser Ser Ala Asp Pro Gly Ala Thr Met Gly
65                  70                  75                  80

Lys Gly Glu Glu Leu Phe Thr Gly Val Val Pro Ile Leu Val Glu Leu
                85                  90                  95

Asp Gly Asp Val Asn Gly His Lys Phe Ser Val Ser Gly Glu Gly Glu
            100                 105                 110

Gly Asp Ala Thr Tyr Gly Lys Leu Thr Leu Lys Phe Ile Cys Thr Thr
        115                 120                 125

Gly Lys Leu Pro Val Pro Trp Pro Thr Leu Val Thr Thr Phe Thr Tyr
    130                 135                 140

Gly Val Gln Cys Phe Ser Arg Tyr Pro Asp His Met Lys Gln His Asp
145                 150                 155                 160

Phe Phe Lys Ser Ala Met Pro Glu Gly Tyr Val Gln Glu Arg Thr Ile
                165                 170                 175

Ser Phe Lys Asp Asp Gly Asn Tyr Lys Thr Arg Ala Glu Val Lys Phe
            180                 185                 190

Glu Gly Asp Thr Leu Val Asn Arg Ile Glu Leu Lys Gly Ile Asp Phe
        195                 200                 205

Lys Glu Asp Gly Asn Ile Leu Gly His Lys Leu Glu Tyr Asn Tyr Asn
    210                 215                 220

Ser His Asn Val Tyr Ile Thr Ala Asp Lys Gln Lys Asn Gly Ile Lys
225                 230                 235                 240

Ala Asn Phe Lys Ile Arg His Asn Ile Glu Asp Gly Ser Val Gln Leu
                245                 250                 255

Ala Asp His Tyr Gln Gln Asn Thr Pro Ile Gly Asp Gly Pro Val Leu
            260                 265                 270

Leu Pro Asp Asn His Tyr Leu Ser Thr Gln Ser Ala Leu Ser Lys Asp
        275                 280                 285

Pro Asn Glu Lys Arg Asp His Met Val Leu Leu Glu Phe Val Thr Ala
    290                 295                 300

Ala Gly Ile Thr His Gly Met Asp Glu Leu Tyr Lys
305                 310                 315
```

<210> SEQ ID NO 54
<211> LENGTH: 297
<212> TYPE: PRT
<213> ORGANISM: Zea mays

<400> SEQUENCE: 54

```
Met Ile Ser Pro Thr Asn Leu Leu Pro Ala Arg Lys Ile Thr Pro Val
1               5                   10                  15

Ser Asn Gly Gly Ala Ala Thr Ala Ser Pro Ser Ser Pro Ser Val Ala
            20                  25                  30

Ala Arg Pro Arg Arg Leu Pro Ser Gly Leu Gln Ser Val Thr Gly Arg
        35                  40                  45
```

```
Gly Lys Val Ser Leu Ala Asp Pro Gly Ala Thr Met Gly Lys Gly Glu
    50                  55                  60

Glu Leu Phe Thr Gly Val Val Pro Ile Leu Val Glu Leu Asp Gly Asp
65                  70                  75                  80

Val Asn Gly His Lys Phe Ser Val Ser Gly Glu Gly Glu Gly Asp Ala
                85                  90                  95

Thr Tyr Gly Lys Leu Thr Leu Lys Phe Ile Cys Thr Thr Gly Lys Leu
            100                 105                 110

Pro Val Pro Trp Pro Thr Leu Val Thr Thr Phe Thr Tyr Gly Val Gln
        115                 120                 125

Cys Phe Ser Arg Tyr Pro Asp His Met Lys Gln His Asp Phe Phe Lys
    130                 135                 140

Ser Ala Met Pro Glu Gly Tyr Val Gln Glu Arg Thr Ile Ser Phe Lys
145                 150                 155                 160

Asp Asp Gly Asn Tyr Lys Thr Arg Ala Glu Val Lys Phe Glu Gly Asp
                165                 170                 175

Thr Leu Val Asn Arg Ile Glu Leu Lys Gly Ile Asp Phe Lys Glu Asp
            180                 185                 190

Gly Asn Ile Leu Gly His Lys Leu Glu Tyr Asn Tyr Asn Ser His Asn
        195                 200                 205

Val Tyr Ile Thr Ala Asp Lys Gln Lys Asn Gly Ile Lys Ala Asn Phe
    210                 215                 220

Lys Ile Arg His Asn Ile Glu Asp Gly Ser Val Gln Leu Ala Asp His
225                 230                 235                 240

Tyr Gln Gln Asn Thr Pro Ile Gly Asp Gly Pro Val Leu Leu Pro Asp
                245                 250                 255

Asn His Tyr Leu Ser Thr Gln Ser Ala Leu Ser Lys Asp Pro Asn Glu
            260                 265                 270

Lys Arg Asp His Met Val Leu Leu Glu Phe Val Thr Ala Ala Gly Ile
        275                 280                 285

Thr His Gly Met Asp Glu Leu Tyr Lys
    290                 295


<210> SEQ ID NO 55
<211> LENGTH: 302
<212> TYPE: PRT
<213> ORGANISM: Zea mays

<400> SEQUENCE: 55

Met Ile Ser Pro Thr Asn Leu Leu Pro Ala Arg Lys Ile Thr Pro Val
1               5                   10                  15

Ser Asn Gly Gly Ala Ala Thr Ala Ser Pro Ser Ser Pro Ser Val Ala
            20                  25                  30

Ala Arg Pro Arg Arg Leu Pro Ser Gly Leu Gln Ser Val Thr Gly Arg
        35                  40                  45

Gly Lys Val Ser Leu Ala Ala Ile Thr Leu Glu Asp Pro Gly Ala Thr
    50                  55                  60

Met Gly Lys Gly Glu Glu Leu Phe Thr Gly Val Val Pro Ile Leu Val
65                  70                  75                  80

Glu Leu Asp Gly Asp Val Asn Gly His Lys Phe Ser Val Ser Gly Glu
                85                  90                  95

Gly Glu Gly Asp Ala Thr Tyr Gly Lys Leu Thr Leu Lys Phe Ile Cys
            100                 105                 110

Thr Thr Gly Lys Leu Pro Val Pro Trp Pro Thr Leu Val Thr Thr Phe
```

```
        115                 120                 125

Thr Tyr Gly Val Gln Cys Phe Ser Arg Tyr Pro Asp His Met Lys Gln
    130                 135                 140

His Asp Phe Phe Lys Ser Ala Met Pro Glu Gly Tyr Val Gln Glu Arg
145                 150                 155                 160

Thr Ile Ser Phe Lys Asp Asp Gly Asn Tyr Lys Thr Arg Ala Glu Val
                165                 170                 175

Lys Phe Glu Gly Asp Thr Leu Val Asn Arg Ile Glu Leu Lys Gly Ile
            180                 185                 190

Asp Phe Lys Glu Asp Gly Asn Ile Leu Gly His Lys Leu Glu Tyr Asn
        195                 200                 205

Tyr Asn Ser His Asn Val Tyr Ile Thr Ala Asp Lys Gln Lys Asn Gly
    210                 215                 220

Ile Lys Ala Asn Phe Lys Ile Arg His Asn Ile Glu Asp Gly Ser Val
225                 230                 235                 240

Gln Leu Ala Asp His Tyr Gln Gln Asn Thr Pro Ile Gly Asp Gly Pro
                245                 250                 255

Val Leu Leu Pro Asp Asn His Tyr Leu Ser Thr Gln Ser Ala Leu Ser
            260                 265                 270

Lys Asp Pro Asn Glu Lys Arg Asp His Met Val Leu Leu Glu Phe Val
        275                 280                 285

Thr Ala Ala Gly Ile Thr His Gly Met Asp Glu Leu Tyr Lys
    290                 295                 300


<210> SEQ ID NO 56
<211> LENGTH: 806
<212> TYPE: PRT
<213> ORGANISM: Arabidopsis thaliana

<400> SEQUENCE: 56

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Glu Lys Met Ala Ala
65                  70                  75                  80

Val Ile Leu Glu Asp Gly Ala Glu Ser Tyr Thr Thr Lys Gly Gly Ile
                85                  90                  95

Val Val Thr Arg Arg Arg Arg Glu Ala Ser Tyr Ser Asp Ala Ile Ala
            100                 105                 110

Gly Tyr Val Asp Arg Leu Asp Glu Arg Arg Gly Ala Val Phe Ser Ser
        115                 120                 125

Asn Tyr Glu Tyr Pro Gly Arg Tyr Thr Arg Trp Asp Thr Ala Val Val
    130                 135                 140

Asp Pro Pro Leu Ala Ile Ser Ser Phe Gly Arg Ser Leu Trp Ile Glu
145                 150                 155                 160

Ala Tyr Asn Glu Arg Gly Glu Val Leu Leu Ala Leu Ile Ala Glu Asp
                165                 170                 175

Leu Lys Ser Val Ala Asp Ile Thr Leu Gly Ser Leu Ala Ala Arg Arg
            180                 185                 190
```

```
Leu Asp Leu Thr Ile Asn Glu Pro Asp Arg Val Phe Thr Glu Glu Glu
        195                 200                 205

Arg Ser Lys Met Pro Thr Val Phe Thr Val Leu Arg Ala Val Thr Asn
    210                 215                 220

Leu Phe His Ser Glu Glu Asp Ser Asn Leu Gly Leu Tyr Gly Ala Phe
225                 230                 235                 240

Gly Tyr Asp Leu Ala Phe Gln Phe Asp Ala Ile Glu Leu Lys Leu Ser
                245                 250                 255

Arg Pro Asp Asp Gln Arg Asp Met Val Leu Phe Leu Pro Asp Glu Ile
            260                 265                 270

Leu Val Val Asp His Tyr Ala Ala Lys Ala Trp Ile Asp Arg Tyr Asp
        275                 280                 285

Phe Ala Arg Glu Asn Leu Ser Thr Glu Gly Lys Ala Ala Asp Ile Ala
    290                 295                 300

Pro Glu Pro Phe Arg Ser Val Asp Ser Ile Pro Pro His Gly Asp His
305                 310                 315                 320

Arg Pro Gly Glu Tyr Ala Glu Leu Val Val Lys Ala Lys Glu Ser Phe
                325                 330                 335

Arg Arg Gly Asp Leu Phe Glu Val Val Pro Gly Gln Lys Phe Tyr Glu
            340                 345                 350

Arg Cys Glu Ser Arg Pro Ser Glu Ile Ser Asn Arg Leu Lys Ala Ile
        355                 360                 365

Asn Pro Ser Pro Tyr Ser Phe Phe Ile Asn Leu Gly Asn Gln Glu Tyr
    370                 375                 380

Leu Val Gly Ala Ser Pro Glu Met Phe Val Arg Val Ser Gly Arg Arg
385                 390                 395                 400

Ile Glu Thr Cys Pro Ile Ser Gly Thr Ile Lys Arg Gly Asp Asp Pro
                405                 410                 415

Ile Ala Asp Ser Glu Gln Ile Leu Lys Leu Leu Asn Ser Lys Lys Asp
            420                 425                 430

Glu Ser Glu Leu Thr Met Cys Ser Asp Val Asp Arg Asn Asp Lys Ser
        435                 440                 445

Arg Val Cys Val Pro Gly Ser Val Lys Val Ile Gly Arg Arg Gln Ile
    450                 455                 460

Glu Met Tyr Ser Arg Leu Ile His Thr Val Asp His Ile Glu Gly Arg
465                 470                 475                 480

Leu Arg Asp Asp Met Asp Ala Phe Asp Gly Phe Leu Ser His Ala Trp
                485                 490                 495

Ala Val Thr Val Thr Gly Ala Pro Lys Leu Trp Ala Met Arg Phe Ile
            500                 505                 510

Glu Ser His Glu Lys Ser Pro Arg Ala Trp Tyr Gly Gly Ala Ile Gly
        515                 520                 525

Met Val Gly Phe Asn Gly Asp Met Asn Thr Gly Leu Thr Leu Arg Thr
    530                 535                 540

Ile Arg Ile Lys Asp Gly Ile Ala Glu Val Arg Ala Gly Ala Thr Leu
545                 550                 555                 560

Leu Tyr Asp Ser Asn Pro Glu Glu Glu Glu Ala Glu Thr Glu Leu Lys
                565                 570                 575

Ala Ser Ala Met Ile Ala Ala Ile Arg Asp Ala Lys Ser Ala Asn Ser
            580                 585                 590

Ala Lys Ser Ala Arg Asp Val Ala Ala Val Gly Ala Gly Val Ser Ile
        595                 600                 605

Leu Leu Val Asp His Glu Asp Ser Phe Val His Thr Leu Ala Asn Tyr
```

610 615 620

Phe Arg Gln Thr Gly Ala Ser Val Thr Thr Val Arg Thr Pro Val Ala
625 630 635 640

Glu Glu Ile Phe Asp Arg Val Lys Pro Asp Leu Val Val Leu Ser Pro
645 650 655

Gly Pro Gly Thr Pro Lys Asp Phe Asp Cys Lys Ala Thr Ile Lys Lys
660 665 670

Ala Arg Ala Arg Asp Leu Pro Ile Phe Gly Val Cys Leu Gly Leu Gln
675 680 685

Ala Leu Ala Glu Ala Tyr Gly Gly Asp Leu Arg Gln Leu Ala Ile Pro
690 695 700

Met His Gly Lys Pro Ser Arg Ile Arg Val Leu Glu Pro Gly Ile Val
705 710 715 720

Phe Ser Gly Leu Gly Lys Glu Val Thr Val Gly Arg Tyr His Ser Ile
725 730 735

Phe Ala Asp Pro Ser Asn Leu Pro Arg Glu Phe Val Ile Thr Ala Glu
740 745 750

Ser Glu Asp Gly Thr Ile Met Gly Ile Glu His Ser Lys Glu Pro Val
755 760 765

Ala Ala Val Gln Phe His Pro Glu Ser Ile Met Thr Leu Gly Gly Asp
770 775 780

Ala Gly Met Arg Met Ile Glu Asn Val Val Ala His Leu Ala Lys Arg
785 790 795 800

Ala Lys Thr Lys Ala Ala
805

<210> SEQ ID NO 57
<211> LENGTH: 815
<212> TYPE: PRT
<213> ORGANISM: Arabidopsis thaliana

<400> SEQUENCE: 57

Met Ala Gln Val Ser Arg Ile Cys Asn Gly Val Gln Asn Pro Ser Leu
1 5 10 15

Ile Ser Asn Leu Ser Lys Ser Ser Gln Arg Lys Ser Pro Leu Ser Val
20 25 30

Ser Leu Lys Thr Gln Gln His Pro Arg Ala Tyr Pro Ile Ser Ser Ser
35 40 45

Trp Gly Leu Lys Lys Ser Gly Met Thr Leu Ile Gly Ser Glu Leu Arg
50 55 60

Pro Leu Lys Val Met Ser Ser Val Ser Thr Ala Glu Lys Ala Ser Glu
65 70 75 80

Ile Val Leu Gln Pro Ile Met Ala Ala Val Ile Leu Glu Asp Gly Ala
85 90 95

Glu Ser Tyr Thr Thr Lys Gly Gly Ile Val Val Thr Arg Arg Arg Arg
100 105 110

Glu Ala Ser Tyr Ser Asp Ala Ile Ala Gly Tyr Val Asp Arg Leu Asp
115 120 125

Glu Arg Arg Gly Ala Val Phe Ser Ser Asn Tyr Glu Tyr Pro Gly Arg
130 135 140

Tyr Thr Arg Trp Asp Thr Ala Val Val Asp Pro Pro Leu Ala Ile Ser
145 150 155 160

Ser Phe Gly Arg Ser Leu Trp Ile Glu Ala Tyr Asn Glu Arg Gly Glu
165 170 175

```
Val Leu Leu Ala Leu Ile Ala Glu Asp Leu Lys Ser Val Ala Asp Ile
            180                 185                 190

Thr Leu Gly Ser Leu Ala Ala Arg Arg Leu Asp Leu Thr Ile Asn Glu
        195                 200                 205

Pro Asp Arg Val Phe Thr Glu Glu Glu Arg Ser Lys Met Pro Thr Val
    210                 215                 220

Phe Thr Val Leu Arg Ala Val Thr Asn Leu Phe His Ser Glu Glu Asp
225                 230                 235                 240

Ser Asn Leu Gly Leu Tyr Gly Ala Phe Gly Tyr Asp Leu Ala Phe Gln
                245                 250                 255

Phe Asp Ala Ile Glu Leu Lys Leu Ser Arg Pro Asp Asp Gln Arg Asp
            260                 265                 270

Met Val Leu Phe Leu Pro Asp Glu Ile Leu Val Val Asp His Tyr Ala
        275                 280                 285

Ala Lys Ala Trp Ile Asp Arg Tyr Asp Phe Ala Arg Glu Asn Leu Ser
    290                 295                 300

Thr Glu Gly Lys Ala Ala Asp Ile Ala Pro Glu Pro Phe Arg Ser Val
305                 310                 315                 320

Asp Ser Ile Pro Pro His Gly Asp His Arg Pro Gly Glu Tyr Ala Glu
                325                 330                 335

Leu Val Val Lys Ala Lys Glu Ser Phe Arg Arg Gly Asp Leu Phe Glu
            340                 345                 350

Val Val Pro Gly Gln Lys Phe Tyr Glu Arg Cys Glu Ser Arg Pro Ser
        355                 360                 365

Glu Ile Ser Asn Arg Leu Lys Ala Ile Asn Pro Ser Pro Tyr Ser Phe
    370                 375                 380

Phe Ile Asn Leu Gly Asn Gln Glu Tyr Leu Val Gly Ala Ser Pro Glu
385                 390                 395                 400

Met Phe Val Arg Val Ser Gly Arg Arg Ile Glu Thr Cys Pro Ile Ser
                405                 410                 415

Gly Thr Ile Lys Arg Gly Asp Asp Pro Ile Ala Asp Ser Glu Gln Ile
            420                 425                 430

Leu Lys Leu Leu Asn Ser Lys Lys Asp Glu Ser Glu Leu Thr Met Cys
        435                 440                 445

Ser Asp Val Asp Arg Asn Asp Lys Ser Arg Val Cys Val Pro Gly Ser
    450                 455                 460

Val Lys Val Ile Gly Arg Arg Gln Ile Glu Met Tyr Ser Arg Leu Ile
465                 470                 475                 480

His Thr Val Asp His Ile Glu Gly Arg Leu Arg Asp Asp Met Asp Ala
                485                 490                 495

Phe Asp Gly Phe Leu Ser His Ala Trp Ala Val Thr Val Thr Gly Ala
            500                 505                 510

Pro Lys Leu Trp Ala Met Arg Phe Ile Glu Ser His Glu Lys Ser Pro
        515                 520                 525

Arg Ala Trp Tyr Gly Gly Ala Ile Gly Met Val Gly Phe Asn Gly Asp
    530                 535                 540

Met Asn Thr Gly Leu Thr Leu Arg Thr Ile Arg Ile Lys Asp Gly Ile
545                 550                 555                 560

Ala Glu Val Arg Ala Gly Ala Thr Leu Leu Tyr Asp Ser Asn Pro Glu
                565                 570                 575

Glu Glu Glu Ala Glu Thr Glu Leu Lys Ala Ser Ala Met Ile Ala Ala
            580                 585                 590

Ile Arg Asp Ala Lys Ser Ala Asn Ser Ala Lys Ser Ala Arg Asp Val
```

```
        595                 600                 605

Ala Ala Val Gly Ala Gly Val Ser Ile Leu Leu Val Asp His Glu Asp
    610                 615                 620

Ser Phe Val His Thr Leu Ala Asn Tyr Phe Arg Gln Thr Gly Ala Ser
625                 630                 635                 640

Val Thr Thr Val Arg Thr Pro Val Ala Glu Glu Ile Phe Asp Arg Val
                645                 650                 655

Lys Pro Asp Leu Val Val Leu Ser Pro Gly Pro Gly Thr Pro Lys Asp
            660                 665                 670

Phe Asp Cys Lys Ala Thr Ile Lys Lys Ala Arg Ala Arg Asp Leu Pro
        675                 680                 685

Ile Phe Gly Val Cys Leu Gly Leu Gln Ala Leu Ala Glu Ala Tyr Gly
    690                 695                 700

Gly Asp Leu Arg Gln Leu Ala Ile Pro Met His Gly Lys Pro Ser Arg
705                 710                 715                 720

Ile Arg Val Leu Glu Pro Gly Ile Val Phe Ser Gly Leu Gly Lys Glu
                725                 730                 735

Val Thr Val Gly Arg Tyr His Ser Ile Phe Ala Asp Pro Ser Asn Leu
            740                 745                 750

Pro Arg Glu Phe Val Ile Thr Ala Glu Ser Glu Asp Gly Thr Ile Met
        755                 760                 765

Gly Ile Glu His Ser Lys Glu Pro Val Ala Ala Val Gln Phe His Pro
    770                 775                 780

Glu Ser Ile Met Thr Leu Gly Gly Asp Ala Gly Met Arg Met Ile Glu
785                 790                 795                 800

Asn Val Val Ala His Leu Ala Lys Arg Ala Lys Thr Lys Ala Ala
                805                 810                 815


<210> SEQ ID NO 58
<211> LENGTH: 776
<212> TYPE: PRT
<213> ORGANISM: Zea mays

<400> SEQUENCE: 58

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Arg Ser Gly Thr Ser Gly Val Lys Cys Ser Met
        35                  40                  45

Ala Ala Val Ile Leu Glu Asp Gly Ala Glu Ser Tyr Thr Thr Lys Gly
    50                  55                  60

Gly Ile Val Val Thr Arg Arg Arg Arg Glu Ala Ser Tyr Ser Asp Ala
65                  70                  75                  80

Ile Ala Gly Tyr Val Asp Arg Leu Asp Glu Arg Arg Gly Ala Val Phe
                85                  90                  95

Ser Ser Asn Tyr Glu Tyr Pro Gly Arg Tyr Thr Arg Trp Asp Thr Ala
            100                 105                 110

Val Val Asp Pro Pro Leu Ala Ile Ser Ser Phe Gly Arg Ser Leu Trp
        115                 120                 125

Ile Glu Ala Tyr Asn Glu Arg Gly Glu Val Leu Leu Ala Leu Ile Ala
    130                 135                 140

Glu Asp Leu Lys Ser Val Ala Asp Ile Thr Leu Gly Ser Leu Ala Ala
145                 150                 155                 160
```

```
Arg Arg Leu Asp Leu Thr Ile Asn Glu Pro Asp Arg Val Phe Thr Glu
                165                 170                 175

Glu Glu Arg Ser Lys Met Pro Thr Val Phe Thr Val Leu Arg Ala Val
            180                 185                 190

Thr Asn Leu Phe His Ser Glu Glu Asp Ser Asn Leu Gly Leu Tyr Gly
        195                 200                 205

Ala Phe Gly Tyr Asp Leu Ala Phe Gln Phe Asp Ala Ile Glu Leu Lys
    210                 215                 220

Leu Ser Arg Pro Asp Asp Gln Arg Asp Met Val Leu Phe Leu Pro Asp
225                 230                 235                 240

Glu Ile Leu Val Val Asp His Tyr Ala Ala Lys Ala Trp Ile Asp Arg
                245                 250                 255

Tyr Asp Phe Ala Arg Glu Asn Leu Ser Thr Glu Gly Lys Ala Ala Asp
            260                 265                 270

Ile Ala Pro Glu Pro Phe Arg Ser Val Asp Ser Ile Pro Pro His Gly
        275                 280                 285

Asp His Arg Pro Gly Glu Tyr Ala Glu Leu Val Val Lys Ala Lys Glu
    290                 295                 300

Ser Phe Arg Arg Gly Asp Leu Phe Glu Val Val Pro Gly Gln Lys Phe
305                 310                 315                 320

Tyr Glu Arg Cys Glu Ser Arg Pro Ser Glu Ile Ser Asn Arg Leu Lys
                325                 330                 335

Ala Ile Asn Pro Ser Pro Tyr Ser Phe Phe Ile Asn Leu Gly Asn Gln
            340                 345                 350

Glu Tyr Leu Val Gly Ala Ser Pro Glu Met Phe Val Arg Val Ser Gly
        355                 360                 365

Arg Arg Ile Glu Thr Cys Pro Ile Ser Gly Thr Ile Lys Arg Gly Asp
    370                 375                 380

Asp Pro Ile Ala Asp Ser Glu Gln Ile Leu Lys Leu Leu Asn Ser Lys
385                 390                 395                 400

Lys Asp Glu Ser Glu Leu Thr Met Cys Ser Asp Val Asp Arg Asn Asp
                405                 410                 415

Lys Ser Arg Val Cys Val Pro Gly Ser Val Lys Val Ile Gly Arg Arg
            420                 425                 430

Gln Ile Glu Met Tyr Ser Arg Leu Ile His Thr Val Asp His Ile Glu
        435                 440                 445

Gly Arg Leu Arg Asp Asp Met Asp Ala Phe Asp Gly Phe Leu Ser His
    450                 455                 460

Ala Trp Ala Val Thr Val Thr Gly Ala Pro Lys Leu Trp Ala Met Arg
465                 470                 475                 480

Phe Ile Glu Ser His Glu Lys Ser Pro Arg Ala Trp Tyr Gly Gly Ala
                485                 490                 495

Ile Gly Met Val Gly Phe Asn Gly Asp Met Asn Thr Gly Leu Thr Leu
            500                 505                 510

Arg Thr Ile Arg Ile Lys Asp Gly Ile Ala Glu Val Arg Ala Gly Ala
        515                 520                 525

Thr Leu Leu Tyr Asp Ser Asn Pro Glu Glu Glu Glu Ala Glu Thr Glu
    530                 535                 540

Leu Lys Ala Ser Ala Met Ile Ala Ala Ile Arg Asp Ala Lys Ser Ala
545                 550                 555                 560

Asn Ser Ala Lys Ser Ala Arg Asp Val Ala Ala Val Gly Ala Gly Val
                565                 570                 575

Ser Ile Leu Leu Val Asp His Glu Asp Ser Phe Val His Thr Leu Ala
```

```
            580                 585                 590

Asn Tyr Phe Arg Gln Thr Gly Ala Ser Val Thr Thr Val Arg Thr Pro
        595                 600                 605

Val Ala Glu Glu Ile Phe Asp Arg Val Lys Pro Asp Leu Val Val Leu
    610                 615                 620

Ser Pro Gly Pro Gly Thr Pro Lys Asp Phe Asp Cys Lys Ala Thr Ile
625                 630                 635                 640

Lys Lys Ala Arg Ala Arg Asp Leu Pro Ile Phe Gly Val Cys Leu Gly
                645                 650                 655

Leu Gln Ala Leu Ala Glu Ala Tyr Gly Gly Asp Leu Arg Gln Leu Ala
            660                 665                 670

Ile Pro Met His Gly Lys Pro Ser Arg Ile Arg Val Leu Glu Pro Gly
        675                 680                 685

Ile Val Phe Ser Gly Leu Gly Lys Glu Val Thr Val Gly Arg Tyr His
    690                 695                 700

Ser Ile Phe Ala Asp Pro Ser Asn Leu Pro Arg Glu Phe Val Ile Thr
705                 710                 715                 720

Ala Glu Ser Glu Asp Gly Thr Ile Met Gly Ile Glu His Ser Lys Glu
                725                 730                 735

Pro Val Ala Ala Val Gln Phe His Pro Glu Ser Ile Met Thr Leu Gly
            740                 745                 750

Gly Asp Ala Gly Met Arg Met Ile Glu Asn Val Val Ala His Leu Ala
        755                 760                 765

Lys Arg Ala Lys Thr Lys Ala Ala
    770                 775


<210> SEQ ID NO 59
<211> LENGTH: 794
<212> TYPE: PRT
<213> ORGANISM: Zea mays

<400> SEQUENCE: 59

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Arg Ser Gly Thr Ser Gly Val Lys Cys Ser Ala
        35                  40                  45

Ala Val Thr Pro Gln Ala Ser Pro Val Ile Ser Arg Ser Ala Ala Ala
    50                  55                  60

Ala Met Ala Ala Val Ile Leu Glu Asp Gly Ala Glu Ser Tyr Thr Thr
65                  70                  75                  80

Lys Gly Gly Ile Val Val Thr Arg Arg Arg Arg Glu Ala Ser Tyr Ser
                85                  90                  95

Asp Ala Ile Ala Gly Tyr Val Asp Arg Leu Asp Glu Arg Arg Gly Ala
            100                 105                 110

Val Phe Ser Ser Asn Tyr Glu Tyr Pro Gly Arg Tyr Thr Arg Trp Asp
        115                 120                 125

Thr Ala Val Val Asp Pro Pro Leu Ala Ile Ser Ser Phe Gly Arg Ser
    130                 135                 140

Leu Trp Ile Glu Ala Tyr Asn Glu Arg Gly Glu Val Leu Leu Ala Leu
145                 150                 155                 160

Ile Ala Glu Asp Leu Lys Ser Val Ala Asp Ile Thr Leu Gly Ser Leu
                165                 170                 175
```

```
Ala Ala Arg Arg Leu Asp Leu Thr Ile Asn Glu Pro Asp Arg Val Phe
            180                 185                 190

Thr Glu Glu Glu Arg Ser Lys Met Pro Thr Val Phe Thr Val Leu Arg
        195                 200                 205

Ala Val Thr Asn Leu Phe His Ser Glu Glu Asp Ser Asn Leu Gly Leu
    210                 215                 220

Tyr Gly Ala Phe Gly Tyr Asp Leu Ala Phe Gln Phe Asp Ala Ile Glu
225                 230                 235                 240

Leu Lys Leu Ser Arg Pro Asp Asp Gln Arg Asp Met Val Leu Phe Leu
                245                 250                 255

Pro Asp Glu Ile Leu Val Val Asp His Tyr Ala Ala Lys Ala Trp Ile
            260                 265                 270

Asp Arg Tyr Asp Phe Ala Arg Glu Asn Leu Ser Thr Glu Gly Lys Ala
        275                 280                 285

Ala Asp Ile Ala Pro Glu Pro Phe Arg Ser Val Asp Ser Ile Pro Pro
    290                 295                 300

His Gly Asp His Arg Pro Gly Glu Tyr Ala Glu Leu Val Val Lys Ala
305                 310                 315                 320

Lys Glu Ser Phe Arg Arg Gly Asp Leu Phe Glu Val Val Pro Gly Gln
                325                 330                 335

Lys Phe Tyr Glu Arg Cys Glu Ser Arg Pro Ser Glu Ile Ser Asn Arg
            340                 345                 350

Leu Lys Ala Ile Asn Pro Ser Pro Tyr Ser Phe Phe Ile Asn Leu Gly
        355                 360                 365

Asn Gln Glu Tyr Leu Val Gly Ala Ser Pro Glu Met Phe Val Arg Val
    370                 375                 380

Ser Gly Arg Arg Ile Glu Thr Cys Pro Ile Ser Gly Thr Ile Lys Arg
385                 390                 395                 400

Gly Asp Asp Pro Ile Ala Asp Ser Glu Gln Ile Leu Lys Leu Leu Asn
                405                 410                 415

Ser Lys Lys Asp Glu Ser Glu Leu Thr Met Cys Ser Asp Val Asp Arg
            420                 425                 430

Asn Asp Lys Ser Arg Val Cys Val Pro Gly Ser Val Lys Val Ile Gly
        435                 440                 445

Arg Arg Gln Ile Glu Met Tyr Ser Arg Leu Ile His Thr Val Asp His
    450                 455                 460

Ile Glu Gly Arg Leu Arg Asp Asp Met Asp Ala Phe Asp Gly Phe Leu
465                 470                 475                 480

Ser His Ala Trp Ala Val Thr Val Thr Gly Ala Pro Lys Leu Trp Ala
                485                 490                 495

Met Arg Phe Ile Glu Ser His Glu Lys Ser Pro Arg Ala Trp Tyr Gly
            500                 505                 510

Gly Ala Ile Gly Met Val Gly Phe Asn Gly Asp Met Asn Thr Gly Leu
        515                 520                 525

Thr Leu Arg Thr Ile Arg Ile Lys Asp Gly Ile Ala Glu Val Arg Ala
    530                 535                 540

Gly Ala Thr Leu Leu Tyr Asp Ser Asn Pro Glu Glu Glu Glu Ala Glu
545                 550                 555                 560

Thr Glu Leu Lys Ala Ser Ala Met Ile Ala Ala Ile Arg Asp Ala Lys
                565                 570                 575

Ser Ala Asn Ser Ala Lys Ser Ala Arg Asp Val Ala Ala Val Gly Ala
            580                 585                 590

Gly Val Ser Ile Leu Leu Val Asp His Glu Asp Ser Phe Val His Thr
```

```
        595                 600                 605

Leu Ala Asn Tyr Phe Arg Gln Thr Gly Ala Ser Val Thr Thr Val Arg
    610                 615                 620

Thr Pro Val Ala Glu Glu Ile Phe Asp Arg Val Lys Pro Asp Leu Val
625                 630                 635                 640

Val Leu Ser Pro Gly Pro Gly Thr Pro Lys Asp Phe Asp Cys Lys Ala
                645                 650                 655

Thr Ile Lys Lys Ala Arg Ala Arg Asp Leu Pro Ile Phe Gly Val Cys
            660                 665                 670

Leu Gly Leu Gln Ala Leu Ala Glu Ala Tyr Gly Gly Asp Leu Arg Gln
        675                 680                 685

Leu Ala Ile Pro Met His Gly Lys Pro Ser Arg Ile Arg Val Leu Glu
    690                 695                 700

Pro Gly Ile Val Phe Ser Gly Leu Gly Lys Glu Val Thr Val Gly Arg
705                 710                 715                 720

Tyr His Ser Ile Phe Ala Asp Pro Ser Asn Leu Pro Arg Glu Phe Val
                725                 730                 735

Ile Thr Ala Glu Ser Glu Asp Gly Thr Ile Met Gly Ile Glu His Ser
            740                 745                 750

Lys Glu Pro Val Ala Ala Val Gln Phe His Pro Glu Ser Ile Met Thr
        755                 760                 765

Leu Gly Gly Asp Ala Gly Met Arg Met Ile Glu Asn Val Val Ala His
    770                 775                 780

Leu Ala Lys Arg Ala Lys Thr Lys Ala Ala
785                 790


<210> SEQ ID NO 60
<211> LENGTH: 793
<212> TYPE: PRT
<213> ORGANISM: Zea mays

<400> SEQUENCE: 60

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Arg Ser Gly Thr Ser Gly Val Lys Cys Ser Ala
        35                  40                  45

Ala Val Thr Pro Gln Ala Ser Pro Val Ile Ser Arg Ser Ala Ala Ala
    50                  55                  60

Ala Val Thr Ile Ile Gln Asp Asp Gly Ala Glu Thr Tyr Glu Thr Lys
65                  70                  75                  80

Gly Gly Ile Gln Val Ser Arg Lys Arg Arg Pro Thr Asp Tyr Ala Asn
                85                  90                  95

Ala Ile Asp Asn Tyr Ile Glu Lys Leu Asp Ser His Arg Gly Ala Val
            100                 105                 110

Phe Ser Ser Asn Tyr Glu Tyr Pro Gly Arg Tyr Thr Arg Trp Asp Thr
        115                 120                 125

Ala Ile Val Asp Pro Pro Leu Gly Ile Ser Cys Phe Gly Arg Lys Met
    130                 135                 140

Trp Ile Glu Ala Tyr Asn Gly Arg Gly Glu Val Leu Leu Asp Phe Ile
145                 150                 155                 160

Thr Glu Lys Leu Lys Ala Thr Pro Asp Leu Thr Leu Gly Ala Ser Ser
                165                 170                 175
```

```
Thr Arg Arg Leu Asp Leu Thr Val Asn Glu Pro Asp Arg Val Phe Thr
            180                 185                 190

Glu Glu Glu Arg Ser Lys Ile Pro Thr Val Phe Thr Ala Leu Arg Ala
        195                 200                 205

Ile Val Asp Leu Phe Tyr Ser Ser Ala Asp Ser Ala Ile Gly Leu Phe
    210                 215                 220

Gly Ala Phe Gly Tyr Asp Leu Ala Phe Gln Phe Asp Ala Ile Lys Leu
225                 230                 235                 240

Ser Leu Ala Arg Pro Glu Asp Gln Arg Asp Met Val Leu Phe Leu Pro
                245                 250                 255

Asp Glu Ile Leu Val Val Asp His Tyr Ser Ala Lys Ala Trp Ile Asp
            260                 265                 270

Arg Tyr Asp Phe Glu Lys Asp Gly Met Thr Thr Asp Gly Lys Ser Ser
        275                 280                 285

Asp Ile Thr Pro Asp Pro Phe Lys Thr Thr Asp Thr Ile Pro Pro Lys
    290                 295                 300

Gly Asp His Arg Pro Gly Glu Tyr Ser Glu Leu Val Val Lys Ala Lys
305                 310                 315                 320

Glu Ser Phe Arg Arg Gly Asp Leu Phe Glu Val Val Pro Gly Gln Lys
                325                 330                 335

Phe Met Glu Arg Cys Glu Ser Asn Pro Ser Ala Ile Ser Arg Arg Leu
            340                 345                 350

Lys Ala Ile Asn Pro Ser Pro Tyr Ser Phe Phe Ile Asn Leu Gly Asp
        355                 360                 365

Gln Glu Tyr Leu Val Gly Ala Ser Pro Glu Met Phe Val Arg Val Ser
    370                 375                 380

Gly Arg Arg Ile Glu Thr Cys Pro Ile Ser Gly Thr Ile Lys Arg Gly
385                 390                 395                 400

Asp Asp Pro Ile Ala Asp Ser Glu Gln Ile Leu Lys Leu Leu Asn Ser
                405                 410                 415

Lys Lys Asp Glu Ser Glu Leu Thr Met Cys Ser Asp Val Asp Arg Asn
            420                 425                 430

Asp Lys Ser Arg Val Cys Glu Pro Gly Ser Val Lys Val Ile Gly Arg
        435                 440                 445

Arg Gln Ile Glu Met Tyr Ser Arg Leu Ile His Thr Val Asp His Ile
    450                 455                 460

Glu Gly Arg Leu Arg Asp Asp Met Asp Ala Phe Asp Gly Phe Leu Ser
465                 470                 475                 480

His Ala Trp Ala Val Thr Val Thr Gly Ala Pro Lys Leu Trp Ala Met
                485                 490                 495

Arg Phe Ile Glu Gly His Glu Lys Ser Pro Arg Ala Trp Tyr Gly Gly
            500                 505                 510

Ala Ile Gly Met Val Gly Phe Asn Gly Asp Met Asn Thr Gly Leu Thr
        515                 520                 525

Leu Arg Thr Ile Arg Ile Lys Asp Gly Ile Ala Glu Val Arg Ala Gly
    530                 535                 540

Ala Thr Leu Leu Asn Asp Ser Asn Pro Gln Glu Glu Glu Ala Glu Thr
545                 550                 555                 560

Glu Leu Lys Ala Ser Ala Met Ile Ser Ala Ile Arg Asp Ala Lys Gly
                565                 570                 575

Thr Asn Ser Ala Ala Thr Lys Arg Asp Ala Ala Lys Val Gly Thr Gly
            580                 585                 590

Val Lys Ile Leu Leu Val Asp His Glu Asp Ser Phe Val His Thr Leu
```

```
        595                 600                 605

Ala Asn Tyr Phe Arg Gln Thr Gly Ala Thr Val Ser Thr Val Arg Ser
    610                 615                 620

Pro Val Ala Ala Asp Val Phe Asp Arg Phe Gln Pro Asp Leu Val Val
625                 630                 635                 640

Leu Ser Pro Gly Pro Gly Ser Pro Thr Asp Phe Asp Cys Lys Ala Thr
                645                 650                 655

Ile Lys Ala Ala Arg Ala Arg Asp Leu Pro Ile Phe Gly Val Cys Leu
            660                 665                 670

Gly Leu Gln Ala Leu Ala Glu Ala Tyr Gly Gly Glu Leu Arg Gln Leu
        675                 680                 685

Ala Val Pro Met His Gly Lys Pro Ser Arg Ile Arg Val Leu Glu Pro
    690                 695                 700

Gly Leu Val Phe Ser Gly Leu Gly Lys Glu Val Thr Val Gly Arg Tyr
705                 710                 715                 720

His Ser Ile Phe Ala Asp Pro Ala Thr Leu Pro Arg Asp Phe Ile Ile
                725                 730                 735

Thr Ala Glu Ser Glu Asp Gly Thr Ile Met Gly Ile Glu His Ala Lys
            740                 745                 750

Glu Pro Val Ala Ala Val Gln Phe His Pro Glu Ser Ile Met Thr Leu
        755                 760                 765

Gly Gln Asp Ala Gly Met Arg Met Ile Glu Asn Val Val Val His Leu
    770                 775                 780

Thr Arg Lys Ala Lys Thr Lys Ala Ala
785                 790


<210> SEQ ID NO 61
<211> LENGTH: 31
<212> TYPE: DNA
<213> ORGANISM: Artificial Sequence
<220> FEATURE:
<223> OTHER INFORMATION: primer

<400> SEQUENCE: 61

tattggatcc agaacaatgg cttcctctat g                                    31


<210> SEQ ID NO 62
<211> LENGTH: 27
<212> TYPE: DNA
<213> ORGANISM: Artificial Sequence
<220> FEATURE:
<223> OTHER INFORMATION: primer

<400> SEQUENCE: 62

tattggatcc atggcctgca tgcagtt                                         27


<210> SEQ ID NO 63
<211> LENGTH: 27
<212> TYPE: DNA
<213> ORGANISM: Artificial Sequence
<220> FEATURE:
<223> OTHER INFORMATION: primer

<400> SEQUENCE: 63

tattggatcc gcggccttgg tcttcgc                                         27


<210> SEQ ID NO 64
<211> LENGTH: 38
<212> TYPE: DNA
<213> ORGANISM: Artificial Sequence
```

<220> FEATURE:
<223> OTHER INFORMATION: primer

<400> SEQUENCE: 64
tattggatcc agaacaatgg taacgatcat tcaggatg 38

<210> SEQ ID NO 65
<211> LENGTH: 36
<212> TYPE: DNA
<213> ORGANISM: Artificial Sequence
<220> FEATURE:
<223> OTHER INFORMATION: primer

<400> SEQUENCE: 65
tattggatcc agaacaatgg aatccctagc cgccac 36

<210> SEQ ID NO 66
<211> LENGTH: 33
<212> TYPE: DNA
<213> ORGANISM: Artificial Sequence
<220> FEATURE:
<223> OTHER INFORMATION: primer

<400> SEQUENCE: 66
tattggatcc tctttgtcta caaaagctga ctc 33

<210> SEQ ID NO 67
<211> LENGTH: 37
<212> TYPE: DNA
<213> ORGANISM: Artificial Sequence
<220> FEATURE:
<223> OTHER INFORMATION: primer

<400> SEQUENCE: 67
tattggatcc agaacaatgg ctgccgtgac gccgcag 37

<210> SEQ ID NO 68
<211> LENGTH: 30
<212> TYPE: DNA
<213> ORGANISM: Artificial Sequence
<220> FEATURE:
<223> OTHER INFORMATION: primer

<400> SEQUENCE: 68
tattggatcc agaaccatgg cggctctcac 30

<210> SEQ ID NO 69
<211> LENGTH: 28
<212> TYPE: DNA
<213> ORGANISM: Artificial Sequence
<220> FEATURE:
<223> OTHER INFORMATION: primer

<400> SEQUENCE: 69
tattggatcc gcaccgtgaa gcatgcac 28

<210> SEQ ID NO 70
<211> LENGTH: 34
<212> TYPE: DNA
<213> ORGANISM: Artificial Sequence
<220> FEATURE:
<223> OTHER INFORMATION: primer

<400> SEQUENCE: 70
tattggatcc agaaccatga gtgcagcggc aacg 34

<210> SEQ ID NO 71
<211> LENGTH: 29
<212> TYPE: DNA
<213> ORGANISM: Artificial Sequence
<220> FEATURE:
<223> OTHER INFORMATION: primer

<400> SEQUENCE: 71
tattggattc cgcggaactg gcggcggac 29

<210> SEQ ID NO 72
<211> LENGTH: 38
<212> TYPE: DNA
<213> ORGANISM: Artificial Sequence
<220> FEATURE:
<223> OTHER INFORMATION: primer

<400> SEQUENCE: 72
tttctagagg atccagaacc atgagtgcag cggcaacg 38

<210> SEQ ID NO 73
<211> LENGTH: 27
<212> TYPE: DNA
<213> ORGANISM: Artificial Sequence
<220> FEATURE:
<223> OTHER INFORMATION: primer

<400> SEQUENCE: 73
ttaacgtacg tctccgctcc gtcatcc 27

<210> SEQ ID NO 74
<211> LENGTH: 22
<212> TYPE: DNA
<213> ORGANISM: Artificial Sequence
<220> FEATURE:
<223> OTHER INFORMATION: primer

<400> SEQUENCE: 74
ctagtctaga atgatttcgc cg 22

<210> SEQ ID NO 75
<211> LENGTH: 24
<212> TYPE: DNA
<213> ORGANISM: Artificial Sequence
<220> FEATURE:
<223> OTHER INFORMATION: primer

<400> SEQUENCE: 75
cgtctcgtac gtctccgctc cgtc 24

<210> SEQ ID NO 76
<211> LENGTH: 27
<212> TYPE: DNA
<213> ORGANISM: Artificial Sequence
<220> FEATURE:
<223> OTHER INFORMATION: primer

<400> SEQUENCE: 76
tgctctagaa tggcgcaagt tagcaga 27

<210> SEQ ID NO 77
<211> LENGTH: 32
<212> TYPE: DNA
<213> ORGANISM: Artificial Sequence
<220> FEATURE:
<223> OTHER INFORMATION: primer

<400> SEQUENCE: 77
tcttctagaa ttaccgctgc catgcacgcc gt 32

<210> SEQ ID NO 78
<211> LENGTH: 35
<212> TYPE: DNA
<213> ORGANISM: Artificial Sequence
<220> FEATURE:
<223> OTHER INFORMATION: primer

<400> SEQUENCE: 78
tcttctagaa ttaccgctgc cattttctcc gccgt 35

<210> SEQ ID NO 79
<211> LENGTH: 38
<212> TYPE: DNA
<213> ORGANISM: Artificial Sequence
<220> FEATURE:
<223> OTHER INFORMATION: primer

<400> SEQUENCE: 79
tcttctagaa ttaccgctgc cataatgggt tgaagtac 38

<210> SEQ ID NO 80
<211> LENGTH: 27
<212> TYPE: DNA
<213> ORGANISM: Artificial Sequence
<220> FEATURE:
<223> OTHER INFORMATION: primer

<400> SEQUENCE: 80
tgctctagaa tggaatccct agccgcc 27

<210> SEQ ID NO 81
<211> LENGTH: 35
<212> TYPE: DNA
<213> ORGANISM: Artificial Sequence
<220> FEATURE:
<223> OTHER INFORMATION: primer

<400> SEQUENCE: 81
tcttctagaa ttaccgctgc catagagcat ttcac 35

<210> SEQ ID NO 82
<211> LENGTH: 21
<212> TYPE: DNA
<213> ORGANISM: Artificial Sequence
<220> FEATURE:
<223> OTHER INFORMATION: primer

<400> SEQUENCE: 82
tgctctagaa tggccaccgc c 21

<210> SEQ ID NO 83
<211> LENGTH: 38
<212> TYPE: DNA
<213> ORGANISM: Artificial Sequence
<220> FEATURE:
<223> OTHER INFORMATION: primer

<400> SEQUENCE: 83
tcttctagaa ttaccgctgc catcgccgcc gcagcgct 38

<210> SEQ ID NO 84

<211> LENGTH: 66
<212> TYPE: DNA
<213> ORGANISM: Artificial Sequence
<220> FEATURE:
<223> OTHER INFORMATION: primer

<400> SEQUENCE: 84
tattggatcc agaaccatgg taacgatcat tcaggatgac ggagcggaga cgtacgagac 60
gaaagg 66

<210> SEQ ID NO 85
<211> LENGTH: 41
<212> TYPE: DNA
<213> ORGANISM: Artificial Sequence
<220> FEATURE:
<223> OTHER INFORMATION: primer

<400> SEQUENCE: 85
tttccatggc gcaagttagc agaatctgca atggtgtgca g 41

<210> SEQ ID NO 86
<211> LENGTH: 40
<212> TYPE: DNA
<213> ORGANISM: Artificial Sequence
<220> FEATURE:
<223> OTHER INFORMATION: primer

<400> SEQUENCE: 86
aacccatctc ttatctccaa tctctcgaaa tccagtcaac 40

<210> SEQ ID NO 87
<211> LENGTH: 39
<212> TYPE: DNA
<213> ORGANISM: Artificial Sequence
<220> FEATURE:
<223> OTHER INFORMATION: primer

<400> SEQUENCE: 87
gcaaatctcc cttatcggtt tctctgaaga cgcagcagc 39

<210> SEQ ID NO 88
<211> LENGTH: 41
<212> TYPE: DNA
<213> ORGANISM: Artificial Sequence
<220> FEATURE:
<223> OTHER INFORMATION: primer

<400> SEQUENCE: 88
atccacgagc ttatccgatt tcgtcgtcgt ggggattgaa g 41

<210> SEQ ID NO 89
<211> LENGTH: 40
<212> TYPE: DNA
<213> ORGANISM: Artificial Sequence
<220> FEATURE:
<223> OTHER INFORMATION: primer

<400> SEQUENCE: 89
aagagtggga tgacgttaat tggctctgag cttcgtcctc 40

<210> SEQ ID NO 90
<211> LENGTH: 40
<212> TYPE: DNA
<213> ORGANISM: Artificial Sequence
<220> FEATURE:
<223> OTHER INFORMATION: primer

<400> SEQUENCE: 90
ttaaggtcat gtcttctgtt tccacggcgt gcatggtaac 40

<210> SEQ ID NO 91
<211> LENGTH: 36
<212> TYPE: DNA
<213> ORGANISM: Artificial Sequence
<220> FEATURE:
<223> OTHER INFORMATION: primer

<400> SEQUENCE: 91
gatcattcag gatgacggag cggagacgta cgagac 36

<210> SEQ ID NO 92
<211> LENGTH: 19
<212> TYPE: DNA
<213> ORGANISM: Artificial Sequence
<220> FEATURE:
<223> OTHER INFORMATION: primer

<400> SEQUENCE: 92
gtctcgtacg tctccgctc 19

<210> SEQ ID NO 93
<211> LENGTH: 40
<212> TYPE: DNA
<213> ORGANISM: Artificial Sequence
<220> FEATURE:
<223> OTHER INFORMATION: primer

<400> SEQUENCE: 93
cgtcatcctg aatgatcgtt accatgcacg ccgtggaaac 40

<210> SEQ ID NO 94
<211> LENGTH: 43
<212> TYPE: DNA
<213> ORGANISM: Artificial Sequence
<220> FEATURE:
<223> OTHER INFORMATION: primer

<400> SEQUENCE: 94
agaagacatg accttaagag gacgaagctc agagccaatt aac 43

<210> SEQ ID NO 95
<211> LENGTH: 39
<212> TYPE: DNA
<213> ORGANISM: Artificial Sequence
<220> FEATURE:
<223> OTHER INFORMATION: primer

<400> SEQUENCE: 95
gtcatcccac tcttcttcaa tccccacgac gacgaaatc 39

<210> SEQ ID NO 96
<211> LENGTH: 38
<212> TYPE: DNA
<213> ORGANISM: Artificial Sequence
<220> FEATURE:
<223> OTHER INFORMATION: primer

<400> SEQUENCE: 96
ggataagctc gtggatgctg ctgcgtcttc agagaaac 38

<210> SEQ ID NO 97

<211> LENGTH: 40
<212> TYPE: DNA
<213> ORGANISM: Artificial Sequence
<220> FEATURE:
<223> OTHER INFORMATION: primer

<400> SEQUENCE: 97
cgataaggga gatttgcgtt gactggattt cgagagattg 40

<210> SEQ ID NO 98
<211> LENGTH: 39
<212> TYPE: DNA
<213> ORGANISM: Artificial Sequence
<220> FEATURE:
<223> OTHER INFORMATION: primer

<400> SEQUENCE: 98
gagataagag atgggttctg cacaccattg cagattctg 39

<210> SEQ ID NO 99
<211> LENGTH: 43
<212> TYPE: DNA
<213> ORGANISM: Artificial Sequence
<220> FEATURE:
<223> OTHER INFORMATION: primer

<400> SEQUENCE: 99
ttaaggtcat gtcttctgtt tccacggcgg agaaaatggt aac 43

<210> SEQ ID NO 100
<211> LENGTH: 43
<212> TYPE: DNA
<213> ORGANISM: Artificial Sequence
<220> FEATURE:
<223> OTHER INFORMATION: primer

<400> SEQUENCE: 100
cgtcatcctg aatgatcgtt accattttct ccgccgtgga aac 43

<210> SEQ ID NO 101
<211> LENGTH: 36
<212> TYPE: DNA
<213> ORGANISM: Artificial Sequence
<220> FEATURE:
<223> OTHER INFORMATION: primer

<400> SEQUENCE: 101
ttaaggtcat gtcttctgtt tccacggcgg agaaag 36

<210> SEQ ID NO 102
<211> LENGTH: 34
<212> TYPE: DNA
<213> ORGANISM: Artificial Sequence
<220> FEATURE:
<223> OTHER INFORMATION: primer

<400> SEQUENCE: 102
cgtcggagat tgtacttcaa cccattatgg taac 34

<210> SEQ ID NO 103
<211> LENGTH: 37
<212> TYPE: DNA
<213> ORGANISM: Artificial Sequence
<220> FEATURE:
<223> OTHER INFORMATION: primer

<400> SEQUENCE: 103
cgtcatcctg aatgatcgta accataatgg gttgaag 37

<210> SEQ ID NO 104
<211> LENGTH: 33
<212> TYPE: DNA
<213> ORGANISM: Artificial Sequence
<220> FEATURE:
<223> OTHER INFORMATION: primer

<400> SEQUENCE: 104
tacaatctcc gacgctttct ccgccgtgga aac 33

<210> SEQ ID NO 105
<211> LENGTH: 55
<212> TYPE: DNA
<213> ORGANISM: Artificial Sequence
<220> FEATURE:
<223> OTHER INFORMATION: primer

<400> SEQUENCE: 105
ttaaggtcat gtcttctgtt tccacggcgg agaaagcgtc ggagattatg gtaac 55

<210> SEQ ID NO 106
<211> LENGTH: 55
<212> TYPE: DNA
<213> ORGANISM: Artificial Sequence
<220> FEATURE:
<223> OTHER INFORMATION: primer

<400> SEQUENCE: 106
cgtcatcctg aatgatcgtt accataatct ccgacgcttt ctccgccgtg gaaac 55

<210> SEQ ID NO 107
<211> LENGTH: 33
<212> TYPE: DNA
<213> ORGANISM: Artificial Sequence
<220> FEATURE:
<223> OTHER INFORMATION: primer

<400> SEQUENCE: 107
tctagaggat ccagaaccat ggccaccgcc agc 33

<210> SEQ ID NO 108
<211> LENGTH: 33
<212> TYPE: DNA
<213> ORGANISM: Artificial Sequence
<220> FEATURE:
<223> OTHER INFORMATION: primer

<400> SEQUENCE: 108
ctgcgcctcg cgccgtactc gcacccgctg agc 33

<210> SEQ ID NO 109
<211> LENGTH: 32
<212> TYPE: DNA
<213> ORGANISM: Artificial Sequence
<220> FEATURE:
<223> OTHER INFORMATION: primer

<400> SEQUENCE: 109
gccgcggcgc cgccggcgtc acctgccgcg cc 32

<210> SEQ ID NO 110
<211> LENGTH: 25
<212> TYPE: DNA

<213> ORGANISM: Artificial Sequence
<220> FEATURE:
<223> OTHER INFORMATION: primer

<400> SEQUENCE: 110
tggccatggt tctggatcct ctaga 25

<210> SEQ ID NO 111
<211> LENGTH: 32
<212> TYPE: DNA
<213> ORGANISM: Artificial Sequence
<220> FEATURE:
<223> OTHER INFORMATION: primer

<400> SEQUENCE: 111
agtacggcgc gaggcgcagc gagagcgcga gg 32

<210> SEQ ID NO 112
<211> LENGTH: 32
<212> TYPE: DNA
<213> ORGANISM: Artificial Sequence
<220> FEATURE:
<223> OTHER INFORMATION: primer

<400> SEQUENCE: 112
acgccggcgg cgccgcggcg gcggaggctc ag 32

<210> SEQ ID NO 113
<211> LENGTH: 33
<212> TYPE: DNA
<213> ORGANISM: Artificial Sequence
<220> FEATURE:
<223> OTHER INFORMATION: primer

<400> SEQUENCE: 113
cgtcatcctg aatgatcgtt accatggcgc ggc 33

<210> SEQ ID NO 114
<211> LENGTH: 32
<212> TYPE: DNA
<213> ORGANISM: Artificial Sequence
<220> FEATURE:
<223> OTHER INFORMATION: primer

<400> SEQUENCE: 114
gccgcggcgc cgccggcgtc acctgccgcg cc 32

<210> SEQ ID NO 115
<211> LENGTH: 33
<212> TYPE: DNA
<213> ORGANISM: Artificial Sequence
<220> FEATURE:
<223> OTHER INFORMATION: primer

<400> SEQUENCE: 115
accagcttga cgccgtcgcg gtgagggagg agc 33

<210> SEQ ID NO 116
<211> LENGTH: 33
<212> TYPE: DNA
<213> ORGANISM: Artificial Sequence
<220> FEATURE:
<223> OTHER INFORMATION: primer

<400> SEQUENCE: 116
gcgacggcgt caagctggtg gaacgtggcg gtc 33

<210> SEQ ID NO 117
<211> LENGTH: 34
<212> TYPE: DNA
<213> ORGANISM: Artificial Sequence
<220> FEATURE:
<223> OTHER INFORMATION: primer

<400> SEQUENCE: 117
cgtcatcctg aatgatcgtt accatcctgg actc 34

<210> SEQ ID NO 118
<211> LENGTH: 40
<212> TYPE: DNA
<213> ORGANISM: Artificial Sequence
<220> FEATURE:
<223> OTHER INFORMATION: primer

<400> SEQUENCE: 118
ctagtctaga ggatccagaa ccatggaatc cctagccgcc 40

<210> SEQ ID NO 119
<211> LENGTH: 40
<212> TYPE: DNA
<213> ORGANISM: Artificial Sequence
<220> FEATURE:
<223> OTHER INFORMATION: primer

<400> SEQUENCE: 119
acctccgtgt tcgcgccctc ccgcgtcgcc gtcccggcgg 40

<210> SEQ ID NO 120
<211> LENGTH: 40
<212> TYPE: DNA
<213> ORGANISM: Artificial Sequence
<220> FEATURE:
<223> OTHER INFORMATION: primer

<400> SEQUENCE: 120
cgcgggccct ggttagggcg gggacggtgg taccaaccag 40

<210> SEQ ID NO 121
<211> LENGTH: 40
<212> TYPE: DNA
<213> ORGANISM: Artificial Sequence
<220> FEATURE:
<223> OTHER INFORMATION: primer

<400> SEQUENCE: 121
gcggacgagc agccggagcg gaaccagcgg ggtgaaatgc 40

<210> SEQ ID NO 122
<211> LENGTH: 40
<212> TYPE: DNA
<213> ORGANISM: Artificial Sequence
<220> FEATURE:
<223> OTHER INFORMATION: primer

<400> SEQUENCE: 122
tctatggtaa cgatcattca ggatgacgga gcggagacgt 40

<210> SEQ ID NO 123
<211> LENGTH: 40
<212> TYPE: DNA
<213> ORGANISM: Artificial Sequence
<220> FEATURE:

<223> OTHER INFORMATION: primer

<400> SEQUENCE: 123
cgtctcgtac gtctccgctc cgtcatcctg aatgatcgtt 40

<210> SEQ ID NO 124
<211> LENGTH: 40
<212> TYPE: DNA
<213> ORGANISM: Artificial Sequence
<220> FEATURE:
<223> OTHER INFORMATION: primer

<400> SEQUENCE: 124
accatagagc atttcacccc gctggttccg ctccggctgc 40

<210> SEQ ID NO 125
<211> LENGTH: 40
<212> TYPE: DNA
<213> ORGANISM: Artificial Sequence
<220> FEATURE:
<223> OTHER INFORMATION: primer

<400> SEQUENCE: 125
tcgtccgcct ggttggtacc accgtccccg ccctaaccag 40

<210> SEQ ID NO 126
<211> LENGTH: 40
<212> TYPE: DNA
<213> ORGANISM: Artificial Sequence
<220> FEATURE:
<223> OTHER INFORMATION: primer

<400> SEQUENCE: 126
ggcccgcgcc gccgggacgg cgacgcggga gggcgcgaac 40

<210> SEQ ID NO 127
<211> LENGTH: 40
<212> TYPE: DNA
<213> ORGANISM: Artificial Sequence
<220> FEATURE:
<223> OTHER INFORMATION: primer

<400> SEQUENCE: 127
acggaggtgg cggctaggga ttccatggtt ctggatcctc 40

<210> SEQ ID NO 128
<211> LENGTH: 40
<212> TYPE: DNA
<213> ORGANISM: Artificial Sequence
<220> FEATURE:
<223> OTHER INFORMATION: primer

<400> SEQUENCE: 128
tctgctgccg tgacgccgat ggtaacgatc attcaggatg 40

<210> SEQ ID NO 129
<211> LENGTH: 30
<212> TYPE: DNA
<213> ORGANISM: Artificial Sequence
<220> FEATURE:
<223> OTHER INFORMATION: primer

<400> SEQUENCE: 129
accatcggcg tcacggcagc agagcatttc 30

<210> SEQ ID NO 130
<211> LENGTH: 24
<212> TYPE: DNA
<213> ORGANISM: Artificial Sequence
<220> FEATURE:
<223> OTHER INFORMATION: primer

<400> SEQUENCE: 130
ccccgctggt tccgctccgg ctgc 24

<210> SEQ ID NO 131
<211> LENGTH: 35
<212> TYPE: DNA
<213> ORGANISM: Artificial Sequence
<220> FEATURE:
<223> OTHER INFORMATION: primer

<400> SEQUENCE: 131
tctgctgccg tgacgccgca ggcgagccca gtgat 35

<210> SEQ ID NO 132
<211> LENGTH: 35
<212> TYPE: DNA
<213> ORGANISM: Artificial Sequence
<220> FEATURE:
<223> OTHER INFORMATION: primer

<400> SEQUENCE: 132
ggtaacgatc attcaggatg acggagcgga gacgt 35

<210> SEQ ID NO 133
<211> LENGTH: 35
<212> TYPE: DNA
<213> ORGANISM: Artificial Sequence
<220> FEATURE:
<223> OTHER INFORMATION: primer

<400> SEQUENCE: 133
accatcactg ggctcgcctg cggcgtcacg gcagc 35

<210> SEQ ID NO 134
<211> LENGTH: 35
<212> TYPE: DNA
<213> ORGANISM: Artificial Sequence
<220> FEATURE:
<223> OTHER INFORMATION: primer

<400> SEQUENCE: 134
agagcatttc accccgctgg ttccgctccg gctgc 35

<210> SEQ ID NO 135
<211> LENGTH: 22
<212> TYPE: DNA
<213> ORGANISM: Artificial Sequence
<220> FEATURE:
<223> OTHER INFORMATION: primer

<400> SEQUENCE: 135
ctagtctaga atggaatccc ta 22

<210> SEQ ID NO 136
<211> LENGTH: 22
<212> TYPE: DNA
<213> ORGANISM: Artificial Sequence
<220> FEATURE:
<223> OTHER INFORMATION: primer

<400> SEQUENCE: 136
tcctggatcc ggcgtcacgg ca 22

<210> SEQ ID NO 137
<211> LENGTH: 33
<212> TYPE: DNA
<213> ORGANISM: Artificial Sequence
<220> FEATURE:
<223> OTHER INFORMATION: primer

<400> SEQUENCE: 137
tctagaggat ccagaaccat ggcggctctc acc 33

<210> SEQ ID NO 138
<211> LENGTH: 33
<212> TYPE: DNA
<213> ORGANISM: Artificial Sequence
<220> FEATURE:
<223> OTHER INFORMATION: primer

<400> SEQUENCE: 138
agctcgccac ctccgccacc ggcttcggca tcg 33

<210> SEQ ID NO 139
<211> LENGTH: 33
<212> TYPE: DNA
<213> ORGANISM: Artificial Sequence
<220> FEATURE:
<223> OTHER INFORMATION: primer

<400> SEQUENCE: 139
gtcggcgccg tcgtcgctgc tccgccacgg gtt 33

<210> SEQ ID NO 140
<211> LENGTH: 33
<212> TYPE: DNA
<213> ORGANISM: Artificial Sequence
<220> FEATURE:
<223> OTHER INFORMATION: primer

<400> SEQUENCE: 140
ctcaagccac gcagcccagc cggcggcgac gcc 33

<210> SEQ ID NO 141
<211> LENGTH: 33
<212> TYPE: DNA
<213> ORGANISM: Artificial Sequence
<220> FEATURE:
<223> OTHER INFORMATION: primer

<400> SEQUENCE: 141
tcagcgtgac gaccagcgcg cgcgcgacgc cca 33

<210> SEQ ID NO 142
<211> LENGTH: 33
<212> TYPE: DNA
<213> ORGANISM: Artificial Sequence
<220> FEATURE:
<223> OTHER INFORMATION: primer

<400> SEQUENCE: 142
cggtcggtgc agcgtcgcag ccggagcttc cca 33

<210> SEQ ID NO 143
<211> LENGTH: 34

<212> TYPE: DNA
<213> ORGANISM: Artificial Sequence
<220> FEATURE:
<223> OTHER INFORMATION: primer

<400> SEQUENCE: 143
gtcgtgtgca tggtaacgat cattcaggat gacc 34

<210> SEQ ID NO 144
<211> LENGTH: 20
<212> TYPE: DNA
<213> ORGANISM: Artificial Sequence
<220> FEATURE:
<223> OTHER INFORMATION: primer

<400> SEQUENCE: 144
atggttctgg atcctctaga 20

<210> SEQ ID NO 145
<211> LENGTH: 33
<212> TYPE: DNA
<213> ORGANISM: Artificial Sequence
<220> FEATURE:
<223> OTHER INFORMATION: primer

<400> SEQUENCE: 145
gtggccgagg tggcgagctg ggacgtggtg aga 33

<210> SEQ ID NO 146
<211> LENGTH: 33
<212> TYPE: DNA
<213> ORGANISM: Artificial Sequence
<220> FEATURE:
<223> OTHER INFORMATION: primer

<400> SEQUENCE: 146
cagcgacgac ggcgccgacc tgtcggcgat gcc 33

<210> SEQ ID NO 147
<211> LENGTH: 33
<212> TYPE: DNA
<213> ORGANISM: Artificial Sequence
<220> FEATURE:
<223> OTHER INFORMATION: primer

<400> SEQUENCE: 147
ctgggctgcg tggcttgagg ccctggaacc cgt 33

<210> SEQ ID NO 148
<211> LENGTH: 33
<212> TYPE: DNA
<213> ORGANISM: Artificial Sequence
<220> FEATURE:
<223> OTHER INFORMATION: primer

<400> SEQUENCE: 148
gcgctggtcg tcacgctgag cgacgtcgcg tcg 33

<210> SEQ ID NO 149
<211> LENGTH: 33
<212> TYPE: DNA
<213> ORGANISM: Artificial Sequence
<220> FEATURE:
<223> OTHER INFORMATION: primer

<400> SEQUENCE: 149
tgccacgctg caccgaccgc tgctgcttcg gcg 33

<210> SEQ ID NO 150
<211> LENGTH: 33
<212> TYPE: DNA
<213> ORGANISM: Artificial Sequence
<220> FEATURE:
<223> OTHER INFORMATION: primer

<400> SEQUENCE: 150
atcgttacca tgcacacgac gacggatggg aac 33

<210> SEQ ID NO 151
<211> LENGTH: 33
<212> TYPE: DNA
<213> ORGANISM: Artificial Sequence
<220> FEATURE:
<223> OTHER INFORMATION: primer

<400> SEQUENCE: 151
gtctcgtacg tctccgctcc gtcatcctga atg 33

<210> SEQ ID NO 152
<211> LENGTH: 33
<212> TYPE: DNA
<213> ORGANISM: Artificial Sequence
<220> FEATURE:
<223> OTHER INFORMATION: primer

<400> SEQUENCE: 152
gtcgtgtacg ccaccggcgc cggcatggta acg 33

<210> SEQ ID NO 153
<211> LENGTH: 33
<212> TYPE: DNA
<213> ORGANISM: Artificial Sequence
<220> FEATURE:
<223> OTHER INFORMATION: primer

<400> SEQUENCE: 153
atcattcagg atgacggagc ggagacgtac gag 33

<210> SEQ ID NO 154
<211> LENGTH: 33
<212> TYPE: DNA
<213> ORGANISM: Artificial Sequence
<220> FEATURE:
<223> OTHER INFORMATION: primer

<400> SEQUENCE: 154
cgccggtggc gtacacgacg acggatggga acc 33

<210> SEQ ID NO 155
<211> LENGTH: 34
<212> TYPE: DNA
<213> ORGANISM: Artificial Sequence
<220> FEATURE:
<223> OTHER INFORMATION: primer

<400> SEQUENCE: 155
gtctcgtacg tctccgctcc gtcatcctga atga 34

<210> SEQ ID NO 156
<211> LENGTH: 33
<212> TYPE: DNA
<213> ORGANISM: Artificial Sequence
<220> FEATURE:
<223> OTHER INFORMATION: primer

<400> SEQUENCE: 156
gtcgtgtacg ccaccggcgc cggcatgaac gtc 33

<210> SEQ ID NO 157
<211> LENGTH: 33
<212> TYPE: DNA
<213> ORGANISM: Artificial Sequence
<220> FEATURE:
<223> OTHER INFORMATION: primer

<400> SEQUENCE: 157
tcggcgccga gatggccccc tggagcaaga tgg 33

<210> SEQ ID NO 158
<211> LENGTH: 33
<212> TYPE: DNA
<213> ORGANISM: Artificial Sequence
<220> FEATURE:
<223> OTHER INFORMATION: primer

<400> SEQUENCE: 158
atcattcagg atgacggagc ggagacgtac gag 33

<210> SEQ ID NO 159
<211> LENGTH: 33
<212> TYPE: DNA
<213> ORGANISM: Artificial Sequence
<220> FEATURE:
<223> OTHER INFORMATION: primer

<400> SEQUENCE: 159
gggccatctc ggcgccgacg aacacgacgt tca 33

<210> SEQ ID NO 160
<211> LENGTH: 34
<212> TYPE: DNA
<213> ORGANISM: Artificial Sequence
<220> FEATURE:
<223> OTHER INFORMATION: primer

<400> SEQUENCE: 160
gtctcgtacg tctccgctcc gtcatcctga atga 34

<210> SEQ ID NO 161
<211> LENGTH: 40
<212> TYPE: DNA
<213> ORGANISM: Artificial Sequence
<220> FEATURE:
<223> OTHER INFORMATION: primer

<400> SEQUENCE: 161
ctagtctaga ggatccagaa ccatgatttc gccgacgaat 40

<210> SEQ ID NO 162
<211> LENGTH: 40
<212> TYPE: DNA
<213> ORGANISM: Artificial Sequence
<220> FEATURE:
<223> OTHER INFORMATION: primer

<400> SEQUENCE: 162
ctcctcccgg cgcggaagat cacccctgtc tcaaatggcg 40

<210> SEQ ID NO 163
<211> LENGTH: 40
<212> TYPE: DNA
<213> ORGANISM: Artificial Sequence
<220> FEATURE:
<223> OTHER INFORMATION: primer

<400> SEQUENCE: 163
gcgcagcgac ggcgagcccc tcttctccct cggtggccgc 40

<210> SEQ ID NO 164
<211> LENGTH: 40
<212> TYPE: DNA
<213> ORGANISM: Artificial Sequence
<220> FEATURE:
<223> OTHER INFORMATION: primer

<400> SEQUENCE: 164
acggccacgg cgactccctt caggcctcca atctgtgact 40

<210> SEQ ID NO 165
<211> LENGTH: 45
<212> TYPE: DNA
<213> ORGANISM: Artificial Sequence
<220> FEATURE:
<223> OTHER INFORMATION: primer

<400> SEQUENCE: 165
ggtagaggga aggtttcctt ggcaatggta acgatcattc aggat 45

<210> SEQ ID NO 166
<211> LENGTH: 45
<212> TYPE: DNA
<213> ORGANISM: Artificial Sequence
<220> FEATURE:
<223> OTHER INFORMATION: primer

<400> SEQUENCE: 166
cgtctcgtac gtctccgctc cgtcatcctg aatgatcgtt accat 45

<210> SEQ ID NO 167
<211> LENGTH: 44
<212> TYPE: DNA
<213> ORGANISM: Artificial Sequence
<220> FEATURE:
<223> OTHER INFORMATION: primer

<400> SEQUENCE: 167
tgccaaggaa accttccctc taccagtcac agattggagg cctg 44

<210> SEQ ID NO 168
<211> LENGTH: 41
<212> TYPE: DNA
<213> ORGANISM: Artificial Sequence
<220> FEATURE:
<223> OTHER INFORMATION: primer

<400> SEQUENCE: 168
aagggagtcg ccgtggccgt gcggccaccg agggagaaga g 41

<210> SEQ ID NO 169
<211> LENGTH: 40
<212> TYPE: DNA
<213> ORGANISM: Artificial Sequence
<220> FEATURE:
<223> OTHER INFORMATION: primer

<400> SEQUENCE: 169
gggctcgccg tcgctgcgcc gccatttgag acaggggtga 40

<210> SEQ ID NO 170
<211> LENGTH: 40
<212> TYPE: DNA
<213> ORGANISM: Artificial Sequence
<220> FEATURE:
<223> OTHER INFORMATION: primer

<400> SEQUENCE: 170
tcttccgcgc cgggaggaga ttcgtcggcg aaatcatggt 40

<210> SEQ ID NO 171
<211> LENGTH: 40
<212> TYPE: DNA
<213> ORGANISM: Artificial Sequence
<220> FEATURE:
<223> OTHER INFORMATION: primer

<400> SEQUENCE: 171
ggtagaggga aggtttcctt ggcagccatc actctggatg 40

<210> SEQ ID NO 172
<211> LENGTH: 40
<212> TYPE: DNA
<213> ORGANISM: Artificial Sequence
<220> FEATURE:
<223> OTHER INFORMATION: primer

<400> SEQUENCE: 172
attaccttcc aatggtaacg atcattcagg atgacggagc 40

<210> SEQ ID NO 173
<211> LENGTH: 40
<212> TYPE: DNA
<213> ORGANISM: Artificial Sequence
<220> FEATURE:
<223> OTHER INFORMATION: primer

<400> SEQUENCE: 173
accattggaa ggtaatcatc cagagtgatg gctgccaagg 40

<210> SEQ ID NO 174
<211> LENGTH: 36
<212> TYPE: DNA
<213> ORGANISM: Artificial Sequence
<220> FEATURE:
<223> OTHER INFORMATION: primer

<400> SEQUENCE: 174
aaaccttccc tctaccagtc acagattgga ggcctg 36

<210> SEQ ID NO 175
<211> LENGTH: 40
<212> TYPE: DNA
<213> ORGANISM: Artificial Sequence
<220> FEATURE:
<223> OTHER INFORMATION: primer

<400> SEQUENCE: 175
attaccttcc aatgcgaagc actgaagtga agaaccggac 40

<210> SEQ ID NO 176

<211> LENGTH: 40
<212> TYPE: DNA
<213> ORGANISM: Artificial Sequence
<220> FEATURE:
<223> OTHER INFORMATION: primer

<400> SEQUENCE: 176
atcaatggta acgatcattc aggatgacgg agcggagacg 40

<210> SEQ ID NO 177
<211> LENGTH: 40
<212> TYPE: DNA
<213> ORGANISM: Artificial Sequence
<220> FEATURE:
<223> OTHER INFORMATION: primer

<400> SEQUENCE: 177
accattgatg tccggttctt cacttcagtg cttcgcattg 40

<210> SEQ ID NO 178
<211> LENGTH: 40
<212> TYPE: DNA
<213> ORGANISM: Artificial Sequence
<220> FEATURE:
<223> OTHER INFORMATION: primer

<400> SEQUENCE: 178
gaaggtaatc atccagagtg atggctgcca aggaaacctt 40

<210> SEQ ID NO 179
<211> LENGTH: 29
<212> TYPE: DNA
<213> ORGANISM: Artificial Sequence
<220> FEATURE:
<223> OTHER INFORMATION: primer

<400> SEQUENCE: 179
ccctctacca gtcacagatt ggaggcctg 29

<210> SEQ ID NO 180
<211> LENGTH: 40
<212> TYPE: DNA
<213> ORGANISM: Artificial Sequence
<220> FEATURE:
<223> OTHER INFORMATION: primer

<400> SEQUENCE: 180
ggtagaggga aggtttcctt ggcagccatc actctggata 40

<210> SEQ ID NO 181
<211> LENGTH: 40
<212> TYPE: DNA
<213> ORGANISM: Artificial Sequence
<220> FEATURE:
<223> OTHER INFORMATION: primer

<400> SEQUENCE: 181
tggtaacgat cattcaggat gacggagcgg agacgtacga 40

<210> SEQ ID NO 182
<211> LENGTH: 40
<212> TYPE: DNA
<213> ORGANISM: Artificial Sequence
<220> FEATURE:
<223> OTHER INFORMATION: primer

<400> SEQUENCE: 182
cgtctcgtac gtctccgctc cgtcatcctg aatgatcgtt 40

<210> SEQ ID NO 183
<211> LENGTH: 40
<212> TYPE: DNA
<213> ORGANISM: Artificial Sequence
<220> FEATURE:
<223> OTHER INFORMATION: primer

<400> SEQUENCE: 183
accatatcca gagtgatggc tgccaaggaa accttccctc 40

<210> SEQ ID NO 184
<211> LENGTH: 24
<212> TYPE: DNA
<213> ORGANISM: Artificial Sequence
<220> FEATURE:
<223> OTHER INFORMATION: primer

<400> SEQUENCE: 184
taccagtcac agattggagg cctg 24

<210> SEQ ID NO 185
<211> LENGTH: 22
<212> TYPE: DNA
<213> ORGANISM: Artificial Sequence
<220> FEATURE:
<223> OTHER INFORMATION: primer

<400> SEQUENCE: 185
ctagtctaga atgatttcgc cg 22

<210> SEQ ID NO 186
<211> LENGTH: 22
<212> TYPE: DNA
<213> ORGANISM: Artificial Sequence
<220> FEATURE:
<223> OTHER INFORMATION: primer

<400> SEQUENCE: 186
tcctggatcc tccagagtga tg 22

<210> SEQ ID NO 187
<211> LENGTH: 40
<212> TYPE: DNA
<213> ORGANISM: Artificial Sequence
<220> FEATURE:
<223> OTHER INFORMATION: primer

<400> SEQUENCE: 187
ctagtctaga ggatccagaa ccatgatttc gccgacgaat 40

<210> SEQ ID NO 188
<211> LENGTH: 40
<212> TYPE: DNA
<213> ORGANISM: Artificial Sequence
<220> FEATURE:
<223> OTHER INFORMATION: primer

<400> SEQUENCE: 188
ctcctcccgg cgcggaagat cacccctgtc tcaaatggcg 40

<210> SEQ ID NO 189
<211> LENGTH: 40
<212> TYPE: DNA

<213> ORGANISM: Artificial Sequence
<220> FEATURE:
<223> OTHER INFORMATION: primer

<400> SEQUENCE: 189
gcgcagcgac ggcgagcccc tcttctccct cggtggccgc 40

<210> SEQ ID NO 190
<211> LENGTH: 40
<212> TYPE: DNA
<213> ORGANISM: Artificial Sequence
<220> FEATURE:
<223> OTHER INFORMATION: primer

<400> SEQUENCE: 190
acggccacgg cgactccctt caggcctcca atctgtgact 40

<210> SEQ ID NO 191
<211> LENGTH: 40
<212> TYPE: DNA
<213> ORGANISM: Artificial Sequence
<220> FEATURE:
<223> OTHER INFORMATION: primer

<400> SEQUENCE: 191
gggctcgccg tcgctgcgcc gccatttgag acaggggtga 40

<210> SEQ ID NO 192
<211> LENGTH: 40
<212> TYPE: DNA
<213> ORGANISM: Artificial Sequence
<220> FEATURE:
<223> OTHER INFORMATION: primer

<400> SEQUENCE: 192
tcttccgcgc cgggaggaga ttcgtcggcg aaatcatggt 40

<210> SEQ ID NO 193
<211> LENGTH: 40
<212> TYPE: DNA
<213> ORGANISM: Artificial Sequence
<220> FEATURE:
<223> OTHER INFORMATION: primer

<400> SEQUENCE: 193
ggtagaggga aggtttcctt ggcagccatc actctggata 40

<210> SEQ ID NO 194
<211> LENGTH: 40
<212> TYPE: DNA
<213> ORGANISM: Artificial Sequence
<220> FEATURE:
<223> OTHER INFORMATION: primer

<400> SEQUENCE: 194
tggtaacgat cattcaggat gacggagcgg agacgtacga 40

<210> SEQ ID NO 195
<211> LENGTH: 40
<212> TYPE: DNA
<213> ORGANISM: Artificial Sequence
<220> FEATURE:
<223> OTHER INFORMATION: primer

<400> SEQUENCE: 195
cgtctcgtac gtctccgctc cgtcatcctg aatgatcgtt 40

<210> SEQ ID NO 196
<211> LENGTH: 40
<212> TYPE: DNA
<213> ORGANISM: Artificial Sequence
<220> FEATURE:
<223> OTHER INFORMATION: primer

<400> SEQUENCE: 196
accatatcca gagtgatggc tgccaaggaa accttccctc 40

<210> SEQ ID NO 197
<211> LENGTH: 24
<212> TYPE: DNA
<213> ORGANISM: Artificial Sequence
<220> FEATURE:
<223> OTHER INFORMATION: primer

<400> SEQUENCE: 197
taccagtcac agattggagg cctg 24

<210> SEQ ID NO 198
<211> LENGTH: 40
<212> TYPE: DNA
<213> ORGANISM: Artificial Sequence
<220> FEATURE:
<223> OTHER INFORMATION: primer

<400> SEQUENCE: 198
accattggaa ggtaatcatc cagagtgatg gctgccaagg 40

<210> SEQ ID NO 199
<211> LENGTH: 2190
<212> TYPE: DNA
<213> ORGANISM: Agrobacterium tumefaciens

<400> SEQUENCE: 199
atggtaacga tcattcagga tgacggagcg gagacctacg agacgaaagg cggcatccag 60
gtcagccgaa agcgccggcc caccgattat gccaacgcca tcgataatta catcgaaaag 120
cttgattccc atcgcggcgc ggtttttttcg tccaactatg aatatccggg ccgttacacc 180
cgctgggata cggccatcgt cgatccgccg ctcggcattt cctgttttgg ccgcaagatg 240
tggatcgaag cctataatgg ccgcggcgaa gtgctgctcg atttcattac ggaaaagctg 300
aaggcgacac ccgatctcac cctcggcgct tcctcgaccc gccggctcga tcttaccgtc 360
aacgaaccgg accgtgtctt caccgaagaa gaacgctcga aatcccgac ggtcttcacc 420 gctctcagag ccatcgtcga cctcttctat tcgagcgcgg attcggccat cggcctgttc 480
ggtgccttcg gttacgatct cgccttccag ttcgacgcga tcaagctttc gctggcgcgt 540
ccggaagacc agcgtgacat ggtgctgttt ctgcccgatg aaatcctcgt cgttgatcac 600
tattccgcca aggcctggat cgaccgttac gatttcgaga aggacggcat gacgacggac 660
ggcaaatcct ccgacattac ccccgatccc ttcaagacca ccgataccat cccgcccaag 720
ggcgatcacc gtcccggcga atattccgag cttgtggtga aggccaagga aagcttccgc 780
cgcggcgacc tgttcgaggt cgttcccggc cagaaattca tggagcgttg cgaaagcaat 840
ccgtcggcga tttcccgccg cctgaaggcg atcaacccgt cgccctattc cttcttcatc 900
aatctcggcg atcaggaata tctggtcggc gcctcgccgg aaatgttcgt gcgcgtctcc 960
ggccgtcgca tcgagacctg cccgatatca ggcaccatca agcgcggcga cgatccgatt 1020

```
gccgacagcg agcagatttt gaaactgctc aactcgaaaa aggacgaatc cgaactgacc   1080

atgtgctcgg acgtggaccg caacgacaag agccgcgtct gcgagccggg ttcggtgaag   1140

gtcattggcc gccgccagat cgagatgtat tcacgcctca tccacaccgt cgatcacatc   1200

gaaggccgcc tgcgcgacga tatggacgcc tttgacggtt tcctcagcca cgcctgggcc   1260

gtcaccgtca ccggtgcacc aaagctgtgg gccatgcgct tcatcgaagg tcatgaaaag   1320

agcccgcgcg cctggtatgg cggtgcgatc ggcatggtcg gcttcaacgg cgacatgaat   1380

accggcctga cgctgcgcac catccggatc aaggacggta ttgccgaagt gcgcgccggc   1440

gcgaccctgc tcaatgattc caacccgcag gaagaagaag ccgaaaccga actgaaggcc   1500

tccgccatga tatcagccat tcgtgacgca aaaggcacca actctgccgc caccaagcgt   1560

gatgccgcca aagtcggcac cggcgtcaag atcctgctcg tcgaccacga agacagcttc   1620

gtgcacacgc tggcgaatta tttccgccag acgggcgcga cggtctcgac cgtcagatca   1680

ccggtcgcag ccgacgtgtt cgatcgcttc cagccggacc tcgttgtcct gtcgcccgga   1740

cccggcagcc cgacggattt cgactgcaag gcaacgatca aggccgcccg cgcccgcgat   1800

ctgccgatct tcggcgtttg cctcggtctg caggcattgg cagaagccta tggcggcgag   1860

ctgcgccagc ttgctgtgcc catgcacggc aagccttcgc gcatccgcgt gctggaaccc   1920

ggcctcgtct tctccggtct cggcaaggaa gtcacggtcg gtcgttacca ttcgatcttc   1980

gccgatcccg ccaccctgcc gcgtgatttc atcatcaccg cagaaagcga ggacggcacg   2040

atcatgggca tcgaacacgc caaggaaccg gtggccgccg ttcagttcca cccggaatcg   2100

atcatgacgc tcggacagga cgcgggcatg cggatgatcg agaatgtcgt ggtgcatctg   2160

acccgcaagg cgaagaccaa ggccgcgtga                                     2190
```

<210> SEQ ID NO 200
<211> LENGTH: 729
<212> TYPE: PRT
<213> ORGANISM: Agrobacterium tumefaciens

<400> SEQUENCE: 200

```
Met Val Thr Ile Ile Gln Asp Asp Gly Ala Glu Thr Tyr Glu Thr Lys
1               5                   10                  15

Gly Gly Ile Gln Val Ser Arg Lys Arg Arg Pro Thr Asp Tyr Ala Asn
            20                  25                  30

Ala Ile Asp Asn Tyr Ile Glu Lys Leu Asp Ser His Arg Gly Ala Val
        35                  40                  45

Phe Ser Ser Asn Tyr Glu Tyr Pro Gly Arg Tyr Thr Arg Trp Asp Thr
    50                  55                  60

Ala Ile Val Asp Pro Pro Leu Gly Ile Ser Cys Phe Gly Arg Lys Met
65                  70                  75                  80

Trp Ile Glu Ala Tyr Asn Gly Arg Gly Glu Val Leu Leu Asp Phe Ile
                85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
        115                 120                 125

Glu Glu Glu Arg Ser Lys Ile Pro Thr Val Phe Thr Ala Leu Arg Ala
    130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
```

```
                165                 170                 175

Ser Leu Ala Arg Pro Glu Asp Gln Arg Asp Met Val Leu Phe Leu Pro
            180                 185                 190

Asp Glu Ile Leu Val Val Asp His Tyr Ser Ala Lys Ala Trp Ile Asp
        195                 200                 205

Arg Tyr Asp Phe Glu Lys Asp Gly Met Thr Thr Asp Gly Lys Ser Ser
    210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
            260                 265                 270

Phe Met Glu Arg Cys Glu Ser Asn Pro Ser Ala Ile Ser Arg Arg Leu
        275                 280                 285

Lys Ala Ile Asn Pro Ser Pro Tyr Ser Phe Phe Ile Asn Leu Gly Asp
    290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Glu Pro Gly Ser Val Lys Val Ile Gly Arg
    370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
        435                 440                 445

Ala Ile Gly Met Val Gly Phe Asn Gly Asp Met Asn Thr Gly Leu Thr
    450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Glu Ala Glu Thr
                485                 490                 495

Glu Leu Lys Ala Ser Ala Met Ile Ser Ala Ile Arg Asp Ala Lys Gly
            500                 505                 510

Thr Asn Ser Ala Ala Thr Lys Arg Asp Ala Ala Lys Val Gly Thr Gly
        515                 520                 525

Val Lys Ile Leu Leu Val Asp His Glu Asp Ser Phe Val His Thr Leu
    530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
            580                 585                 590
```

```
Ile Lys Ala Ala Arg Ala Arg Asp Leu Pro Ile Phe Gly Val Cys Leu
        595                 600                 605

Gly Leu Gln Ala Leu Ala Glu Ala Tyr Gly Gly Glu Leu Arg Gln Leu
    610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
            660                 665                 670

Thr Ala Glu Ser Glu Asp Gly Thr Ile Met Gly Ile Glu His Ala Lys
        675                 680                 685

Glu Pro Val Ala Ala Val Gln Phe His Pro Glu Ser Ile Met Thr Leu
    690                 695                 700

Gly Gln Asp Ala Gly Met Arg Met Ile Glu Asn Val Val Val His Leu
705                 710                 715                 720

Thr Arg Lys Ala Lys Thr Lys Ala Ala
                725


<210> SEQ ID NO 201
<211> LENGTH: 2190
<212> TYPE: DNA
<213> ORGANISM: Agrobacterium tumefaciens

<400> SEQUENCE: 201

atggtaacga tcattcagga tgacggagcg gagacctacg agacgaaagg cggcatccag      60

gtcagccgaa agcgccggcc caccgattat gccaacgcca tcgataatta catcgaaaag     120

cttgattccc atcgcggcgc ggtttttttcg tccaactatg aatatccggg ccgttacacc    180

cgctgggata cggccatcgt cgatccgccg ctcggcattt cctgttttgg ccgcaagatg     240

tggatcgaag cctataatgg ccgcggcgaa gtgctgctcg atttcattac ggaaaagctg     300

aaggcgacac ccgatctcac cctcggcgct tcctcgaccc gccggctcga tcttaccgtc     360

aacgaaccgg accgtgtctt caccgaagaa gaacgctcga aaatcccgac ggtcttcacc     420

gctctcagag ccatcgtcga cctcttctat tcgagcgcgg attcggccat cggcctgttc     480

ggtgccttcg gttacgatct cgccttccag ttcgacgcga tcaagctttc gctggcgcgt     540

ccggaagacc agcgtgacat ggtgctgttt ctgcccgatg aaatcctcgt cgttgatcac     600

tattccgcca aggcctggat cgaccgttac gatttcgaga aggacggcat gacgacggac     660

ggcaaatcct ccgacattac ccccgatccc ttcaagacca ccgataccat cccgcccaag     720

ggcgatcacc gtcccggcga atattccgag cttgtggtga aggccaagga aagcttccgc     780

cgcggcgacc tgttcgaggt cgttcccggc cagaaattca tggagcgttg cgaaagcaat     840

ccgtcggcga tttcccgccg cctgaaggcg atcaacccgt cgccctattc ctggttcatc     900

aatctcggcg atcaggaata tctggtcggc gcctcgccgg aaatgttcgt gcgcgtctcc     960

ggccgtcgca tcgagacctg cccgatatca ggcaccatca agcgcggcga cgatccgatt    1020

gccgacagcg agcagatttt gaaactgctc aactcgaaaa aggacgaatc cgaactgacc    1080

atgtgctcgg acgtggaccg caacgacaag agccgcgtct gcgagccggg ttcggtgaag    1140

gtcattggcc gccgccagat cgagatgtat tcacgcctca tccacaccgt cgatcacatc    1200

gaaggccgcc tgcgcgacga tatggacgcc tttgacggtt tcctcagcca cgcctgggcc    1260

gtcaccgtca ccggtgcacc aaagctgtgg gccatgcgct tcatcgaagg tcatgaaaag    1320
```

```
agcccgcgcg cctggtatgg cggtgcgatc ggcatggtcg gcttcaacgg cgacatgaat   1380

accggcctga cgctgcgcac catccggatc aaggacggta ttgccgaagt gcgcgccggc   1440

gcgaccctgc tcaatgattc caacccgcag gaagaagaag ccgaaaccga actgaaggcc   1500

tccgccatga tatcagccat tcgtgacgca aaaggcacca actctgccgc caccaagcgt   1560

gatgccgcca aagtcggcac cggcgtcaag atcctgctcg tcgaccacga agacagcttc   1620

gtgcacacgc tggcgaatta tttccgccag acgggcgcga cggtctcgac cgtcagatca   1680

ccggtcgcag ccgacgtgtt cgatcgcttc cagccggacc tcgttgtcct gtcgcccgga   1740

cccggcagcc cgacggattt cgactgcaag gcaacgatca aggccgcccg cgcccgcgat   1800

ctgccgatct tcggcgtttg cctcggtctg caggcattgg cagaagccta tggcggcgag   1860

ctgcgccagc ttgctgtgcc catgcacggc aagccttcgc gcatccgcgt gctggaaccc   1920

ggcctcgtct tctccggtct cggcaaggaa gtcacggtcg gtcgttacca ttcgatcttc   1980

gccgatcccg ccaccctgcc gcgtgatttc atcatcaccg cagaaagcga ggacggcacg   2040

atcatgggca tcgaacacgc caaggaaccg gtggccgccg ttcagttcca cccggaatcg   2100

atcatgacgc tcggacagga cgcgggcatg cggatgatcg agaatgtcgt ggtgcatctg   2160

acccgcaagg cgaagaccaa ggccgcgtga                                    2190
```

<210> SEQ ID NO 202
<211> LENGTH: 729
<212> TYPE: PRT
<213> ORGANISM: Agrobacterium tumefaciens

<400> SEQUENCE: 202

```
Met Val Thr Ile Ile Gln Asp Asp Gly Ala Glu Thr Tyr Glu Thr Lys
1               5                   10                  15

Gly Gly Ile Gln Val Ser Arg Lys Arg Arg Pro Thr Asp Tyr Ala Asn
            20                  25                  30

Ala Ile Asp Asn Tyr Ile Glu Lys Leu Asp Ser His Arg Gly Ala Val
        35                  40                  45

Phe Ser Ser Asn Tyr Glu Tyr Pro Gly Arg Tyr Thr Arg Trp Asp Thr
    50                  55                  60

Ala Ile Val Asp Pro Pro Leu Gly Ile Ser Cys Phe Gly Arg Lys Met
65                  70                  75                  80

Trp Ile Glu Ala Tyr Asn Gly Arg Gly Glu Val Leu Leu Asp Phe Ile
                85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
        115                 120                 125

Glu Glu Glu Arg Ser Lys Ile Pro Thr Val Phe Thr Ala Leu Arg Ala
    130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
            180                 185                 190

Asp Glu Ile Leu Val Val Asp His Tyr Ser Ala Lys Ala Trp Ile Asp
        195                 200                 205

Arg Tyr Asp Phe Glu Lys Asp Gly Met Thr Thr Asp Gly Lys Ser Ser
```

```
    210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
            260                 265                 270

Phe Met Glu Arg Cys Glu Ser Asn Pro Ser Ala Ile Ser Arg Arg Leu
        275                 280                 285

Lys Ala Ile Asn Pro Ser Pro Tyr Ser Trp Phe Ile Asn Leu Gly Asp
    290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Glu Pro Gly Ser Val Lys Val Ile Gly Arg
    370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
        435                 440                 445

Ala Ile Gly Met Val Gly Phe Asn Gly Asp Met Asn Thr Gly Leu Thr
    450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Glu Ala Glu Thr
                485                 490                 495

Glu Leu Lys Ala Ser Ala Met Ile Ser Ala Ile Arg Asp Ala Lys Gly
            500                 505                 510

Thr Asn Ser Ala Ala Thr Lys Arg Asp Ala Ala Lys Val Gly Thr Gly
        515                 520                 525

Val Lys Ile Leu Leu Val Asp His Glu Asp Ser Phe Val His Thr Leu
    530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
            580                 585                 590

Ile Lys Ala Ala Arg Ala Arg Asp Leu Pro Ile Phe Gly Val Cys Leu
        595                 600                 605

Gly Leu Gln Ala Leu Ala Glu Ala Tyr Gly Gly Glu Leu Arg Gln Leu
    610                 615                 620

Ala Val Pro Met His Gly Lys Pro Ser Arg Ile Arg Val Leu Glu Pro
625                 630                 635                 640
```

```
Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
            660                 665                 670

Thr Ala Glu Ser Glu Asp Gly Thr Ile Met Gly Ile Glu His Ala Lys
        675                 680                 685

Glu Pro Val Ala Ala Val Gln Phe His Pro Glu Ser Ile Met Thr Leu
    690                 695                 700

Gly Gln Asp Ala Gly Met Arg Met Ile Glu Asn Val Val Val His Leu
705                 710                 715                 720

Thr Arg Lys Ala Lys Thr Lys Ala Ala
                725


<210> SEQ ID NO 203
<211> LENGTH: 2190
<212> TYPE: DNA
<213> ORGANISM: Agrobacterium tumefaciens

<400> SEQUENCE: 203

gtaacgatca ttcaggatga cggagcggag acctacgaga cgaaaggcgg catccaggtc      60

agccgaaagc gccggcccac cgattatgcc aacgccatcg ataattacat cgaaaagctt     120

gattcccatc gcggcgcggt tttttcgttc aactatgaat atccgggccg ttacacccgc     180

tgggatacgg ccatcgtcga tccgccgctc ggcatttcct gttttggccg caagatgtgg     240

atcgaagcct ataatggccg cggcgaagtg ctgctcgatt tcattacgga aaagctgaag     300

gcgacacccg atctcaccct cggcgcttcc tcgacccgcc ggctcgatct taccgtcaac     360

gaaccggacc gtgtcttcac cgaagaagaa cgctcgaaaa tcccgacggt cttcaccgct     420

ctcagagcca tcgtcgacct cttctattcg agcgcggatt cggccatcgg cctgttcggt     480

gccttcggtt acgatctcgc cttccagttc gacgcgatca agctttcgct ggcgcgtccg     540

gaagaccagc gtgacatggt gctgtttctg cccgatgaaa tcctcgtcgt tgatcactat     600

tccgccaagg cctggatcga ccgttacgat ttcgagaagg acggcatgac gacggacggc     660

aaatcctccg acattacccc cgatcccttc aagaccaccg ataccatccc gcccaagggc     720

gatcaccgtc ccggcgaata ttccgagctt gtggtgaagg ccaaggaaag cttccgccgc     780

ggcgacctgt tcgaggtcgt tcccggccag aaattcatgg agcgttgcga aagcaatccg     840

tcggcgattt cccgccgcct gaaggcgatc aacccgtcgc cctattcctt cttcatcaat     900

ctcggcgatc aggaatatct ggtcggcgcc tcgccggaaa tgttcgtgcg cgtctccggc     960

cgtcgcatcg agacctgccc gatatcaggc accatcaagc gcggcgacga tccgattgcc    1020

gacagcgagc agattttgaa actgctcaac tcgaaaaagg acgaatccga actgaccatg    1080

tgctcggacg tggaccgcaa cgacaagagc cgcgtctgcg agccgggttc ggtgaaggtc    1140

attggccgcc gccagatcga gatgtattca cgcctcatcc acaccgtcga tcacatcgaa    1200

ggccgcctgc gcgacgatat ggacgccttt gacggtttcc tcagccacgc ctgggccgtc    1260

accgtcaccg gtgcaccaaa gctgtgggcc atgcgcttca tcgaaggtca tgaaaagagc    1320

ccgcgcgcct ggtatggcgg tgcgatcggc atggtcggct tcaacggcga catgaatacc    1380

ggcctgacgc tgcgcaccat ccggatcaag gacggtattg ccgaagtgcg cgccggcgcg    1440

accctgctca atgattccaa cccgcaggaa gaagaagccg aaaccgaact gaaggcctcc    1500

gccatgatat cagccattcg tgacgcaaaa ggcaccaact ctgccgccac caagcgtgat    1560
```

```
gccgccaaag tcggcaccgg cgtcaagatc ctgctcgtcg accacgaaga cagcttcgtg   1620

cacacgctgg cgaattattt ccgccagacg ggcgcgacgg tctcgaccgt cagatcaccg   1680

gtcgcagccg acgtgttcga tcgcttccag ccggacctcg ttgtcctgtc gcccggaccc   1740

ggcagcccga cggatttcga ctgcaaggca acgatcaagg ccgcccgcgc ccgcgatctg   1800

ccgatcttcg gcgtttgcct cggtctgcag gcattggcag aagcctatgg cggcgagctg   1860

cgccagcttg ctgtgcccat gcacggcaag ccttcgcgca tccgcgtgct ggaacccggc   1920

ctcgtcttct ccggtctcgg caaggaagtc acggtcggtc gttaccattc gatcttcgcc   1980

gatcccgcca ccctgccgcg tgatttcatc atcaccgcag aaagcgagga cggcacgatc   2040

atgggcatcg aacacgccaa ggaaccggtg gccgccgttc agttccaccc ggaatcgatc   2100

atgacgctcg gacaggacgc gggcatgcgg atgatcgaga atgtcgtggt gcatctgacc   2160

cgcaaggcga agaccaaggc cgcgtgatgg                                    2190


<210> SEQ ID NO 204
<211> LENGTH: 728
<212> TYPE: PRT
<213> ORGANISM: Agrobacterium tumefaciens

<400> SEQUENCE: 204

Val Thr Ile Ile Gln Asp Asp Gly Ala Glu Thr Tyr Glu Thr Lys Gly
1               5                   10                  15

Gly Ile Gln Val Ser Arg Lys Arg Arg Pro Thr Asp Tyr Ala Asn Ala
            20                  25                  30

Ile Asp Asn Tyr Ile Glu Lys Leu Asp Ser His Arg Gly Ala Val Phe
        35                  40                  45

Ser Phe Asn Tyr Glu Tyr Pro Gly Arg Tyr Thr Arg Trp Asp Thr Ala
    50                  55                  60

Ile Val Asp Pro Pro Leu Gly Ile Ser Cys Phe Gly Arg Lys Met Trp
65                  70                  75                  80

Ile Glu Ala Tyr Asn Gly Arg Gly Glu Val Leu Leu Asp Phe Ile Thr
                85                  90                  95

Glu Lys Leu Lys Ala Thr Pro Asp Leu Thr Leu Gly Ala Ser Ser Thr
            100                 105                 110

Arg Arg Leu Asp Leu Thr Val Asn Glu Pro Asp Arg Val Phe Thr Glu
        115                 120                 125

Glu Glu Arg Ser Lys Ile Pro Thr Val Phe Thr Ala Leu Arg Ala Ile
    130                 135                 140

Val Asp Leu Phe Tyr Ser Ser Ala Asp Ser Ala Ile Gly Leu Phe Gly
145                 150                 155                 160

Ala Phe Gly Tyr Asp Leu Ala Phe Gln Phe Asp Ala Ile Lys Leu Ser
                165                 170                 175

Leu Ala Arg Pro Glu Asp Gln Arg Asp Met Val Leu Phe Leu Pro Asp
            180                 185                 190

Glu Ile Leu Val Val Asp His Tyr Ser Ala Lys Ala Trp Ile Asp Arg
        195                 200                 205

Tyr Asp Phe Glu Lys Asp Gly Met Thr Thr Asp Gly Lys Ser Ser Asp
    210                 215                 220

Ile Thr Pro Asp Pro Phe Lys Thr Thr Asp Thr Ile Pro Pro Lys Gly
225                 230                 235                 240

Asp His Arg Pro Gly Glu Tyr Ser Glu Leu Val Val Lys Ala Lys Glu
                245                 250                 255

Ser Phe Arg Arg Gly Asp Leu Phe Glu Val Val Pro Gly Gln Lys Phe
```

```
            260                 265                 270

Met Glu Arg Cys Glu Ser Asn Pro Ser Ala Ile Ser Arg Arg Leu Lys
        275                 280                 285

Ala Ile Asn Pro Ser Pro Tyr Ser Phe Phe Ile Asn Leu Gly Asp Gln
    290                 295                 300

Glu Tyr Leu Val Gly Ala Ser Pro Glu Met Phe Val Arg Val Ser Gly
305                 310                 315                 320

Arg Arg Ile Glu Thr Cys Pro Ile Ser Gly Thr Ile Lys Arg Gly Asp
                325                 330                 335

Asp Pro Ile Ala Asp Ser Glu Gln Ile Leu Lys Leu Leu Asn Ser Lys
            340                 345                 350

Lys Asp Glu Ser Glu Leu Thr Met Cys Ser Asp Val Asp Arg Asn Asp
        355                 360                 365

Lys Ser Arg Val Cys Glu Pro Gly Ser Val Lys Val Ile Gly Arg Arg
    370                 375                 380

Gln Ile Glu Met Tyr Ser Arg Leu Ile His Thr Val Asp His Ile Glu
385                 390                 395                 400

Gly Arg Leu Arg Asp Asp Met Asp Ala Phe Asp Gly Phe Leu Ser His
                405                 410                 415

Ala Trp Ala Val Thr Val Thr Gly Ala Pro Lys Leu Trp Ala Met Arg
            420                 425                 430

Phe Ile Glu Gly His Glu Lys Ser Pro Arg Ala Trp Tyr Gly Gly Ala
        435                 440                 445

Ile Gly Met Val Gly Phe Asn Gly Asp Met Asn Thr Gly Leu Thr Leu
    450                 455                 460

Arg Thr Ile Arg Ile Lys Asp Gly Ile Ala Glu Val Arg Ala Gly Ala
465                 470                 475                 480

Thr Leu Leu Asn Asp Ser Asn Pro Gln Glu Glu Glu Ala Glu Thr Glu
                485                 490                 495

Leu Lys Ala Ser Ala Met Ile Ser Ala Ile Arg Asp Ala Lys Gly Thr
            500                 505                 510

Asn Ser Ala Ala Thr Lys Arg Asp Ala Ala Lys Val Gly Thr Gly Val
        515                 520                 525

Lys Ile Leu Leu Val Asp His Glu Asp Ser Phe Val His Thr Leu Ala
    530                 535                 540

Asn Tyr Phe Arg Gln Thr Gly Ala Thr Val Ser Thr Val Arg Ser Pro
545                 550                 555                 560

Val Ala Ala Asp Val Phe Asp Arg Phe Gln Pro Asp Leu Val Val Leu
                565                 570                 575

Ser Pro Gly Pro Gly Ser Pro Thr Asp Phe Asp Cys Lys Ala Thr Ile
            580                 585                 590

Lys Ala Ala Arg Ala Arg Asp Leu Pro Ile Phe Gly Val Cys Leu Gly
        595                 600                 605

Leu Gln Ala Leu Ala Glu Ala Tyr Gly Gly Glu Leu Arg Gln Leu Ala
    610                 615                 620

Val Pro Met His Gly Lys Pro Ser Arg Ile Arg Val Leu Glu Pro Gly
625                 630                 635                 640

Leu Val Phe Ser Gly Leu Gly Lys Glu Val Thr Val Gly Arg Tyr His
                645                 650                 655

Ser Ile Phe Ala Asp Pro Ala Thr Leu Pro Arg Asp Phe Ile Ile Thr
            660                 665                 670

Ala Glu Ser Glu Asp Gly Thr Ile Met Gly Ile Glu His Ala Lys Glu
        675                 680                 685
```

```
Pro Val Ala Ala Val Gln Phe His Pro Glu Ser Ile Met Thr Leu Gly
    690                 695                 700

Gln Asp Ala Gly Met Arg Met Ile Glu Asn Val Val Val His Leu Thr
705                 710                 715                 720

Arg Lys Ala Lys Thr Lys Ala Ala
                725


<210> SEQ ID NO 205
<211> LENGTH: 2190
<212> TYPE: DNA
<213> ORGANISM: Agrobacterium tumefaciens

<400> SEQUENCE: 205

atggtaacga tcattcagga tgacggagcg gagacctacg agacgaaagg cggcatccag      60

gtcagccgaa agcgccggcc caccgattat gccaacgcca tcgataatta catcgaaaag     120

cttgattccc atcgcggcgc ggtttttttcg tgcaactatg aatatccggg ccgttacacc    180

cgctgggata cggccatcgt cgatccgccg ctcggcattt cctgttttgg ccgcaagatg     240

tggatcgaag cctataatgg ccgcggcgaa gtgctgctcg atttcattac ggaaaagctg     300

aaggcgacac ccgatctcac cctcggcgct tcctcgaccc gccggctcga tcttaccgtc     360

aacgaaccgg accgtgtctt caccgaagaa gaacgctcga aaatcccgac ggtcttcacc     420

gctctcagag ccatcgtcga cctcttctat tcgagcgcgg attcggccat cggcctgttc     480

ggtgccttcg gttacgatct cgccttccag ttcgacgcga tcaagctttc gctggcgcgt     540

ccggaagacc agcgtgacat ggtgctgttt ctgcccgatg aaatcctcgt cgttgatcac     600

tattccgcca aggcctggat cgaccgttac gatttcgaga aggacggcat gacgacggac     660

ggcaaatcct ccgacattac ccccgatccc ttcaagacca ccgataccat cccgcccaag     720

ggcgatcacc gtcccggcga atattccgag cttgtggtga aggccaagga aagcttccgc     780

cgcggcgacc tgttcgaggt cgttcccggc cagaaattca tggagcgttg cgaaagcaat     840

ccgtcggcga tttcccgccg cctgaaggcg atcaacccgt cgccctattc cttcttcatc     900

aatctcggcg atcaggaata tctggtcggc gcctcgccgg aaatgttcgt gcgcgtctcc     960

ggccgtcgca tcgagacctg cccgatatca ggcaccatca agcgcggcga cgatccgatt    1020

gccgacagcg agcagatttt gaaactgctc aactcgaaaa aggacgaatc cgaactgacc    1080

atgtgctcgg acgtggaccg caacgacaag agccgcgtct gcgagccggg ttcggtgaag    1140

gtcattggcc gccgccagat cgagatgtat tcacgcctca tccacaccgt cgatcacatc    1200

gaaggccgcc tgcgcgacga tatggacgcc tttgacggtt tcctcagcca cgcctgggcc    1260

gtcaccgtca ccggtgcacc aaagctgtgg gccatgcgct tcatcgaagg tcatgaaaag    1320

agcccgcgcg cctggtatgg cggtgcgatc ggcatggtcg gcttcaacgg cgacatgaat    1380

accggcctga cgctgcgcac catccggatc aaggacggta ttgccgaagt gcgcgccggc    1440

gcgaccctgc tcaatgattc caacccgcag gaagaagaag ccgaaaccga actgaaggcc    1500

tccgccatga tatcagccat tcgtgacgca aaaggcacca actctgccgc caccaagcgt    1560

gatgccgcca aagtcggcac cggcgtcaag atcctgctcg tcgaccacga agacagcttc    1620

gtgcacacgc tggcgaatta tttccgccag acgggcgcga cggtctcgac cgtcagatca    1680

ccggtcgcag ccgacgtgtt cgatcgcttc cagccggacc tcgttgtcct gtcgcccgga    1740

cccggcagcc cgacggattt cgactgcaag gcaacgatca aggccgcccg cgcccgcgat    1800

ctgccgatct tcggcgtttg cctcggtctg caggcattgg cagaagccta tggcggcgag    1860
```

```
ctgcgccagc ttgctgtgcc catgcacggc aagccttcgc gcatccgcgt gctggaaccc   1920

ggcctcgtct tctccggtct cggcaaggaa gtcacggtcg gtcgttacca ttcgatcttc   1980

gccgatcccg ccaccctgcc gcgtgatttc atcatcaccg cagaaagcga ggacggcacg   2040

atcatgggca tcgaacacgc caaggaaccg gtggccgccg ttcagttcca cccggaatcg   2100

atcatgacgc tcggacagga cgcgggcatg cggatgatcg agaatgtcgt ggtgcatctg   2160

acccgcaagg cgaagaccaa ggccgcgtga                                    2190


<210> SEQ ID NO 206
<211> LENGTH: 729
<212> TYPE: PRT
<213> ORGANISM: Agrobacterium tumefaciens

<400> SEQUENCE: 206

Met Val Thr Ile Ile Gln Asp Asp Gly Ala Glu Thr Tyr Glu Thr Lys
1               5                   10                  15

Gly Gly Ile Gln Val Ser Arg Lys Arg Arg Pro Thr Asp Tyr Ala Asn
            20                  25                  30

Ala Ile Asp Asn Tyr Ile Glu Lys Leu Asp Ser His Arg Gly Ala Val
        35                  40                  45

Phe Ser Cys Asn Tyr Glu Tyr Pro Gly Arg Tyr Thr Arg Trp Asp Thr
    50                  55                  60

Ala Ile Val Asp Pro Pro Leu Gly Ile Ser Cys Phe Gly Arg Lys Met
65                  70                  75                  80

Trp Ile Glu Ala Tyr Asn Gly Arg Gly Glu Val Leu Leu Asp Phe Ile
                85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
        115                 120                 125

Glu Glu Glu Arg Ser Lys Ile Pro Thr Val Phe Thr Ala Leu Arg Ala
    130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
            180                 185                 190

Asp Glu Ile Leu Val Val Asp His Tyr Ser Ala Lys Ala Trp Ile Asp
        195                 200                 205

Arg Tyr Asp Phe Glu Lys Asp Gly Met Thr Thr Asp Gly Lys Ser Ser
    210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
            260                 265                 270

Phe Met Glu Arg Cys Glu Ser Asn Pro Ser Ala Ile Ser Arg Arg Leu
        275                 280                 285

Lys Ala Ile Asn Pro Ser Pro Tyr Ser Phe Phe Ile Asn Leu Gly Asp
    290                 295                 300

Gln Glu Tyr Leu Val Gly Ala Ser Pro Glu Met Phe Val Arg Val Ser
```

-continued

```
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Glu Pro Gly Ser Val Lys Val Ile Gly Arg
    370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
        435                 440                 445

Ala Ile Gly Met Val Gly Phe Asn Gly Asp Met Asn Thr Gly Leu Thr
    450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Glu Ala Glu Thr
                485                 490                 495

Glu Leu Lys Ala Ser Ala Met Ile Ser Ala Ile Arg Asp Ala Lys Gly
            500                 505                 510

Thr Asn Ser Ala Ala Thr Lys Arg Asp Ala Ala Lys Val Gly Thr Gly
        515                 520                 525

Val Lys Ile Leu Leu Val Asp His Glu Asp Ser Phe Val His Thr Leu
    530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
            580                 585                 590

Ile Lys Ala Ala Arg Ala Arg Asp Leu Pro Ile Phe Gly Val Cys Leu
        595                 600                 605

Gly Leu Gln Ala Leu Ala Glu Ala Tyr Gly Gly Glu Leu Arg Gln Leu
    610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
            660                 665                 670

Thr Ala Glu Ser Glu Asp Gly Thr Ile Met Gly Ile Glu His Ala Lys
        675                 680                 685

Glu Pro Val Ala Ala Val Gln Phe His Pro Glu Ser Ile Met Thr Leu
    690                 695                 700

Gly Gln Asp Ala Gly Met Arg Met Ile Glu Asn Val Val Val His Leu
705                 710                 715                 720

Thr Arg Lys Ala Lys Thr Lys Ala Ala
                725
```

<210> SEQ ID NO 207
<211> LENGTH: 2190
<212> TYPE: DNA
<213> ORGANISM: Artificial Sequence
<220> FEATURE:
<223> OTHER INFORMATION: codon-optimized S51C allele from Agrobacterium tumefaciens anthranilate synthase

<400> SEQUENCE: 207
atggtgacca tcattcagga cgacggcgct gagacctacg agactaaggg cggtatccaa 60
gtgagccgta agcgtaggcc cactgactac gctaacgcca tcgacaacta catcgagaag 120
ctagactccc atcgcggcgc tgtgttctcc tgcaactacg aataccctgg gcgctacacg 180
aggtgggata ccgccatcgt cgatcctcca ttgggcatct cctgttttgg gcgtaagatg 240
tggatcgagg cgtacaacgg ccgtggcgaa gtcttgctgg acttcatcac ggagaagctc 300
aaggccacac cggacctcac cctcggcgct tcctcgaccc gccgcctcga ccttacggtc 360
aacgagccgg accgcgtgtt caccgaggaa gagcgtagca agatcccgac tgtcttcacc 420
gcgctcagag ccatcgtgga cctattctac tcttctgcgg acagcgccat cgggttgttc 480
ggtgccttcg gttacgacct cgcgttccag ttcgacgcca tcaagctctc gctcgcgcgg 540
ccggaggacc agcgagacat ggtgctcttc ctccctgacg agatcctggt cgtcgatcac 600
tattccgcga aggcgtggat cgaccggtac gacttcgaga aggatggcat gaccacggat 660
ggcaagagca gcgacatcac tcccgaccca ttcaagacca ccgacaccat ccctccaaag 720
ggcgatcacc gccctggcga gtattccgaa ctcgtggtga aggccaagga atccttccgg 780
cgcggcgatc tgtttgaggt ggttcccggc caaaagttca tggagaggtg cgagtcgaat 840
ccgtctgcga tcagtcgccg actgaaagcg atcaacccga gcccgtattc cttcttcatc 900
aacctcggcg atcaggaata tctggtcgga gcctcacccg agatgttcgt caggtctcc 960 ggccgccgga tcgagacgtg cccaatttcc ggaaccatca agcgcggaga tgacccgata 1020
gccgactctg agcagatcct gaaactcttg aacagcaaga aggacgagtc cgagctgact 1080
atgtgctcag atgtggaccg aaacgacaag tcacgtgtct gcgagcccgg tagcgtcaag 1140
gtcattggcc gccgtcagat cgagatgtac tccaggctga ttcacacggt cgatcatatc 1200
gaagggcggc tgcgcgacga tatggacgca ttcgacgggt tcctcagtca cgcctgggcc 1260
gttactgtca ccggagcgcc taagctctgg gctatgaggt tcatcgaggg ccacgagaag 1320
agccctaggg cttggtatgg tggtgccatc ggcatggttg ggttcaacgg cgacatgaac 1380
accgggctga cgctccggac catcaggatc aaagacggca ttgccgaggt gagggccggt 1440
gccacgcttc tcaacgatag caaccctcag gaggaagagg cggagaccga gctgaaagcc 1500
tctgcgatga tctccgcgat tagagatgca aagggtacga acagtgctgc caccaagcgg 1560
gacgcagcca aggtgggcac cggcgtcaag attttacttg tcgatcacga ggactccttc 1620
gtgcacactc tggcgaacta cttccgccag acaggcgcga cggtctccac cgttaggtca 1680
ccggtggccg ctgacgtgtt cgataggttc cagcccgacc ttgtggtgct ctctcccggt 1740
cccggctcgc ccacggactt cgactgcaag gccaccatta aggccgccag ggccagggat 1800
ctgccaatct tcggcgtttg cctcgggctt caggcattgg ccgaggcata cggtggagag 1860
ctgaggcagc tcgccgtccc gatgcacggg aagccatccc gcatcagagt cctggagccc 1920
ggcctcgtct tctccggtct cgggaaggag gtcacggtcg gtcggtatca ttcgatcttc 1980
gccgatccgg caaccctccc gcgcgacttc atcataaccg ccgagtcgga ggacggaacg 2040
atcatgggaa tcgaacacgc caaggagccc gtagctgcgg ttcagttcca ccctgagtcc 2100
atcatgaccc tcggtcaaga tgcgggtatg cggatgatcg agaatgtggt ggttcacctc 2160
acccgcaagg ccaagaccaa ggcagcatga 2190

<210> SEQ ID NO 208
<211> LENGTH: 729
<212> TYPE: PRT
<213> ORGANISM: Artificial Sequence
<220> FEATURE:
<223> OTHER INFORMATION: codon-optimized S51C allele from Agrobacterium tumefaciens anthranilate synthase

<400> SEQUENCE: 208

Met Val Thr Ile Ile Gln Asp Asp Gly Ala Glu Thr Tyr Glu Thr Lys
1 5 10 15

Gly Gly Ile Gln Val Ser Arg Lys Arg Arg Pro Thr Asp Tyr Ala Asn
20 25 30

Ala Ile Asp Asn Tyr Ile Glu Lys Leu Asp Ser His Arg Gly Ala Val
35 40 45

Phe Ser Cys Asn Tyr Glu Tyr Pro Gly Arg Tyr Thr Arg Trp Asp Thr
50 55 60

Ala Ile Val Asp Pro Pro Leu Gly Ile Ser Cys Phe Gly Arg Lys Met
65 70 75 80

Trp Ile Glu Ala Tyr Asn Gly Arg Gly Glu Val Leu Leu Asp Phe Ile
85 90 95

Thr Glu Lys Leu Lys Ala Thr Pro Asp Leu Thr Leu Gly Ala Ser Ser
100 105 110

Thr Arg Arg Leu Asp Leu Thr Val Asn Glu Pro Asp Arg Val Phe Thr
115 120 125

Glu Glu Glu Arg Ser Lys Ile Pro Thr Val Phe Thr Ala Leu Arg Ala
130 135 140

Ile Val Asp Leu Phe Tyr Ser Ser Ala Asp Ser Ala Ile Gly Leu Phe
145 150 155 160

Gly Ala Phe Gly Tyr Asp Leu Ala Phe Gln Phe Asp Ala Ile Lys Leu
165 170 175

Ser Leu Ala Arg Pro Glu Asp Gln Arg Asp Met Val Leu Phe Leu Pro
180 185 190

Asp Glu Ile Leu Val Val Asp His Tyr Ser Ala Lys Ala Trp Ile Asp
195 200 205

Arg Tyr Asp Phe Glu Lys Asp Gly Met Thr Thr Asp Gly Lys Ser Ser
210 215 220

Asp Ile Thr Pro Asp Pro Phe Lys Thr Thr Asp Thr Ile Pro Pro Lys
225 230 235 240

Gly Asp His Arg Pro Gly Glu Tyr Ser Glu Leu Val Val Lys Ala Lys
245 250 255

Glu Ser Phe Arg Arg Gly Asp Leu Phe Glu Val Val Pro Gly Gln Lys
260 265 270

Phe Met Glu Arg Cys Glu Ser Asn Pro Ser Ala Ile Ser Arg Arg Leu
275 280 285

Lys Ala Ile Asn Pro Ser Pro Tyr Ser Phe Phe Ile Asn Leu Gly Asp
290 295 300

Gln Glu Tyr Leu Val Gly Ala Ser Pro Glu Met Phe Val Arg Val Ser
305 310 315 320

Gly Arg Arg Ile Glu Thr Cys Pro Ile Ser Gly Thr Ile Lys Arg Gly

```
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Glu Pro Gly Ser Val Lys Val Ile Gly Arg
    370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
        435                 440                 445

Ala Ile Gly Met Val Gly Phe Asn Gly Asp Met Asn Thr Gly Leu Thr
    450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Glu Ala Glu Thr
                485                 490                 495

Glu Leu Lys Ala Ser Ala Met Ile Ser Ala Ile Arg Asp Ala Lys Gly
            500                 505                 510

Thr Asn Ser Ala Ala Thr Lys Arg Asp Ala Ala Lys Val Gly Thr Gly
        515                 520                 525

Val Lys Ile Leu Leu Val Asp His Glu Asp Ser Phe Val His Thr Leu
    530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
            580                 585                 590

Ile Lys Ala Ala Arg Ala Arg Asp Leu Pro Ile Phe Gly Val Cys Leu
        595                 600                 605

Gly Leu Gln Ala Leu Ala Glu Ala Tyr Gly Gly Glu Leu Arg Gln Leu
    610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
            660                 665                 670

Thr Ala Glu Ser Glu Asp Gly Thr Ile Met Gly Ile Glu His Ala Lys
        675                 680                 685

Glu Pro Val Ala Ala Val Gln Phe His Pro Glu Ser Ile Met Thr Leu
    690                 695                 700

Gly Gln Asp Ala Gly Met Arg Met Ile Glu Asn Val Val Val His Leu
705                 710                 715                 720

Thr Arg Lys Ala Lys Thr Lys Ala Ala
                725
```

<210> SEQ ID NO 209

<211> LENGTH: 2191
<212> TYPE: DNA
<213> ORGANISM: Sinorhizobium meliloti

<400> SEQUENCE: 209

```
atggcagcgg taattctgga agacggcgcg gagagttata ccacgaaggg tggcatcgtc     60
gtcacccgca ggcggcgtga ggcatcctac agcgacgcga tcgccggtta tgtcgaccgg    120
ctggacgaac gccgcggcgc ggtcttttcc tcgaactacg aatatcccgg ccgctatacc    180
cgctgggaca ctgcggtggt cgacccgccg cttgccatct cctccttcgg tcgctcgctc    240
tggatcgaag cctataacga acgcggcgaa gtgctgctgg cgctgatcgc cgaggatctg    300
aagtccgttg ccgacatcac gctcggctca cttgccgccc gccgcctcga cctcaccatc    360
aacgagcccg atcgtgtctt caccgaggaa gagcggtcga agatgccgac ggtctttacg    420
gttcttcgcg cggtgacgaa cctcttccac tcggaggagg actcgaacct cggcctctat    480
ggcgccttcg gctacgacct cgccttccag ttcgatgcga tcgaactgaa gctttcgcgt    540
ccggacgacc agcgcgacat ggttctcttt ctgccggacg agatccttgt ggtcgatcac    600
tatgcggcca aggcctggat cgaccgctac gatttcgcca gggagaacct ttcgaccgag    660
ggcaaggcag cggacattgc tcccgagccg ttccgcagcg tcgacagcat cccgccgcac    720
ggggatcacc gcccgggcga atatgccgag ctcgtcgtca aggcgaagga aagcttccgt    780
cgcggcgatc ttttcgaagt ggtgccgggg cagaaattct acgagcgctg cgaaagccgc    840
ccgtccgaga tttccaaccg gctgaaggcg atcaatccgt cgccctattc cttcttcatc    900
aatctcggca accaggaata tctcgtcggt gcttcgccgg agatgttcgt gcgcgtttcc    960
ggccggcgca tcgagacctg cccgatctcc ggtacgatca agcgcggcga cgatccgatc   1020
gccgacagcg agcagatcct gaagctcttg aactcgaaga aggacgagtc cgagctcacc   1080
atgtgctcgg acgtcgaccg caacgacaag agccgggtct gcgtgccggg ctcggtcaag   1140
gtgatcggcc ggcgtcagat cgagatgtat tcgcggctga tccacacggt cgatcacatc   1200
gaggggcgcc tgcgcgacga tatggacgcc ttcgacgggt tcctcagcca cgcctgggcg   1260
gtgaccgtta ccggcgcgcc aaagctctgg gccatgcgct tcatcgagag ccacgagaag   1320
agcccgcgtg cctggtatgg cggcgcgatc ggcatggtcg gcttcaacgg cgacatgaat   1380
accgggctga ccttgcgtac catccgcatc aaggacggga tcgccgaggt gagggcgggt   1440
gcgacgctcc tctatgattc caatccggaa gaagaagaag ccgaaaccga actgaaggcc   1500
tctgccatga ttgcagccat ccgcgacgcg aaatccgcaa acagcgccaa atccgcgcgc   1560
gatgtcgccg ccgtcggcgc cggagtcagc atcctgctcg tcgatcacga ggacagcttc   1620
gtccataccc tcgcgaacta cttccgccag accggcgcgt ccgtcaccac cgtgcgcacg   1680
ccggtggccg aggaaatctt cgaccgggtc aagccggacc tcgtcgtgct ttcgcccggt   1740
cccggcaccc cgaaggactt cgactgcaag gcgacgatca agaaggcgcg ggcgcgggac   1800
ctgccgatct tcggcgtctg cctggggctg caggcgctcg cggaggccta tggcggcgac   1860
cttcgtcaac tggcgatccc gatgcatggg aagccctcgc gcatccgcgt gctcgaaccc   1920
ggcatcgtct tctccggcct cggcaaggag gtgacggtcg ggcgctatca ttcgattttc   1980
gccgatccgt ccaacctgcc gcgcgaattc gtgatcacgg ccgaaagcga agatggtacg   2040
atcatgggca tcgaacacag caaggagccg gtggcggccg tgcagttcca tccggaatcg   2100
atcatgacgc tgggcggcga cgccggcatg cggatgatcg agaacgtggt tgcccatctc   2160
gccaagcggg cgaagaccaa ggcagcctga a                                  2191
```

<210> SEQ ID NO 210
<211> LENGTH: 729
<212> TYPE: PRT
<213> ORGANISM: Sinorhizobium meliloti

<400> SEQUENCE: 210

```
Met Ala Ala Val Ile Leu Glu Asp Gly Ala Glu Ser Tyr Thr Thr Lys
1               5                   10                  15

Gly Gly Ile Val Val Thr Arg Arg Arg Arg Glu Ala Ser Tyr Ser Asp
            20                  25                  30

Ala Ile Ala Gly Tyr Val Asp Arg Leu Asp Glu Arg Arg Gly Ala Val
        35                  40                  45

Phe Ser Ser Asn Tyr Glu Tyr Pro Gly Arg Tyr Thr Arg Trp Asp Thr
    50                  55                  60

Ala Val Val Asp Pro Pro Leu Ala Ile Ser Ser Phe Gly Arg Ser Leu
65                  70                  75                  80

Trp Ile Glu Ala Tyr Asn Glu Arg Gly Glu Val Leu Leu Ala Leu Ile
                85                  90                  95

Ala Glu Asp Leu Lys Ser Val Ala Asp Ile Thr Leu Gly Ser Leu Ala
            100                 105                 110

Ala Arg Arg Leu Asp Leu Thr Ile Asn Glu Pro Asp Arg Val Phe Thr
        115                 120                 125

Glu Glu Glu Arg Ser Lys Met Pro Thr Val Phe Thr Val Leu Arg Ala
    130                 135                 140

Val Thr Asn Leu Phe His Ser Glu Glu Asp Ser Asn Leu Gly Leu Tyr
145                 150                 155                 160

Gly Ala Phe Gly Tyr Asp Leu Ala Phe Gln Phe Asp Ala Ile Glu Leu
                165                 170                 175

Lys Leu Ser Arg Pro Asp Asp Gln Arg Asp Met Val Leu Phe Leu Pro
            180                 185                 190

Asp Glu Ile Leu Val Val Asp His Tyr Ala Ala Lys Ala Trp Ile Asp
        195                 200                 205

Arg Tyr Asp Phe Ala Arg Glu Asn Leu Ser Thr Glu Gly Lys Ala Ala
    210                 215                 220

Asp Ile Ala Pro Glu Pro Phe Arg Ser Val Asp Ser Ile Pro Pro His
225                 230                 235                 240

Gly Asp His Arg Pro Gly Glu Tyr Ala Glu Leu Val Val Lys Ala Lys
                245                 250                 255

Glu Ser Phe Arg Arg Gly Asp Leu Phe Glu Val Val Pro Gly Gln Lys
            260                 265                 270

Phe Tyr Glu Arg Cys Glu Ser Arg Pro Ser Glu Ile Ser Asn Arg Leu
        275                 280                 285

Lys Ala Ile Asn Pro Ser Pro Tyr Ser Phe Phe Ile Asn Leu Gly Asn
    290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Val Pro Gly Ser Val Lys Val Ile Gly Arg
```

```
    370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Ser His Glu Lys Ser Pro Arg Ala Trp Tyr Gly Gly
        435                 440                 445

Ala Ile Gly Met Val Gly Phe Asn Gly Asp Met Asn Thr Gly Leu Thr
    450                 455                 460

Leu Arg Thr Ile Arg Ile Lys Asp Gly Ile Ala Glu Val Arg Ala Gly
465                 470                 475                 480

Ala Thr Leu Leu Tyr Asp Ser Asn Pro Glu Glu Glu Glu Ala Glu Thr
                485                 490                 495

Glu Leu Lys Ala Ser Ala Met Ile Ala Ala Ile Arg Asp Ala Lys Ser
            500                 505                 510

Ala Asn Ser Ala Lys Ser Ala Arg Asp Val Ala Ala Val Gly Ala Gly
        515                 520                 525

Val Ser Ile Leu Leu Val Asp His Glu Asp Ser Phe Val His Thr Leu
    530                 535                 540

Ala Asn Tyr Phe Arg Gln Thr Gly Ala Ser Val Thr Thr Val Arg Thr
545                 550                 555                 560

Pro Val Ala Glu Glu Ile Phe Asp Arg Val Lys Pro Asp Leu Val Val
                565                 570                 575

Leu Ser Pro Gly Pro Gly Thr Pro Lys Asp Phe Asp Cys Lys Ala Thr
            580                 585                 590

Ile Lys Lys Ala Arg Ala Arg Asp Leu Pro Ile Phe Gly Val Cys Leu
        595                 600                 605

Gly Leu Gln Ala Leu Ala Glu Ala Tyr Gly Gly Asp Leu Arg Gln Leu
    610                 615                 620

Ala Ile Pro Met His Gly Lys Pro Ser Arg Ile Arg Val Leu Glu Pro
625                 630                 635                 640

Gly Ile Val Phe Ser Gly Leu Gly Lys Glu Val Thr Val Gly Arg Tyr
                645                 650                 655

His Ser Ile Phe Ala Asp Pro Ser Asn Leu Pro Arg Glu Phe Val Ile
            660                 665                 670

Thr Ala Glu Ser Glu Asp Gly Thr Ile Met Gly Ile Glu His Ser Lys
        675                 680                 685

Glu Pro Val Ala Ala Val Gln Phe His Pro Glu Ser Ile Met Thr Leu
    690                 695                 700

Gly Gly Asp Ala Gly Met Arg Met Ile Glu Asn Val Val Ala His Leu
705                 710                 715                 720

Ala Lys Arg Ala Lys Thr Lys Ala Ala
                725
```

<210> SEQ ID NO 211
<211> LENGTH: 2190
<212> TYPE: DNA
<213> ORGANISM: Sinorhizobium meliloti

<400> SEQUENCE: 211

```
atggcagcgg taattctgga agacggcgcg gagagttata ccacgaaggg tggcatcgtc      60

gtcacccgca ggcggcgtga ggcatcctac agcgacgcga tcgccggtta tgtcgaccgg     120
```

```
ctggacgaac gccgcggcgc ggtcttttcc tgcaactacg aatatcccgg ccgctatacc    180
cgctgggaca ctgcggtggt cgacccgccg cttgccatct cctccttcgg tcgctcgctc    240
tggatcgaag cctataacga acgcggcgaa gtgctgctgg cgctgatcgc cgaggatctg    300
aagtccgttg ccgacatcac gctcggctca cttgccgccc gccgcctcga cctcaccatc    360
aacgagcccg atcgtgtctt caccgaggaa gagcggtcga agatgccgac ggtctttacg    420
gttcttcgcg cggtgacgaa cctcttccac tcggaggagg actcgaacct cggcctctat    480
ggcgccttcg gctacgacct cgccttccag ttcgatgcga tcgaactgaa gctttcgcgt    540
ccggacgacc agcgcgacat ggttctcttt ctgccggacg agatccttgt ggtcgatcac    600
tatgcggcca aggcctggat cgaccgctac gatttcgcca gggagaacct ttcgaccgag    660
ggcaaggcag cggacattgc tcccgagccg ttccgcagcg tcgacagcat cccgccgcac    720
ggggatcacc gcccgggcga atatgccgag ctcgtcgtca aggcgaagga aagcttccgt    780
cgcggcgatc ttttcgaagt ggtgccgggg cagaaattct acgagcgctg cgaaagccgc    840
ccgtccgaga tttccaaccg gctgaaggcg atcaatccgt cgccctattc cttcttcatc    900
aatctcggca accaggaata tctcgtcggt gcttcgccgg agatgttcgt gcgcgtttcc    960
ggccggcgca tcgagacctg cccgatctcc ggtacgatca agcgcggcga cgatccgatc   1020
gccgacagcg agcagatcct gaagctcttg aactcgaaga aggacgagtc cgagctcacc   1080
atgtgctcgg acgtcgaccg caacgacaag agccgggtct gcgtgccggg ctcggtcaag   1140
gtgatcggcc ggcgtcagat cgagatgtat tcgcggctga tccacacggt cgatcacatc   1200
gaggggcgcc tgcgcgacga tatggacgcc ttcgacgggt tcctcagcca cgcctgggcg   1260
gtgaccgtta ccggcgcgcc aaagctctgg gccatgcgct tcatcgagag ccacgagaag   1320
agcccgcgtg cctggtatgg cggcgcgatc ggcatggtcg gcttcaacgg cgacatgaat   1380
accgggctga ccttgcgtac catccgcatc aaggacggga tcgccgaggt gagggcgggt   1440
gcgacgctcc tctatgattc caatccggaa gaagaagaag ccgaaaccga actgaaggcc   1500
tctgccatga ttgcagccat ccgcgacgcg aaatccgcaa acagcgccaa atccgcgcgc   1560
gatgtcgccg ccgtcggcgc cggagtcagc atcctgctcg tcgatcacga ggacagcttc   1620
gtccataccc tcgcgaacta cttccgccag accggcgcgt ccgtcaccac cgtgcgcacg   1680
ccggtggccg aggaaatctt cgaccgggtc aagccggacc tcgtcgtgct ttcgcccggt   1740
cccggcaccc cgaaggactt cgactgcaag gcgacgatca agaaggcgcg ggcgcgggac   1800
ctgccgatct tcggcgtctg cctggggctg caggcgctcg cggaggccta tggcggcgac   1860
cttcgtcaac tggcgatccc gatgcatggg aagccctcgc gcatccgcgt gctcgaaccc   1920
ggcatcgtct tctccggcct cggcaaggag gtgacggtcg ggcgctatca ttcgattttc   1980
gccgatccgt ccaacctgcc gcgcgaattc gtgatcacgg ccgaaagcga agatggtacg   2040
atcatgggca tcgaacacag caaggagccg gtggcggccg tgcagttcca tccggaatcg   2100
atcatgacgc tgggcggcga cgccggcatg cggatgatcg agaacgtggt tgcccatctc   2160
gccaagcggg cgaagaccaa ggcagcctga                                    2190
```

<210> SEQ ID NO 212
<211> LENGTH: 729
<212> TYPE: PRT
<213> ORGANISM: Sinorhizobium meliloti

<400> SEQUENCE: 212

```
Met Ala Ala Val Ile Leu Glu Asp Gly Ala Glu Ser Tyr Thr Thr Lys
1               5                   10                  15

Gly Gly Ile Val Val Thr Arg Arg Arg Arg Glu Ala Ser Tyr Ser Asp
            20                  25                  30

Ala Ile Ala Gly Tyr Val Asp Arg Leu Asp Glu Arg Arg Gly Ala Val
        35                  40                  45

Phe Ser Cys Asn Tyr Glu Tyr Pro Gly Arg Tyr Thr Arg Trp Asp Thr
    50                  55                  60

Ala Val Val Asp Pro Pro Leu Ala Ile Ser Ser Phe Gly Arg Ser Leu
65                  70                  75                  80

Trp Ile Glu Ala Tyr Asn Glu Arg Gly Glu Val Leu Leu Ala Leu Ile
                85                  90                  95

Ala Glu Asp Leu Lys Ser Val Ala Asp Ile Thr Leu Gly Ser Leu Ala
            100                 105                 110

Ala Arg Arg Leu Asp Leu Thr Ile Asn Glu Pro Asp Arg Val Phe Thr
        115                 120                 125

Glu Glu Glu Arg Ser Lys Met Pro Thr Val Phe Thr Val Leu Arg Ala
    130                 135                 140

Val Thr Asn Leu Phe His Ser Glu Glu Asp Ser Asn Leu Gly Leu Tyr
145                 150                 155                 160

Gly Ala Phe Gly Tyr Asp Leu Ala Phe Gln Phe Asp Ala Ile Glu Leu
                165                 170                 175

Lys Leu Ser Arg Pro Asp Asp Gln Arg Asp Met Val Leu Phe Leu Pro
            180                 185                 190

Asp Glu Ile Leu Val Val Asp His Tyr Ala Ala Lys Ala Trp Ile Asp
        195                 200                 205

Arg Tyr Asp Phe Ala Arg Glu Asn Leu Ser Thr Glu Gly Lys Ala Ala
    210                 215                 220

Asp Ile Ala Pro Glu Pro Phe Arg Ser Val Asp Ser Ile Pro Pro His
225                 230                 235                 240

Gly Asp His Arg Pro Gly Glu Tyr Ala Glu Leu Val Val Lys Ala Lys
                245                 250                 255

Glu Ser Phe Arg Arg Gly Asp Leu Phe Glu Val Val Pro Gly Gln Lys
            260                 265                 270

Phe Tyr Glu Arg Cys Glu Ser Arg Pro Ser Glu Ile Ser Asn Arg Leu
        275                 280                 285

Lys Ala Ile Asn Pro Ser Pro Tyr Ser Phe Phe Ile Asn Leu Gly Asn
    290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Val Pro Gly Ser Val Lys Val Ile Gly Arg
    370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
```

```
            420                 425                 430

Arg Phe Ile Glu Ser His Glu Lys Ser Pro Arg Ala Trp Tyr Gly Gly
        435                 440                 445

Ala Ile Gly Met Val Gly Phe Asn Gly Asp Met Asn Thr Gly Leu Thr
    450                 455                 460

Leu Arg Thr Ile Arg Ile Lys Asp Gly Ile Ala Glu Val Arg Ala Gly
465                 470                 475                 480

Ala Thr Leu Leu Tyr Asp Ser Asn Pro Glu Glu Glu Glu Ala Glu Thr
                485                 490                 495

Glu Leu Lys Ala Ser Ala Met Ile Ala Ala Ile Arg Asp Ala Lys Ser
            500                 505                 510

Ala Asn Ser Ala Lys Ser Ala Arg Asp Val Ala Ala Val Gly Ala Gly
        515                 520                 525

Val Ser Ile Leu Leu Val Asp His Glu Asp Ser Phe Val His Thr Leu
    530                 535                 540

Ala Asn Tyr Phe Arg Gln Thr Gly Ala Ser Val Thr Thr Val Arg Thr
545                 550                 555                 560

Pro Val Ala Glu Glu Ile Phe Asp Arg Val Lys Pro Asp Leu Val Val
                565                 570                 575

Leu Ser Pro Gly Pro Gly Thr Pro Lys Asp Phe Asp Cys Lys Ala Thr
            580                 585                 590

Ile Lys Lys Ala Arg Ala Arg Asp Leu Pro Ile Phe Gly Val Cys Leu
        595                 600                 605

Gly Leu Gln Ala Leu Ala Glu Ala Tyr Gly Gly Asp Leu Arg Gln Leu
    610                 615                 620

Ala Ile Pro Met His Gly Lys Pro Ser Arg Ile Arg Val Leu Glu Pro
625                 630                 635                 640

Gly Ile Val Phe Ser Gly Leu Gly Lys Glu Val Thr Val Gly Arg Tyr
                645                 650                 655

His Ser Ile Phe Ala Asp Pro Ser Asn Leu Pro Arg Glu Phe Val Ile
            660                 665                 670

Thr Ala Glu Ser Glu Asp Gly Thr Ile Met Gly Ile Glu His Ser Lys
        675                 680                 685

Glu Pro Val Ala Ala Val Gln Phe His Pro Glu Ser Ile Met Thr Leu
    690                 695                 700

Gly Gly Asp Ala Gly Met Arg Met Ile Glu Asn Val Val Ala His Leu
705                 710                 715                 720

Ala Lys Arg Ala Lys Thr Lys Ala Ala
                725


<210> SEQ ID NO 213
<211> LENGTH: 13596
<212> TYPE: DNA
<213> ORGANISM: Artificial Sequence
<220> FEATURE:
<223> OTHER INFORMATION: pMON68065;Figure 48; the expression vector for
      Zm-ASA2-CTP +18::AgroAS(S51C) mutant allele

<400> SEQUENCE: 213

gcgccaaatc gtgaagtttc tcatctaagc ccccatttgg acgtgaatgt agacacgtcg      60

aaataaagat ttccgaatta gaataatttg tttattgctt tcgcctataa atacgacgga     120

tcgtaatttg tcgttttatc aaaatgtact ttcattttat aataacgctg cggacatcta     180

catttttgaa ttgaaaaaaa attggtaatt actctttctt tttctccata ttgaccatca     240

tactcattgc tgatccatgt agatttcccg gacatgaagc catttacaat tgaatatatc     300
```

```
ctgccgccgc tgccgctttg cacccggtgg agcttgcatg ttggtttcta cgcagaactg    360
agccggttag gcagataatt tccattgaga actgagccat gtgcaccttc cccccaacac    420
ggtgagcgac ggggcaacgg agtgatccac atgggacttt tcctagcttg gctgccattt    480
ttggggtgag gccgttcgcg gccgaggggc gcagcccctg gggggatggg aggcccgcgt    540
tagcgggccg ggagggttcg agaagggggg gcacccccct tcggcgtgcg cggtcacgcg    600
cacagggcgc agccctggtt aaaaacaagg tttataaata ttggtttaaa agcaggttaa    660
aagacaggtt agcggtggcc gaaaaacggg cggaaaccct tgcaaatgct ggattttctg    720
cctgtggaca gcccctcaaa tgtcaatagg tgcgcccctc atctgtcagc actctgcccc    780
tcaagtgtca aggatcgcgc ccctcatctg tcagtagtcg cgcccctcaa gtgtcaatac    840
cgcagggcac ttatccccag gcttgtccac atcatctgtg ggaaactcgc gtaaaatcag    900
gcgttttcgc cgatttgcga ggctggccag ctccacgtcg ccggccgaaa tcgagcctgc    960
ccctcatctg tcaacgccgc gccgggtgag tcggcccctc aagtgtcaac gtccgcccct   1020
catctgtcag tgagggccaa gttttccgcg aggtatccac aacgccggcg gccggccgcg   1080
gtgtctcgca cacggcttcg acggcgtttc tggcgcgttt gcagggccat agacggccgc   1140
cagcccagcg gcgagggcaa ccagcccggt gagcgtcgga aagggtcgat cgaccgatgc   1200
ccttgagagc cttcaaccca gtcagctcct tccggtgggc gcggggcatg actatcgtcg   1260
ccgcacttat gactgtcttc tttatcatgc aactcgtagg acaggtgccg gcagcgctct   1320
gggtcatttt cggcgaggac cgctttcgct ggagcgcgac gatgatcggc ctgtcgcttg   1380
cggtattcgg aatcttgcac gccctcgctc aagccttcgt cactggtccc gccaccaaac   1440
gtttcggcga gaagcaggcc attatcgccg gcatggcggc cgacgcgctg ggctacgtct   1500
tgctggcgtt cgcgacgcga ggctggatgg ccttccccat tatgattctt ctcgcttccg   1560
gcggcatcgg gatgcccgcg ttgcaggcca tgctgtccag gcaggtagat gacgaccatc   1620
agggacagct tcaaggatcg ctcgcggctc ttaccagcct aacttcgatc attggaccgc   1680
tgatcgtcac ggcgatttat gccgcctcgg cgagcacatg gaacgggttg gcatggattg   1740
taggcgccgc cctatacctt gtctgcctcc ccgcgttgcg tcgcggtgca tggagccggg   1800
ccacctcgac ctgaatggaa gccggcggca cctcgctaac ggattcacca ctccaagaat   1860
tggagccaat caattcttgc ggagaactgt gaatgcgcaa accaaccctt ggcagaacat   1920
atccatcgcg tccgccatct ccagcagccg cacgcggcgc atctcgggca gcgttgggtc   1980
ctggccacgg gtgcgcatga tcgtgctcct gtcgttgagg acccggctag gctggcgggg   2040
ttgccttact ggttagcaga atgaatcacc gatacgcgag cgaacgtgaa gcgactgctg   2100
ctgcaaaacg tctgcgacct gagcaacaac atgaatggtc ttcggtttcc gtgtttcgta   2160
aagtctggaa acgcggaagt cagcgccctg caccattatg ttccggatct gcatcgcagg   2220
atgctgctgg ctaccctgtg gaacacctac atctgtatta acgaagcgct ggcattgacc   2280
ctgagtgatt tttctctggt cccgccgcat ccataccgcc agttgtttac cctcacaacg   2340
ttccagtaac cgggcatgtt catcatcagt aacccgtatc gtgagcatcc tctctcgttt   2400
catcggtatc attaccccca tgaacagaaa tcccccttac acggaggcat cagtgaccaa   2460
acaggaaaaa accgccctta acatggcccg ctttatcaga agccagacat taacgcttct   2520
ggagaaactc aacgagctgg acgcggatga acaggcagac atctgtgaat cgcttcacga   2580
ccacgctgat gagctttacc gcagctgcct cgcgcgtttc ggtgatgacg gtgaaaacct   2640
```

-continued

```
ctgacacatg cagctcccgg agacggtcac agcttgtctg taagcggatg ccgggagcag   2700
acaagcccgt cagggcgcgt cagcgggtgt tggcgggtgt cggggcgcag ccatgaccca   2760
gtcacgtagc gatagcggag tgtatactgg cttaactatg cggcatcaga gcagattgta   2820
ctgagagtgc accatatgcg gtgtgaaata ccgcacagat gcgtaaggag aaaataccgc   2880
atcaggcgct cttccgcttc ctcgctcact gactcgctgc gctcggtcgt tcggctgcgg   2940
cgagcggtat cagctcactc aaaggcggta atacggttat ccacagaatc aggggataac   3000
gcaggaaaga acatgtgagc aaaaggccag caaaaggcca ggaaccgtaa aaaggccgcg   3060
ttgctggcgt ttttccatag gctccgcccc cctgacgagc atcacaaaaa tcgacgctca   3120
agtcagaggt ggcgaaaccc gacaggacta taaagatacc aggcgtttcc ccctggaagc   3180
tccctcgtgc gctctcctgt tccgaccctg ccgcttaccg gatacctgtc cgcctttctc   3240
ccttcgggaa gcgtggcgct ttctcatagc tcacgctgta ggtatctcag ttcggtgtag   3300
gtcgttcgct ccaagctggg ctgtgtgcac gaaccccccg ttcagcccga ccgctgcgcc   3360
ttatccggta actatcgtct tgagtccaac ccggtaagac acgacttatc gccactggca   3420
gcagccactg gtaacaggat tagcagagcg aggtatgtag gcggtgctac agagttcttg   3480
aagtggtggc ctaactacgg ctacactaga aggacagtat ttggtatctg cgctctgctg   3540
aagccagtta ccttcggaaa aagagttggt agctcttgat ccggcaaaca aaccaccgct   3600
ggtagcggtg gtttttttgt ttgcaagcag cagattacgc gcagaaaaaa aggatctcaa   3660
gaagatcctt tgatcttttc tacggggtct gacgctcagt ggaacgaaaa ctcacgttaa   3720
gggattttgg tcatgagatt atcaaaaagg atcttcacct agatcctttt aaattaaaaa   3780
tgaagtttta aatcaatcta aagtatatat gagtaaactt ggtctgacag ttaccaatgc   3840
ttaatcagtg aggcacctat ctcagcgatc tgtctatttc gttcatccat agttgcctga   3900
ctccccgtcg tgtagataac tacgatacgg gagggcttac catctggccc cagtgctgca   3960
atgataccgc gagacccacg ctcaccggct ccagatttat cagcaataaa ccagccagcc   4020
ggaagggccg agcgcagaag tggtcctgca actttatccg cctccatcca gtctattaat   4080
tgttgccggg aagctagagt aagtagttcg ccagttaata gtttgcgcaa cgttgttgcc   4140
attgctgcag gtcgggagca caggatgacg cctaacaatt cattcaagcc gacaccgctt   4200
cgcggcgcgg cttaattcag gagttaaaca tcatgaggga agcggtgatc gccgaagtat   4260
cgactcaact atcagaggta gttggcgtca tcgagcgcca tctcgaaccg acgttgctgg   4320
ccgtacattt gtacggctcc gcagtggatg gcggcctgaa gccacacagt gatattgatt   4380
tgctggttac ggtgaccgta aggcttgatg aaacaacgcg gcgagctttg atcaacgacc   4440
ttttggaaac ttcggcttcc cctggagaga gcgagattct ccgcgctgta gaagtcacca   4500
ttgttgtgca cgacgacatc attccgtggc gttatccagc taagcgcgaa ctgcaatttg   4560
gagaatggca gcgcaatgac attcttgcag gtatcttcga gccagccacg atcgacattg   4620
atctggctat cttgctgaca aaagcaagag aacatagcgt tgccttggta ggtccagcgg   4680
cggaggaact ctttgatccg gttcctgaac aggatctatt tgaggcgcta aatgaaacct   4740
taacgctatg gaactcgccg cccgactggg ctggcgatga gcgaaatgta gtgcttacgt   4800
tgtcccgcat ttggtacagc gcagtaaccg gcaaaatcgc gccgaaggat gtcgctgccg   4860
actgggcaat ggagcgcctg ccggcccagt atcagcccgt catacttgaa gctaggcagg   4920
cttatcttgg acaagaagat cgcttggcct cgcgcgcaga tcagttggaa gaatttgttc   4980
actacgtgaa aggcgagatc accaaggtag tcggcaaata atgtctaaca attcgttcaa   5040
```

-continued

```
gccgacgccg cttcgcggcg cggcttaact caagcgttag atgctgcagg catcgtggtg   5100
tcacgctcgt cgtttggtat ggcttcattc agctccggtt cccaacgatc aaggcgagtt   5160
acatgatccc ccatgttgtg caaaaaagcg gttagctcct tcggtcctcc gatcgaggat   5220
ttttcggcgc tgcgctacgt ccgcgaccgc gttgagggat caagccacag cagcccactc   5280
gaccttctag ccgacccaga cgagccaagg gatctttttg gaatgctgct ccgtcgtcag   5340
gctttccgac gtttgggtgg ttgaacagaa gtcattatcg cacggaatgc caagcactcc   5400
cgaggggaac cctgtggttg gcatgcacat acaaatggac gaacggataa accttttcac   5460
gcccttttaa atatccgatt attctaataa acgctctttt ctcttaggtt tacccgccaa   5520
tatatcctgt caaacactga tagtttaaac tgaaggcggg aaacgacaat ctgatcccca   5580
tcaagctagc ttctgcaggt cctgctcgag gtcactaagc aactaacttt gaggaatgag   5640
gtgatgatga attaactcac tccattccac aaaccaaaca aaaatttgag gagtgagaag   5700
atgattgact atctcattcc tcaaaccaaa cacctcaaat atatctgcta tcgggattgg   5760
cattcctgta tccctacgcc cgtgtacccc ctgtttagag aacctccaaa ggtataagat   5820
ggcgaagatt attgttgtct tgtctttcat catatatcga gtctttccct aggatattat   5880
tattggcaat gagcattaca cggttaatcg attgagagaa catgcatctc accttcagca   5940
aataattacg ataatccata ttttacgctt cgtaacttct catgagtttc gatatacaaa   6000
tttgttttct ggacacccta ccattcatcc tcttcggaga agagaggaag tgtcctcaat   6060
ttaaatatgt tgtcatgctg tagttcttca caaaatctca acaggtacca agcacattgt   6120
ttccacaaat tatattttag tcacaataaa tctatattat tattaatata ctaaaactat   6180
actgacgctc agatgctttt actagttctt gctagtatgt gatgtaggtc tacgtggacc   6240
agaaaatagt gagacacgga agacaaaaga agtaaaagag gcccggacta cggcccacat   6300
gagattcggc cccgccacct ccggcaacca gcggccgatc caacggcagt gcgcgcacac   6360
acacaacctc gtatatatcg ccgcgcggaa gcggcgcgac cgaggaagcc ttgtcctcga   6420
caccccctac acaggtgtcg cgctgccccc gacacgagtc ccgcatgcgt cccacgcggc   6480
cgcgccagat cccgcctccg cgcgttgcca cgccctctat aaacacccag ctctccctcg   6540
ccctcatcta cctcactcgt agtcgtagct caagcatcag cggcagcggc agcggcagga   6600
tctctgggca gcgtgcgcac gtggggtatc tagctcgctc tgctagccta ccaatcgaat   6660
tcctgcaggt cgactctaga ggatctaccg tcttcggtac gcgctcactc cgccctctgc   6720
ctttgttact gccacgtttc tctgaatgct ctcttgtgtg gtgattgctg agagtggttt   6780
agctggatct agaattacac tctgaaatcg tgttctgcct gtgctgatta cttgccgtcc   6840
tttgtagcag caaaatatag ggacatggta gtacgaaacg aagatagaac ctacacagca   6900
atacgagaaa tgtgtaattt ggtgcttagc ggtatttatt taagcacatg ttggtgttat   6960
agggcacttg gattcagaag tttgctgtta atttaggcac aggcttcata ctacatgggt   7020
caatagtata gggattcata ttataggcga tactataata atttgttcgt ctgcagagct   7080
tattatttgc caaaattaga tattcctatt ctgtttttgt ttgtgtgctg ttaaattgtt   7140
aacgcctgaa ggaataaata taaatgacga aattttgatg tttatctctg ctcctttatt   7200
gtgaccataa gtcaagatca gatgcacttg ttttaaatat tgttgtctga agaaataagt   7260
actgacagta ttttgatgca ttgatctgct tgtttgttgt aacaaaattt aaaaataaag   7320
agtttccttt ttgttgctct ccttacctcc tgatggtatc tagtatctac caactgacac   7380
```

```
tatattgctt ctctttacat acgtatcttg ctcgatgcct tctccctagt gttgaccagt   7440
gttactcaca tagtctttgc tcatttcatt gtaatgcaga taccaagcgg cctctagagg   7500
actccgatct atggaatccc tagccgccac ctccgtgttc gcgccctccc gcgtcgccgt   7560
cccggcggcg cgggccctgg ttagggcggg gacggtggta ccaaccaggc ggacgagcag   7620
ccggagcgga accagcgggg tgaaatgctc tgctgccgtg acgccgcagg cgagcccagt   7680
gattagcagg agcgctgcgg cggccatggt aacgatcatt caggatgacg gagcggagac   7740
ctacgagacg aaaggcggca tccaggtcag ccgaaagcgc cggcccaccg attatgccaa   7800
cgccatcgat aattacatcg aaaagcttga ttcccatcgc ggcgcggttt tttcgtgcaa   7860
ctatgaatat ccgggccgtt acacccgctg ggatacggcc atcgtcgatc cgccgctcgg   7920
catttcctgt tttggccgca agatgtggat cgaagcctat aatggccgcg gcgaagtgct   7980
gctcgatttc attacggaaa agctgaaggc gacacccgat ctcaccctcg gcgcttcctc   8040
gacccgccgg ctcgatctta ccgtcaacga accggaccgt gtcttcaccg aagaagaacg   8100
ctcgaaaatc ccgacggtct tcaccgctct cagagccatc gtcgacctct tctattcgag   8160
cgcggattcg gccatcggcc tgttcggtgc cttcggttac gatctcgcct tccagttcga   8220
cgcgatcaag ctttcgctgg cgcgtccgga agaccagcgt gacatggtgc tgtttctgcc   8280
cgatgaaatc ctcgtcgttg atcactattc cgccaaggcc tggatcgacc gttacgattt   8340
cgagaaggac ggcatgacga cggacggcaa atcctccgac attacccccg atcccttcaa   8400
gaccaccgat accatcccgc ccaagggcga tcaccgtccc ggcgaatatt ccgagcttgt   8460
ggtgaaggcc aaggaaagct tccgccgcgg cgacctgttc gaggtcgttc ccggccagaa   8520
attcatggag cgttgcgaaa gcaatccgtc ggcgatttcc cgccgcctga aggcgatcaa   8580
cccgtcgccc tattccttct tcatcaatct cggcgatcag gaatatctgg tcggcgcctc   8640
gccggaaatg ttcgtgcgcg tctccggccg tcgcatcgag acctgcccga tatcaggcac   8700
catcaagcgc ggcgacgatc cgattgccga cagcgagcag attttgaaac tgctcaactc   8760
gaaaaaggac gaatccgaac tgaccatgtg ctcggacgtg gaccgcaacg acaagagccg   8820
cgtctgcgag ccgggttcgg tgaaggtcat tggccgccgc cagatcgaga tgtattcacg   8880
cctcatccac accgtcgatc acatcgaagg ccgcctgcgc gacgatatgg acgcctttga   8940
cggtttcctc agccacgcct gggccgtcac cgtcaccggt gcaccaaagc tgtgggccat   9000
gcgcttcatc gaaggtcatg aaaagagccc gcgcgcctgg tatggcggtg cgatcggcat   9060
ggtcggcttc aacggcgaca tgaataccgg cctgacgctg cgcaccatcc ggatcaagga   9120
cggtattgcc gaagtgcgcg ccggcgcgac cctgctcaat gattccaacc cgcaggaaga   9180
agaagccgaa accgaactga aggcctccgc catgatatca gccattcgtg acgcaaaagg   9240
caccaactct gccgccacca agcgtgatgc cgccaaagtc ggcaccggcg tcaagatcct   9300
gctcgtcgac cacgaagaca gcttcgtgca cacgctggcg aattatttcc gccagacggg   9360
cgcgacggtc tcgaccgtca gatcaccggt cgcagccgac gtgttcgatc gcttccagcc   9420
ggacctcgtt gtcctgtcgc ccggacccgg cagcccgacg gatttcgact gcaaggcaac   9480
gatcaaggcc gcccgcgccc gcgatctgcc gatcttcggc gtttgcctcg gtctgcaggc   9540
attggcagaa gcctatggcg gcgagctgcg ccagcttgct gtgcccatgc acggcaagcc   9600
ttcgcgcatc cgcgtgctgg aacccggcct cgtcttctcc ggtctcggca aggaagtcac   9660
ggtcggtcgt taccattcga tcttcgccga tcccgccacc ctgccgcgtg atttcatcat   9720
caccgcagaa agcgaggacg gcacgatcat gggcatcgaa cacgccaagg aaccggtggc   9780
```

```
cgccgttcag ttccacccgg aatcgatcat gacgctcgga caggacgcgg gcatgcggat   9840
gatcgagaat gtcgtggtgc atctgacccg caaggcgaag accaaggccg cgtgatggcg   9900
ctcgatgaca cggttatatc actagtgcgg ccatcggatc cgttggcaat gcggataaag   9960
aataactaaa taaataaata aataaattgc aagcaattgc gttgctgcta tgtactgtaa  10020
aagtttctta taatatcagt tctgaatgct aaggacatcc ctcaagatgg tctttctatt  10080
tttgtgttcc cgttccaatg tactgttggt atcctcttgg agattcatca atatgagaaa  10140
acagagaatg gacaaccctc ccttatctta tggctcgagc ggccgctcta gaactagtgg  10200
atcccccct taattaaggg ggctgcagga attcataact tcgtataatg tatgctatac  10260
gaagttatgt ttcgaggtca ttcatatgct tgagaagaga gtcgggatag tccaaaataa  10320
aacaaaggta agattacctg gtcaaaagtg aaaacatcag ttaaaaggtg gtataaagta  10380
aaatatcggt aataaaaggt ggcccaaagt gaaatttact cttttctact attataaaaa  10440
ttgaggatgt ttttgtcggt actttgatac gtcatttttg tatgaattgg tttttaagtt  10500
tattcgcttt tggaaatgca tatctgtatt tgagtcgggt tttaagttcg tttgcttttg  10560
taaatacaga gggatttgta taagaaatat ctttagaaaa acccatatgc taatttgaca  10620
taatttttga gaaaaatata tattcaggcg aattctcaca atgaacaata ataagattaa  10680
aatagctttc cccgttgca gcgcatgggt attttttcta gtaaaaataa aagataaact  10740
tagactcaaa acatttacaa aaacaacccc taaagttcct aaagcccaaa gtgctatcca  10800
cgatccatag caagcccagc ccaacccaac ccaacccaac ccaccccagt ccagccaact  10860
ggacaatagt ctccacaccc ccccactatc accgtgagtt gtccgcacgc accgcacgtc  10920
tcgcagccaa aaaaaaaaag aaagaaaaaa aagaaaaaga aaaaacagca ggtgggtccg  10980
ggtcgtgggg gccggaaacg cgaggaggat cgcgagccag cgacgaggcc ggccctccct  11040
ccgcttccaa agaaacgccc cccatcgcca ctatatacat acccccccct ctcctcccat  11100
ccccccaacc ctaccaccac caccaccacc acctccacct cctccccct cgctgccgga  11160
cgacgagctc ctcccccctc cccctccgcc gccgccgcgc cggtaaccac cccgcccctc  11220
tcctctttct ttctccgttt ttttttccgt ctcggtctcg atctttggcc ttggtagttt  11280
gggtgggcga gaggcggctt cgtgcgcgcc cagatcggtg cgcgggaggg gcgggatctc  11340
gcggctgggg ctctcgccgg cgtggatccg gcccggatct cgcggggaat ggggctctcg  11400
gatgtagatc tgcgatccgc cgttgttggg ggagatgatg gggggtttaa aatttccgcc  11460
gtgctaaaca agatcaggaa gaggggaaaa gggcactatg gtttatattt ttatatattt  11520
ctgctgcttc gtcaggctta gatgtgctag atctttcttt cttcttttg tgggtagaat  11580
ttgaatccct cagcattgtt catcggtagt ttttcttttc atgatttgtg acaaatgcag  11640
cctcgtgcgg agcttttttg taggtagaag tgatcaacca tggcgcaagt tagcagaatc  11700
tgcaatggtg tgcagaaccc atctcttatc tccaatctct cgaaatccag tcaacgcaaa  11760
tctcccttat cggtttctct gaagacgcag cagcatccac gagcttatcc gatttcgtcg  11820
tcgtggggat tgaagaagag tgggatgacg ttaattggct ctgagcttcg tcctcttaag  11880
gtcatgtctt ctgtttccac ggcgtgcatg cttcacggtg caagcagccg gcccgcaacc  11940
gcccgcaaat cctctggcct ttccggaacc gtccgcattc ccggcgacaa gtcgatctcc  12000
caccggtcct tcatgttcgg cggtctcgcg agcggtgaaa cgcgcatcac cggccttctg  12060
gaaggcgagg acgtcatcaa tacgggcaag gccatgcagg cgatgggcgc ccgcatccgt  12120
```

```
aaggaaggcg acacctggat catcgatggc gtcggcaatg gcggcctcct ggcgcctgag  12180

gcgccgctcg atttcggcaa tgccgccacg ggctgccgcc tgacgatggg cctcgtcggg  12240

gtctacgatt tcgacagcac cttcatcggc gacgcctcgc tcacaaagcg cccgatgggc  12300

cgcgtgttga acccgctgcg cgaaatgggc gtgcaggtga aatcggaaga cggtgaccgt  12360

cttcccgtta ccttgcgcgg gccgaagacg ccgacgccga tcacctaccg cgtgccgatg  12420

gcctccgcac aggtgaagtc cgccgtgctg ctcgccggcc tcaacacgcc cggcatcacg  12480

acggtcatcg agccgatcat gacgcgcgat catacggaaa agatgctgca gggctttggc  12540

gccaacctta ccgtcgagac ggatgcggac ggcgtgcgca ccatccgcct ggaaggccgc  12600

ggcaagctca ccggccaagt catcgacgtg ccgggcgacc cgtcctcgac ggccttcccg  12660

ctggttgcgg ccctgcttgt tccgggctcc gacgtcacca tcctcaacgt gctgatgaac  12720

cccacccgca ccggcctcat cctgacgctg caggaaatgg gcgccgacat cgaagtcatc  12780

aacccgcgcc ttgccggcgg cgaagacgtg gcggacctgc gcgttcgctc ctccacgctg  12840

aagggcgtca cggtgccgga agaccgcgcg ccttcgatga tcgacgaata tccgattctc  12900

gctgtcgccg ccgccttcgc ggaaggggcg accgtgatga acggtctgga agaactccgc  12960

gtcaaggaaa gcgaccgcct ctcggccgtc gccaatggcc tcaagctcaa tggcgtggat  13020

tgcgatgagg gcgagacgtc gctcgtcgtg cgtggccgcc ctgacggcaa ggggctcggc  13080

aacgcctcgg gcgccgccgt cgccacccat ctcgatcacc gcatcgccat gagcttcctc  13140

gtcatgggcc tcgtgtcgga aaaccctgtc acggtggacg atgccacgat gatcgccacg  13200

agcttcccgg agttcatgga cctgatggcc gggctgggcg cgaagatcga actctccgat  13260

acgaaggctg cctgatgagc tcgaattccc gatcgttcaa acatttggca ataaagtttc  13320

ttaagattga atcctgttgc cggtcttgcg atgattatca tataatttct gttgaattac  13380

gttaagcatg taataattaa catgtaatgc atgacgttat ttatgagatg ggtttttatg  13440

attagagtcc cgcaattata catttaatac gcgatagaaa acaaaatata gcgcgcaaac  13500

taggataaat tatcgcgcgc ggtgtcatct atgttactag atcggggata acgatcaagc  13560

tataacttcg tataatgtat gctatacgaa gttatc                           13596
```

```
<210> SEQ ID NO 214
<211> LENGTH: 13559
<212> TYPE: DNA
<213> ORGANISM: Artificial Sequence
<220> FEATURE:
<223> OTHER INFORMATION: pMON68066;Figure 49;the expression vector for
      Zm-ASA2-CTP +18::AgroAS(S51C)-nno

<400> SEQUENCE: 214
```

```
gcgccaaatc gtgaagtttc tcatctaagc ccccatttgg acgtgaatgt agacacgtcg     60

aaataaagat ttccgaatta gaataatttg tttattgctt tcgcctataa atacgacgga    120

tcgtaatttg tcgttttatc aaaatgtact ttcattttat aataacgctg cggacatcta    180

catttttgaa ttgaaaaaaa attggtaatt actctttctt tttctccata ttgaccatca    240

tactcattgc tgatccatgt agatttcccg gacatgaagc catttacaat tgaatatatc    300

ctgccgccgc tgccgctttg cacccggtgg agcttgcatg ttggtttcta cgcagaactg    360

agccggttag gcagataatt tccattgaga actgagccat gtgcaccttc cccccaacac    420

ggtgagcgac ggggcaacgg agtgatccac atgggacttt tcctagcttg gctgccattt    480

ttggggtgag gccgttcgcg gccgaggggc gcagcccctg gggggatggg aggcccgcgt    540
```

-continued

```
tagcgggccg ggagggttcg agaagggggg gcacccccct tcggcgtgcg cggtcacgcg    600
cacagggcgc agccctggtt aaaaacaagg tttataaata ttggtttaaa agcaggttaa    660
aagacaggtt agcggtggcc gaaaaacggg cggaaaccct tgcaaatgct ggattttctg    720
cctgtggaca gcccctcaaa tgtcaatagg tgcgcccctc atctgtcagc actctgcccc    780
tcaagtgtca aggatcgcgc ccctcatctg tcagtagtcg cgcccctcaa gtgtcaatac    840
cgcagggcac ttatccccag gcttgtccac atcatctgtg ggaaactcgc gtaaaatcag    900
gcgttttcgc cgatttgcga ggctggccag ctccacgtcg ccggccgaaa tcgagcctgc    960
ccctcatctg tcaacgccgc gccgggtgag tcggcccctc aagtgtcaac gtccgcccct   1020
catctgtcag tgagggccaa gttttccgcg aggtatccac aacgccggcg gccggccgcg   1080
gtgtctcgca cacggcttcg acggcgtttc tggcgcgttt gcagggccat agacggccgc   1140
cagcccagcg gcgagggcaa ccagcccggt gagcgtcgga aagggtcgat cgaccgatgc   1200
ccttgagagc cttcaaccca gtcagctcct tccggtgggc gcggggcatg actatcgtcg   1260
ccgcacttat gactgtcttc tttatcatgc aactcgtagg acaggtgccg gcagcgctct   1320
gggtcatttt cggcgaggac cgctttcgct ggagcgcgac gatgatcggc ctgtcgcttg   1380
cggtattcgg aatcttgcac gccctcgctc aagccttcgt cactggtccc gccaccaaac   1440
gtttcggcga gaagcaggcc attatcgccg gcatggcggc cgacgcgctg ggctacgtct   1500
tgctggcgtt cgcgacgcga ggctggatgg ccttccccat tatgattctt ctcgcttccg   1560
gcggcatcgg gatgcccgcg ttgcaggcca tgctgtccag gcaggtagat gacgaccatc   1620
agggacagct tcaaggatcg ctcgcggctc ttaccagcct aacttcgatc attggaccgc   1680
tgatcgtcac ggcgatttat gccgcctcgg cgagcacatg gaacgggttg gcatggattg   1740
taggcgccgc cctatacctt gtctgcctcc ccgcgttgcg tcgcggtgca tggagccggg   1800
ccacctcgac ctgaatggaa gccggcggca cctcgctaac ggattcacca ctccaagaat   1860
tggagccaat caattcttgc ggagaactgt gaatgcgcaa accaaccctt ggcagaacat   1920
atccatcgcg tccgccatct ccagcagccg cacgcggcgc atctcgggca gcgttgggtc   1980
ctggccacgg gtgcgcatga tcgtgctcct gtcgttgagg acccggctag gctggcgggg   2040
ttgccttact ggttagcaga atgaatcacc gatacgcgag cgaacgtgaa gcgactgctg   2100
ctgcaaaacg tctgcgacct gagcaacaac atgaatggtc ttcggtttcc gtgtttcgta   2160
aagtctggaa acgcggaagt cagcgccctg caccattatg ttccggatct gcatcgcagg   2220
atgctgctgg ctaccctgtg gaacacctac atctgtatta acgaagcgct ggcattgacc   2280
ctgagtgatt tttctctggt cccgccgcat ccataccgcc agttgtttac cctcacaacg   2340
ttccagtaac cgggcatgtt catcatcagt aacccgtatc gtgagcatcc tctctcgttt   2400
catcggtatc attaccccca tgaacagaaa tcccccttac acggaggcat cagtgaccaa   2460
acaggaaaaa accgccctta acatggcccg ctttatcaga agccagacat taacgcttct   2520
ggagaaactc aacgagctgg acgcggatga acaggcagac atctgtgaat cgcttcacga   2580
ccacgctgat gagctttacc gcagctgcct cgcgcgtttc ggtgatgacg gtgaaaacct   2640
ctgacacatg cagctcccgg agacggtcac agcttgtctg taagcggatg ccgggagcag   2700
acaagcccgt cagggcgcgt cagcgggtgt tggcgggtgt cggggcgcag ccatgaccca   2760
gtcacgtagc gatagcggag tgtatactgg cttaactatg cggcatcaga gcagattgta   2820
ctgagagtgc accatatgcg gtgtgaaata ccgcacagat gcgtaaggag aaaataccgc   2880
atcaggcgct cttccgcttc ctcgctcact gactcgctgc gctcggtcgt tcggctgcgg   2940
```

-continued

```
cgagcggtat cagctcactc aaaggcggta atacggttat ccacagaatc aggggataac   3000

gcaggaaaga acatgtgagc aaaaggccag caaaaggcca ggaaccgtaa aaaggccgcg   3060

ttgctggcgt ttttccatag gctccgcccc cctgacgagc atcacaaaaa tcgacgctca   3120

agtcagaggt ggcgaaaccc gacaggacta taaagatacc aggcgtttcc ccctggaagc   3180

tccctcgtgc gctctcctgt tccgaccctg ccgcttaccg gatacctgtc cgcctttctc   3240

ccttcgggaa gcgtggcgct ttctcatagc tcacgctgta ggtatctcag ttcggtgtag   3300

gtcgttcgct ccaagctggg ctgtgtgcac gaaccccccg ttcagcccga ccgctgcgcc   3360

ttatccggta actatcgtct tgagtccaac ccggtaagac acgacttatc gccactggca   3420

gcagccactg gtaacaggat tagcagagcg aggtatgtag gcggtgctac agagttcttg   3480

aagtggtggc ctaactacgg ctacactaga aggacagtat ttggtatctg cgctctgctg   3540

aagccagtta ccttcggaaa aagagttggt agctcttgat ccggcaaaca aaccaccgct   3600

ggtagcggtg gtttttttgt ttgcaagcag cagattacgc gcagaaaaaa aggatctcaa   3660

gaagatcctt tgatcttttc tacggggtct gacgctcagt ggaacgaaaa ctcacgttaa   3720

gggattttgg tcatgagatt atcaaaaagg atcttcacct agatcctttt aaattaaaaa   3780

tgaagtttta aatcaatcta aagtatatat gagtaaactt ggtctgacag ttaccaatgc   3840

ttaatcagtg aggcacctat ctcagcgatc tgtctatttc gttcatccat agttgcctga   3900

ctccccgtcg tgtagataac tacgatacgg gagggcttac catctggccc cagtgctgca   3960

atgataccgc gagacccacg ctcaccggct ccagatttat cagcaataaa ccagccagcc   4020

ggaagggccg agcgcagaag tggtcctgca actttatccg cctccatcca gtctattaat   4080

tgttgccggg aagctagagt aagtagttcg ccagttaata gtttgcgcaa cgttgttgcc   4140

attgctgcag gtcgggagca caggatgacg cctaacaatt cattcaagcc gacaccgctt   4200

cgcggcgcgg cttaattcag gagttaaaca tcatgaggga agcggtgatc gccgaagtat   4260

cgactcaact atcagaggta gttggcgtca tcgagcgcca tctcgaaccg acgttgctgg   4320

ccgtacattt gtacggctcc gcagtggatg gcggcctgaa gccacacagt gatattgatt   4380

tgctggttac ggtgaccgta aggcttgatg aaacaacgcg gcgagctttg atcaacgacc   4440

ttttggaaac ttcggcttcc cctggagaga gcgagattct ccgcgctgta gaagtcacca   4500

ttgttgtgca cgacgacatc attccgtggc gttatccagc taagcgcgaa ctgcaatttg   4560

gagaatggca gcgcaatgac attcttgcag gtatcttcga gccagccacg atcgacattg   4620

atctggctat cttgctgaca aaagcaagag aacatagcgt tgccttggta ggtccagcgg   4680

cggaggaact ctttgatccg gttcctgaac aggatctatt tgaggcgcta aatgaaacct   4740

taacgctatg gaactcgccg cccgactggg ctggcgatga gcgaaatgta gtgcttacgt   4800

tgtcccgcat ttggtacagc gcagtaaccg gcaaaatcgc gccgaaggat gtcgctgccg   4860

actgggcaat ggagcgcctg ccggcccagt atcagcccgt catacttgaa gctaggcagg   4920

cttatcttgg acaagaagat cgcttggcct cgcgcgcaga tcagttggaa gaatttgttc   4980

actacgtgaa aggcgagatc accaaggtag tcggcaaata atgtctaaca attcgttcaa   5040

gccgacgccg cttcgcggcg cggcttaact caagcgttag atgctgcagg catcgtggtg   5100

tcacgctcgt cgtttggtat ggcttcattc agctccggtt cccaacgatc aaggcgagtt   5160

acatgatccc ccatgttgtg caaaaaagcg gttagctcct tcggtcctcc gatcgaggat   5220

ttttcggcgc tgcgctacgt ccgcgaccgc gttgagggat caagccacag cagcccactc   5280
```

```
gaccttctag ccgacccaga cgagccaagg gatctttttg gaatgctgct ccgtcgtcag   5340
gctttccgac gtttgggtgg ttgaacagaa gtcattatcg cacggaatgc caagcactcc   5400
cgaggggaac cctgtggttg gcatgcacat acaaatggac gaacggataa accttttcac   5460
gcccttttaa atatccgatt attctaataa acgctctttt ctcttaggtt tacccgccaa   5520
tatatcctgt caaacactga tagtttaaac tgaaggcggg aaacgacaat ctgatcccca   5580
tcaagctagc ttctgcaggt cctgctcgag gtcactaagc aactaacttt gaggaatgag   5640
gtgatgatga attaactcac tccattccac aaaccaaaca aaaatttgag gagtgagaag   5700
atgattgact atctcattcc tcaaaccaaa cacctcaaat atatctgcta tcgggattgg   5760
cattcctgta tccctacgcc cgtgtacccc ctgtttagag aacctccaaa ggtataagat   5820
ggcgaagatt attgttgtct tgtctttcat catatatcga gtctttccct aggatattat   5880
tattggcaat gagcattaca cggttaatcg attgagagaa catgcatctc accttcagca   5940
aataattacg ataatccata ttttacgctt cgtaacttct catgagtttc gatatacaaa   6000
tttgttttct ggacacccta ccattcatcc tcttcggaga agagaggaag tgtcctcaat   6060
ttaaatatgt tgtcatgctg tagttcttca caaaatctca acaggtacca agcacattgt   6120
ttccacaaat tatattttag tcacaataaa tctatattat tattaatata ctaaaactat   6180
actgacgctc agatgctttt actagttctt gctagtatgt gatgtaggtc tacgtggacc   6240
agaaaatagt gagacacgga agacaaaaga agtaaaagag gcccggacta cggcccacat   6300
gagattcggc cccgccacct ccggcaacca gcggccgatc caacggcagt gcgcgcacac   6360
acacaacctc gtatatatcg ccgcgcggaa gcggcgcgac cgaggaagcc ttgtcctcga   6420
cacccccctac acaggtgtcg cgctgccccc gacacgagtc ccgcatgcgt cccacgcggc   6480
cgcgccagat cccgcctccg cgcgttgcca cgccctctat aaacacccag ctctccctcg   6540
ccctcatcta cctcactcgt agtcgtagct caagcatcag cggcagcggc agcggcagga   6600
tctctgggca gcgtgcgcac gtggggtatc tagctcgctc tgctagccta ccaatcgaat   6660
tcctgcaggt cgactctaga ggatctaccg tcttcggtac gcgctcactc cgccctctgc   6720
ctttgttact gccacgtttc tctgaatgct ctcttgtgtg gtgattgctg agagtggttt   6780
agctggatct agaattacac tctgaaatcg tgttctgcct gtgctgatta cttgccgtcc   6840
tttgtagcag caaaatatag ggacatggta gtacgaaacg aagatagaac ctacacagca   6900
atacgagaaa tgtgtaattt ggtgcttagc ggtatttatt taagcacatg ttggtgttat   6960
agggcacttg gattcagaag tttgctgtta atttaggcac aggcttcata ctacatgggt   7020
caatagtata gggattcata ttataggcga tactataata atttgttcgt ctgcagagct   7080
tattatttgc caaaattaga tattcctatt ctgtttttgt ttgtgtgctg ttaaattgtt   7140
aacgcctgaa ggaataaata taaatgacga aattttgatg tttatctctg ctcctttatt   7200
gtgaccataa gtcaagatca gatgcacttg ttttaaatat tgttgtctga agaaataagt   7260
actgacagta ttttgatgca ttgatctgct tgtttgttgt aacaaaattt aaaaataaag   7320
agtttccttt ttgttgctct ccttacctcc tgatggtatc tagtatctac caactgacac   7380
tatattgctt ctctttacat acgtatcttg ctcgatgcct tctccctagt gttgaccagt   7440
gttactcaca tagtctttgc tcatttcatt gtaatgcaga taccaagcgg cctctagagg   7500
actccgatct atggaatccc tagccgccac ctccgtgttc gcgccctccc gcgtcgccgt   7560
cccggcggcg cgggccctgg ttagggcggg gacggtggta ccaaccaggc ggacgagcag   7620
ccggagcgga accagcgggg tgaaatgctc tgctgccgtg acgccgcagg cgagcccagt   7680
```

```
gattagcagg agcgctgcgg cggccatggt gaccatcatt caggacgacg gcgctgagac   7740
ctacgagact aagggcggta tccaagtgag ccgtaagcgt aggcccactg actacgctaa   7800
cgccatcgac aactacatcg agaagctaga ctcccatcgc ggcgctgtgt tctcctgcaa   7860
ctacgaatac cctgggcgct acacgaggtg ggataccgcc atcgtcgatc ctccattggg   7920
catctcctgt tttgggcgta agatgtggat cgaggcgtac aacggccgtg gcgaagtctt   7980
gctggacttc atcacggaga agctcaaggc cacaccggac ctcaccctcg gcgcttcctc   8040
gacccgccgc ctcgacctta cggtcaacga gccggaccgc gtgttcaccg aggaagagcg   8100
tagcaagatc ccgactgtct tcaccgcgct cagagccatc gtggacctat tctactcttc   8160
tgcggacagc gccatcgggt tgttcggtgc cttcggttac gacctcgcgt tccagttcga   8220
cgccatcaag ctctcgctcg cgcggccgga ggaccagcga gacatggtgc tcttcctccc   8280
tgacgagatc ctggtcgtcg atcactattc cgcgaaggcg tggatcgacc ggtacgactt   8340
cgagaaggat ggcatgacca cggatggcaa gagcagcgac atcactcccg acccattcaa   8400
gaccaccgac accatccctc caaagggcga tcaccgccct ggcgagtatt ccgaactcgt   8460
ggtgaaggcc aaggaatcct tccggcgcgg cgatctgttt gaggtggttc ccggccaaaa   8520
gttcatggag aggtgcgagt cgaatccgtc tgcgatcagt cgccgactga aagcgatcaa   8580
cccgagcccg tattccttct tcatcaacct cggcgatcag gaatatctgg tcggagcctc   8640
acccgagatg ttcgtcaggg tctccggccg ccggatcgag acgtgcccaa tttccggaac   8700
catcaagcgc ggagatgacc cgatagccga ctctgagcag atcctgaaac tcttgaacag   8760
caagaaggac gagtccgagc tgactatgtg ctcagatgtg gaccgaaacg acaagtcacg   8820
tgtctgcgag cccggtagcg tcaaggtcat tggccgccgt cagatcgaga tgtactccag   8880
gctgattcac acggtcgatc atatcgaagg gcggctgcgc gacgatatgg acgcattcga   8940
cgggttcctc agtcacgcct gggccgttac tgtcaccgga gcgcctaagc tctgggctat   9000
gaggttcatc gagggccacg agaagagccc tagggcttgg tatggtggtg ccatcggcat   9060
ggttgggttc aacggcgaca tgaacaccgg gctgacgctc cggaccatca ggatcaaaga   9120
cggcattgcc gaggtgaggg ccggtgccac gcttctcaac gatagcaacc ctcaggagga   9180
agaggcggag accgagctga aagcctctgc gatgatctcc gcgattagag atgcaaaggg   9240
tacgaacagt gctgccacca agcgggacgc agccaaggtg ggcaccggcg tcaagatttt   9300
acttgtcgat cacgaggact ccttcgtgca cactctggcg aactacttcc gccagacagg   9360
cgcgacggtc tccaccgtta ggtcaccggt ggccgctgac gtgttcgata ggttccagcc   9420
cgaccttgtg gtgctctctc ccggtcccgg ctcgcccacg gacttcgact gcaaggccac   9480
cattaaggcc gccagggcca gggatctgcc aatcttcggc gtttgcctcg ggcttcaggc   9540
attggccgag gcatacggtg gagagctgag gcagctcgcc gtcccgatgc acgggaagcc   9600
atcccgcatc agagtcctgg agcccggcct cgtcttctcc ggtctcggga aggaggtcac   9660
ggtcggtcgg tatcattcga tcttcgccga tccggcaacc ctcccgcgcg acttcatcat   9720
aaccgccgag tcggaggacg gaacgatcat gggaatcgaa cacgccaagg agcccgtagc   9780
tgcggttcag ttccaccctg agtccatcat gaccctcggt caagatgcgg gtatgcggat   9840
gatcgagaat gtggtggttc acctcacccg caaggccaag accaaggcag catgataggg   9900
atccgttggc aatgcggata aagaataact aaataaataa ataaataaat tgcaagcaat   9960
tgcgttgctg ctatgtactg taaaagtttc ttataatatc agttctgaat gctaaggaca  10020
```

```
tccctcaaga tggtctttct atttttgtgt tcccgttcca atgtactgtt ggtatcctct  10080
tggagattca tcaatatgag aaaacagaga atggacaacc ctcccttatc ttatggctcg  10140
agcggccgct ctagaactag tggatccccc ccttaattaa gggggctgca ggaattcata  10200
acttcgtata atgtatgcta tacgaagtta tgtttcgagg tcattcatat gcttgagaag  10260
agagtcggga tagtccaaaa taaaacaaag gtaagattac ctggtcaaaa gtgaaaacat  10320
cagttaaaag gtggtataaa gtaaaatatc ggtaataaaa ggtggcccaa agtgaaattt  10380
actcttttct actattataa aaattgagga tgtttttgtc ggtactttga tacgtcattt  10440
ttgtatgaat tggtttttaa gtttattcgc ttttggaaat gcatatctgt atttgagtcg  10500
ggttttaagt tcgtttgctt ttgtaaatac agagggattt gtataagaaa tatctttaga  10560
aaaacccata tgctaatttg acataatttt tgagaaaaat atatattcag gcgaattctc  10620
acaatgaaca ataataagat taaaatagct ttcccccgtt gcagcgcatg ggtatttttt  10680
ctagtaaaaa taaaagataa acttagactc aaaacattta caaaaacaac ccctaaagtt  10740
cctaaagccc aaagtgctat ccacgatcca tagcaagccc agcccaaccc aacccaaccc  10800
aacccacccc agtccagcca actggacaat agtctccaca cccccccact atcaccgtga  10860
gttgtccgca cgcaccgcac gtctcgcagc caaaaaaaaa aagaaagaaa aaaaagaaaa  10920
agaaaaaaca gcaggtgggt ccgggtcgtg gggggccggaa acgcgaggag gatcgcgagc  10980
cagcgacgag gccggccctc cctccgcttc caaagaaacg ccccccatcg ccactatata  11040
catacccccc cctctcctcc catcccccca accctaccac caccaccacc accacctcca  11100
cctcctcccc cctcgctgcc ggacgacgag ctcctccccc ctccccctcc gccgccgccg  11160
cgccggtaac cacccgccc ctctcctctt tctttctccg ttttttttc cgtctcggtc  11220
tcgatctttg gccttggtag tttgggtggg cgagaggcgg cttcgtgcgc gcccagatcg  11280
gtgcgcggga ggggcgggat ctcgcggctg gggctctcgc cggcgtggat ccggcccgga  11340
tctcgcgggg aatggggctc tcggatgtag atctgcgatc cgccgttgtt gggggagatg  11400
atggggggtt taaaatttcc gccgtgctaa acaagatcag gaagagggga aaagggcact  11460
atggtttata tttttatata tttctgctgc ttcgtcaggc ttagatgtgc tagatctttc  11520
tttcttcttt ttgtgggtag aatttgaatc cctcagcatt gttcatcggt agtttttctt  11580
ttcatgattt gtgacaaatg cagcctcgtg cggagctttt ttgtaggtag aagtgatcaa  11640
ccatggcgca agttagcaga atctgcaatg gtgtgcagaa cccatctctt atctccaatc  11700
tctcgaaatc cagtcaacgc aaatctccct tatcggtttc tctgaagacg cagcagcatc  11760
cacgagctta tccgatttcg tcgtcgtggg gattgaagaa gagtgggatg acgttaattg  11820
gctctgagct tcgtcctctt aaggtcatgt cttctgtttc cacggcgtgc atgcttcacg  11880
gtgcaagcag ccggcccgca accgcccgca aatcctctgg cctttccgga accgtccgca  11940
ttcccggcga caagtcgatc tcccaccggt ccttcatgtt cggcggtctc gcgagcggtg  12000
aaacgcgcat caccggcctt ctggaaggcg aggacgtcat caatacgggc aaggccatgc  12060
aggcgatggg cgcccgcatc cgtaaggaag gcgacacctg gatcatcgat ggcgtcggca  12120
atggcggcct cctggcgcct gaggcgccgc tcgatttcgg caatgccgcc acgggctgcc  12180
gcctgacgat gggcctcgtc ggggtctacg atttcgacag caccttcatc ggcgacgcct  12240
cgctcacaaa gcgcccgatg ggccgcgtgt tgaacccgct gcgcgaaatg ggcgtgcagg  12300
tgaaatcgga agacggtgac cgtcttcccg ttaccttgcg cgggccgaag acgccgacgc  12360
cgatcaccta ccgcgtgccg atggcctccg cacaggtgaa gtccgccgtg ctgctcgccg  12420
```

```
gcctcaacac gcccggcatc acgacggtca tcgagccgat catgacgcgc gatcatacgg  12480

aaaagatgct gcagggcttt ggcgccaacc ttaccgtcga gacggatgcg gacggcgtgc  12540

gcaccatccg cctggaaggc cgcggcaagc tcaccggcca agtcatcgac gtgccgggcg  12600

acccgtcctc gacggccttc ccgctggttg cggccctgct tgttccgggc tccgacgtca  12660

ccatcctcaa cgtgctgatg aaccccaccc gcaccggcct catcctgacg ctgcaggaaa  12720

tgggcgccga catcgaagtc atcaacccgc gccttgccgg cggcgaagac gtggcggacc  12780

tgcgcgttcg ctcctccacg ctgaagggcg tcacggtgcc ggaagaccgc gcgccttcga  12840

tgatcgacga atatccgatt ctcgctgtcg ccgccgcctt cgcggaaggg gcgaccgtga  12900

tgaacggtct ggaagaactc cgcgtcaagg aaagcgaccg cctctcggcc gtcgccaatg  12960

gcctcaagct caatggcgtg gattgcgatg agggcgagac gtcgctcgtc gtgcgtggcc  13020

gccctgacgg caaggggctc ggcaacgcct cgggcgccgc cgtcgccacc catctcgatc  13080

accgcatcgc catgagcttc ctcgtcatgg gcctcgtgtc ggaaaaccct gtcacggtgg  13140

acgatgccac gatgatcgcc acgagcttcc cggagttcat ggacctgatg gccgggctgg  13200

gcgcgaagat cgaactctcc gatacgaagg ctgcctgatg agctcgaatt cccgatcgtt  13260

caaacatttg gcaataaagt ttcttaagat tgaatcctgt tgccggtctt gcgatgatta  13320

tcatataatt tctgttgaat tacgttaagc atgtaataat taacatgtaa tgcatgacgt  13380

tatttatgag atgggttttt atgattagag tcccgcaatt atacatttaa tacgcgatag  13440

aaaacaaaat atagcgcgca aactaggata aattatcgcg cgcggtgtca tctatgttac  13500

tagatcgggg ataacgatca agctataact tcgtataatg tatgctatac gaagttatc   13559
```

<210> SEQ ID NO 215
<211> LENGTH: 13905
<212> TYPE: DNA
<213> ORGANISM: Artificial Sequence
<220> FEATURE:
<223> OTHER INFORMATION: pMON69757;Figure 33;the expression vector for the construct containing the AgroAS(F298W) mutant allele

<400> SEQUENCE: 215

```
gtcctccgat cgaggatttt tcggcgctgc gctacgtccg cgaccgcgtt gagggatcaa     60

gccacagcag cccactcgac cttctagccg acccagacga gccaagggat ctttttggaa    120

tgctgctccg tcgtcaggct ttccgacgtt tgggtggttg aacagaagtc attatcgcac    180

ggaatgccaa gcactcccga ggggaaccct gtggttggca tgcacataca aatggacgaa    240

cggataaacc ttttcacgcc cttttaaata tccgattatt ctaataaacg ctcttttctc    300

ttaggtttac ccgccaatat atcctgtcaa acactgatag tttaaactga aggcgggaaa    360

cgacaatctg atccccatca agctagcttc tgcaggtcct gctcgaggtc actaagcaac    420

taactttgag gaatgaggtg atgatgaatt aactcactcc attccacaaa ccaaacaaaa    480

atttgaggag tgagaagatg attgactatc tcattcctca aaccaaacac ctcaaatata    540

tctgctatcg ggattggcat tcctgtatcc ctacgcccgt gtacccectg tttagagaac    600

ctccaaaggt ataagatggc gaagattatt gttgtcttgt ctttcatcat atatcgagtc    660

tttccctagg atattattat tggcaatgag cattacacgg ttaatcgatt gagagaacat    720

gcatctcacc ttcagcaaat aattacgata atccatattt tacgcttcgt aacttctcat    780

gagtttcgat atacaaattt gttttctgga caccctacca ttcatcctct tcggagaaga    840

gaggaagtgt cctcaattta aatatgttgt catgctgtag ttcttcacaa aatctcaaca    900
```

```
ggtaccaagc acattgtttc cacaaattat attttagtca caataaatct atattattat    960
taatatacta aaactatact gacgctcaga tgcttttact agttcttgct agtatgtgat   1020
gtaggtctac gtggaccaga aaatagtgag acacggaaga caaaagaagt aaaagaggcc   1080
cggactacgg cccacatgag attcggcccc gccacctccg gcaaccagcg gccgatccaa   1140
cggcagtgcg cgcacacaca caacctcgta tatatcgccg cgcggaagcg gcgcgaccga   1200
ggaagccttg tcctcgacac cccctacaca ggtgtcgcgc tgcccccgac acgagtcccg   1260
catgcgtccc acgcggccgc gccagatccc gcctccgcgc gttgccacgc cctctataaa   1320
cacccagctc tccctcgccc tcatctacct cactcgtagt cgtagctcaa gcatcagcgg   1380
cagcggcagc ggcaggatct ctgggcagcg tgcgcacgtg gggtatctag ctcgctctgc   1440
tagcctacca atcgaattcc tgcaggtcga ctctagagga tctaccgtct tcggtacgcg   1500
ctcactccgc cctctgcctt tgttactgcc acgtttctct gaatgctctc ttgtgtggtg   1560
attgctgaga gtggtttagc tggatctaga attacactct gaaatcgtgt tctgcctgtg   1620
ctgattactt gccgtccttt gtagcagcaa aatataggga catggtagta cgaaacgaag   1680
atagaaccta cacagcaata cgagaaatgt gtaatttggt gcttagcggt atttatttaa   1740
gcacatgttg gtgttatagg gcacttggat tcagaagttt gctgttaatt taggcacagg   1800
cttcatacta catgggtcaa tagtataggg attcatatta taggcgatac tataataatt   1860
tgttcgtctg cagagcttat tatttgccaa aattagatat tcctattctg tttttgtttg   1920
tgtgctgtta aattgttaac gcctgaagga ataaatataa atgacgaaat tttgatgttt   1980
atctctgctc ctttattgtg accataagtc aagatcagat gcacttgttt taaatattgt   2040
tgtctgaaga aataagtact gacagtattt tgatgcattg atctgcttgt ttgttgtaac   2100
aaaatttaaa aataaagagt ttcctttttg ttgctctcct tacctcctga tggtatctag   2160
tatctaccaa ctgacactat attgcttctc tttacatacg tatcttgctc gatgccttct   2220
ccctagtgtt gaccagtgtt actcacatag tctttgctca tttcattgta atgcagatac   2280
caagcggcct ctagaggact ccgatctatg gaatccctag ccgccacctc cgtgttcgcg   2340
ccctcccgcg tcgccgtccc ggcggcgcgg gccctggtta gggcggggac ggtggtacca   2400
accaggcgga cgagcagccg gagcggaacc agcggggtga aatgctctgc tgccgtgacg   2460
ccgcaggcga gcccagtgat tagcaggagc gctgcggcgg ccatggtaac gatcattcag   2520
gatgacggag cggagaccta cgagacgaaa ggcggcatcc aggtcagccg aaagcgccgg   2580
cccaccgatt atgccaacgc catcgataat tacatcgaaa agcttgattc ccatcgcggc   2640
gcggtttttt cgtccaacta tgaatatccg ggccgttaca cccgctggga tacggccatc   2700
gtcgatccgc cgctcggcat ttcctgtttt ggccgcaaga tgtggatcga agcctataat   2760
ggccgcggcg aagtgctgct cgatttcatt acggaaaagc tgaaggcgac acccgatctc   2820
accctcggcg cttcctcgac ccgccggctc gatcttaccg tcaacgaacc ggaccgtgtc   2880
ttcaccgaag aagaacgctc gaaaatcccg acggtcttca ccgctctcag agccatcgtc   2940
gacctcttct attcgagcgc ggattcggcc atcggcctgt tcggtgcctt cggttacgat   3000
ctcgccttcc agttcgacgc gatcaagctt tcgctggcgc gtccggaaga ccagcgtgac   3060
atggtgctgt ttctgcccga tgaaatcctc gtcgttgatc actattccgc caaggcctgg   3120
atcgaccgtt acgatttcga gaaggacggc atgacgacgg acggcaaatc ctccgacatt   3180
acccccgatc ccttcaagac caccgatacc atcccgccca agggcgatca ccgtcccggc   3240
```

```
gaatattccg agcttgtggt gaaggccaag gaaagcttcc gccgcggcga cctgttcgag   3300
gtcgttcccg gccagaaatt catggagcgt tgcgaaagca atccgtcggc gatttcccgc   3360
cgcctgaagg cgatcaaccc gtcgccctat tcctggttca tcaatctcgg cgatcaggaa   3420
tatctggtcg gcgcctcgcc ggaaatgttc gtgcgcgtct ccggccgtcg catcgagacc   3480
tgcccgatat caggcaccat caagcgcggc gacgatccga ttgccgacag cgagcagatt   3540
ttgaaactgc tcaactcgaa aaaggacgaa tccgaactga ccatgtgctc ggacgtggac   3600
cgcaacgaca agagccgcgt ctgcgagccg ggttcggtga aggtcattgg ccgccgccag   3660
atcgagatgt attcacgcct catccacacc gtcgatcaca tcgaaggccg cctgcgcgac   3720
gatatggacg cctttgacgg tttcctcagc cacgcctggg ccgtcaccgt caccggtgca   3780
ccaaagctgt gggccatgcg cttcatcgaa ggtcatgaaa agagcccgcg cgcctggtat   3840
ggcggtgcga tcggcatggt cggcttcaac ggcgacatga ataccggcct gacgctgcgc   3900
accatccgga tcaaggacgg tattgccgaa gtgcgcgccg gcgcgaccct gctcaatgat   3960
tccaacccgc aggaagaaga agccgaaacc gaactgaagg cctccgccat gatatcagcc   4020
attcgtgacg caaaaggcac caactctgcc gccaccaagc gtgatgccgc caaagtcggc   4080
accggcgtca agatcctgct cgtcgaccac gaagacagct tcgtgcacac gctggcgaat   4140
tatttccgcc agacgggcgc gacggtctcg accgtcagat caccggtcgc agccgacgtg   4200
ttcgatcgct tccagccgga cctcgttgtc ctgtcgcccg gacccggcag cccgacggat   4260
ttcgactgca aggcaacgat caaggccgcc cgcgcccgcg atctgccgat cttcggcgtt   4320
tgcctcggtc tgcaggcatt ggcagaagcc tatggcggcg agctgcgcca gcttgctgtg   4380
cccatgcacg gcaagccttc gcgcatccgc gtgctggaac ccggcctcgt cttctccggt   4440
ctcggcaagg aagtcacggt cggtcgttac cattcgatct tcgccgatcc cgccaccctg   4500
ccgcgtgatt tcatcatcac cgcagaaagc gaggacggca cgatcatggg catcgaacac   4560
gccaaggaac cggtggccgc cgttcagttc cacccggaat cgatcatgac gctcggacag   4620
gacgcgggca tgcggatgat cgagaatgtc gtggtgcatc tgacccgcaa ggcgaagacc   4680
aaggccgcgt gatggcgctc gatgacacgg ttatatcact agtgcggcca tcggatccgg   4740
ggatcgatga gctaagctag ctatatcatc aatttatgta ttacacataa tatcgcactc   4800
agtctttcat ctacggcaat gtaccagctg atataatcag ttattgaaat atttctgaat   4860
ttaaacttgc atcaataaat ttatgttttt gcttggacta taatacctga cttgttattt   4920
tatcaataaa tatttaaact atatttcttt caagatatca ttctttacaa gtatacgtgt   4980
ttaaattgaa taccataaat ttttattttt caaatacatg taaaattatg aaatgggagt   5040
ggtggcgacc gagctcaagc acacttcaat tcctataacg gaccaaatcg caaaaattat   5100
aataacatat tatttcatcc tggattaaaa gaaagtcacc ggggattatt ttgtgacgcc   5160
gattacatac ggcgacaata aagacattgg aaatcgtagt acatattgga atacactgat   5220
tatattaatg atgaatacat actttaatat ccttacgtag gatcgatccg aatttcgacc   5280
tcgagcggcc gctctagaac tagtggatcc ccccttaat taagggggct gcaggaattc   5340
ataacttcgt ataatgtatg ctatacgaag ttatgtttcg aggtcattca tatgcttgag   5400
aagagagtcg ggatagtcca aaataaaaca aaggtaagat tacctggtca aaagtgaaaa   5460
catcagttaa aaggtggtat aaagtaaaat atcggtaata aaaggtggcc caaagtgaaa   5520
tttactcttt tctactatta taaaaattga ggatgttttt gtcggtactt tgatacgtca   5580
tttttgtatg aattggtttt taagtttatt cgcttttgga aatgcatatc tgtatttgag   5640
```

```
tcgggtttta agttcgtttg cttttgtaaa tacagaggga tttgtataag aaatatcttt   5700
agaaaaaccc atatgctaat ttgacataat ttttgagaaa aatatatatt caggcgaatt   5760
ctcacaatga acaataataa gattaaaata gctttccccc gttgcagcgc atgggtattt   5820
tttctagtaa aaataaaaga taaacttaga ctcaaaacat ttacaaaaac aacccctaaa   5880
gttcctaaag cccaaagtgc tatccacgat ccatagcaag cccagcccaa cccaacccaa   5940
cccaacccac cccagtccag ccaactggac aatagtctcc acaccccccc actatcaccg   6000
tgagttgtcc gcacgcaccg cacgtctcgc agccaaaaaa aaaaagaaag aaaaaaaaga   6060
aaaagaaaaa acagcaggtg ggtccgggtc gtgggggccg gaaacgcgag gaggatcgcg   6120
agccagcgac gaggccggcc ctccctccgc ttccaaagaa acgcccccca tcgccactat   6180
atacataccc ccccctctcc tcccatcccc ccaaccctac caccaccacc accaccacct   6240
ccacctcctc ccccctcgct gccggacgac gagctcctcc cccctccccc tccgccgccg   6300
ccgcgccggt aaccaccccg cccctctcct ctttctttct ccgttttttt ttccgtctcg   6360
gtctcgatct ttggccttgg tagtttgggt gggcgagagg cggcttcgtg cgcgcccaga   6420
tcggtgcgcg ggaggggcgg gatctcgcgg ctggggctct cgccggcgtg gatccggccc   6480
ggatctcgcg gggaatgggg ctctcggatg tagatctgcg atccgccgtt gttgggggag   6540
atgatggggg gtttaaaatt tccgccgtgc taaacaagat caggaagagg ggaaaagggc   6600
actatggttt atatttttat atatttctgc tgcttcgtca ggcttagatg tgctagatct   6660
ttctttcttc tttttgtggg tagaatttga atccctcagc attgttcatc ggtagttttt   6720
cttttcatga tttgtgacaa atgcagcctc gtgcggagct tttttgtagg tagaagtgat   6780
caaccatggc gcaagttagc agaatctgca atggtgtgca gaacccatct cttatctcca   6840
atctctcgaa atccagtcaa cgcaaatctc ccttatcggt ttctctgaag acgcagcagc   6900
atccacgagc ttatccgatt tcgtcgtcgt ggggattgaa gaagagtggg atgacgttaa   6960
ttggctctga gcttcgtcct cttaaggtca tgtcttctgt ttccacggcg tgcatgcttc   7020
acggtgcaag cagccggccc gcaaccgccc gcaaatcctc tggcctttcc ggaaccgtcc   7080
gcattcccgg cgacaagtcg atctcccacc ggtccttcat gttcggcggt ctcgcgagcg   7140
gtgaaacgcg catcaccggc cttctggaag gcgaggacgt catcaatacg ggcaaggcca   7200
tgcaggcgat gggcgcccgc atccgtaagg aaggcgacac ctggatcatc gatggcgtcg   7260
gcaatggcgg cctcctggcg cctgaggcgc cgctcgattt cggcaatgcc gccacgggct   7320
gccgcctgac gatgggcctc gtcggggtct acgatttcga cagcaccttc atcggcgacg   7380
cctcgctcac aaagcgcccg atgggccgcg tgttgaaccc gctgcgcgaa atgggcgtgc   7440
aggtgaaatc ggaagacggt gaccgtcttc ccgttacctt gcgcgggccg aagacgccga   7500
cgccgatcac ctaccgcgtg ccgatggcct ccgcacaggt gaagtccgcc gtgctgctcg   7560
ccggcctcaa cacgcccggc atcacgacgg tcatcgagcc gatcatgacg cgcgatcata   7620
cggaaaagat gctgcagggc tttggcgcca accttaccgt cgagacggat gcggacggcg   7680
tgcgcaccat ccgcctggaa ggccgcggca agctcaccgg ccaagtcatc gacgtgccgg   7740
gcgacccgtc ctcgacggcc ttcccgctgg ttgcggccct gcttgttccg ggctccgacg   7800
tcaccatcct caacgtgctg atgaacccca cccgcaccgg cctcatcctg acgctgcagg   7860
aaatgggcgc cgacatcgaa gtcatcaacc cgcgccttgc cggcggcgaa gacgtggcgg   7920
acctgcgcgt tcgctcctcc acgctgaagg gcgtcacggt gccggaagac cgcgcgcctt   7980
```

```
cgatgatcga cgaatatccg attctcgctg tcgccgccgc cttcgcggaa ggggcgaccg   8040
tgatgaacgg tctggaagaa ctccgcgtca aggaaagcga ccgcctctcg gccgtcgcca   8100
atggcctcaa gctcaatggc gtggattgcg atgagggcga gacgtcgctc gtcgtgcgtg   8160
gccgccctga cggcaagggg ctcggcaacg cctcgggcgc cgccgtcgcc acccatctcg   8220
atcaccgcat cgccatgagc ttcctcgtca tgggcctcgt gtcggaaaac cctgtcacgg   8280
tggacgatgc cacgatgatc gccacgagct tcccggagtt catggacctg atggccgggc   8340
tgggcgcgaa gatcgaactc tccgatacga aggctgcctg atgagctcga attcccgatc   8400
gttcaaacat ttggcaataa agtttcttaa gattgaatcc tgttgccggt cttgcgatga   8460
ttatcatata atttctgttg aattacgtta agcatgtaat aattaacatg taatgcatga   8520
cgttatttat gagatgggtt tttatgatta gagtcccgca attatacatt taatacgcga   8580
tagaaaacaa aatatagcgc gcaaactagg ataaattatc gcgcgcggtg tcatctatgt   8640
tactagatcg gggataacga tcaagctata acttcgtata atgtatgcta tacgaagtta   8700
tcgcgccaaa tcgtgaagtt tctcatctaa gcccccattt ggacgtgaat gtagacacgt   8760
cgaaataaag atttccgaat tagaataatt tgtttattgc tttcgcctat aaatacgacg   8820
gatcgtaatt tgtcgtttta tcaaaatgta ctttcatttt ataataacgc tgcggacatc   8880
tacattttttg aattgaaaaa aaattggtaa ttactctttc tttttctcca tattgaccat   8940
catactcatt gctgatccat gtagatttcc cggacatgaa gccatttaca attgaatata   9000
tcctgccgcc gctgccgctt tgcacccggt ggagcttgca tgttggtttc tacgcagaac   9060
tgagccggtt aggcagataa tttccattga gaactgagcc atgtgcacct tccccccaac   9120
acggtgagcg acggggcaac ggagtgatcc acatgggact tttcctagct tggctgccat   9180
ttttggggtg aggccgttcg cggccgaggg gcgcagcccc tggggggatg ggaggcccgc   9240
gttagcgggc cgggagggtt cgagaagggg gggcaccccc cttcggcgtg cgcggtcacg   9300
cgcacagggc gcagccctgg ttaaaaacaa ggtttataaa tattggttta aaagcaggtt   9360
aaaagacagg ttagcggtgg ccgaaaaacg ggcggaaacc cttgcaaatg ctggattttc   9420
tgcctgtgga cagcccctca aatgtcaata ggtgcgcccc tcatctgtca gcactctgcc   9480
cctcaagtgt caaggatcgc gcccctcatc tgtcagtagt cgcgcccctc aagtgtcaat   9540
accgcagggc acttatcccc aggcttgtcc acatcatctg tgggaaactc gcgtaaaatc   9600
aggcgttttc gccgatttgc gaggctggcc agctccacgt cgccggccga aatcgagcct   9660
gcccctcatc tgtcaacgcc gcgccgggtg agtcggcccc tcaagtgtca acgtccgccc   9720
ctcatctgtc agtgagggcc aagttttccg cgaggtatcc acaacgccgg cggccggccg   9780
cggtgtctcg cacacggctt cgacggcgtt tctggcgcgt ttgcagggcc atagacggcc   9840
gccagcccag cggcgagggc aaccagcccg gtgagcgtcg gaaagggtcg atcgaccgat   9900
gcccttgaga gccttcaacc cagtcagctc cttccggtgg gcgcggggca tgactatcgt   9960
cgccgcactt atgactgtct tctttatcat gcaactcgta ggacaggtgc cggcagcgct  10020
ctgggtcatt ttcggcgagg accgctttcg ctggagcgcg acgatgatcg gcctgtcgct  10080
tgcggtattc ggaatcttgc acgccctcgc tcaagccttc gtcactggtc ccgccaccaa  10140
acgtttcggc gagaagcagg ccattatcgc cggcatggcg gccgacgcgc tgggctacgt  10200
cttgctggcg ttcgcgacgc gaggctggat ggccttcccc attatgattc ttctcgcttc  10260
cggcggcatc gggatgcccg cgttgcaggc catgctgtcc aggcaggtag atgacgacca  10320
tcagggacag cttcaaggat cgctcgcggc tcttaccagc ctaacttcga tcattggacc  10380
```

```
gctgatcgtc acggcgattt atgccgcctc ggcgagcaca tggaacgggt tggcatggat  10440
tgtaggcgcc gccctatacc ttgtctgcct ccccgcgttg cgtcgcggtg catggagccg  10500
ggccacctcg acctgaatgg aagccggcgg cacctcgcta acggattcac cactccaaga  10560
attggagcca atcaattctt gcggagaact gtgaatgcgc aaaccaaccc ttggcagaac  10620
atatccatcg cgtccgccat ctccagcagc cgcacgcggc gcatctcggg cagcgttggg  10680
tcctggccac gggtgcgcat gatcgtgctc ctgtcgttga ggacccggct aggctggcgg  10740
ggttgcctta ctggttagca gaatgaatca ccgatacgcg agcgaacgtg aagcgactgc  10800
tgctgcaaaa cgtctgcgac ctgagcaaca acatgaatgg tcttcggttt ccgtgtttcg  10860
taaagtctgg aaacgcggaa gtcagcgccc tgcaccatta tgttccggat ctgcatcgca  10920
ggatgctgct ggctaccctg tggaacacct acatctgtat taacgaagcg ctggcattga  10980
ccctgagtga tttttctctg gtcccgccgc atccataccg ccagttgttt accctcacaa  11040
cgttccagta accgggcatg ttcatcatca gtaacccgta tcgtgagcat cctctctcgt  11100
ttcatcggta tcattacccc catgaacaga aatcccctt acacggaggc atcagtgacc  11160
aaacaggaaa aaaccgccct taacatggcc cgctttatca gaagccagac attaacgctt  11220
ctggagaaac tcaacgagct ggacgcggat gaacaggcag acatctgtga atcgcttcac  11280
gaccacgctg atgagcttta ccgcagctgc ctcgcgcgtt tcggtgatga cggtgaaaac  11340
ctctgacaca tgcagctccc ggagacggtc acagcttgtc tgtaagcgga tgccgggagc  11400
agacaagccc gtcagggcgc gtcagcgggt gttggcgggt gtcggggcgc agccatgacc  11460
cagtcacgta gcgatagcgg agtgtatact ggcttaacta tgcggcatca gagcagattg  11520
tactgagagt gcaccatatg cggtgtgaaa taccgcacag atgcgtaagg agaaaatacc  11580
gcatcaggcg ctcttccgct tcctcgctca ctgactcgct gcgctcggtc gttcggctgc  11640
ggcgagcggt atcagctcac tcaaaggcgg taatacggtt atccacagaa tcaggggata  11700
acgcaggaaa gaacatgtga gcaaaaggcc agcaaaaggc caggaaccgt aaaaaggccg  11760
cgttgctggc gtttttccat aggctccgcc cccctgacga gcatcacaaa aatcgacgct  11820
caagtcagag gtggcgaaac ccgacaggac tataaagata ccaggcgttt ccccctggaa  11880
gctccctcgt gcgctctcct gttccgaccc tgccgcttac cggatacctg tccgcctttc  11940
tcccttcggg aagcgtggcg ctttctcata gctcacgctg taggtatctc agttcggtgt  12000
aggtcgttcg ctccaagctg ggctgtgtgc acgaaccccc cgttcagccc gaccgctgcg  12060
ccttatccgg taactatcgt cttgagtcca acccggtaag acacgactta tcgccactgg  12120
cagcagccac tggtaacagg attagcagag cgaggtatgt aggcggtgct acagagttct  12180
tgaagtggtg gcctaactac ggctacacta gaaggacagt atttggtatc tgcgctctgc  12240
tgaagccagt taccttcgga aaaagagttg gtagctcttg atccggcaaa caaaccaccg  12300
ctggtagcgg tggttttttt gtttgcaagc agcagattac gcgcagaaaa aaaggatctc  12360
aagaagatcc tttgatcttt tctacggggt ctgacgctca gtggaacgaa aactcacgtt  12420
aagggatttt ggtcatgaga ttatcaaaaa ggatcttcac ctagatcctt ttaaattaaa  12480
aatgaagttt taaatcaatc taaagtatat atgagtaaac ttggtctgac agttaccaat  12540
gcttaatcag tgaggcacct atctcagcga tctgtctatt tcgttcatcc atagttgcct  12600
gactccccgt cgtgtagata actacgatac gggagggctt accatctggc cccagtgctg  12660
caatgatacc gcgagaccca cgctcaccgg ctccagattt atcagcaata aaccagccag  12720
```

```
ccggaagggc cgagcgcaga agtggtcctg caactttatc cgcctccatc cagtctatta  12780

attgttgccg ggaagctaga gtaagtagtt cgccagttaa tagtttgcgc aacgttgttg  12840

ccattgctgc aggtcgggag cacaggatga cgcctaacaa ttcattcaag ccgacaccgc  12900

ttcgcggcgc ggcttaattc aggagttaaa catcatgagg gaagcggtga tcgccgaagt  12960

atcgactcaa ctatcagagg tagttggcgt catcgagcgc catctcgaac cgacgttgct  13020

ggccgtacat ttgtacggct ccgcagtgga tggcggcctg aagccacaca gtgatattga  13080

tttgctggtt acggtgaccg taaggcttga tgaaacaacg cggcgagctt tgatcaacga  13140

ccttttggaa acttcggctt cccctggaga gagcgagatt ctccgcgctg tagaagtcac  13200

cattgttgtg cacgacgaca tcattccgtg gcgttatcca gctaagcgcg aactgcaatt  13260

tggagaatgg cagcgcaatg acattcttgc aggtatcttc gagccagcca cgatcgacat  13320

tgatctggct atcttgctga caaaagcaag agaacatagc gttgccttgg taggtccagc  13380

ggcggaggaa ctctttgatc cggttcctga acaggatcta tttgaggcgc taaatgaaac  13440

cttaacgcta tggaactcgc cgcccgactg ggctggcgat gagcgaaatg tagtgcttac  13500

gttgtcccgc atttggtaca gcgcagtaac cggcaaaatc gcgccgaagg atgtcgctgc  13560

cgactgggca atggagcgcc tgccggccca gtatcagccc gtcatacttg aagctaggca  13620

ggcttatctt ggacaagaag atcgcttggc ctcgcgcgca gatcagttgg aagaatttgt  13680

tcactacgtg aaaggcgaga tcaccaaggt agtcggcaaa taatgtctaa caattcgttc  13740

aagccgacgc cgcttcgcgg cgcggcttaa ctcaagcgtt agatgctgca ggcatcgtgg  13800

tgtcacgctc gtcgtttggt atggcttcat tcagctccgg ttcccaacga tcaaggcgag  13860

ttacatgatc ccccatgttg tgcaaaaaag cggttagctc cttcg                  13905
```

<210> SEQ ID NO 216
<211> LENGTH: 13905
<212> TYPE: DNA
<213> ORGANISM: Artificial Sequence
<220> FEATURE:
<223> OTHER INFORMATION: pMON69770;Figure 37;the expression vector for the construct containing the AgroAS(S51C) non-optimized allele

<400> SEQUENCE: 216

```
tcgaggattt ttcggcgctg cgctacgtcc gcgaccgcgt tgagggatca agccacagca     60

gcccactcga ccttctagcc gacccagacg agccaaggga tctttttgga atgctgctcc    120

gtcgtcaggc tttccgacgt ttgggtggtt gaacagaagt cattatcgca cggaatgcca    180

agcactcccg aggggaaccc tgtggttggc atgcacatac aaatggacga acggataaac    240

cttttcacgc ccttttaaat atccgattat tctaataaac gctcttttct cttaggttta    300

cccgccaata tatcctgtca aacactgata gtttaaactg aaggcgggaa acgacaatct    360

gatccccatc aagctagctt ctgcaggtcc tgctcgaggt cactaagcaa ctaactttga    420

ggaatgaggt gatgatgaat taactcactc cattccacaa accaaacaaa aatttgagga    480

gtgagaagat gattgactat ctcattcctc aaaccaaaca cctcaaatat atctgctatc    540

gggattggca ttcctgtatc cctacgcccg tgtacccccct gtttagagaa cctccaaagg    600

tataagatgg cgaagattat tgttgtcttg tctttcatca tatatcgagt ctttccctag    660

gatattatta ttggcaatga gcattacacg gttaatcgat tgagagaaca tgcatctcac    720

cttcagcaaa taattacgat aatccatatt ttacgcttcg taacttctca tgagtttcga    780

tatacaaatt tgttttctgg acaccctacc attcatcctc ttcggagaag agaggaagtg    840
```

-continued

```
tcctcaattt aaatatgttg tcatgctgta gttcttcaca aaatctcaac aggtaccaag    900
cacattgttt ccacaaatta tattttagtc acaataaatc tatattatta ttaatatact    960
aaaactatac tgacgctcag atgcttttac tagttcttgc tagtatgtga tgtaggtcta   1020
cgtggaccag aaaatagtga gacacggaag acaaaagaag taaaagaggc ccggactacg   1080
gcccacatga gattcggccc cgccacctcc ggcaaccagc ggccgatcca acggcagtgc   1140
gcgcacacac acaacctcgt atatatcgcc gcgcggaagc ggcgcgaccg aggaagcctt   1200
gtcctcgaca ccccctacac aggtgtcgcg ctgcccccga cacgagtccc gcatgcgtcc   1260
cacgcggccg cgccagatcc cgcctccgcg cgttgccacg ccctctataa acacccagct   1320
ctccctcgcc ctcatctacc tcactcgtag tcgtagctca agcatcagcg gcagcggcag   1380
cggcaggatc tctgggcagc gtgcgcacgt ggggtatcta gctcgctctg ctagcctacc   1440
aatcgaattc ctgcaggtcg actctagagg atctaccgtc ttcggtacgc gctcactccg   1500
ccctctgcct ttgttactgc cacgtttctc tgaatgctct cttgtgtggt gattgctgag   1560
agtggtttag ctggatctag aattacactc tgaaatcgtg ttctgcctgt gctgattact   1620
tgccgtcctt tgtagcagca aaatataggg acatggtagt acgaaacgaa gatagaacct   1680
acacagcaat acgagaaatg tgtaatttgg tgcttagcgg tatttattta agcacatgtt   1740
ggtgttatag ggcacttgga ttcagaagtt tgctgttaat ttaggcacag gcttcatact   1800
acatgggtca atagtatagg gattcatatt ataggcgata ctataataat ttgttcgtct   1860
gcagagctta ttatttgcca aaattagata ttcctattct gtttttgttt gtgtgctgtt   1920
aaattgttaa cgcctgaagg aataaatata aatgacgaaa ttttgatgtt tatctctgct   1980
cctttattgt gaccataagt caagatcaga tgcacttgtt ttaaatattg ttgtctgaag   2040
aaataagtac tgacagtatt ttgatgcatt gatctgcttg tttgttgtaa caaaatttaa   2100
aaataaagag tttccttttt gttgctctcc ttacctcctg atggtatcta gtatctacca   2160
actgacacta tattgcttct ctttacatac gtatcttgct cgatgccttc tccctagtgt   2220
tgaccagtgt tactcacata gtctttgctc atttcattgt aatgcagata ccaagcggcc   2280
tctagaggac tccgatctat ggaatcccta gccgccacct ccgtgttcgc gccctcccgc   2340
gtcgccgtcc cggcggcgcg ggccctggtt agggcgggga cggtggtacc aaccaggcgg   2400
acgagcagcc ggagcggaac cagcggggtg aaatgctctg ctgccgtgac gccgcaggcg   2460
agcccagtga ttagcaggag cgctgcggcg gccatggtaa cgatcattca ggatgacgga   2520
gcggagacct acgagacgaa aggcggcatc caggtcagcc gaaagcgccg gcccaccgat   2580
tatgccaacg ccatcgataa ttacatcgaa aagcttgatt cccatcgcgg cgcggttttt   2640
tcgtgcaact atgaatatcc gggccgttac acccgctggg atacggccat cgtcgatccg   2700
ccgctcggca tttcctgttt tggccgcaag atgtggatcg aagcctataa tggccgcggc   2760
gaagtgctgc tcgatttcat tacggaaaag ctgaaggcga cacccgatct caccctcggc   2820
gcttcctcga cccgccggct cgatcttacc gtcaacgaac cggaccgtgt cttcaccgaa   2880
gaagaacgct cgaaaatccc gacggtcttc accgctctca gagccatcgt cgacctcttc   2940
tattcgagcg cggattcggc catcggcctg ttcggtgcct tcggttacga tctcgccttc   3000
cagttcgacg cgatcaagct ttcgctggcg cgtccggaag accagcgtga catggtgctg   3060
tttctgcccg atgaaatcct cgtcgttgat cactattccg ccaaggcctg gatcgaccgt   3120
tacgatttcg agaaggacgg catgacgacg gacggcaaat cctccgacat tacccccgat   3180
cccttcaaga ccaccgatac catcccgccc aagggcgatc accgtcccgg cgaatattcc   3240
```

```
gagcttgtgg tgaaggccaa ggaaagcttc cgccgcggcg acctgttcga ggtcgttccc   3300
ggccagaaat tcatggagcg ttgcgaaagc aatccgtcgg cgatttcccg ccgcctgaag   3360
gcgatcaacc cgtcgcccta ttccttcttc atcaatctcg gcgatcagga atatctggtc   3420
ggcgcctcgc cggaaatgtt cgtgcgcgtc tccggccgtc gcatcgagac ctgcccgata   3480
tcaggcacca tcaagcgcgg cgacgatccg attgccgaca gcgagcagat tttgaaactg   3540
ctcaactcga aaaaggacga atccgaactg accatgtgct cggacgtgga ccgcaacgac   3600
aagagccgcg tctgcgagcc gggttcggtg aaggtcattg gccgccgcca gatcgagatg   3660
tattcacgcc tcatccacac cgtcgatcac atcgaaggcc gcctgcgcga cgatatggac   3720
gcctttgacg gtttcctcag ccacgcctgg gccgtcaccg tcaccggtgc accaaagctg   3780
tgggccatgc gcttcatcga aggtcatgaa aagagcccgc gcgcctggta tggcggtgcg   3840
atcggcatgg tcggcttcaa cggcgacatg aataccggcc tgacgctgcg caccatccgg   3900
atcaaggacg gtattgccga agtgcgcgcc ggcgcgaccc tgctcaatga ttccaacccg   3960
caggaagaag aagccgaaac cgaactgaag gcctccgcca tgatatcagc cattcgtgac   4020
gcaaaaggca ccaactctgc cgccaccaag cgtgatgccg ccaaagtcgg caccggcgtc   4080
aagatcctgc tcgtcgacca cgaagacagc ttcgtgcaca cgctggcgaa ttatttccgc   4140
cagacgggcg cgacggtctc gaccgtcaga tcaccggtcg cagccgacgt gttcgatcgc   4200
ttccagccgg acctcgttgt cctgtcgccc ggacccggca gcccgacgga tttcgactgc   4260
aaggcaacga tcaaggccgc ccgcgcccgc gatctgccga tcttcggcgt ttgcctcggt   4320
ctgcaggcat tggcagaagc ctatggcggc gagctgcgcc agcttgctgt gcccatgcac   4380
ggcaagcctt cgcgcatccg cgtgctggaa cccggcctcg tcttctccgg tctcggcaag   4440
gaagtcacgg tcggtcgtta ccattcgatc ttcgccgatc ccgccaccct gccgcgtgat   4500
ttcatcatca ccgcagaaag cgaggacggc acgatcatgg gcatcgaaca cgccaaggaa   4560
ccggtggccg ccgttcagtt ccacccggaa tcgatcatga cgctcggaca ggacgcgggc   4620
atgcggatga tcgagaatgt cgtggtgcat ctgacccgca aggcgaagac caaggccgcg   4680
tgatggcgct cgatgacacg gttatatcac tagtgcggcc atcggatccg ggatcgatg   4740
agctaagcta gctatatcat caatttatgt attacacata atatcgcact cagtctttca   4800
tctacggcaa tgtaccagct gatataatca gttattgaaa tatttctgaa tttaaacttg   4860
catcaataaa tttatgtttt tgcttggact ataatacctg acttgttatt ttatcaataa   4920
atatttaaac tatatttctt tcaagatatc attctttaca agtatacgtg tttaaattga   4980
ataccataaa tttttatttt tcaaatacat gtaaaattat gaaatgggag tggtggcgac   5040
cgagctcaag cacacttcaa ttcctataac ggaccaaatc gcaaaaatta taataacata   5100
ttatttcatc ctggattaaa agaaagtcac cggggattat tttgtgacgc cgattacata   5160
cggcgacaat aaagacattg gaaatcgtag tacatattgg aatacactga ttatattaat   5220
gatgaataca tactttaata tccttacgta ggatcgatcc gaatttcgac ctcgagcggc   5280
cgctctagaa ctagtggatc ccccccttaa ttaagggggc tgcaggaatt cataacttcg   5340
tataatgtat gctatacgaa gttatgtttc gaggtcattc atatgcttga gaagagagtc   5400
gggatagtcc aaaataaaac aaaggtaaga ttacctggtc aaaagtgaaa acatcagtta   5460
aaaggtggta taaagtaaaa tatcggtaat aaaaggtggc ccaaagtgaa atttactctt   5520
ttctactatt ataaaaattg aggatgtttt tgtcggtact ttgatacgtc atttttgtat   5580
```

```
gaattggttt ttaagtttat tcgcttttgg aaatgcatat ctgtatttga gtcgggtttt   5640
aagttcgttt gcttttgtaa atacagaggg atttgtataa gaaatatctt tagaaaaacc   5700
catatgctaa tttgacataa tttttgagaa aaatatatat tcaggcgaat tctcacaatg   5760
aacaataata agattaaaat agctttcccc cgttgcagcg catgggtatt ttttctagta   5820
aaaataaaag ataaacttag actcaaaaca tttacaaaaa caacccctaa agttcctaaa   5880
gcccaaagtg ctatccacga tccatagcaa gcccagccca acccaaccca acccaaccca   5940
ccccagtcca gccaactgga caatagtctc cacacccccc cactatcacc gtgagttgtc   6000
cgcacgcacc gcacgtctcg cagccaaaaa aaaaaagaaa gaaaaaaaag aaaaagaaaa   6060
aacagcaggt gggtccgggt cgtgggggcc ggaaacgcga ggaggatcgc gagccagcga   6120
cgaggccggc cctccctccg cttccaaaga aacgccccccc atcgccacta tatacatacc   6180
cccccctctc ctcccatccc cccaacccta ccaccaccac caccaccacc tccacctcct   6240
cccccctcgc tgccggacga cgagctcctc ccccctcccc ctccgccgcc gccgcgccgg   6300
taaccacccc gcccctctcc tctttctttc tccgtttttt tttccgtctc ggtctcgatc   6360
tttggccttg gtagtttggg tgggcgagag gcggcttcgt gcgcgcccag atcggtgcgc   6420
gggaggggcg ggatctcgcg gctggggctc tcgccggcgt ggatccggcc cggatctcgc   6480
ggggaatggg gctctcggat gtagatctgc gatccgccgt tgttggggga gatgatgggg   6540
ggtttaaaat ttccgccgtg ctaaacaaga tcaggaagag gggaaaaggg cactatggtt   6600
tatattttta tatatttctg ctgcttcgtc aggcttagat gtgctagatc tttctttctt   6660
ctttttgtgg gtagaatttg aatccctcag cattgttcat cggtagtttt tcttttcatg   6720
atttgtgaca aatgcagcct cgtgcggagc ttttttgtag gtagaagtga tcaaccatgg   6780
cgcaagttag cagaatctgc aatggtgtgc agaacccatc tcttatctcc aatctctcga   6840
aatccagtca acgcaaatct cccttatcgg tttctctgaa gacgcagcag catccacgag   6900
cttatccgat ttcgtcgtcg tggggattga agaagagtgg gatgacgtta attggctctg   6960
agcttcgtcc tcttaaggtc atgtcttctg tttccacggc gtgcatgctt cacggtgcaa   7020
gcagccggcc cgcaaccgcc cgcaaatcct ctggcctttc cggaaccgtc cgcattcccg   7080
gcgacaagtc gatctcccac cggtccttca tgttcggcgg tctcgcgagc ggtgaaacgc   7140
gcatcaccgg ccttctggaa ggcgaggacg tcatcaatac gggcaaggcc atgcaggcga   7200
tgggcgcccg catccgtaag gaaggcgaca cctggatcat cgatggcgtc ggcaatggcg   7260
gcctcctggc gcctgaggcg ccgctcgatt tcggcaatgc cgccacgggc tgccgcctga   7320
cgatgggcct cgtcggggtc tacgatttcg acagcacctt catcggcgac gcctcgctca   7380
caaagcgccc gatgggccgc gtgttgaacc cgctgcgcga aatgggcgtg caggtgaaat   7440
cggaagacgg tgaccgtctt cccgttacct tgcgcgggcc gaagacgccg acgccgatca   7500
cctaccgcgt gccgatggcc tccgcacagg tgaagtccgc cgtgctgctc gccggcctca   7560
acacgcccgg catcacgacg gtcatcgagc cgatcatgac gcgcgatcat acggaaaaga   7620
tgctgcaggg ctttggcgcc aaccttaccg tcgagacgga tgcggacggc gtgcgcacca   7680
tccgcctgga aggccgcggc aagctcaccg gccaagtcat cgacgtgccg ggcgacccgt   7740
cctcgacggc cttcccgctg gttgcggccc tgcttgttcc gggctccgac gtcaccatcc   7800
tcaacgtgct gatgaacccc acccgcaccg gcctcatcct gacgctgcag gaaatgggcg   7860
ccgacatcga agtcatcaac ccgcgccttg ccggcggcga agacgtggcg gacctgcgcg   7920
ttcgctcctc cacgctgaag ggcgtcacgg tgccggaaga ccgcgcgcct tcgatgatcg   7980
```

```
acgaatatcc gattctcgct gtcgccgccg ccttcgcgga aggggcgacc gtgatgaacg   8040
gtctggaaga actccgcgtc aaggaaagcg accgcctctc ggccgtcgcc aatggcctca   8100
agctcaatgg cgtggattgc gatgagggcg agacgtcgct cgtcgtgcgt ggccgccctg   8160
acggcaaggg gctcggcaac gcctcgggcg ccgccgtcgc cacccatctc gatcaccgca   8220
tcgccatgag cttcctcgtc atgggcctcg tgtcggaaaa ccctgtcacg gtggacgatg   8280
ccacgatgat cgccacgagc ttcccggagt tcatggacct gatggccggg ctgggcgcga   8340
agatcgaact ctccgatacg aaggctgcct gatgagctcg aattcccgat cgttcaaaca   8400
tttggcaata aagtttctta agattgaatc ctgttgccgg tcttgcgatg attatcatat   8460
aatttctgtt gaattacgtt aagcatgtaa taattaacat gtaatgcatg acgttattta   8520
tgagatgggt ttttatgatt agagtcccgc aattatacat ttaatacgcg atagaaaaca   8580
aaatatagcg cgcaaactag gataaattat cgcgcgcggt gtcatctatg ttactagatc   8640
ggggataacg atcaagctat aacttcgtat aatgtatgct atacgaagtt atcgcgccaa   8700
atcgtgaagt ttctcatcta agcccccatt tggacgtgaa tgtagacacg tcgaaataaa   8760
gatttccgaa ttagaataat ttgtttattg ctttcgccta taaatacgac ggatcgtaat   8820
ttgtcgtttt atcaaaatgt actttcattt tataataacg ctgcggacat ctacattttt   8880
gaattgaaaa aaaattggta attactcttt ctttttctcc atattgacca tcatactcat   8940
tgctgatcca tgtagatttc ccggacatga agccatttac aattgaatat atcctgccgc   9000
cgctgccgct ttgcacccgg tggagcttgc atgttggttt ctacgcagaa ctgagccggt   9060
taggcagata atttccattg agaactgagc catgtgcacc ttccccccaa cacggtgagc   9120
gacggggcaa cggagtgatc cacatgggac ttttcctagc ttggctgcca tttttggggt   9180
gaggccgttc gcggccgagg ggcgcagccc ctgggggat gggaggcccg cgttagcggg    9240
ccgggagggt tcgagaaggg ggggcacccc ccttcggcgt gcgcggtcac gcgcacaggg   9300
cgcagccctg gttaaaaaca aggtttataa atattggttt aaaagcaggt taaaagacag   9360
gttagcggtg gccgaaaaac gggcggaaac ccttgcaaat gctggatttt ctgcctgtgg   9420
acagcccctc aaatgtcaat aggtgcgccc ctcatctgtc agcactctgc ccctcaagtg   9480
tcaaggatcg cgcccctcat ctgtcagtag tcgcgcccct caagtgtcaa taccgcaggg   9540
cacttatccc caggcttgtc cacatcatct gtgggaaact cgcgtaaaat caggcgtttt   9600
cgccgatttg cgaggctggc cagctccacg tcgccggccg aaatcgagcc tgcccctcat   9660
ctgtcaacgc cgcgccgggt gagtcggccc ctcaagtgtc aacgtccgcc cctcatctgt   9720
cagtgagggc caagttttcc gcgaggtatc cacaacgccg gcggccggcc gcggtgtctc   9780
gcacacggct tcgacggcgt ttctggcgcg tttgcagggc catagacggc cgccagccca   9840
gcggcgaggg caaccagccc ggtgagcgtc ggaaagggtc gatcgaccga tgcccttgag   9900
agccttcaac ccagtcagct ccttccggtg ggcgcggggc atgactatcg tcgccgcact   9960
tatgactgtc ttctttatca tgcaactcgt aggacaggtg ccggcagcgc tctgggtcat  10020
tttcggcgag gaccgctttc gctggagcgc gacgatgatc ggcctgtcgc ttgcggtatt  10080
cggaatcttg cacgccctcg ctcaagcctt cgtcactggt cccgccacca aacgtttcgg  10140
cgagaagcag gccattatcg ccggcatggc ggccgacgcg ctgggctacg tcttgctggc  10200
gttcgcgacg cgaggctgga tggccttccc cattatgatt cttctcgctt ccggcggcat  10260
cgggatgccc gcgttgcagg ccatgctgtc caggcaggta gatgacgacc atcagggaca  10320
```

```
gcttcaagga tcgctcgcgg ctcttaccag cctaacttcg atcattggac cgctgatcgt  10380
cacggcgatt tatgccgcct cggcgagcac atggaacggg ttggcatgga ttgtaggcgc  10440
cgccctatac cttgtctgcc tccccgcgtt gcgtcgcggt gcatggagcc gggccacctc  10500
gacctgaatg gaagccggcg gcacctcgct aacggattca ccactccaag aattggagcc  10560
aatcaattct tgcggagaac tgtgaatgcg caaaccaacc cttggcagaa catatccatc  10620
gcgtccgcca tctccagcag ccgcacgcgg cgcatctcgg gcagcgttgg gtcctggcca  10680
cgggtgcgca tgatcgtgct cctgtcgttg aggacccggc taggctggcg gggttgcctt  10740
actggttagc agaatgaatc accgatacgc gagcgaacgt gaagcgactg ctgctgcaaa  10800
acgtctgcga cctgagcaac aacatgaatg gtcttcggtt tccgtgtttc gtaaagtctg  10860
gaaacgcgga agtcagcgcc ctgcaccatt atgttccgga tctgcatcgc aggatgctgc  10920
tggctaccct gtggaacacc tacatctgta ttaacgaagc gctggcattg accctgagtg  10980
atttttctct ggtcccgccg catccatacc gccagttgtt taccctcaca acgttccagt  11040
aaccgggcat gttcatcatc agtaacccgt atcgtgagca tcctctctcg tttcatcggt  11100
atcattaccc ccatgaacag aaatcccct tacacggagg catcagtgac caaacaggaa  11160
aaaaccgccc ttaacatggc ccgctttatc agaagccaga cattaacgct tctggagaaa  11220
ctcaacgagc tggacgcgga tgaacaggca gacatctgtg aatcgcttca cgaccacgct  11280
gatgagcttt accgcagctg cctcgcgcgt ttcggtgatg acggtgaaaa cctctgacac  11340
atgcagctcc cggagacggt cacagcttgt ctgtaagcgg atgccgggag cagacaagcc  11400
cgtcagggcg cgtcagcggg tgttggcggg tgtcggggcg cagccatgac ccagtcacgt  11460
agcgatagcg gagtgtatac tggcttaact atgcggcatc agagcagatt gtactgagag  11520
tgcaccatat gcggtgtgaa ataccgcaca gatgcgtaag gagaaaatac cgcatcaggc  11580
gctcttccgc ttcctcgctc actgactcgc tgcgctcggt cgttcggctg cggcgagcgg  11640
tatcagctca ctcaaaggcg gtaatacggt tatccacaga atcaggggat aacgcaggaa  11700
agaacatgtg agcaaaaggc cagcaaaagg ccaggaaccg taaaaaggcc gcgttgctgg  11760
cgtttttcca taggctccgc ccccctgacg agcatcacaa aaatcgacgc tcaagtcaga  11820
ggtggcgaaa cccgacagga ctataaagat accaggcgtt tccccctgga agctccctcg  11880
tgcgctctcc tgttccgacc ctgccgctta ccggatacct gtccgccttt ctcccttcgg  11940
gaagcgtggc gctttctcat agctcacgct gtaggtatct cagttcggtg taggtcgttc  12000
gctccaagct gggctgtgtg cacgaacccc ccgttcagcc cgaccgctgc gccttatccg  12060
gtaactatcg tcttgagtcc aacccggtaa gacacgactt atcgccactg gcagcagcca  12120
ctggtaacag gattagcaga gcgaggtatg taggcggtgc tacagagttc ttgaagtggt  12180
ggcctaacta cggctacact agaaggacag tatttggtat ctgcgctctg ctgaagccag  12240
ttaccttcgg aaaaagagtt ggtagctctt gatccggcaa acaaaccacc gctggtagcg  12300
gtggtttttt tgtttgcaag cagcagatta cgcgcagaaa aaaaggatct caagaagatc  12360
ctttgatctt ttctacgggg tctgacgctc agtggaacga aaactcacgt taagggattt  12420
tggtcatgag attatcaaaa aggatcttca cctagatcct tttaaattaa aaatgaagtt  12480
ttaaatcaat ctaaagtata tatgagtaaa cttggtctga cagttaccaa tgcttaatca  12540
gtgaggcacc tatctcagcg atctgtctat ttcgttcatc catagttgcc tgactccccg  12600
tcgtgtagat aactacgata cgggagggct taccatctgg ccccagtgct gcaatgatac  12660
cgcgagaccc acgctcaccg gctccagatt tatcagcaat aaaccagcca gccggaaggg  12720
```

ccgagcgcag aagtggtcct gcaactttat ccgcctccat ccagtctatt aattgttgcc 12780
gggaagctag agtaagtagt tcgccagtta atagtttgcg caacgttgtt gccattgctg 12840
caggtcggga gcacaggatg acgcctaaca attcattcaa gccgacaccg cttcgcggcg 12900
cggcttaatt caggagttaa acatcatgag ggaagcggtg atcgccgaag tatcgactca 12960
actatcagag gtagttggcg tcatcgagcg ccatctcgaa ccgacgttgc tggccgtaca 13020
tttgtacggc tccgcagtgg atggcggcct gaagccacac agtgatattg atttgctggt 13080
tacggtgacc gtaaggcttg atgaaacaac gcggcgagct ttgatcaacg accttttgga 13140
aacttcggct tcccctggag agagcgagat tctccgcgct gtagaagtca ccattgttgt 13200
gcacgacgac atcattccgt ggcgttatcc agctaagcgc gaactgcaat ttggagaatg 13260
gcagcgcaat gacattcttg caggtatctt cgagccagcc acgatcgaca ttgatctggc 13320
tatcttgctg acaaaagcaa gagaacatag cgttgccttg gtaggtccag cggcggagga 13380
actctttgat ccggttcctg aacaggatct atttgaggcg ctaaatgaaa ccttaacgct 13440
atggaactcg ccgcccgact gggctggcga tgagcgaaat gtagtgctta cgttgtcccg 13500
catttggtac agcgcagtaa ccggcaaaat cgcgccgaag gatgtcgctg ccgactgggc 13560
aatggagcgc ctgccggccc agtatcagcc cgtcatactt gaagctaggc aggcttatct 13620
tggacaagaa gatcgcttgg cctcgcgcgc agatcagttg gaagaatttg ttcactacgt 13680
gaaaggcgag atcaccaagg tagtcggcaa ataatgtcta acaattcgtt caagccgacg 13740
ccgcttcgcg gcgcggctta actcaagcgt tagatgctgc aggcatcgtg gtgtcacgct 13800
cgtcgtttgg tatggcttca ttcagctccg gttcccaacg atcaaggcga gttacatgat 13860
cccccatgtt gtgcaaaaaa gcggttagct ccttcggtcc tccga 13905

<210> SEQ ID NO 217
<211> LENGTH: 13905
<212> TYPE: DNA
<213> ORGANISM: Artificial Sequence
<220> FEATURE:
<223> OTHER INFORMATION: pMON69768;Figure 36;the expression vector for the construct containing the AgroAS(S51F) mutant allele

<400> SEQUENCE: 217
tcgaggattt ttcggcgctg cgctacgtcc gcgaccgcgt tgagggatca agccacagca 60
gcccactcga ccttctagcc gacccagacg agccaaggga tctttttgga atgctgctcc 120
gtcgtcaggc tttccgacgt ttgggtggtt gaacagaagt cattatcgca cggaatgcca 180
agcactcccg aggggaaccc tgtggttggc atgcacatac aaatggacga acggataaac 240
cttttcacgc ccttttaaat atccgattat tctaataaac gctcttttct cttaggttta 300
cccgccaata tatcctgtca aacactgata gtttaaactg aaggcgggaa acgacaatct 360
gatccccatc aagctagctt ctgcaggtcc tgctcgaggt cactaagcaa ctaactttga 420
ggaatgaggt gatgatgaat taactcactc cattccacaa accaaacaaa aatttgagga 480
gtgagaagat gattgactat ctcattcctc aaaccaaaca cctcaaatat atctgctatc 540
gggattggca ttcctgtatc cctacgcccg tgtacccct gtttagagaa cctccaaagg 600
tataagatgg cgaagattat tgttgtcttg tctttcatca tatatcgagt ctttccctag 660
gatattatta ttggcaatga gcattacacg gttaatcgat tgagagaaca tgcatctcac 720
cttcagcaaa taattacgat aatccatatt ttacgcttcg taacttctca tgagtttcga 780
tatacaaatt tgttttctgg acaccctacc attcatcctc ttcggagaag agaggaagtg 840

```
tcctcaattt aaatatgttg tcatgctgta gttcttcaca aaatctcaac aggtaccaag    900
cacattgttt ccacaaatta tattttagtc acaataaatc tatattatta ttaatatact    960
aaaactatac tgacgctcag atgcttttac tagttcttgc tagtatgtga tgtaggtcta   1020
cgtggaccag aaaatagtga gacacggaag acaaaagaag taaaagaggc ccggactacg   1080
gcccacatga gattcggccc cgccacctcc ggcaaccagc ggccgatcca acggcagtgc   1140
gcgcacacac acaacctcgt atatatcgcc gcgcggaagc ggcgcgaccg aggaagcctt   1200
gtcctcgaca ccccctacac aggtgtcgcg ctgcccccga cacgagtccc gcatgcgtcc   1260
cacgcggccg cgccagatcc cgcctccgcg cgttgccacg ccctctataa acacccagct   1320
ctccctcgcc ctcatctacc tcactcgtag tcgtagctca agcatcagcg gcagcggcag   1380
cggcaggatc tctgggcagc gtgcgcacgt ggggtatcta gctcgctctg ctagcctacc   1440
aatcgaattc ctgcaggtcg actctagagg atctaccgtc ttcggtacgc gctcactccg   1500
ccctctgcct ttgttactgc cacgtttctc tgaatgctct cttgtgtggt gattgctgag   1560
agtggtttag ctggatctag aattacactc tgaaatcgtg ttctgcctgt gctgattact   1620
tgccgtcctt tgtagcagca aaatataggg acatggtagt acgaaacgaa gatagaacct   1680
acacagcaat acgagaaatg tgtaatttgg tgcttagcgg tatttattta agcacatgtt   1740
ggtgttatag ggcacttgga ttcagaagtt tgctgttaat ttaggcacag gcttcatact   1800
acatgggtca atagtatagg gattcatatt ataggcgata ctataataat ttgttcgtct   1860
gcagagctta ttatttgcca aaattagata ttcctattct gtttttgttt gtgtgctgtt   1920
aaattgttaa cgcctgaagg aataaatata aatgacgaaa ttttgatgtt tatctctgct   1980
cctttattgt gaccataagt caagatcaga tgcacttgtt ttaaatattg ttgtctgaag   2040
aaataagtac tgacagtatt ttgatgcatt gatctgcttg tttgttgtaa caaaatttaa   2100
aaataaagag tttccttttt gttgctctcc ttacctcctg atggtatcta gtatctacca   2160
actgacacta tattgcttct ctttacatac gtatcttgct cgatgccttc tccctagtgt   2220
tgaccagtgt tactcacata gtctttgctc atttcattgt aatgcagata ccaagcggcc   2280
tctagaggac tccgatctat ggaatcccta gccgccacct ccgtgttcgc gccctcccgc   2340
gtcgccgtcc cggcggcgcg ggccctggtt agggcgggga cggtggtacc aaccaggcgg   2400
acgagcagcc ggagcggaac cagcggggtg aaatgctctg ctgccgtgac gccgcaggcg   2460
agcccagtga ttagcaggag cgctgcggcg gccatggtaa cgatcattca ggatgacgga   2520
gcggagacct acgagacgaa aggcggcatc caggtcagcc gaaagcgccg gcccaccgat   2580
tatgccaacg ccatcgataa ttacatcgaa aagcttgatt cccatcgcgg cgcggttttt   2640
tcgttcaact atgaatatcc gggccgttac acccgctggg atacggccat cgtcgatccg   2700
ccgctcggca tttcctgttt tggccgcaag atgtggatcg aagcctataa tggccgcggc   2760
gaagtgctgc tcgatttcat tacggaaaag ctgaaggcga cacccgatct caccctcggc   2820
gcttcctcga cccgccggct cgatcttacc gtcaacgaac cggaccgtgt cttcaccgaa   2880
gaagaacgct cgaaaatccc gacggtcttc accgctctca gagccatcgt cgacctcttc   2940
tattcgagcg cggattcggc catcggcctg ttcggtgcct tcggttacga tctcgccttc   3000
cagttcgacg cgatcaagct ttcgctggcg cgtccggaag accagcgtga catggtgctg   3060
tttctgcccg atgaaatcct cgtcgttgat cactattccg ccaaggcctg gatcgaccgt   3120
tacgatttcg agaaggacgg catgacgacg gacggcaaat cctccgacat tacccccgat   3180
```

```
cccttcaaga ccaccgatac catcccgccc aagggcgatc accgtcccgg cgaatattcc   3240
gagcttgtgg tgaaggccaa ggaaagcttc cgccgcggcg acctgttcga ggtcgttccc   3300
ggccagaaat tcatggagcg ttgcgaaagc aatccgtcgg cgatttcccg ccgcctgaag   3360
gcgatcaacc cgtcgcccta ttccttcttc atcaatctcg gcgatcagga atatctggtc   3420
ggcgcctcgc cggaaatgtt cgtgcgcgtc tccggccgtc gcatcgagac ctgcccgata   3480
tcaggcacca tcaagcgcgg cgacgatccg attgccgaca gcgagcagat tttgaaactg   3540
ctcaactcga aaaaggacga atccgaactg accatgtgct cggacgtgga ccgcaacgac   3600
aagagccgcg tctgcgagcc gggttcggtg aaggtcattg gccgccgcca gatcgagatg   3660
tattcacgcc tcatccacac cgtcgatcac atcgaaggcc gcctgcgcga cgatatggac   3720
gcctttgacg gtttcctcag ccacgcctgg gccgtcaccg tcaccggtgc accaaagctg   3780
tgggccatgc gcttcatcga aggtcatgaa aagagcccgc gcgcctggta tggcggtgcg   3840
atcggcatgg tcggcttcaa cggcgacatg aataccggcc tgacgctgcg caccatccgg   3900
atcaaggacg gtattgccga agtgcgcgcc ggcgcgaccc tgctcaatga ttccaacccg   3960
caggaagaag aagccgaaac cgaactgaag gcctccgcca tgatatcagc cattcgtgac   4020
gcaaaaggca ccaactctgc cgccaccaag cgtgatgccg ccaaagtcgg caccggcgtc   4080
aagatcctgc tcgtcgacca cgaagacagc ttcgtgcaca cgctggcgaa ttatttccgc   4140
cagacgggcg cgacggtctc gaccgtcaga tcaccggtcg cagccgacgt gttcgatcgc   4200
ttccagccgg acctcgttgt cctgtcgccc ggacccggca gcccgacgga tttcgactgc   4260
aaggcaacga tcaaggccgc ccgcgcccgc gatctgccga tcttcggcgt ttgcctcggt   4320
ctgcaggcat tggcagaagc ctatggcggc gagctgcgcc agcttgctgt gcccatgcac   4380
ggcaagcctt cgcgcatccg cgtgctggaa cccggcctcg tcttctccgg tctcggcaag   4440
gaagtcacgg tcggtcgtta ccattcgatc ttcgccgatc ccgccaccct gccgcgtgat   4500
ttcatcatca ccgcagaaag cgaggacggc acgatcatgg gcatcgaaca cgccaaggaa   4560
ccggtggccg ccgttcagtt ccacccggaa tcgatcatga cgctcggaca ggacgcgggc   4620
atgcggatga tcgagaatgt cgtggtgcat ctgacccgca aggcgaagac caaggccgcg   4680
tgatggcgct cgatgacacg gttatatcac tagtgcggcc atcggatccg gggatcgatg   4740
agctaagcta gctatatcat caatttatgt attacacata atatcgcact cagtctttca   4800
tctacggcaa tgtaccagct gatataatca gttattgaaa tatttctgaa tttaaacttg   4860
catcaataaa tttatgtttt tgcttggact ataatacctg acttgttatt ttatcaataa   4920
atatttaaac tatatttctt tcaagatatc attctttaca agtatacgtg tttaaattga   4980
ataccataaa tttttatttt tcaaatacat gtaaaattat gaaatgggag tggtggcgac   5040
cgagctcaag cacacttcaa ttcctataac ggaccaaatc gcaaaaatta taataacata   5100
ttatttcatc ctggattaaa agaaagtcac cggggattat tttgtgacgc cgattacata   5160
cggcgacaat aaagacattg gaaatcgtag tacatattgg aatacactga ttatattaat   5220
gatgaataca tactttaata tccttacgta ggatcgatcc gaatttcgac ctcgagcggc   5280
cgctctagaa ctagtggatc ccccccttaa ttaagggggc tgcaggaatt cataacttcg   5340
tataatgtat gctatacgaa gttatgtttc gaggtcattc atatgcttga gaagagagtc   5400
gggatagtcc aaaataaaac aaaggtaaga ttacctggtc aaaagtgaaa acatcagtta   5460
aaaggtggta taaagtaaaa tatcggtaat aaaaggtggc ccaaagtgaa atttactctt   5520
ttctactatt ataaaaattg aggatgtttt tgtcggtact ttgatacgtc atttttgtat   5580
```

```
gaattggttt ttaagtttat tcgcttttgg aaatgcatat ctgtatttga gtcgggtttt   5640
aagttcgttt gcttttgtaa atacagaggg atttgtataa gaaatatctt tagaaaaacc   5700
catatgctaa tttgacataa tttttgagaa aaatatatat tcaggcgaat tctcacaatg   5760
aacaataata agattaaaat agctttcccc cgttgcagcg catgggtatt ttttctagta   5820
aaaataaaag ataaacttag actcaaaaca tttacaaaaa caacccctaa agttcctaaa   5880
gcccaaagtg ctatccacga tccatagcaa gcccagccca acccaaccca acccaaccca   5940
ccccagtcca gccaactgga caatagtctc cacacccccc cactatcacc gtgagttgtc   6000
cgcacgcacc gcacgtctcg cagccaaaaa aaaaaagaaa gaaaaaaaag aaaaagaaaa   6060
aacagcaggt gggtccgggt cgtgggggcc ggaaacgcga ggaggatcgc gagccagcga   6120
cgaggccggc cctccctccg cttccaaaga aacgcccccc atcgccacta tatacatacc   6180
ccccccctctc ctcccatccc cccaacccta ccaccaccac caccaccacc tccacctcct   6240
ccccccctcgc tgccggacga cgagctcctc ccccctcccc ctccgccgcc gccgcgccgg   6300
taaccacccc gcccctctcc tctttctttc tccgtttttt tttccgtctc ggtctcgatc   6360
tttggccttg gtagtttggg tgggcgagag gcggcttcgt gcgcgcccag atcggtgcgc   6420
gggagggggcg ggatctcgcg gctggggctc tcgccggcgt ggatccggcc cggatctcgc   6480
ggggaatggg gctctcggat gtagatctgc gatccgccgt tgttgggggga gatgatgggg   6540
ggtttaaaat ttccgccgtg ctaaacaaga tcaggaagag gggaaaaggg cactatggtt   6600
tatattttta tatatttctg ctgcttcgtc aggcttagat gtgctagatc tttctttctt   6660
ctttttgtgg gtagaatttg aatccctcag cattgttcat cggtagtttt tcttttcatg   6720
atttgtgaca aatgcagcct cgtgcggagc ttttttgtag gtagaagtga tcaaccatgg   6780
cgcaagttag cagaatctgc aatggtgtgc agaacccatc tcttatctcc aatctctcga   6840
aatccagtca acgcaaatct cccttatcgg tttctctgaa gacgcagcag catccacgag   6900
cttatccgat ttcgtcgtcg tggggattga agaagagtgg gatgacgtta attggctctg   6960
agcttcgtcc tcttaaggtc atgtcttctg tttccacggc gtgcatgctt cacggtgcaa   7020
gcagccggcc cgcaaccgcc cgcaaatcct ctggcctttc cggaaccgtc cgcattcccg   7080
gcgacaagtc gatctcccac cggtccttca tgttcggcgg tctcgcgagc ggtgaaacgc   7140
gcatcaccgg ccttctggaa ggcgaggacg tcatcaatac gggcaaggcc atgcaggcga   7200
tgggcgcccg catccgtaag gaaggcgaca cctggatcat cgatggcgtc ggcaatggcg   7260
gcctcctggc gcctgaggcg ccgctcgatt tcggcaatgc cgccacgggc tgccgcctga   7320
cgatgggcct cgtcggggtc tacgatttcg acagcacctt catcggcgac gcctcgctca   7380
caaagcgccc gatgggccgc gtgttgaacc cgctgcgcga aatgggcgtg caggtgaaat   7440
cggaagacgg tgaccgtctt cccgttacct tgcgcgggcc gaagacgccg acgccgatca   7500
cctaccgcgt gccgatggcc tccgcacagg tgaagtccgc cgtgctgctc gccggcctca   7560
acacgcccgg catcacgacg gtcatcgagc cgatcatgac gcgcgatcat acggaaaaga   7620
tgctgcaggg ctttggcgcc aaccttaccg tcgagacgga tgcggacggc gtgcgcacca   7680
tccgcctgga aggccgcggc aagctcaccg gccaagtcat cgacgtgccg ggcgacccgt   7740
cctcgacggc cttcccgctg gttgcggccc tgcttgttcc gggctccgac gtcaccatcc   7800
tcaacgtgct gatgaacccc acccgcaccg gcctcatcct gacgctgcag gaaatgggcg   7860
ccgacatcga agtcatcaac ccgcgccttg ccggcggcga agacgtggcg gacctgcgcg   7920
```

```
ttcgctcctc cacgctgaag ggcgtcacgg tgccggaaga ccgcgcgcct tcgatgatcg   7980
acgaatatcc gattctcgct gtcgccgccg ccttcgcgga aggggcgacc gtgatgaacg   8040
gtctggaaga actccgcgtc aaggaaagcg accgcctctc ggccgtcgcc aatggcctca   8100
agctcaatgg cgtggattgc gatgagggcg agacgtcgct cgtcgtgcgt ggccgccctg   8160
acggcaaggg gctcggcaac gcctcgggcg ccgccgtcgc cacccatctc gatcaccgca   8220
tcgccatgag cttcctcgtc atgggcctcg tgtcggaaaa ccctgtcacg gtggacgatg   8280
ccacgatgat cgccacgagc ttcccggagt tcatggacct gatggccggg ctgggcgcga   8340
agatcgaact ctccgatacg aaggctgcct gatgagctcg aattcccgat cgttcaaaca   8400
tttggcaata aagtttctta agattgaatc ctgttgccgg tcttgcgatg attatcatat   8460
aatttctgtt gaattacgtt aagcatgtaa taattaacat gtaatgcatg acgttattta   8520
tgagatgggt ttttatgatt agagtcccgc aattatacat ttaatacgcg atagaaaaca   8580
aaatatagcg cgcaaactag gataaattat cgcgcgcggt gtcatctatg ttactagatc   8640
ggggataacg atcaagctat aacttcgtat aatgtatgct atacgaagtt atcgcgccaa   8700
atcgtgaagt ttctcatcta agcccccatt tggacgtgaa tgtagacacg tcgaaataaa   8760
gatttccgaa ttagaataat ttgtttattg ctttcgccta taaatacgac ggatcgtaat   8820
ttgtcgtttt atcaaaatgt actttcattt tataataacg ctgcggacat ctacattttt   8880
gaattgaaaa aaaattggta attactcttt ctttttctcc atattgacca tcatactcat   8940
tgctgatcca tgtagatttc ccggacatga agccatttac aattgaatat atcctgccgc   9000
cgctgccgct ttgcacccgg tggagcttgc atgttggttt ctacgcagaa ctgagccggt   9060
taggcagata atttccattg agaactgagc catgtgcacc ttccccccaa cacggtgagc   9120
gacggggcaa cggagtgatc cacatgggac ttttcctagc ttggctgcca tttttggggt   9180
gaggccgttc gcggccgagg ggcgcagccc ctggggggat gggaggcccg cgttagcggg   9240
ccgggagggt tcgagaaggg ggggcacccc ccttcggcgt gcgcggtcac gcgcacaggg   9300
cgcagccctg gttaaaaaca aggtttataa atattggttt aaaagcaggt taaaagacag   9360
gttagcggtg gccgaaaaac gggcggaaac ccttgcaaat gctggatttt ctgcctgtgg   9420
acagcccctc aaatgtcaat aggtgcgccc ctcatctgtc agcactctgc ccctcaagtg   9480
tcaaggatcg cgcccctcat ctgtcagtag tcgcgcccct caagtgtcaa taccgcaggg   9540
cacttatccc caggcttgtc cacatcatct gtgggaaact cgcgtaaaat caggcgtttt   9600
cgccgatttg cgaggctggc cagctccacg tcgccggccg aaatcgagcc tgcccctcat   9660
ctgtcaacgc cgcgccgggt gagtcggccc ctcaagtgtc aacgtccgcc cctcatctgt   9720
cagtgagggc caagttttcc gcgaggtatc cacaacgccg gcggccggcc gcggtgtctc   9780
gcacacggct tcgacggcgt ttctggcgcg tttgcagggc catagacggc cgccagccca   9840
gcggcgaggg caaccagccc ggtgagcgtc ggaaagggtc gatcgaccga tgcccttgag   9900
agccttcaac ccagtcagct ccttccggtg ggcgcggggc atgactatcg tcgccgcact   9960
tatgactgtc ttctttatca tgcaactcgt aggacaggtg ccggcagcgc tctgggtcat  10020
tttcggcgag gaccgctttc gctggagcgc gacgatgatc ggcctgtcgc ttgcggtatt  10080
cggaatcttg cacgccctcg ctcaagcctt cgtcactggt cccgccacca aacgtttcgg  10140
cgagaagcag gccattatcg ccggcatggc ggccgacgcg ctgggctacg tcttgctggc  10200
gttcgcgacg cgaggctgga tggccttccc cattatgatt cttctcgctt ccggcggcat  10260
cgggatgccc gcgttgcagg ccatgctgtc caggcaggta gatgacgacc atcagggaca  10320
```

```
gcttcaagga tcgctcgcgg ctcttaccag cctaacttcg atcattggac cgctgatcgt  10380
cacggcgatt tatgccgcct cggcgagcac atggaacggg ttggcatgga ttgtaggcgc  10440
cgccctatac cttgtctgcc tccccgcgtt gcgtcgcggt gcatggagcc gggccacctc  10500
gacctgaatg gaagccggcg gcacctcgct aacggattca ccactccaag aattggagcc  10560
aatcaattct tgcggagaac tgtgaatgcg caaaccaacc cttggcagaa catatccatc  10620
gcgtccgcca tctccagcag ccgcacgcgg cgcatctcgg gcagcgttgg gtcctggcca  10680
cgggtgcgca tgatcgtgct cctgtcgttg aggacccggc taggctggcg gggttgcctt  10740
actggttagc agaatgaatc accgatacgc gagcgaacgt gaagcgactg ctgctgcaaa  10800
acgtctgcga cctgagcaac aacatgaatg gtcttcggtt tccgtgtttc gtaaagtctg  10860
gaaacgcgga agtcagcgcc ctgcaccatt atgttccgga tctgcatcgc aggatgctgc  10920
tggctaccct gtggaacacc tacatctgta ttaacgaagc gctggcattg accctgagtg  10980
atttttctct ggtcccgccg catccatacc gccagttgtt taccctcaca acgttccagt  11040
aaccgggcat gttcatcatc agtaacccgt atcgtgagca tcctctctcg tttcatcggt  11100
atcattaccc ccatgaacag aaatccccct tacacggagg catcagtgac caaacaggaa  11160
aaaaccgccc ttaacatggc ccgctttatc agaagccaga cattaacgct tctggagaaa  11220
ctcaacgagc tggacgcgga tgaacaggca gacatctgtg aatcgcttca cgaccacgct  11280
gatgagcttt accgcagctg cctcgcgcgt ttcggtgatg acggtgaaaa cctctgacac  11340
atgcagctcc cggagacggt cacagcttgt ctgtaagcgg atgccgggag cagacaagcc  11400
cgtcagggcg cgtcagcggg tgttggcggg tgtcggggcg cagccatgac ccagtcacgt  11460
agcgatagcg gagtgtatac tggcttaact atgcggcatc agagcagatt gtactgagag  11520
tgcaccatat gcggtgtgaa ataccgcaca gatgcgtaag gagaaaatac cgcatcaggc  11580
gctcttccgc ttcctcgctc actgactcgc tgcgctcggt cgttcggctg cggcgagcgg  11640
tatcagctca ctcaaaggcg gtaatacggt tatccacaga atcaggggat aacgcaggaa  11700
agaacatgtg agcaaaaggc cagcaaaagg ccaggaaccg taaaaaggcc gcgttgctgg  11760
cgtttttcca taggctccgc ccccctgacg agcatcacaa aaatcgacgc tcaagtcaga  11820
ggtggcgaaa cccgacagga ctataaagat accaggcgtt tccccctgga agctccctcg  11880
tgcgctctcc tgttccgacc ctgccgctta ccggatacct gtccgccttt ctcccttcgg  11940
gaagcgtggc gctttctcat agctcacgct gtaggtatct cagttcggtg taggtcgttc  12000
gctccaagct gggctgtgtg cacgaacccc ccgttcagcc cgaccgctgc gccttatccg  12060
gtaactatcg tcttgagtcc aacccggtaa gacacgactt atcgccactg gcagcagcca  12120
ctggtaacag gattagcaga gcgaggtatg taggcggtgc tacagagttc ttgaagtggt  12180
ggcctaacta cggctacact agaaggacag tatttggtat ctgcgctctg ctgaagccag  12240
ttaccttcgg aaaaagagtt ggtagctctt gatccggcaa acaaaccacc gctggtagcg  12300
gtggtttttt tgtttgcaag cagcagatta cgcgcagaaa aaaaggatct caagaagatc  12360
ctttgatctt ttctacgggg tctgacgctc agtggaacga aaactcacgt taagggattt  12420
tggtcatgag attatcaaaa aggatcttca cctagatcct tttaaattaa aaatgaagtt  12480
ttaaatcaat ctaaagtata tatgagtaaa cttggtctga cagttaccaa tgcttaatca  12540
gtgaggcacc tatctcagcg atctgtctat ttcgttcatc catagttgcc tgactccccg  12600
tcgtgtagat aactacgata cgggagggct taccatctgg ccccagtgct gcaatgatac  12660
```

```
cgcgagaccc acgctcaccg gctccagatt tatcagcaat aaaccagcca gccggaaggg  12720
ccgagcgcag aagtggtcct gcaactttat ccgcctccat ccagtctatt aattgttgcc  12780
gggaagctag agtaagtagt tcgccagtta atagtttgcg caacgttgtt gccattgctg  12840
caggtcggga gcacaggatg acgcctaaca attcattcaa gccgacaccg cttcgcggcg  12900
cggcttaatt caggagttaa acatcatgag ggaagcggtg atcgccgaag tatcgactca  12960
actatcagag gtagttggcg tcatcgagcg ccatctcgaa ccgacgttgc tggccgtaca  13020
tttgtacggc tccgcagtgg atggcggcct gaagccacac agtgatattg atttgctggt  13080
tacggtgacc gtaaggcttg atgaaacaac gcggcgagct ttgatcaacg accttttgga  13140
aacttcggct tcccctggag agagcgagat tctccgcgct gtagaagtca ccattgttgt  13200
gcacgacgac atcattccgt ggcgttatcc agctaagcgc gaactgcaat ttggagaatg  13260
gcagcgcaat gacattcttg caggtatctt cgagccagcc acgatcgaca ttgatctggc  13320
tatcttgctg acaaaagcaa gagaacatag cgttgccttg gtaggtccag cggcggagga  13380
actctttgat ccggttcctg aacaggatct atttgaggcg ctaaatgaaa ccttaacgct  13440
atggaactcg ccgcccgact gggctggcga tgagcgaaat gtagtgctta cgttgtcccg  13500
catttggtac agcgcagtaa ccggcaaaat cgcgccgaag gatgtcgctg ccgactgggc  13560
aatggagcgc ctgccggccc agtatcagcc cgtcatactt gaagctaggc aggcttatct  13620
tggacaagaa gatcgcttgg cctcgcgcgc agatcagttg gaagaatttg ttcactacgt  13680
gaaaggcgag atcaccaagg tagtcggcaa ataatgtcta acaattcgtt caagccgacg  13740
ccgcttcgcg gcgcggctta actcaagcgt tagatgctgc aggcatcgtg gtgtcacgct  13800
cgtcgtttgg tatggcttca ttcagctccg gttcccaacg atcaaggcga gttacatgat  13860
cccccatgtt gtgcaaaaaa gcggttagct ccttcggtcc tccga                 13905
```

<210> SEQ ID NO 218
<211> LENGTH: 13888
<212> TYPE: DNA
<213> ORGANISM: Artificial Sequence
<220> FEATURE:
<223> OTHER INFORMATION: pMON78850;Figure 47;the expression vector for the construct containing the Rhizobium meliloti anthranilate synthase wild type allele

<400> SEQUENCE: 218

```
ccaaatcgtg aagtttctca tctaagcccc catttggacg tgaatgtaga cacgtcgaaa     60
taaagatttc cgaattagaa taatttgttt attgctttcg cctataaata cgacggatcg    120
taatttgtcg ttttatcaaa atgtactttc attttataat aacgctgcgg acatctacat    180
ttttgaattg aaaaaaaatt ggtaattact ctttcttttt ctccatattg accatcatac    240
tcattgctga tccatgtaga tttcccggac atgaagccat ttacaattga atatatcctg    300
ccgccgctgc cgctttgcac ccggtggagc ttgcatgttg gtttctacgc agaactgagc    360
cggttaggca gataatttcc attgagaact gagccatgtg caccttcccc ccaacacggt    420
gagcgacggg gcaacggagt gatccacatg ggacttttcc tagcttggct gccatttttg    480
gggtgaggcc gttcgcggcc gaggggcgca gcccctgggg ggatgggagg cccgcgttag    540
cgggccggga gggttcgaga aggggggca cccccttcg gcgtgcgcgg tcacgcgcac    600
agggcgcagc cctggttaaa aacaaggttt ataaatattg gtttaaaagc aggttaaaag    660
acaggttagc ggtggccgaa aaacgggcgg aaacccttgc aaatgctgga ttttctgcct    720
gtggacagcc cctcaaatgt caataggtgc gcccctcatc tgtcagcact ctgcccctca    780
```

-continued

```
agtgtcaagg atcgcgcccc tcatctgtca gtagtcgcgc ccctcaagtg tcaataccgc    840
agggcactta tccccaggct tgtccacatc atctgtggga aactcgcgta aaatcaggcg    900
ttttcgccga tttgcgaggc tggccagctc cacgtcgccg gccgaaatcg agcctgcccc    960
tcatctgtca acgccgcgcc gggtgagtcg gcccctcaag tgtcaacgtc cgcccctcat   1020
ctgtcagtga gggccaagtt ttccgcgagg tatccacaac gccggcggcc ggccgcggtg   1080
tctcgcacac ggcttcgacg gcgtttctgg cgcgtttgca gggccataga cggccgccag   1140
cccagcggcg agggcaacca gcccggtgag cgtcggaaag ggtcgatcga ccgatgccct   1200
tgagagcctt caacccagtc agctccttcc ggtgggcgcg gggcatgact atcgtcgccg   1260
cacttatgac tgtcttcttt atcatgcaac tcgtaggaca ggtgccggca gcgctctggg   1320
tcattttcgg cgaggaccgc tttcgctgga gcgcgacgat gatcggcctg tcgcttgcgg   1380
tattcggaat cttgcacgcc ctcgctcaag ccttcgtcac tggtcccgcc accaaacgtt   1440
tcggcgagaa gcaggccatt atcgccggca tggcggccga cgcgctgggc tacgtcttgc   1500
tggcgttcgc gacgcgaggc tggatggcct tccccattat gattcttctc gcttccggcg   1560
gcatcgggat gcccgcgttg caggccatgc tgtccaggca ggtagatgac gaccatcagg   1620
gacagcttca aggatcgctc gcggctctta ccagcctaac ttcgatcatt ggaccgctga   1680
tcgtcacggc gatttatgcc gcctcggcga gcacatggaa cgggttggca tggattgtag   1740
gcgccgccct ataccttgtc tgcctccccg cgttgcgtcg cggtgcatgg agccgggcca   1800
cctcgacctg aatggaagcc ggcggcacct cgctaacgga ttcaccactc caagaattgg   1860
agccaatcaa ttcttgcgga gaactgtgaa tgcgcaaacc aacccttggc agaacatatc   1920
catcgcgtcc gccatctcca gcagccgcac gcggcgcatc tcgggcagcg ttgggtcctg   1980
gccacgggtg cgcatgatcg tgctcctgtc gttgaggacc cggctaggct ggcggggttg   2040
ccttactggt tagcagaatg aatcaccgat acgcgagcga acgtgaagcg actgctgctg   2100
caaaacgtct gcgacctgag caacaacatg aatggtcttc ggtttccgtg tttcgtaaag   2160
tctggaaacg cggaagtcag cgccctgcac cattatgttc cggatctgca tcgcaggatg   2220
ctgctggcta ccctgtggaa cacctacatc tgtattaacg aagcgctggc attgaccctg   2280
agtgattttt ctctggtccc gccgcatcca taccgccagt tgtttaccct cacaacgttc   2340
cagtaaccgg gcatgttcat catcagtaac ccgtatcgtg agcatcctct ctcgtttcat   2400
cggtatcatt acccccatga acagaaatcc cccttacacg gaggcatcag tgaccaaaca   2460
ggaaaaaacc gcccttaaca tggcccgctt tatcagaagc cagacattaa cgcttctgga   2520
gaaactcaac gagctggacg cggatgaaca ggcagacatc tgtgaatcgc ttcacgacca   2580
cgctgatgag ctttaccgca gctgcctcgc gcgtttcggt gatgacggtg aaaacctctg   2640
acacatgcag ctcccggaga cggtcacagc ttgtctgtaa gcggatgccg ggagcagaca   2700
agcccgtcag ggcgcgtcag cgggtgttgg cgggtgtcgg ggcgcagcca tgacccagtc   2760
acgtagcgat agcggagtgt atactggctt aactatgcgg catcagagca gattgtactg   2820
agagtgcacc atatgcggtg tgaaataccg cacagatgcg taaggagaaa ataccgcatc   2880
aggcgctctt ccgcttcctc gctcactgac tcgctgcgct cggtcgttcg gctgcggcga   2940
gcggtatcag ctcactcaaa ggcggtaata cggttatcca cagaatcagg ggataacgca   3000
ggaaagaaca tgtgagcaaa aggccagcaa aaggccagga accgtaaaaa ggccgcgttg   3060
ctggcgtttt tccataggct ccgcccccct gacgagcatc acaaaaatcg acgctcaagt   3120
```

```
cagaggtggc gaaacccgac aggactataa agataccagg cgtttccccc tggaagctcc   3180
ctcgtgcgct ctcctgttcc gaccctgccg cttaccggat acctgtccgc ctttctccct   3240
tcgggaagcg tggcgctttc tcatagctca cgctgtaggt atctcagttc ggtgtaggtc   3300
gttcgctcca agctgggctg tgtgcacgaa ccccccgttc agcccgaccg ctgcgcctta   3360
tccggtaact atcgtcttga gtccaacccg gtaagacacg acttatcgcc actggcagca   3420
gccactggta acaggattag cagagcgagg tatgtaggcg gtgctacaga gttcttgaag   3480
tggtggccta actacggcta cactagaagg acagtatttg gtatctgcgc tctgctgaag   3540
ccagttacct tcggaaaaag agttggtagc tcttgatccg gcaaacaaac caccgctggt   3600
agcggtggtt tttttgtttg caagcagcag attacgcgca gaaaaaaagg atctcaagaa   3660
gatcctttga tcttttctac ggggtctgac gctcagtgga acgaaaactc acgttaaggg   3720
attttggtca tgagattatc aaaaaggatc ttcacctaga tccttttaaa ttaaaaatga   3780
agttttaaat caatctaaag tatatatgag taaacttggt ctgacagtta ccaatgctta   3840
atcagtgagg cacctatctc agcgatctgt ctatttcgtt catccatagt tgcctgactc   3900
cccgtcgtgt agataactac gatacgggag ggcttaccat ctggccccag tgctgcaatg   3960
ataccgcgag acccacgctc accggctcca gatttatcag caataaacca gccagccgga   4020
agggccgagc gcagaagtgg tcctgcaact ttatccgcct ccatccagtc tattaattgt   4080
tgccgggaag ctagagtaag tagttcgcca gttaatagtt tgcgcaacgt tgttgccatt   4140
gctgcaggtc gggagcacag gatgacgcct aacaattcat tcaagccgac accgcttcgc   4200
ggcgcggctt aattcaggag ttaaacatca tgagggaagc ggtgatcgcc gaagtatcga   4260
ctcaactatc agaggtagtt ggcgtcatcg agcgccatct cgaaccgacg ttgctggccg   4320
tacatttgta cggctccgca gtggatggcg gcctgaagcc acacagtgat attgatttgc   4380
tggttacggt gaccgtaagg cttgatgaaa caacgcggcg agctttgatc aacgaccttt   4440
tggaaacttc ggcttcccct ggagagagcg agattctccg cgctgtagaa gtcaccattg   4500
ttgtgcacga cgacatcatt ccgtggcgtt atccagctaa gcgcgaactg caatttggag   4560
aatggcagcg caatgacatt cttgcaggta tcttcgagcc agccacgatc gacattgatc   4620
tggctatctt gctgacaaaa gcaagagaac atagcgttgc cttggtaggt ccagcggcgg   4680
aggaactctt tgatccggtt cctgaacagg atctatttga ggcgctaaat gaaaccttaa   4740
cgctatggaa ctcgccgccc gactgggctg gcgatgagcg aaatgtagtg cttacgttgt   4800
cccgcatttg gtacagcgca gtaaccggca aaatcgcgcc gaaggatgtc gctgccgact   4860
gggcaatgga gcgcctgccg gcccagtatc agcccgtcat acttgaagct aggcaggctt   4920
atcttggaca agaagatcgc ttggcctcgc gcgcagatca gttggaagaa tttgttcact   4980
acgtgaaagg cgagatcacc aaggtagtcg gcaaataatg tctaacaatt cgttcaagcc   5040
gacgccgctt cgcggcgcgg cttaactcaa gcgttagatg ctgcaggcat cgtggtgtca   5100
cgctcgtcgt ttggtatggc ttcattcagc tccggttccc aacgatcaag gcgagttaca   5160
tgatccccca tgttgtgcaa aaaagcggtt agctccttcg gtcctccgat cgaggatttt   5220
tcggcgctgc gctacgtccg cgaccgcgtt gagggatcaa gccacagcag cccactcgac   5280
cttctagccg acccagacga gccaagggat ctttttggaa tgctgctccg tcgtcaggct   5340
ttccgacgtt tgggtggttg aacagaagtc attatcgcac ggaatgccaa gcactcccga   5400
ggggaaccct gtggttggca tgcacataca aatggacgaa cggataaacc ttttcacgcc   5460
cttttaaata tccgattatt ctaataaacg ctcttttctc ttaggtttac ccgccaatat   5520
```

```
atcctgtcaa acactgatag tttaaactga aggcgggaaa cgacaatctg atccccatca   5580
agctagcttc tgcaggtcct gctcgaggtc actaagcaac taactttgag gaatgaggtg   5640
atgatgaatt aactcactcc attccacaaa ccaaacaaaa atttgaggag tgagaagatg   5700
attgactatc tcattcctca aaccaaacac ctcaaatata tctgctatcg ggattggcat   5760
tcctgtatcc ctacgcccgt gtacccctg tttagagaac ctccaaaggt ataagatggc   5820
gaagattatt gttgtcttgt ctttcatcat atatcgagtc tttccctagg atattattat   5880
tggcaatgag cattacacgg ttaatcgatt gagagaacat gcatctcacc ttcagcaaat   5940
aattacgata atccatattt tacgcttcgt aacttctcat gagtttcgat atacaaattt   6000
gttttctgga caccctacca ttcatcctct tcggagaaga gaggaagtgt cctcaattta   6060
aatatgttgt catgctgtag ttcttcacaa aatctcaaca ggtaccaagc acattgtttc   6120
cacaaattat attttagtca caataaatct atattattat taatatacta aaactatact   6180
gacgctcaga tgcttttact agttcttgct agtatgtgat gtaggtctac gtggaccaga   6240
aaatagtgag acacggaaga caaaagaagt aaaagaggcc cggactacgg cccacatgag   6300
attcggcccc gccacctccg gcaaccagcg gccgatccaa cggcagtgcg cgcacacaca   6360
caacctcgta tatatcgccg cgcggaagcg gcgcgaccga ggaagccttg tcctcgacac   6420
cccctacaca ggtgtcgcgc tgcccccgac acgagtcccg catgcgtccc acgcggccgc   6480
gccagatccc gcctccgcgc gttgccacgc cctctataaa cacccagctc tccctcgccc   6540
tcatctacct cactcgtagt cgtagctcaa gcatcagcgg cagcggcagc ggcaggatct   6600
ctgggcagcg tgcgcacgtg ggtatctag ctcgctctgc tagcctacca atcgaattcc   6660
tgcaggtcga ctctagagga tctaccgtct tcggtacgcg ctcactccgc cctctgcctt   6720
tgttactgcc acgtttctct gaatgctctc ttgtgtggtg attgctgaga gtggtttagc   6780
tggatctaga attacactct gaaatcgtgt tctgcctgtg ctgattactt gccgtccttt   6840
gtagcagcaa aatataggga catggtagta cgaaacgaag atagaaccta cacagcaata   6900
cgagaaatgt gtaatttggt gcttagcggt atttatttaa gcacatgttg gtgttatagg   6960
gcacttggat tcagaagttt gctgttaatt taggcacagg cttcatacta catgggtcaa   7020
tagtataggg attcatatta taggcgatac tataataatt tgttcgtctg cagagcttat   7080
tatttgccaa aattagatat tcctattctg tttttgtttg tgtgctgtta aattgttaac   7140
gcctgaagga ataaatataa atgacgaaat tttgatgttt atctctgctc ctttattgtg   7200
accataagtc aagatcagat gcacttgttt taaatattgt tgtctgaaga aataagtact   7260
gacagtattt tgatgcattg atctgcttgt ttgttgtaac aaaatttaaa aataaagagt   7320
ttcctttttg ttgctctcct tacctcctga tggtatctag tatctaccaa ctgacactat   7380
attgcttctc tttacatacg tatcttgctc gatgccttct ccctagtgtt gaccagtgtt   7440
actcacatag tctttgctca tttcattgta atgcagatac caagcggcct ctagaggatc   7500
tccctagagg atctccagat ctatggaatc cctagccgcc acctccgtgt tcgcgccctc   7560
ccgcgtcgcc gtcccggcgg cgcgggccct ggttagggcg gggacggtgg taccaaccag   7620
gcggacgagc agccggagcg gaaccagcgg ggtgaaatgc tctgctgccg tgacgccgca   7680
ggcgagccca gtgattagca ggagcgctgc ggcggccatg gcagcggtaa ttctggaaga   7740
cggcgcggag agttatacca cgaagggtgg catcgtcgtc acccgcaggc ggcgtgaggc   7800
atcctacagc gacgcgatcg ccggttatgt cgaccggctg gacgaacgcc gcggcgcggt   7860
```

```
cttttcctcg aactacgaat atcccggccg ctatacccgc tgggacactg cggtggtcga   7920
cccgccgctt gccatctcct ccttcggtcg ctcgctctgg atcgaagcct ataacgaacg   7980
cggcgaagtg ctgctggcgc tgatcgccga ggatctgaag tccgttgccg acatcacgct   8040
cggctcactt gccgcccgcc gcctcgacct caccatcaac gagcccgatc gtgtcttcac   8100
cgaggaagag cggtcgaaga tgccgacggt ctttacggtt cttcgcgcgg tgacgaacct   8160
cttccactcg gaggaggact cgaacctcgg cctctatggc gccttcggct acgacctcgc   8220
cttccagttc gatgcgatcg aactgaagct ttcgcgtccg gacgaccagc gcgacatggt   8280
tctctttctg ccggacgaga tccttgtggt cgatcactat gcggccaagg cctggatcga   8340
ccgctacgat ttcgccaggg agaacctttc gaccgagggc aaggcagcgg acattgctcc   8400
cgagccgttc cgcagcgtcg acagcatccc gccgcacggg gatcaccgcc cgggcgaata   8460
tgccgagctc gtcgtcaagg cgaaggaaag cttccgtcgc ggcgatcttt tcgaagtggt   8520
gccggggcag aaattctacg agcgctgcga aagccgcccg tccgagattt ccaaccggct   8580
gaaggcgatc aatccgtcgc cctattcctt cttcatcaat ctcggcaacc aggaatatct   8640
cgtcggtgct tcgccggaga tgttcgtgcg cgtttccggc cggcgcatcg agacctgccc   8700
gatctccggt acgatcaagc gcggcgacga tccgatcgcc gacagcgagc agatcctgaa   8760
gctcttgaac tcgaagaagg acgagtccga gctcaccatg tgctcggacg tcgaccgcaa   8820
cgacaagagc cgggtctgcg tgccgggctc ggtcaaggtg atcggccggc gtcagatcga   8880
gatgtattcg cggctgatcc acacggtcga tcacatcgag gggcgcctgc gcgacgatat   8940
ggacgccttc gacgggttcc tcagccacgc ctgggcggtg accgttaccg gcgcgccaaa   9000
gctctgggcc atgcgcttca tcgagagcca cgagaagagc ccgcgtgcct ggtatggcgg   9060
cgcgatcggc atggtcggct tcaacggcga catgaatacc gggctgacct tgcgtaccat   9120
ccgcatcaag gacgggatcg ccgaggtgag ggcgggtgcg acgctcctct atgattccaa   9180
tccggaagaa gaagaagccg aaaccgaact gaaggcctct gccatgattg cagccatccg   9240
cgacgcgaaa tccgcaaaca gcgccaaatc cgcgcgcgat gtcgccgccg tcggcgccgg   9300
agtcagcatc ctgctcgtcg atcacgagga cagcttcgtc cataccctcg cgaactactt   9360
ccgccagacc ggcgcgtccg tcaccaccgt gcgcacgccg gtggccgagg aaatcttcga   9420
ccgggtcaag ccggacctcg tcgtgctttc gcccggtccc ggcaccccga aggacttcga   9480
ctgcaaggcg acgatcaaga aggcgcgggc gcgggacctg ccgatcttcg gcgtctgcct   9540
ggggctgcag gcgctcgcgg aggcctatgg cggcgacctt cgtcaactgg cgatcccgat   9600
gcatgggaag ccctcgcgca tccgcgtgct cgaacccggc atcgtcttct ccggcctcgg   9660
caaggaggtg acggtcgggc gctatcattc gattttcgcc gatccgtcca acctgccgcg   9720
cgaattcgtg atcacggccg aaagcgaaga tggtacgatc atgggcatcg aacacagcaa   9780
ggagccggtg gcggccgtgc agttccatcc ggaatcgatc atgacgctgg gcggcgacgc   9840
cggcatgcgg atgatcgaga acgtggttgc ccatctcgcc aagcgggcga agaccaaggc   9900
agcctgaact agatcggatc cggggatcga tgagctaagc tagctatatc atcaatttat   9960
gtattacaca taatatcgca ctcagtcttt catctacggc aatgtaccag ctgatataat  10020
cagttattga aatatttctg aatttaaact tgcatcaata aatttatgtt tttgcttgga  10080
ctataatacc tgacttgtta ttttatcaat aaatatttaa actatatttc tttcaagata  10140
tcattcttta caagtatacg tgtttaaatt gaataccata aatttttatt tttcaaatac  10200
atgtaaaatt atgaaatggg agtggtggcg accgagctca agcacacttc aattcctata  10260
```

```
acggaccaaa tcgcaaaaat tataataaca tattatttca tcctggatta aaagaaagtc  10320
accggggatt attttgtgac gccgattaca tacggcgaca ataaagacat tggaaatcgt  10380
agtacatatt ggaatacact gattatatta atgatgaata catactttaa tatccttacg  10440
taggatcgat ccgaatttcg acctcgagcg gccgctctag aactagtgga tccccccctt  10500
aattaagggg gctgcaggaa ttcataactt cgtataatgt atgctatacg aagttatgtt  10560
tcgaggtcat tcatatgctt gagaagagag tcgggatagt ccaaaataaa acaaaggtaa  10620
gattacctgg tcaaaagtga aaacatcagt taaaaggtgg tataaagtaa aatatcggta  10680
ataaaaggtg gcccaaagtg aaatttactc ttttctacta ttataaaaat tgaggatgtt  10740
tttgtcggta ctttgatacg tcatttttgt atgaattggt ttttaagttt attcgctttt  10800
ggaaatgcat atctgtattt gagtcgggtt ttaagttcgt ttgcttttgt aaatacagag  10860
ggatttgtat aagaaatatc tttagaaaaa cccatatgct aatttgacat aatttttgag  10920
aaaaatatat attcaggcga attctcacaa tgaacaataa taagattaaa atagctttcc  10980
cccgttgcag cgcatgggta ttttttctag taaaaataaa agataaactt agactcaaaa  11040
catttacaaa aacaacccct aaagttccta aagcccaaag tgctatccac gatccatagc  11100
aagcccagcc caacccaacc caacccaacc caccccagtc cagccaactg gacaatagtc  11160
tccacacccc cccactatca ccgtgagttg tccgcacgca ccgcacgtct cgcagccaaa  11220
aaaaaaaaga aagaaaaaaa agaaaaagaa aaaacagcag gtgggtccgg gtcgtggggg  11280
ccggaaacgc gaggaggatc gcgagccagc gacgaggccg gccctccctc cgcttccaaa  11340
gaaacgcccc ccatcgccac tatatacata cccccccctc tcctcccatc cccccaaccc  11400
taccaccacc accaccacca cctccacctc ctcccccctc gctgccggac gacgagctcc  11460
tcccccctcc ccctccgccg ccgccgcgcc ggtaaccacc ccgcccctct cctctttctt  11520
tctccgtttt tttttccgtc tcggtctcga tctttggcct tggtagtttg ggtgggcgag  11580
aggcggcttc gtgcgcgccc agatcggtgc gcgggagggg cgggatctcg cggctggggc  11640
tctcgccggc gtggatccgg cccggatctc gcggggaatg gggctctcgg atgtagatct  11700
gcgatccgcc gttgttgggg gagatgatgg ggggtttaaa atttccgccg tgctaaacaa  11760
gatcaggaag aggggaaaag ggcactatgg tttatatttt tatatatttc tgctgcttcg  11820
tcaggcttag atgtgctaga tctttctttc ttcttttttgt gggtagaatt tgaatccctc  11880
agcattgttc atcggtagtt tttcttttca tgatttgtga caaatgcagc ctcgtgcgga  11940
gcttttttgt aggtagaagt gatcaaccat ggcgcaagtt agcagaatct gcaatggtgt  12000
gcagaaccca tctcttatct ccaatctctc gaaatccagt caacgcaaat ctcccttatc  12060
ggtttctctg aagacgcagc agcatccacg agcttatccg atttcgtcgt cgtggggatt  12120
gaagaagagt gggatgacgt taattggctc tgagcttcgt cctcttaagg tcatgtcttc  12180
tgtttccacg gcgtgcatgc ttcacggtgc aagcagccgg cccgcaaccg cccgcaaatc  12240
ctctggcctt tccggaaccg tccgcattcc cggcgacaag tcgatctccc accggtcctt  12300
catgttcggc ggtctcgcga gcggtgaaac gcgcatcacc ggccttctgg aaggcgagga  12360
cgtcatcaat acgggcaagg ccatgcaggc gatgggcgcc cgcatccgta aggaaggcga  12420
cacctggatc atcgatggcg tcggcaatgg cggcctcctg gcgcctgagg cgccgctcga  12480
tttcggcaat gccgccacgg gctgccgcct gacgatgggc ctcgtcgggg tctacgattt  12540
cgacagcacc ttcatcggcg acgcctcgct cacaaagcgc ccgatgggcc gcgtgttgaa  12600
```

```
cccgctgcgc gaaatgggcg tgcaggtgaa atcggaagac ggtgaccgtc ttcccgttac  12660

cttgcgcggg ccgaagacgc cgacgccgat cacctaccgc gtgccgatgg cctccgcaca  12720

ggtgaagtcc gccgtgctgc tcgccggcct caacacgccc ggcatcacga cggtcatcga  12780

gccgatcatg acgcgcgatc atacggaaaa gatgctgcag ggctttggcg ccaaccttac  12840

cgtcgagacg gatgcggacg gcgtgcgcac catccgcctg gaaggccgcg gcaagctcac  12900

cggccaagtc atcgacgtgc cgggcgaccc gtcctcgacg gccttcccgc tggttgcggc  12960

cctgcttgtt ccgggctccg acgtcaccat cctcaacgtg ctgatgaacc ccacccgcac  13020

cggcctcatc ctgacgctgc aggaaatggg cgccgacatc gaagtcatca acccgcgcct  13080

tgccggcggc gaagacgtgg cggacctgcg cgttcgctcc tccacgctga agggcgtcac  13140

ggtgccggaa gaccgcgcgc cttcgatgat cgacgaatat ccgattctcg ctgtcgccgc  13200

cgccttcgcg gaaggggcga ccgtgatgaa cggtctggaa gaactccgcg tcaaggaaag  13260

cgaccgcctc tcggccgtcg ccaatggcct caagctcaat ggcgtggatt gcgatgaggg  13320

cgagacgtcg ctcgtcgtgc gtggccgccc tgacggcaag ggctcggca acgcctcggg  13380

cgccgccgtc gccacccatc tcgatcaccg catcgccatg agcttcctcg tcatgggcct  13440

cgtgtcggaa aaccctgtca cggtggacga tgccacgatg atcgccacga gcttcccgga  13500

gttcatggac ctgatggccg ggctgggcgc gaagatcgaa ctctccgata cgaaggctgc  13560

ctgatgagct cgaattcccg atcgttcaaa catttggcaa taaagtttct taagattgaa  13620

tcctgttgcc ggtcttgcga tgattatcat ataatttctg ttgaattacg ttaagcatgt  13680

aataattaac atgtaatgca tgacgttatt tatgagatgg gtttttatga ttagagtccc  13740

gcaattatac atttaatacg cgatagaaaa caaaatatag cgcgcaaact aggataaatt  13800

atcgcgcgcg gtgtcatcta tgttactaga tcggggataa cgatcaagct ataacttcgt  13860

ataatgtatg ctatacgaag ttatcgcg                                    13888
```

<210> SEQ ID NO 219
<211> LENGTH: 13888
<212> TYPE: DNA
<213> ORGANISM: Artificial Sequence
<220> FEATURE:
<223> OTHER INFORMATION: pMON78851;Figure 48;the expression vector for the construct containing the Rhizobium meliloti anthranilate synthase S51C allele

<400> SEQUENCE: 219

```
ccaaatcgtg aagtttctca tctaagcccc catttggacg tgaatgtaga cacgtcgaaa     60

taaagatttc cgaattagaa taatttgttt attgctttcg cctataaata cgacggatcg    120

taatttgtcg ttttatcaaa atgtactttc attttataat aacgctgcgg acatctacat    180

ttttgaattg aaaaaaaatt ggtaattact ctttcttttt ctccatattg accatcatac    240

tcattgctga tccatgtaga tttcccggac atgaagccat ttacaattga atatatcctg    300

ccgccgctgc cgctttgcac ccggtggagc ttgcatgttg gtttctacgc agaactgagc    360

cggttaggca gataatttcc attgagaact gagccatgtg caccttcccc ccaacacggt    420

gagcgacggg gcaacggagt gatccacatg ggacttttcc tagcttggct gccatttttg    480

gggtgaggcc gttcgcggcc gaggggcgca gcccctgggg ggatgggagg cccgcgttag    540

cgggccggga gggttcgaga aggggggca cccccttcg gcgtgcgcgg tcacgcgcac    600

agggcgcagc cctggttaaa aacaaggttt ataaatattg gtttaaaagc aggttaaaag    660

acaggttagc ggtggccgaa aaacgggcgg aaacccttgc aaatgctgga ttttctgcct    720
```

```
gtggacagcc cctcaaatgt caataggtgc gcccctcatc tgtcagcact ctgcccctca    780
agtgtcaagg atcgcgcccc tcatctgtca gtagtcgcgc ccctcaagtg tcaataccgc    840
agggcactta tccccaggct tgtccacatc atctgtggga aactcgcgta aaatcaggcg    900
ttttcgccga tttgcgaggc tggccagctc cacgtcgccg gccgaaatcg agcctgcccc    960
tcatctgtca acgccgcgcc gggtgagtcg gcccctcaag tgtcaacgtc cgcccctcat   1020
ctgtcagtga gggccaagtt ttccgcgagg tatccacaac gccggcggcc ggccgcggtg   1080
tctcgcacac ggcttcgacg gcgtttctgg cgcgtttgca gggccataga cggccgccag   1140
cccagcggcg agggcaacca gcccggtgag cgtcggaaag ggtcgatcga ccgatgccct   1200
tgagagcctt caacccagtc agctccttcc ggtgggcgcg gggcatgact atcgtcgccg   1260
cacttatgac tgtcttcttt atcatgcaac tcgtaggaca ggtgccggca gcgctctggg   1320
tcattttcgg cgaggaccgc tttcgctgga gcgcgacgat gatcggcctg tcgcttgcgg   1380
tattcggaat cttgcacgcc ctcgctcaag ccttcgtcac tggtcccgcc accaaacgtt   1440
tcggcgagaa gcaggccatt atcgccggca tggcggccga cgcgctgggc tacgtcttgc   1500
tggcgttcgc gacgcgaggc tggatggcct tccccattat gattcttctc gcttccggcg   1560
gcatcgggat gcccgcgttg caggccatgc tgtccaggca ggtagatgac gaccatcagg   1620
gacagcttca aggatcgctc gcggctctta ccagcctaac ttcgatcatt ggaccgctga   1680
tcgtcacggc gatttatgcc gcctcggcga gcacatggaa cgggttggca tggattgtag   1740
gcgccgccct ataccttgtc tgcctccccg cgttgcgtcg cggtgcatgg agccgggcca   1800
cctcgacctg aatggaagcc ggcggcacct cgctaacgga ttcaccactc caagaattgg   1860
agccaatcaa ttcttgcgga gaactgtgaa tgcgcaaacc aacccttggc agaacatatc   1920
catcgcgtcc gccatctcca gcagccgcac gcggcgcatc tcgggcagcg ttgggtcctg   1980
gccacgggtg cgcatgatcg tgctcctgtc gttgaggacc cggctaggct ggcggggttg   2040
ccttactggt tagcagaatg aatcaccgat acgcgagcga acgtgaagcg actgctgctg   2100
caaaacgtct gcgacctgag caacaacatg aatggtcttc ggtttccgtg tttcgtaaag   2160
tctggaaacg cggaagtcag cgccctgcac cattatgttc cggatctgca tcgcaggatg   2220
ctgctggcta ccctgtggaa cacctacatc tgtattaacg aagcgctggc attgaccctg   2280
agtgattttt ctctggtccc gccgcatcca taccgccagt tgtttaccct cacaacgttc   2340
cagtaaccgg gcatgttcat catcagtaac ccgtatcgtg agcatcctct ctcgtttcat   2400
cggtatcatt acccccatga acagaaatcc cccttacacg gaggcatcag tgaccaaaca   2460
ggaaaaaacc gcccttaaca tggcccgctt tatcagaagc cagacattaa cgcttctgga   2520
gaaactcaac gagctggacg cggatgaaca ggcagacatc tgtgaatcgc ttcacgacca   2580
cgctgatgag ctttaccgca gctgcctcgc gcgtttcggt gatgacggtg aaaacctctg   2640
acacatgcag ctcccggaga cggtcacagc ttgtctgtaa gcggatgccg ggagcagaca   2700
agcccgtcag ggcgcgtcag cgggtgttgg cgggtgtcgg ggcgcagcca tgacccagtc   2760
acgtagcgat agcggagtgt atactggctt aactatgcgg catcagagca gattgtactg   2820
agagtgcacc atatgcggtg tgaaataccg cacagatgcg taaggagaaa ataccgcatc   2880
aggcgctctt ccgcttcctc gctcactgac tcgctgcgct cggtcgttcg gctgcggcga   2940
gcggtatcag ctcactcaaa ggcggtaata cggttatcca cagaatcagg ggataacgca   3000
ggaaagaaca tgtgagcaaa aggccagcaa aaggccagga accgtaaaaa ggccgcgttg   3060
```

-continued

```
ctggcgtttt tccataggct ccgcccccct gacgagcatc acaaaaatcg acgctcaagt   3120
cagaggtggc gaaacccgac aggactataa agataccagg cgtttccccc tggaagctcc   3180
ctcgtgcgct ctcctgttcc gaccctgccg cttaccggat acctgtccgc ctttctccct   3240
tcgggaagcg tggcgctttc tcatagctca cgctgtaggt atctcagttc ggtgtaggtc   3300
gttcgctcca agctgggctg tgtgcacgaa ccccccgttc agcccgaccg ctgcgcctta   3360
tccggtaact atcgtcttga gtccaacccg gtaagacacg acttatcgcc actggcagca   3420
gccactggta acaggattag cagagcgagg tatgtaggcg gtgctacaga gttcttgaag   3480
tggtggccta actacggcta cactagaagg acagtatttg gtatctgcgc tctgctgaag   3540
ccagttacct tcggaaaaag agttggtagc tcttgatccg gcaaacaaac caccgctggt   3600
agcggtggtt tttttgtttg caagcagcag attacgcgca gaaaaaaagg atctcaagaa   3660
gatcctttga tcttttctac ggggtctgac gctcagtgga acgaaaactc acgttaaggg   3720
attttggtca tgagattatc aaaaaggatc ttcacctaga tccttttaaa ttaaaaatga   3780
agttttaaat caatctaaag tatatatgag taaacttggt ctgacagtta ccaatgctta   3840
atcagtgagg cacctatctc agcgatctgt ctatttcgtt catccatagt tgcctgactc   3900
cccgtcgtgt agataactac gatacgggag ggcttaccat ctggccccag tgctgcaatg   3960
ataccgcgag acccacgctc accggctcca gatttatcag caataaacca gccagccgga   4020
agggccgagc gcagaagtgg tcctgcaact ttatccgcct ccatccagtc tattaattgt   4080
tgccgggaag ctagagtaag tagttcgcca gttaatagtt tgcgcaacgt tgttgccatt   4140
gctgcaggtc gggagcacag gatgacgcct aacaattcat tcaagccgac accgcttcgc   4200
ggcgcggctt aattcaggag ttaaacatca tgagggaagc ggtgatcgcc gaagtatcga   4260
ctcaactatc agaggtagtt ggcgtcatcg agcgccatct cgaaccgacg ttgctggccg   4320
tacatttgta cggctccgca gtggatggcg gcctgaagcc acacagtgat attgatttgc   4380
tggttacggt gaccgtaagg cttgatgaaa caacgcggcg agctttgatc aacgaccttt   4440
tggaaacttc ggcttcccct ggagagagcg agattctccg cgctgtagaa gtcaccattg   4500
ttgtgcacga cgacatcatt ccgtggcgtt atccagctaa gcgcgaactg caatttggag   4560
aatggcagcg caatgacatt cttgcaggta tcttcgagcc agccacgatc gacattgatc   4620
tggctatctt gctgacaaaa gcaagagaac atagcgttgc cttggtaggt ccagcggcgg   4680
aggaactctt tgatccggtt cctgaacagg atctatttga ggcgctaaat gaaaccttaa   4740
cgctatggaa ctcgccgccc gactgggctg gcgatgagcg aaatgtagtg cttacgttgt   4800
cccgcatttg gtacagcgca gtaaccggca aaatcgcgcc gaaggatgtc gctgccgact   4860
gggcaatgga gcgcctgccg gcccagtatc agcccgtcat acttgaagct aggcaggctt   4920
atcttggaca agaagatcgc ttggcctcgc gcgcagatca gttggaagaa tttgttcact   4980
acgtgaaagg cgagatcacc aaggtagtcg gcaaataatg tctaacaatt cgttcaagcc   5040
gacgccgctt cgcggcgcgg cttaactcaa gcgttagatg ctgcaggcat cgtggtgtca   5100
cgctcgtcgt ttggtatggc ttcattcagc tccggttccc aacgatcaag gcgagttaca   5160
tgatccccca tgttgtgcaa aaaagcggtt agctccttcg gtcctccgat cgaggatttt   5220
tcggcgctgc gctacgtccg cgaccgcgtt gagggatcaa gccacagcag cccactcgac   5280
cttctagccg acccagacga gccaagggat ctttttggaa tgctgctccg tcgtcaggct   5340
ttccgacgtt tgggtggttg aacagaagtc attatcgcac ggaatgccaa gcactcccga   5400
ggggaaccct gtggttggca tgcacataca aatggacgaa cggataaacc ttttcacgcc   5460
```

```
cttttaaata tccgattatt ctaataaacg ctcttttctc ttaggtttac ccgccaatat   5520
atcctgtcaa acactgatag tttaaactga aggcgggaaa cgacaatctg atccccatca   5580
agctagcttc tgcaggtcct gctcgaggtc actaagcaac taactttgag gaatgaggtg   5640
atgatgaatt aactcactcc attccacaaa ccaaacaaaa atttgaggag tgagaagatg   5700
attgactatc tcattcctca aaccaaacac ctcaaatata tctgctatcg ggattggcat   5760
tcctgtatcc ctacgcccgt gtacccccctg tttagagaac ctccaaaggt ataagatggc   5820
gaagattatt gttgtcttgt ctttcatcat atatcgagtc tttccctagg atattattat   5880
tggcaatgag cattacacgg ttaatcgatt gagagaacat gcatctcacc ttcagcaaat   5940
aattacgata atccatattt tacgcttcgt aacttctcat gagtttcgat atacaaattt   6000
gttttctgga caccctacca ttcatcctct tcggagaaga gaggaagtgt cctcaattta   6060
aatatgttgt catgctgtag ttcttcacaa aatctcaaca ggtaccaagc acattgtttc   6120
cacaaattat attttagtca caataaatct atattattat taatatacta aaactatact   6180
gacgctcaga tgcttttact agttcttgct agtatgtgat gtaggtctac gtggaccaga   6240
aaatagtgag acacggaaga caaaagaagt aaaagaggcc cggactacgg cccacatgag   6300
attcggcccc gccacctccg gcaaccagcg gccgatccaa cggcagtgcg cgcacacaca   6360
caacctcgta tatatcgccg cgcggaagcg gcgcgaccga ggaagccttg tcctcgacac   6420
cccctacaca ggtgtcgcgc tgcccccgac acgagtcccg catgcgtccc acgcggccgc   6480
gccagatccc gcctccgcgc gttgccacgc cctctataaa cacccagctc tccctcgccc   6540
tcatctacct cactcgtagt cgtagctcaa gcatcagcgg cagcggcagc ggcaggatct   6600
ctgggcagcg tgcgcacgtg gggtatctag ctcgctctgc tagcctacca atcgaattcc   6660
tgcaggtcga ctctagagga tctaccgtct tcggtacgcg ctcactccgc cctctgcctt   6720
tgttactgcc acgtttctct gaatgctctc ttgtgtggtg attgctgaga gtggtttagc   6780
tggatctaga attacactct gaaatcgtgt tctgcctgtg ctgattactt gccgtccttt   6840
gtagcagcaa aatataggga catggtagta cgaaacgaag atagaaccta cacagcaata   6900
cgagaaatgt gtaatttggt gcttagcggt atttatttaa gcacatgttg gtgttatagg   6960
gcacttggat tcagaagttt gctgttaatt taggcacagg cttcatacta catgggtcaa   7020
tagtataggg attcatatta taggcgatac tataataatt tgttcgtctg cagagcttat   7080
tatttgccaa aattagatat tcctattctg tttttgtttg tgtgctgtta aattgttaac   7140
gcctgaagga ataaatataa atgacgaaat tttgatgttt atctctgctc ctttattgtg   7200
accataagtc aagatcagat gcacttgttt taaatattgt tgtctgaaga aataagtact   7260
gacagtattt tgatgcattg atctgcttgt ttgttgtaac aaaatttaaa aataaagagt   7320
ttcctttttg ttgctctcct tacctcctga tggtatctag tatctaccaa ctgacactat   7380
attgcttctc tttacatacg tatcttgctc gatgccttct ccctagtgtt gaccagtgtt   7440
actcacatag tctttgctca tttcattgta atgcagatac caagcggcct ctagaggatc   7500
tccctagagg atctccagat ctatggaatc cctagccgcc acctccgtgt tcgcgccctc   7560
ccgcgtcgcc gtcccggcgg cgcgggccct ggttagggcg gggacggtgg taccaaccag   7620
gcggacgagc agccggagcg gaaccagcgg ggtgaaatgc tctgctgccg tgacgccgca   7680
ggcgagccca gtgattagca ggagcgctgc ggcggccatg gcagcggtaa ttctggaaga   7740
cggcgcggag agttatacca cgaagggtgg catcgtcgtc acccgcaggc ggcgtgaggc   7800
```

```
atcctacagc gacgcgatcg ccggttatgt cgaccggctg gacgaacgcc gcggcgcggt   7860
cttttcctgc aactacgaat atcccggccg ctatacccgc tgggacactg cggtggtcga   7920
cccgccgctt gccatctcct ccttcggtcg ctcgctctgg atcgaagcct ataacgaacg   7980
cggcgaagtg ctgctggcgc tgatcgccga ggatctgaag tccgttgccg acatcacgct   8040
cggctcactt gccgcccgcc gcctcgacct caccatcaac gagcccgatc gtgtcttcac   8100
cgaggaagag cggtcgaaga tgccgacggt ctttacggtt cttcgcgcgg tgacgaacct   8160
cttccactcg gaggaggact cgaacctcgg cctctatggc gccttcggct acgacctcgc   8220
cttccagttc gatgcgatcg aactgaagct ttcgcgtccg gacgaccagc gcgacatggt   8280
tctctttctg ccggacgaga tccttgtggt cgatcactat gcggccaagg cctggatcga   8340
ccgctacgat ttcgccaggg agaacctttc gaccgagggc aaggcagcgg acattgctcc   8400
cgagccgttc cgcagcgtcg acagcatccc gccgcacggg gatcaccgcc cgggcgaata   8460
tgccgagctc gtcgtcaagg cgaaggaaag cttccgtcgc ggcgatcttt tcgaagtggt   8520
gccggggcag aaattctacg agcgctgcga aagccgcccg tccgagattt ccaaccggct   8580
gaaggcgatc aatccgtcgc cctattcctt cttcatcaat ctcggcaacc aggaatatct   8640
cgtcggtgct tcgccggaga tgttcgtgcg cgtttccggc cggcgcatcg agacctgccc   8700
gatctccggt acgatcaagc gcggcgacga tccgatcgcc gacagcgagc agatcctgaa   8760
gctcttgaac tcgaagaagg acgagtccga gctcaccatg tgctcggacg tcgaccgcaa   8820
cgacaagagc cgggtctgcg tgccgggctc ggtcaaggtg atcggccggc gtcagatcga   8880
gatgtattcg cggctgatcc acacggtcga tcacatcgag gggcgcctgc gcgacgatat   8940
ggacgccttc gacgggttcc tcagccacgc ctgggcggtg accgttaccg gcgcgccaaa   9000
gctctgggcc atgcgcttca tcgagagcca cgagaagagc ccgcgtgcct ggtatggcgg   9060
cgcgatcggc atggtcggct tcaacggcga catgaatacc gggctgacct tgcgtaccat   9120
ccgcatcaag gacgggatcg ccgaggtgag ggcgggtgcg acgctcctct atgattccaa   9180
tccggaagaa gaagaagccg aaaccgaact gaaggcctct gccatgattg cagccatccg   9240
cgacgcgaaa tccgcaaaca gcgccaaatc cgcgcgcgat gtcgccgccg tcggcgccgg   9300
agtcagcatc ctgctcgtcg atcacgagga cagcttcgtc cataccctcg cgaactactt   9360
ccgccagacc ggcgcgtccg tcaccaccgt gcgcacgccg gtggccgagg aaatcttcga   9420
ccgggtcaag ccggacctcg tcgtgctttc gcccggtccc ggcacccccga aggacttcga   9480
ctgcaaggcg acgatcaaga aggcgcgggc gcgggacctg ccgatcttcg gcgtctgcct   9540
ggggctgcag gcgctcgcgg aggcctatgg cggcgacctt cgtcaactgg cgatcccgat   9600
gcatgggaag ccctcgcgca tccgcgtgct cgaacccggc atcgtcttct ccggcctcgg   9660
caaggaggtg acggtcgggc gctatcattc gattttcgcc gatccgtcca acctgccgcg   9720
cgaattcgtg atcacggccg aaagcgaaga tggtacgatc atgggcatcg aacacagcaa   9780
ggagccggtg gcggccgtgc agttccatcc ggaatcgatc atgacgctgg gcggcgacgc   9840
cggcatgcgg atgatcgaga acgtggttgc ccatctcgcc aagcgggcga agaccaaggc   9900
agcctgaact agatcggatc cggggatcga tgagctaagc tagctatatc atcaatttat   9960
gtattacaca taatatcgca ctcagtcttt catctacggc aatgtaccag ctgatataat  10020
cagttattga aatatttctg aatttaaact tgcatcaata aatttatgtt tttgcttgga  10080
ctataatacc tgacttgtta ttttatcaat aaatatttaa actatatttc tttcaagata  10140
tcattcttta caagtatacg tgtttaaatt gaataccata aatttttatt tttcaaatac  10200
```

```
atgtaaaatt atgaaatggg agtggtggcg accgagctca agcacacttc aattcctata  10260
acggaccaaa tcgcaaaaat tataataaca tattatttca tcctggatta aaagaaagtc  10320
accggggatt attttgtgac gccgattaca tacggcgaca ataaagacat tggaaatcgt  10380
agtacatatt ggaatacact gattatatta atgatgaata catactttaa tatccttacg  10440
taggatcgat ccgaatttcg acctcgagcg gccgctctag aactagtgga tcccccccctt  10500
aattaagggg gctgcaggaa ttcataactt cgtataatgt atgctatacg aagttatgtt  10560
tcgaggtcat tcatatgctt gagaagagag tcgggatagt ccaaaataaa acaaaggtaa  10620
gattacctgg tcaaaagtga aaacatcagt taaaaggtgg tataaagtaa aatatcggta  10680
ataaaaggtg gcccaaagtg aaatttactc ttttctacta ttataaaaat tgaggatgtt  10740
tttgtcggta ctttgatacg tcatttttgt atgaattggt ttttaagttt attcgctttt  10800
ggaaatgcat atctgtattt gagtcgggtt ttaagttcgt ttgcttttgt aaatacagag  10860
ggatttgtat aagaaatatc tttagaaaaa cccatatgct aatttgacat aatttttgag  10920
aaaaatatat attcaggcga attctcacaa tgaacaataa taagattaaa atagctttcc  10980
cccgttgcag cgcatgggta ttttttctag taaaaataaa agataaactt agactcaaaa  11040
catttacaaa aacaacccct aaagttccta aagcccaaag tgctatccac gatccatagc  11100
aagcccagcc caacccaacc caacccaacc caccccagtc cagccaactg gacaatagtc  11160
tccacacccc cccactatca ccgtgagttg tccgcacgca ccgcacgtct cgcagccaaa  11220
aaaaaaaaga aagaaaaaaa agaaaaagaa aaaacagcag gtgggtccgg gtcgtggggg  11280
ccggaaacgc gaggaggatc gcgagccagc gacgaggccg gccctccctc cgcttccaaa  11340
gaaacgcccc ccatcgccac tatatacata cccccccctc tcctcccatc cccccaaccc  11400
taccaccacc accaccacca cctccacctc ctcccccctc gctgccggac gacgagctcc  11460
tccccccctcc ccctccgccg ccgccgcgcc ggtaaccacc ccgcccctct cctctttctt  11520
tctccgtttt tttttccgtc tcggtctcga tctttggcct tggtagtttg ggtgggcgag  11580
aggcggcttc gtgcgcgccc agatcggtgc gcgggagggg cgggatctcg cggctggggc  11640
tctcgccggc gtggatccgg cccggatctc gcggggaatg gggctctcgg atgtagatct  11700
gcgatccgcc gttgttgggg gagatgatgg ggggtttaaa atttccgccg tgctaaacaa  11760
gatcaggaag aggggaaaag ggcactatgg tttatatttt tatatatttc tgctgcttcg  11820
tcaggcttag atgtgctaga tctttctttc ttctttttgt gggtagaatt tgaatccctc  11880
agcattgttc atcggtagtt tttcttttca tgatttgtga caaatgcagc ctcgtgcgga  11940
gctttttttgt aggtagaagt gatcaaccat ggcgcaagtt agcagaatct gcaatggtgt  12000
gcagaaccca tctcttatct ccaatctctc gaaatccagt caacgcaaat ctcccttatc  12060
ggtttctctg aagacgcagc agcatccacg agcttatccg atttcgtcgt cgtggggatt  12120
gaagaagagt gggatgacgt taattggctc tgagcttcgt cctcttaagg tcatgtcttc  12180
tgtttccacg gcgtgcatgc ttcacggtgc aagcagccgg cccgcaaccg cccgcaaatc  12240
ctctggcctt tccggaaccg tccgcattcc cggcgacaag tcgatctccc accggtcctt  12300
catgttcggc ggtctcgcga gcggtgaaac gcgcatcacc ggccttctgg aaggcgagga  12360
cgtcatcaat acgggcaagg ccatgcaggc gatgggcgcc cgcatccgta aggaaggcga  12420
cacctggatc atcgatggcg tcggcaatgg cggcctcctg gcgcctgagg cgccgctcga  12480
tttcggcaat gccgccacgg gctgccgcct gacgatgggc ctcgtcgggg tctacgattt  12540
```

```
cgacagcacc ttcatcggcg acgcctcgct cacaaagcgc ccgatgggcc gcgtgttgaa  12600

cccgctgcgc gaaatgggcg tgcaggtgaa atcggaagac ggtgaccgtc ttcccgttac  12660

cttgcgcggg ccgaagacgc cgacgccgat cacctaccgc gtgccgatgg cctccgcaca  12720

ggtgaagtcc gccgtgctgc tcgccggcct caacacgccc ggcatcacga cggtcatcga  12780

gccgatcatg acgcgcgatc atacggaaaa gatgctgcag ggctttggcg ccaaccttac  12840

cgtcgagacg gatgcggacg gcgtgcgcac catccgcctg gaaggccgcg gcaagctcac  12900

cggccaagtc atcgacgtgc cgggcgaccc gtcctcgacg gccttcccgc tggttgcggc  12960

cctgcttgtt ccgggctccg acgtcaccat cctcaacgtg ctgatgaacc ccacccgcac  13020

cggcctcatc ctgacgctgc aggaaatggg cgccgacatc gaagtcatca acccgcgcct  13080

tgccggcggc gaagacgtgg cggacctgcg cgttcgctcc tccacgctga agggcgtcac  13140

ggtgccggaa gaccgcgcgc cttcgatgat cgacgaatat ccgattctcg ctgtcgccgc  13200

cgccttcgcg gaaggggcga ccgtgatgaa cggtctggaa gaactccgcg tcaaggaaag  13260

cgaccgcctc tcggccgtcg ccaatggcct caagctcaat ggcgtggatt gcgatgaggg  13320

cgagacgtcg ctcgtcgtgc gtggccgccc tgacggcaag gggctcggca acgcctcggg  13380

cgccgccgtc gccacccatc tcgatcaccg catcgccatg agcttcctcg tcatgggcct  13440

cgtgtcggaa aaccctgtca cggtggacga tgccacgatg atcgccacga gcttcccgga  13500

gttcatggac ctgatggccg ggctgggcgc gaagatcgaa ctctccgata cgaaggctgc  13560

ctgatgagct cgaattcccg atcgttcaaa catttggcaa taaagtttct taagattgaa  13620

tcctgttgcc ggtcttgcga tgattatcat ataatttctg ttgaattacg ttaagcatgt  13680

aataattaac atgtaatgca tgacgttatt tatgagatgg gtttttatga ttagagtccc  13740

gcaattatac atttaatacg cgatagaaaa caaaatatag cgcgcaaact aggataaatt  13800

atcgcgcgcg gtgtcatcta tgttactaga tcggggataa cgatcaagct ataacttcgt  13860

ataatgtatg ctatacgaag ttatcgcg                                     13888
```

<210> SEQ ID NO 220
<211> LENGTH: 866
<212> TYPE: DNA
<213> ORGANISM: Hordeum vulgare

<400> SEQUENCE: 220

```
ggtttacata tttaaaggaa aaaatgttca tcgattttaa aaaaaagttc atacctttca     60

aaaacgttca tcaatttttt taaaaagttc actaaaaatg aaaaaaagtt catccaattt    120

aaaaaaagtt cattaatttt ttataaattt caataaattt gaaaaaactt cataaaattc    180

aacaaaagtt cattgaagtg aaaaaagctc ataaatcttt aaaaagtgca tccattttca    240

aaaagatgtt catcaaaatt caatatagtt caccaatatt caaaaaagtt cattaatctt    300

aaaaaatatt cgctaaaatt taaaaaatgt ttatcaatat ttaaacggcg tctagatgag    360

ccggtctatt tacaaacacc ataggcgcca attaacaaaa atgcacgtta gatcacgtct    420

acggcgtcaa ataggaaatg cccatcggcc ttactattaa gagttgtttt ggttatcctt    480

taggatttat gctgtgggct ggacttaaca caaaacccac agccatggta ggccggaatc    540

tattattcag ctcacaaacg atgttctact caaaagaaga aaaaaatctg ttgtcagaaa    600

aagagaacaa aaaaggctca cgaacatgcc gcggctcgca caggtggccg tgagcttctg    660

aatgacttgg ccacccggca tgtccactgc ccccctagac ggtgtgggtg ggtggacagg    720

tcaagcgcat tgaacaaggt caccctgcgt tctgccacga ggccaactgc gtggccctca    780
```

tgcaacgcgc cttgctgcca cttctacaca cgccctcgcc ggccgaccgc tgctataaaa 840
gcagctcccc gttgcgtcct cgacgg 866

<210> SEQ ID NO 221
<211> LENGTH: 392
<212> TYPE: DNA
<213> ORGANISM: Zea mays

<400> SEQUENCE: 221
gatctcgtca atttttccct tttgtaattt tgtaatttat aatttacttt cctgtatgct 60
tctaactctg tcgttttaaa attttaataa aatttcagta ggggcttgcc cctcctgtcc 120
tataaaaaaa agttgacgtg aatagatttc attaagaggt tggatgttag tgggatgaca 180
tgactattag taggacgaga tgatgtggaa agttagtggg agatgatatg gatagttttt 240
gctttcatcg aaaggttgga agttagtatg atgacatggc taatatagat acatagatat 300
agactaccaa catggctgca tgcccccaag ctctcccact atatatatct ctggtagcac 360
atcatcccaa ttcacaatgc ttacaaaaac cc 392

<210> SEQ ID NO 222
<211> LENGTH: 1041
<212> TYPE: DNA
<213> ORGANISM: Zea mays

<400> SEQUENCE: 222
gtcccgcgtc aatattatta aaaaactcct acatttcttt ataatcaacc cgcactctta 60
taatctcttc tctactacta taataagaga gtttatgtac aaaataaggt gaaattatgt 120
ataagtgttc tggatattgg ttgttggctc catattcaca caacctaatc aatagaaaac 180
atatgtttta ttaaaacaaa atttatcata tatcatatat atatatatac atatatatat 240
atatatatat aaaccgtagc aatgcacggg catataacta gtgcaactta atacatgtgt 300
gtattaagat gaataagagg gtatccaaat aaaaaacttg ttcgcttacg tctggatcga 360
aaggggttgg aaacgattaa atctcttcct agtcaaaatt gaatagaagg agatttaatc 420
tctcccaatc cccttcgatc atccaggtgc aaccgtataa gtcctaaagt ggtgaggaac 480
acgaaacaac catgcattgg catgtaaagc tccaagaatt tgttgtatcc ttaacaactc 540
acagaacatc aaccaaaatt gcacgtcaag ggtattgggt aagaaacaat caaacaaatc 600
ctctctgtgt gcaaagaaac acggtgagtc atgccgagat catactcatc tgatatacat 660
gcttacagct cacaagacat tacaaacaac tcatattgca ttacaaagat cgtttcatga 720
aaaataaaat aggccggaca ggacaaaaat ccttgacgtg taaagtaaat ttacaacaaa 780
aaaaaagcca tatgtcaagc taaatctaat tcgttttacg tagatcaaca acctgtagaa 840
ggcaacaaaa ctgagccacg cagaagtaca gaatgattcc agatgaacca tcgacgtgct 900
acgtaaagag agtgacgagt catatacatt tggcaagaaa ccatgaagct gcctacagcc 960
gtctcggtgg cataagaaca caagaaattg tgttaattaa tcaaagctat aaataacgct 1020
cgcatgcctg tgcacttctc c 1041

<210> SEQ ID NO 223
<211> LENGTH: 1401
<212> TYPE: DNA
<213> ORGANISM: Zea mays

<400> SEQUENCE: 223

```
aagcttgccg agtgccatcc ttggacactc gataaagtat attttatttt ttttattttg     60
ccaaccaaac tttttgtggt atgttcctac actatgtaga tctacatgta ccattttggc    120
acaattacat atttacaaaa atgttttcta taaatattag atttagttcg tttatttgaa    180
tttcttcgga aaattcacat ttaaactgca agtcactcga aacatggaaa accgtgcatg    240
caaaataaat gatatgcatg ttatctagca caagttacga ccgatttcag aagcagacca    300
gaatcttcaa gcaccatgct cactaaacat gaccgtgaac ttgttatcta gttgtttaaa    360
aattgtataa aacacaaata aagtcagaaa ttaatgaaac ttgtccacat gtcatgatat    420
catatataga ggttgtgata aaaatttgat aatgtttcgg taaagttgtg acgtactatg    480
tgtagaaacc taagtgacct acacataaaa tcatagagtt tcaatgtagt tcactcgaca    540
aagactttgt caagtgtccg ataaaaagta ctcgacaaag aagccgttgt cgatgtactg    600
ttcgtcgaga tctctttgtc gagtgtcaca ctaggcaaag tctttacgga gtgtttttca    660
ggctttgaca ctcggcaaag cgctcgattc cagtagtgac agtaatttgc atcaaaaata    720
gctgagagat ttaggccccg tttcaatctc acgggataaa gtttagcttc ctgctaaact    780
ttagctatat gaattgaagt gctaaagttt agtttcaatt accaccatta gctctcctgt    840
ttagattaca aatggctaaa agtagctaaa aaatagctgc taaagtttat ctcgcgagat    900
tgaaacaggg ccttaaaatg agtcaactaa tagaccaact aattattagc tattagtcgt    960
tagcttcttt aatctaagct aaaaccaact aatagcttat ttgttgaatt acaattagct   1020
caacggaatt ctctgttttt ctaaaaaaaa actgcccctc tcttacagca aattgtccgc   1080
tgcccgtcgt ccagatacaa tgaacgtacc tagtaggaac tcttttacac gctcggtcgc   1140
tcgccgcgga tcggagtccc cggaacacga caccactgtg gaacacgaca aagtctgctc   1200
agaggcggcc acaccctggc gtgcaccgag ccggagcccg gataagcacg gtaaggagag   1260
tacggcggga cgtggcgacc cgtgtgtctg ctgccacgca gccttcctcc acgtagccgc   1320
gcggccgcgc cacgtaccag ggcccggcgc tggtataaat gcgcgccacc tccgctttag   1380
ttctgcatac agccaaccca a                                             1401
```

<210> SEQ ID NO 224
<211> LENGTH: 1805
<212> TYPE: DNA
<213> ORGANISM: Coix lacryma-jobi

<400> SEQUENCE: 224

```
ggcggaagtt ttgcggcgga gctccggtcg gtgttggaga agacgaccac agcggtggcg     60
ttacggttca ccggagtagg ctagcgaggg ctcaacgaaa gctcaggagg cggcgggatc    120
agaagcacgg ccaatttggc cgtagacggc gtaacgacgg cgaggtgtgg aagcggagct    180
tggcgatttc agaggagcag aggaggaaaa cggggatggt accggcgatg aggaggctta    240
tatagccggc caaggacctg gggcgaaggg cacgtcaaag gcggtcacca cagtgcaagc    300
aggaggtggc ctggtggcgt ggcatggtcg gcagaggata cggcggtgtg gcggccgacg    360
agcagagcac gactctgctc tgatattttt tcccctccgg ttactgttca ccagagaaca    420
tctagatctt ctttccccta tttctccaaa aacattatac aacaggaaaa actcccaaca    480
tgaaagttgt tccaaaaatt aggacctaca actttcattt aaggagcaca accaaaatct    540
gcctagattt taaaatcaca ttttgaattt gaaaaacatt caaacttgaa ttcaaaatta    600
cttttgaatt ttctgaacga cttcaaattt tatcaatata aaagttgttc ctcattaaat    660
tatctacaac tttgtttttg gtcatatatc caaattgtgc ttaattttga aactaaaaaa    720
```

gggataaaac taggttttgg gaattgattt tcaatttgaa accaaatcaa acttgttttc 780
caaatcactt cagattctct ttagtaactt gaaaatctat cttaataaaa gttgtttctt 840
ttaatcctct ctacaacttt gattaaaaga cccaagtcta attcttttta gtttttgaaa 900
tctagtttag ggtcaaatt cagggtttga aacatttcaa atttattcaa aattttgtac 960
agaaacttta aaaactttga ataccaaagt tgtacatctc aacaagagct acaactttgc 1020
ttttgaaatc attttgaaat ttgacatact ttttgactta ttaaaaaggg gacaaaaaga 1080
gagatttaaa aaccaaggtt ttctcacttg ccctatcatg taacaccaaa catctcaatc 1140
aagccacata tatatcaaac atggaaatca acactcaaaa acatacaaca ctcttgtcaa 1200
acatacaaag catcatattt atgccttaaa cataaaaaca tgaaatgctt ttatgccatg 1260
atgccagatg attatgcata ctaaacaact taattaaaat tttaattaat gtttaacacc 1320
aggggtgtta cattaggcaa ttagtccatg ccaaacattt ctattgcatc cagagaccag 1380
aatagctttt tttttaatat ttaaccaaaa aaagaagaaa atgaggtgaa tgaatgggcc 1440
gacgggcaca taaactattg catggaccca gactattgaa ggcccgctaa tgttgagaca 1500
cggaacgcaa aaggaaaaga gggcccagac tacggcccac gcgtgggatt cggcccggcc 1560
acctccggca accagcggct catcatccaa cgccactacg ccagggcgtt cgtccacaac 1620
ctcctcgtac atatcgccgg gcggaagcgg cgcgaccgcg caagcgcaag cttgtcctcg 1680
acagcccgca caggtgtcgc gcggccccgg acacgagtcc cgcatgcgcc ccacgcggcc 1740
gcgccaggtc ccgcctcccc gcatccccac gccctctata aaccccgcgc tctccctggc 1800
cctcg 1805

<210> SEQ ID NO 225
<211> LENGTH: 232
<212> TYPE: DNA
<213> ORGANISM: Oryza sativa

<400> SEQUENCE: 225
gttggcaatg cggataaaga ataactaaat aaataaataa ataaattgca agcaattgcg 60
ttgctgctat gtactgtaaa agtttcttat aatatcagtt ctgaatgcta aggacatccc 120
tcaagatggt ctttctattt ttgtgttccc gttccaatgt actgttggta tcctcttgga 180
gattcatcaa tatgagaaaa cagagaatgg acaaccctcc cttatcttat gg 232

<210> SEQ ID NO 226
<211> LENGTH: 24
<212> TYPE: DNA
<213> ORGANISM: Artificial Sequence
<220> FEATURE:
<223> OTHER INFORMATION: primer

<400> SEQUENCE: 226
atgagtataa gaatgctgtt ctgc 24

<210> SEQ ID NO 227
<211> LENGTH: 21
<212> TYPE: DNA
<213> ORGANISM: Artificial Sequence
<220> FEATURE:
<223> OTHER INFORMATION: primer

<400> SEQUENCE: 227
gcacactgtt tttcacttaa c 21

```
<210> SEQ ID NO 228
<211> LENGTH: 24
<212> TYPE: DNA
<213> ORGANISM: Artificial Sequence
<220> FEATURE:
<223> OTHER INFORMATION: primer

<400> SEQUENCE: 228

tcgcgcccct caagtgtcaa tacc                                          24


<210> SEQ ID NO 229
<211> LENGTH: 24
<212> TYPE: DNA
<213> ORGANISM: Artificial Sequence
<220> FEATURE:
<223> OTHER INFORMATION: primer

<400> SEQUENCE: 229

caccgcctac atacctcgct ctgc                                          24


<210> SEQ ID NO 230
<211> LENGTH: 16
<212> TYPE: DNA
<213> ORGANISM: Artificial Sequence
<220> FEATURE:
<223> OTHER INFORMATION: primer

<400> SEQUENCE: 230

ggacagcccc tcaaat                                                   16


<210> SEQ ID NO 231
<211> LENGTH: 20
<212> TYPE: DNA
<213> ORGANISM: Artificial Sequence
<220> FEATURE:
<223> OTHER INFORMATION: primer

<400> SEQUENCE: 231

cctacatacc tcgctctgct                                               20
```